United States Patent
Ho et al.

(10) Patent No.: US 9,409,892 B2
(45) Date of Patent: Aug. 9, 2016

(54) 4-HYDROXY-ISOQUINOLINE COMPOUNDS AS HIF HYDROXYLASE INHIBITORS

(71) Applicant: FIBROGEN, INC., San Francisco, CA (US)

(72) Inventors: Wen-Bin Ho, Los Altos, CA (US); Hongda Zhao, Dublin, CA (US); Shaojiang Deng, Foster City, CA (US); Danny Ng, Daly City, CA (US); Lee R. Wright, Redwood City, CA (US); Min Wu, Sunnyvale, CA (US); Xiaoti Zhou, Burlingame, CA (US); Michael P. Arend, Foster City, CA (US); Lee A. Flippin, Woodside, CA (US)

(73) Assignee: FibroGen, Inc., San Francisco, CA (US)

( * ) Notice: Subject to any disclaimer, the term of this patent is extended or adjusted under 35 U.S.C. 154(b) by 0 days.

(21) Appl. No.: 14/383,874

(22) PCT Filed: Mar. 8, 2013

(86) PCT No.: PCT/US2013/029912
§ 371 (c)(1),
(2) Date: Sep. 8, 2014

(87) PCT Pub. No.: WO2013/134660
PCT Pub. Date: Sep. 12, 2013

(65) Prior Publication Data
US 2015/0038528 A1    Feb. 5, 2015

Related U.S. Application Data

(60) Provisional application No. 61/609,022, filed on Mar. 9, 2012.

(51) Int. Cl.
| | |
|---|---|
| C07D 217/26 | (2006.01) |
| C07D 401/12 | (2006.01) |
| A61K 31/44 | (2006.01) |
| A61K 31/47 | (2006.01) |
| C07D 409/12 | (2006.01) |
| C07D 401/04 | (2006.01) |
| C07D 405/12 | (2006.01) |

(52) U.S. Cl.
CPC ............ *C07D 409/12* (2013.01); *C07D 217/26* (2013.01); *C07D 401/04* (2013.01); *C07D 401/12* (2013.01); *C07D 405/12* (2013.01)

(58) Field of Classification Search
None
See application file for complete search history.

(56) References Cited

U.S. PATENT DOCUMENTS

| | | | |
|---|---|---|---|
| 3,989,704 A | 11/1976 | Houlihan et al. | |
| 4,036,964 A | 7/1977 | Buckle et al. | |
| 4,260,611 A | 4/1981 | Bartmann et al. | |
| 4,559,403 A | 12/1985 | Bruderer et al. | |
| 4,584,379 A | 4/1986 | Wagner | |
| 4,673,682 A | 6/1987 | Konz et al. | |
| 4,822,800 A | 4/1989 | Faltico et al. | |
| 4,952,588 A | 8/1990 | Glamkowski et al. | |
| 4,966,906 A | 10/1990 | Glamkowski et al. | |
| 5,620,995 A | 4/1997 | Weidmann et al. | |
| 5,658,933 A | 8/1997 | Weidmann et al. | |
| 5,719,164 A | 2/1998 | Weidmann et al. | |
| 5,726,305 A | 3/1998 | Weidmann et al. | |
| 6,093,730 A | 7/2000 | Weidmann et al. | |
| 6,319,931 B1 | 11/2001 | Kroemer et al. | |
| 6,358,973 B1 | 3/2002 | Napoletano et al. | |
| 6,358,976 B1 | 3/2002 | Wityak et al. | |
| 6,369,053 B1 | 4/2002 | Yuan et al. | |
| 6,762,318 B2 | 7/2004 | Kodra et al. | |
| 6,777,425 B2 | 8/2004 | Burli et al. | |
| 6,903,114 B2 | 6/2005 | Backstrom et al. | |
| 7,208,601 B2 | 4/2007 | Mjalli et al. | |
| 7,323,475 B2 | 1/2008 | Arend et al. | |
| 7,629,357 B2 | 12/2009 | Arend et al. | |
| 7,696,223 B2 | 4/2010 | Deng et al. | |
| 7,863,292 B2 | 1/2011 | Arend et al. | |

(Continued)

FOREIGN PATENT DOCUMENTS

| | | |
|---|---|---|
| CA | 2134866 | 5/1995 |
| EP | 0650960 | 5/1995 |

(Continued)

OTHER PUBLICATIONS

International Search Report and Written Opinion for PCT/US2013/029912 dated Mar. 8, 2013, 3 pages.

(Continued)

*Primary Examiner* — Zinna Northington Davis

(74) *Attorney, Agent, or Firm* — Leanne C. Price; Sheppard Mullin Richter & Hampton LLP

(57) ABSTRACT

The present invention relates to novel compounds of formula (I), and compositions capable of inhibiting PHD1 enzyme activity selectively over other isoforms, for example, PHD2 and/or PHD3 enzymes. The invention also relates to compounds of formula (I) for use in disorders such as muscle degeneration, colitis, IBD, and certain ischemias.

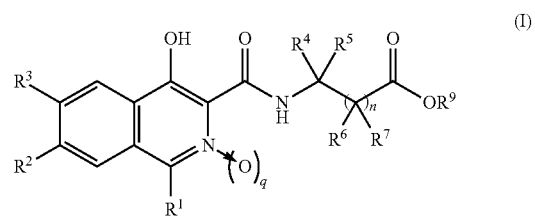

30 Claims, No Drawings

(56) References Cited

U.S. PATENT DOCUMENTS

| | | |
|---|---|---|
| 7,928,120 B2 | 4/2011 | Arend et al. |
| 8,017,625 B2 | 9/2011 | Arend et al. |
| 8,278,325 B2 | 10/2012 | Arend et al. |
| 8,765,956 B2 | 7/2014 | Arend et al. |
| 8,916,585 B2 | 12/2014 | Arend et al. |
| 2003/0153503 A1 | 8/2003 | Klaus et al. |
| 2003/0176317 A1 | 9/2003 | Guenzler-Pukall et al. |
| 2004/0204356 A1 | 10/2004 | Guenzler-Pukall et al. |
| 2004/0235082 A1 | 11/2004 | Fourney et al. |
| 2004/0254215 A1 | 12/2004 | Arend et al. |
| 2005/0020487 A1 | 1/2005 | Klaus et al. |
| 2006/0178316 A1 | 8/2006 | Klaus et al. |
| 2006/0178317 A1 | 8/2006 | Klaus et al. |
| 2006/0183695 A1 | 8/2006 | Klaus et al. |
| 2006/0199836 A1 | 9/2006 | Turtle et al. |
| 2006/0217416 A1 | 9/2006 | Arend et al. |
| 2006/0251638 A1 | 11/2006 | Guenzler-Pukall et al. |
| 2006/0258660 A1 | 11/2006 | Guenzler-Pukall et al. |
| 2006/0258702 A1 | 11/2006 | Guenzler-Pukall et al. |
| 2006/0270699 A1 | 11/2006 | Guenzler-Pukall et al. |
| 2006/0276477 A1 | 12/2006 | Klaus et al. |
| 2007/0004627 A1 | 1/2007 | Seeley et al. |
| 2007/0155784 A1 | 7/2007 | Arend et al. |
| 2007/0185159 A1 | 8/2007 | Arend et al. |
| 2007/0292433 A1 | 12/2007 | Seeley et al. |
| 2007/0293575 A1 | 12/2007 | Seeley et al. |
| 2007/0298104 A1 | 12/2007 | Arend et al. |
| 2008/0004309 A1 | 1/2008 | Deng et al. |
| 2010/0047367 A1 | 2/2010 | Deng et al. |
| 2010/0303928 A1 | 12/2010 | Arend et al. |
| 2010/0330199 A1 | 12/2010 | Zhou et al. |
| 2010/0331400 A1 | 12/2010 | Ho et al. |
| 2011/0212959 A1 | 9/2011 | Arend et al. |
| 2011/0305776 A1 | 12/2011 | Ho et al. |
| 2012/0029011 A1 | 2/2012 | Arend et al. |
| 2014/0343094 A1 | 11/2014 | Arend et al. |

FOREIGN PATENT DOCUMENTS

| | | |
|---|---|---|
| EP | 0650961 | 5/1995 |
| EP | 0911340 | 4/1999 |
| JP | A-H07-224039 | 8/1995 |
| JP | A-H07-228571 | 8/1995 |
| JP | A-H11302257 | 11/1999 |
| JP | 2005-524612 | 8/2005 |
| JP | 2006-514113 | 4/2006 |
| JP | 2006-137763 | 6/2006 |
| JP | 2006-527199 | 11/2006 |
| WO | WO 96/18616 | 6/1996 |
| WO | WO 01/58892 | 8/2001 |
| WO | WO 02/070510 | 9/2002 |
| WO | WO 02/100832 | 12/2002 |
| WO | WO 02/101073 | 12/2002 |
| WO | WO 03/053997 | 7/2003 |
| WO | WO 2004/052285 | 6/2004 |
| WO | WO 2004/108121 | 12/2004 |
| WO | WO 2004/108681 | 12/2004 |
| WO | WO 2005/007192 | 1/2005 |
| WO | WO 2005/009962 | 2/2005 |
| WO | WO 2005/011696 | 2/2005 |
| WO | WO 2005/014533 | 2/2005 |

OTHER PUBLICATIONS

Bruick et al., A Conserved Family of Proly-4-Hydroxylases That Modify HIF, Science, vol. 294, pp. 1337-1340, (2001).

Cunliffe et al., Novel Inhibitors of Prolyl 4-Hydroxylase 3 Inhibition by the Substrate Analogue N-Oxaloglycine and Its Derivatives, *J. Med. Chem.*, vol. 35, pp. 2652-2658, (1992).

Duro et al., Sintesi Ed Attivita Farmacologica D1 Ammmino-E Dialchilamminoalchilammidi-D1 Derivati Della 3-Carbossi-4-Fenillisochinolina, *Ed. Sc.*, vol. 36, pp. 400-411, (1980) (Abstract in English).

Franklin et al., Approaches to the Design of Anti-Fibrotic Drugs, *Biochem. Soc. Trans.*, 19(4):812-815, (1991).

Guo et al., Selective Protection of 2',2'-Difluorodeoxycytidine (Gemcitabine), *J. Org. Chem.*, vol. 64, pp. 8319-8322, (1999).

Ivan et al., HIFα Targeted for VHL-Mediated Destruction by Proline Hydroxylation: Implications for $O_2$ Sensing, *Science*, 292:464-468, (2001).

Jaakkola et al., Targeting of HIF-α to the von Hippel-Lindau Ubiquitylation Complex by $O_2$-Regulated Prolyl Hydroxylation, *Science*, 292(5516):468-472, (2001).

Lando et al., Oxygen-Dependent Regulation of Hypoxia-Inducible Factors by Polyl and Asparaginyl Hydroxylation, *Eur. J. Biochem*, 270:781-790, (2003).

Richard et al., Nonhypoxic Pathway Mediates the Induction of Hypoxia-Inducible Factor 1α in Vascular Smooth Muscle Cells, *J. Bio. Chm.*, 275:26765-26771, (2000).

Safran et al., HIF Hydroxylation and the Mammalian Oxygen-Sensing Pathway, *J. Clin. Invest.*, 111(6):779-783, (2003).

Sandau et al., Induction of Hypoxia-Inducible-Factor 1 by Nitric Oxide Is Mediated Via the P1 3K Pathway, *Biochem. Biophys. Res. Commun.*, 278:263-267, (2000).

Sato et al., Stability and Physicochemical Properties of Viracept Tablets, *Antibiotics and Chemotherapy*, 14(9):1589-1592, (1998)—English Translation Not Available.

Sodhi et al., MAPK and Akt Act Cooperatively But Independently on Hypoxia Inducible Factor-1 α in rasV12 Unpregulation of VEGF, *Biochem. Biophys. Res. Commun.*, 287:292-300, (2001).

Tacchini et al., Hepatocyte Growth Factor Signaling Stimulates Hypoxia Inducible Factor-1 (HIF-1) Activity in HepG2 Hepatoma Cells, *Carcinogenesis*, 22:1363-1371, (2001).

Wu et al., Regulatory Perspectives of Type II Prodrug Development and Time-Dependent Toxicity Management: Nonclinical Pharm/Tox Analysis and the Role of Comparative Toxicology, *Toxicology*, 236, pp. 1-6, (2007).

4-HYDROXY-ISOQUINOLINE COMPOUNDS AS HIF HYDROXYLASE INHIBITORS

CROSS REFERENCE TO RELATED APPLICATIONS

This application is a U.S. National Stage Application under 35 U.S.C. §371 of International Application No. PCT/US2013/029912, filed Mar. 8, 2013, which claims the benefit under 35 U.S.C. §119(e) of U.S. Provisional Application 61/609,022 filed Mar. 9, 2012, the contents of which are hereby incorporated by reference in their entirety.

BACKGROUND

1. Field

The present invention relates to novel compounds and compositions capable of inhibiting PHD1 enzyme activity selectively over other isoforms, for example, PHD2 and/or PHD3 enzymes. Selective inhibition of PHD1 has useful therapeutic applications. Therefore, methods of using the compounds and compositions are also included.

2. State of the Art

Hypoxia occurs when cells are deprived of an adequate oxygen supply. A decline in the supply of oxygen can be due to the restriction of blood flow to organs and occurs under ischemic conditions in many vascular diseases including stroke, myocardial infarction, and acute kidney injury. The result of hypoxia is a functional impairment of cells and structural tissue damage. The body has many natural cellular defenses to combat states of hypoxia. These include angiogenesis, erythropoiesis, glycolysis, and induction of antioxidative enzymes. The activation of cellular defense mechanisms during hypoxia is mediated by HIF (Hypoxia-inducible factor) protein. HIF is a heterodimeric nuclear protein (HIFα/β) that responds to changes in the oxygen supply in the environment. During conditions of normoxia, the HIF subunits are constitutively expressed, but the α subunit of HIF is targeted for proteasome-mediated degradation by prolyl hydroxylation. (Fong and Takeda (2008) Cell Death and Differentiation. 15:635-641; Bernhardt et al. (2007) Methods in Enzymology. 435:221-245.) In response to hypoxic conditions, levels of HIFα are elevated in most cells because of a decrease in HIFα prolyl hydroxylation.

Prolyl hydroxylation of HIFα is accomplished by a family of proteins variously termed the prolyl hydroxylase domain-containing proteins (PHD1, 2, and 3), also known as HIF prolyl hydroxylases (HPH-3, 2, and 1) or EGLN-2, 1, and 3. The PHD proteins are oxygen sensors and regulate the stability of HIF in an oxygen dependent manner. The three PHD isoforms function differently in their regulation of HIF and may have other non-HIF related regulatory roles.

A number of studies have been done to better define the roles of each of the PHD isoforms. Many of these studies were done using genetically engineered knockout or knockdown animals for each of the PHD genes, or using siRNA, shRNA, or RNAi specific for a single isoform to inhibit or reduce gene expression. For PHD1, studies have suggested that inhibition of this protein could be therapeutically beneficial for treating skeletal muscle cell degeneration (U.S. Pat. No. 7,858,593), for protection of myofibers against ischemia (Aragones et al. (2008) Nat. Genet. 40:170-180), for treatment of colitis and other forms of inflammatory bowel disease (Tambuwala et al. (2010) Gastroenterology 139:2093-2101, and for treatment of heart failure and anemia in patients with concomitant cardiac and renal disease (Bao et al. (2010) J. Cardiovasc. Pharmacol. 56:147-155).

Numerous small molecule inhibitors for PHD proteins have been identified (for example, Arend, et al., U.S. Pat. Nos. 7,323,475; 7,629,357; 7,863,292; and 7,928,120; and Deng, et al., U.S. Pat. No. 7,696,223), however, few of these have been described as selective for inhibition of PHD1 in preference to the PHD2 and PHD3 isoforms Inhibitors that are selective for PHD1 would be preferable for the therapeutic uses described above in order to minimize unwanted side effects that could occur from significant inhibition of PHD2 and PHD3. Murray et al. (J. Comb. Chem. 13:676-686 (2010)) describe some dipeptidyl-quinolone derivatives that were found to be about 10-fold more potent against PHD1 and PHD3 than against PHD2. Bao et al. (supra) describe a fluoroquinolone derivative that is selective for PHD1.

Given the potential therapeutic benefit of selectively inhibiting the activity of PHD1 in disorders such as muscle degeneration, colitis, IBD, and certain ischemias, there is a need for compounds that can achieve this selective inhibition. Compounds that selectively inhibit PHD1 are described herein.

SUMMARY

The present invention relates to novel compounds and compositions capable of inhibiting PHD1 enzyme activity selectively over other isoforms, for example, PHD2 and/or PHD3 enzymes.

In one aspect, there are provided compounds of Formula I:

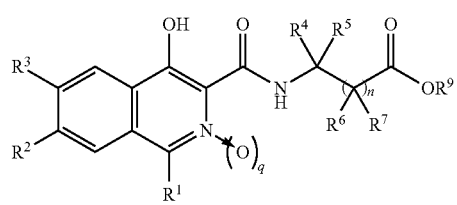

wherein
n is 1, 2, or 3;
q is 0 or 1;
$R^1$ is hydrogen, cyano, $C_1$-$C_4$ alkyl, aryl, or heteroaryl;
  wherein said $C_1$-$C_4$ alkyl, aryl, or heteroaryl is optionally substituted with 1, 2, or 3 trifluoromethyl, $C_1$-$C_4$ alkyl, or halo;
one of $R^2$ or $R^3$ is -L-$R^8$ and the other is hydrogen;
$R^4$ and $R^5$ are independently hydrogen, halo, $C_1$-$C_4$ alkyl, cycloalkyl, aryl, heterocyclyl, or heteroaryl;
  wherein said $C_1$-$C_4$ alkyl, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;
each $R^6$ and $R^7$ are independently hydrogen, halo, hydroxy, $C_1$-$C_4$ alkyl, $C_1$-$C_4$ alkoxy, amino, substituted amino, acylamino, carboxyl, carboxyl ester, carboxamide, oxycarbonylamino, aminocarbonyloxy, aminocarbonylamino, cycloalkyl, aryl, heterocyclyl, or heteroaryl, or wherein $R^6$ and $R^7$ together with the carbon atom attached thereto, form a carbonyl;

wherein said $C_1$-$C_4$ alkyl, $C_1$-$C_4$ alkoxy, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;

or wherein any of $R^4$ and $R^5$, $R^6$ and $R^7$, $R^4$ and $R^6$, or $R^5$ and $R^7$ groups, together with the carbon atom(s) attached thereto, join to form a cycloalkyl, aryl, heterocyclyl, or heteroaryl group, each optionally substituted with 1 to 4 halogen, oxo, $C_1$-$C_4$ alkyl, $C_1$-$C_4$ alkoxy, carboxyl, carboxyl ester, carboxamide, oxycarbonylamino, aminocarbonyloxy, aminocarbonylamino, or aryl;

$R^8$ is cycloalkyl, aryl, or heteroaryl;
wherein said cycloalkyl, aryl, or heteroaryl is optionally substituted with 1, 2, or 3 $C_1$-$C_4$ alkyl, $C_1$-$C_4$ alkoxy, or halo;

L is a covalent bond, $C_1$-$C_4$ alkylene, —O—, —S—, —SO—, —$SO_2$—, —NH—, —C(O)NH—, —NHC(O)—, —NHC(O)NH—, —O-alkylene-, —NH-alkylene-, or —NHC(O)NH-alkylene; and $R^9$ is hydrogen or $C_1$-$C_4$ alkyl;
wherein said $C_1$-$C_4$ alkyl is optionally substituted with 1, 2, or 3 $C_1$-$C_4$ alkoxy, halo, cycloalkyl, heterocyclyl, aryl, or heteroaryl;

or a pharmaceutically acceptable salt, single stereoisomer, mixture of stereoisomers, ester, tautomer or prodrug thereof.

The invention also provides pharmaceutical compositions comprising one or more compounds of Formula I and a pharmaceutically acceptable excipient. In some embodiments, the composition further comprises or is used in combination with at least one additional therapeutic agent.

The invention is also directed to methods and compositions capable of inhibiting PHD1 enzyme activity selectively over other isoforms, for example, PHD2 and/or PHD3 enzymes. Selective inhibition of PHD1 may be of particular benefit in treating skeletal muscle cell degeneration, colitis and other forms of inflammatory bowel disease, and heart failure in patients with concomitant cardiac and renal disease. In one embodiment, the method of the invention comprises administering to a patient in need a therapeutically effective amount of a compound of Formula I, or a pharmaceutical composition comprising one or more compounds of Formula I.

DETAILED DESCRIPTION

Before the present compositions and methods are described, it is to be understood that the invention is not limited to the particular compounds, compositions, methodologies, protocols, cell lines, assays, and reagents described, as these may vary. It is also to be understood that the terminology used herein is intended to describe particular embodiments of the present invention, and is in no way intended to limit the scope of the present invention as set forth in the appended claims.

1. Compounds

The invention is directed to compounds of Formula I:

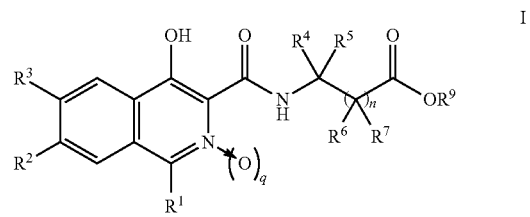

wherein
n is 1, 2, or 3;
q is 0 or 1;
$R^1$ is hydrogen, cyano, $C_1$-$C_4$ alkyl, aryl, or heteroaryl;
wherein said $C_1$-$C_4$ alkyl, aryl, or heteroaryl is optionally substituted with 1, 2, or 3 trifluoromethyl, $C_1$-$C_4$ alkyl, or halo;
one of $R^2$ or $R^3$ is -L-$R^8$ and the other is hydrogen;
$R^4$ and $R^5$ are independently hydrogen, halo, $C_1$-$C_4$ alkyl, cycloalkyl, aryl, heterocyclyl, or heteroaryl;
wherein said $C_1$-$C_4$ alkyl, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;
each $R^6$ and $R^7$ are independently hydrogen, halo, hydroxy, $C_1$-$C_4$ alkyl, $C_1$-$C_4$ alkoxy, amino, substituted amino, acylamino, carboxyl, carboxyl ester, carboxamide, oxycarbonylamino, aminocarbonyloxy, aminocarbonylamino, cycloalkyl, aryl, heterocyclyl, or heteroaryl, or wherein $R^6$ and $R^7$ together with the carbon atom attached thereto, form a carbonyl;
wherein said $C_1$-$C_4$ alkyl, $C_1$-$C_4$ alkoxy, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;
or wherein any of $R^4$ and $R^5$, $R^6$ and $R^7$, $R^4$ and $R^6$, or $R^5$ and $R^7$ groups, together with the carbon atom(s) attached thereto, join to form a cycloalkyl, aryl, heterocyclyl, or heteroaryl group, each optionally substituted with 1 to 4 halogen, oxo, $C_1$-$C_4$ alkyl, $C_1$-$C_4$ alkoxy, carboxyl, carboxyl ester, carboxamide, oxycarbonylamino, aminocarbonyloxy, aminocarbonylamino, or aryl;
$R^8$ is cycloalkyl, aryl, or heteroaryl;
wherein said cycloalkyl, aryl, or heteroaryl is optionally substituted with 1, 2, or 3 $C_1$-$C_4$ alkyl, $C_1$-$C_4$ alkoxy, or halo;
L is a covalent bond, $C_1$-$C_4$ alkylene, —O—, —S—, —SO—, —$SO_2$—, —NH—, —C(O)NH—, —NHC (O)—, —NHC(O)NH—, —O-alkylene-, —NH-alkylene-, or —NHC(O)NH-alkylene; and
$R^9$ is hydrogen or $C_1$-$C_4$ alkyl;
  wherein said $C_1$-$C_4$ alkyl is optionally substituted with 1, 2, or 3 $C_1$-$C_4$ alkoxy, halo, cycloalkyl, heterocyclyl, aryl, or heteroaryl;
or a pharmaceutically acceptable salt, single stereoisomer, mixture of stereoisomers, ester, tautomer or prodrug thereof.

In certain embodiments, the compounds of Formula I are represented by Formula II:

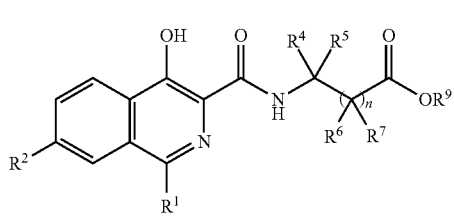

wherein n, $R^1$, $R^2$, $R^4$, $R^5$, $R^6$, $R^7$ and $R^9$ are as defined for Formula I.

In certain embodiments, the compounds of Formula I are represented by Formula III:

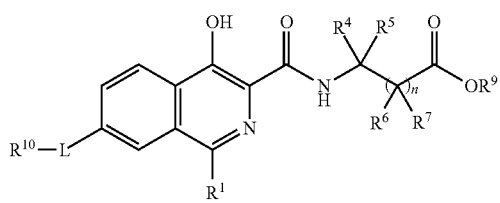

wherein n, L, $R^1$, $R^4$, $R^5$, $R^6$, $R^7$ and $R^9$ are as defined for Formula I, and $R^{10}$ is aryl optionally substituted with 1, 2, or 3 $C_1$-$C_4$ alkyl, $C_1$-$C_4$ alkoxy, or halo.

In certain embodiments of Formula I, q is 0.
In certain embodiments of Formula I, II or III, n is 1.
In certain embodiments of Formula I, II or III, n is 2 or 3.
In certain embodiments of Formula I, II or III, $R^9$ is hydrogen. In certain embodiments of Formula I, II or III, $R^9$ is $C_1$-$C_4$ alkyl.
In certain embodiments of Formula I, II or III, $R^1$ is hydrogen or cyano. In one embodiment, $R^1$ is hydrogen. In another embodiment, $R^1$ is cyano.
In certain embodiments of Formula I, II or III, $R^1$ is $C_1$-$C_4$ alkyl, aryl, or heteroaryl; wherein said $C_1$-$C_4$ alkyl, aryl, or heteroaryl is optionally substituted with 1, 2, or 3 substituents selected from trifluoromethyl, $C_1$-$C_4$ alkyl, and halo. In one embodiment of Formula I, II or III, $R^1$ is $C_1$-$C_4$ alkyl, such as methyl.
In another embodiment of Formula I, II or III, $R^1$ is aryl, such as phenyl. In yet another embodiment of Formula I, II or III, $R^1$ is heteroaryl, such as pyridyl.
In certain embodiments of Formula I, II or III, $R^4$ and $R^5$ are independently hydrogen, $C_1$-$C_4$ alkyl, or aryl; wherein said $C_1$-$C_4$ alkyl is optionally substituted with 1, 2, or 3 hydroxy or aryl; or wherein $R^4$ and $R^5$ together with the carbon atom attached thereto, join to form a cycloalkyl or heterocyclyl group, optionally substituted with carboxyl ester.
In one embodiment of Formula I, II or III, $R^4$ and $R^5$ are independently hydrogen, $C_1$-$C_4$ alkyl, or aryl; wherein said $C_1$-$C_4$ alkyl is optionally substituted with 1, 2, or 3 hydroxy or aryl.

In another embodiment of Formula I, II or III, $R^4$ and $R^5$ together with the carbon atom attached thereto, join to form a cycloalkyl or heterocyclyl group, optionally substituted with carboxyl ester.
In certain embodiments of Formula I, II or III, $R^4$ and $R^5$ are independently hydrogen, methyl, or phenyl.
In certain embodiments of compounds of Formula I, II or III, $R^4$ and $R^5$ are hydrogen.
In certain embodiments of Formula I, II or III, each $R^6$ and $R^7$ are independently hydrogen, halo, hydroxy, $C_1$-$C_4$ alkyl, $C_1$-$C_4$ alkoxy, aryl, amino, acylamino, or aminocarbonylamino, or $R^6$ and $R^7$ together with the carbon atom attached thereto, form a carbonyl; wherein said $C_1$-$C_4$ alkyl or aryl, is optionally substituted with 1, 2, or 3 substituents selected from hydroxy, halo, and aryl; or $R^6$ and $R^7$ together with the carbon atom attached thereto, join to form a cycloalkyl or heterocyclyl group, each optionally substituted with oxo.
In certain embodiments of Formula I, II or III, each $R^6$ and $R^7$ are independently hydrogen, halo, hydroxy, $C_1$-$C_4$ alkyl, $C_1$-$C_4$ alkoxy, aryl, amino, acylamino, and aminocarbonylamino, or $R^6$ and $R^7$ together with the carbon atom attached thereto, form a carbonyl; wherein said $C_1$-$C_4$ alkyl or aryl, is optionally substituted with 1, 2, or 3 substituents selected from hydroxy, halo, and aryl.
In one embodiment of Formula I, II or III, each $R^6$ and $R^7$ are independently hydrogen, halo, hydroxy, $C_1$-$C_4$ alkyl, $C_1$-$C_4$ alkoxy, aryl, amino, acylamino, or aminocarbonylamino, or $R^6$ and $R^7$ together with the carbon atom attached thereto, form a carbonyl.
In one embodiment of Formula I, II or III, each $R^6$ and $R^7$ are independently hydrogen or $C_1$-$C_4$ alkyl.
In another embodiment of Formula I, II or III, $R^6$ and $R^7$ together with the carbon atom attached thereto, join to form a cycloalkyl or heterocyclyl group, each optionally substituted with oxo.
In certain embodiments of Formula I or II, $R^8$ is aryl, optionally substituted with 1, 2, or 3 substituents selected from $C_1$-$C_4$ alkyl, $C_1$-$C_4$ alkoxy, and halo.
In another embodiment of Formula I or II, $R^8$ is cycloalkyl, optionally substituted with 1, 2, or 3 substituents selected from $C_1$-$C_4$ alkyl, $C_1$-$C_4$ alkoxy, and halo.
In one embodiment of Formula I or II, $R^8$ is heteroaryl, optionally substituted with 1, 2, or 3 substituents selected from $C_1$-$C_4$ alkyl, $C_1$-$C_4$ alkoxy, and halo.
In certain embodiments of Formula I, II or III, L is —O—, —S—, —SO—, —SO$_2$—, —NH—, —C(O)NH—, —NHC(O)—, or —NHC(O)NH—.
In one embodiment of Formula I, II or III, L is a covalent bond or $C_1$-$C_4$ alkylene.
In one embodiment of Formula I, II or III, L is —O-alkylene-, —NH-alkylene-, or —NHC(O)NH-alkylene.
In one embodiment of Formula I, II or III, L is —O— or —S—. In one embodiment of Formula I, II or III, L is —O—.
In certain embodiments of Formula II, L is —O— or —S—; $R^9$ is hydrogen; $R^1$ is hydrogen or cyano; and $R^8$ is aryl.
In certain embodiments of Formula III, L is —O— or —S—; $R^9$ is hydrogen; and $R^1$ is hydrogen or cyano.
In certain embodiments of Formula I, II or III, the compound is capable of inhibiting PHD1 enzyme activity selectively over other PHD isoforms, such as PHD2 and/or PHD3 enzymes. In one embodiment of Formula I, II or III, the compound is capable of inhibiting PHD1 enzyme activity selectively over PHD2 enzyme. In another embodiment of Formula I, II or III, the compound is capable of inhibiting PHD1 enzyme activity selectively over PHD3 enzyme. In certain embodiments of Formula I, II or III, the compound is at least five times more active in inhibiting PHD1 enzyme over PHD2 enzyme; namely, the ratio of the $IC_{50}$ for PHD2 over the $IC_{50}$ for PHD1 (i.e., $IC_{50}$ PHD2/$IC_{50}$ PHD1) is greater than or equal to five. In certain embodiments of Formula I, II or III, the compound is at least eight times more active in inhibiting PHD1 enzyme over PHD2 enzyme; namely, the ratio of the $IC_{50}$ for PHD2 over the $IC_{50}$ for PHD1 (i.e., $IC_{50}$ PHD2/$IC_{50}$ PHD1) is greater than or equal to eight. In certain embodiments of Formula I, II or III, the compound is at least ten times more active in inhibiting PHD1 enzyme over PHD2 enzyme; namely, the ratio of the $IC_{50}$ for PHD2 over the $IC_{50}$ for PHD1 (i.e., $IC_{50}$ PHD2/$IC_{50}$ PHD1) is greater than or equal to ten. In certain embodiments of Formula I, II or III, the compound is at least five times more active in inhibiting PHD1 enzyme over PHD3 enzyme; i.e., $IC_{50}$ PHD3/$IC_{50}$ PHD1 is greater than or equal to five.

In certain embodiments, the compound of Formula I, II or III is the pharmaceutically acceptable salt thereof. In some embodiments, the salt is the trifluoroacetic acid salt thereof.

In certain embodiments of Formula I, II or III, when n is 1 and $R^6$ and $R^7$ are hydrogen, then $R^1$ is cyano.

In certain embodiments of Formula I, II or III, the compound is selected from

3-[(4-Hydroxy-7-phenoxy-isoquinoline-3-carbonyl)-amino]-propionic acid;
3-[(4-Hydroxy-7-phenoxy-isoquinoline-3-carbonyl)-amino]-2,2-dimethyl-propionic acid;
2-(S)-Hydroxy-3-[(4-hydroxy-7-phenoxy-isoquinoline-3-carbonyl)-amino]-propionic acid;
4-[(4-Hydroxy-7-phenoxy-isoquinoline-3-carbonyl)-amino]-butyric acid;
5-[(4-Hydroxy-7-phenoxy-isoquinoline-3-carbonyl)-amino]-pentanoic acid;
3-[(4-Hydroxy-7-phenoxy-isoquinoline-3-carbonyl)-amino]-3-methyl-butyric acid;
2-(S)-Hydroxy-4-[(4-hydroxy-7-phenoxy-isoquinoline-3-carbonyl)-amino]-butyric acid;
4-[(4-Hydroxy-7-phenoxy-isoquinoline-3-carbonyl)-amino]-2,2-dimethyl-butyric acid;
2-(S)-Amino-3-[(4-hydroxy-7-phenoxy-isoquinoline-3-carbonyl)-amino]-propionic acid;
3-[(1-Cyano-4-hydroxy-7-phenoxy-isoquinoline-3-carbonyl)-amino]-propionic acid;
3-[(1-Cyano-4-hydroxy-7-phenoxy-isoquinoline-3-carbonyl)-amino]-butyric acid;
1-{[(1-Cyano-4-hydroxy-7-phenoxy-isoquinoline-3-carbonyl)-amino]-methyl}-cyclopropanecarboxylic acid;
1-{[(4-Hydroxy-7-phenoxy-isoquinoline-3-carbonyl)-amino]-methyl}-cyclobutanecarboxylic acid;
1-{[(1-Cyano-4-hydroxy-7-phenoxy-isoquinoline-3-carbonyl)-amino]-methyl}-cyclobutanecarboxylic acid;
4-{[(4-Hydroxy-7-phenoxy-isoquinoline-3-carbonyl)-amino]-methyl}-tetrahydro-pyran-4-carboxylic acid;
4-{[(1-Cyano-4-hydroxy-7-phenoxy-isoquinoline-3-carbonyl)-amino]-methyl}-tetrahydro-pyran-4-carboxylic acid;
2-{[(1-Cyano-4-hydroxy-7-phenoxy-isoquinoline-3-carbonyl)-amino]-methyl}-pentanoic acid;
2-{[(1-Cyano-4-hydroxy-7-phenoxy-isoquinoline-3-carbonyl)-amino]-methyl}-2-propyl-pentanoic acid;
1-{[(1-Cyano-4-hydroxy-7-phenoxy-isoquinoline-3-carbonyl)-amino]-methyl}-cyclopentanecarboxylic acid;
3-{[1-Cyano-4-hydroxy-7-(4-methoxy-phenoxy)-isoquinoline-3-carbonyl]-amino}-2,2-dimethyl-propionic acid;
3-{[1-Cyano-4-hydroxy-7-(4-methoxy-phenoxy)-isoquinoline-3-carbonyl]-amino}-3-methyl-butyric acid;
3-{[1-Cyano-7-(2,6-difluoro-phenoxy)-4-hydroxy-isoquinoline-3-carbonyl]-amino}-2,2-dimethyl-propionic acid;
3-{[7-(4-Chloro-3-fluoro-phenoxy)-4-hydroxy-isoquinoline-3-carbonyl]-amino}-2,2-dimethyl-propionic acid;
3-{[4-Hydroxy-7-(pyridin-3-yloxy)-isoquinoline-3-carbonyl]-amino}-propionic acid;
3-{[4-Hydroxy-7-(pyridin-2-yloxy)-isoquinoline-3-carbonyl]-amino}-propionic acid;
1-({[1-Cyano-7-(2,6-difluoro-phenoxy)-4-hydroxy-isoquinoline-3-carbonyl]-amino}-methyl)-cyclobutanecarboxylic acid;
3-{[1-Cyano-4-hydroxy-7-(pyridin-3-yloxy)-isoquinoline-3-carbonyl]-amino}-2,2-dimethyl-propionic acid;
1-({[1-Cyano-4-hydroxy-7-(pyridin-3-yloxy)-isoquinoline-3-carbonyl]-amino}-methyl)-cyclobutanecarboxylic acid;
4-{[(1-Cyano-4-hydroxy-7-phenoxy-isoquinoline-3-carbonyl)-amino]-methyl}-1,1-dioxo-hexahydro-1$\lambda^6$-thiopyran-4-carboxylic acid;
4-{[(1-Cyano-4-hydroxy-7-phenoxy-isoquinoline-3-carbonyl)-amino]-methyl}-1-oxo-hexahydro-1$\lambda^4$-thiopyran-4-carboxylic acid;
3-{[7-(2-Chloro-5-fluoro-phenoxy)-1-cyano-4-hydroxy-isoquinoline-3-carbonyl]-amino}-2,2-dimethyl-propionic acid;
cis-2-(1-Cyano-4-hydroxy-7-phenoxyisoquinoline-3-carboxamido)cyclohexanecarboxylic acid;
cis-2-[(1-Cyano-4-hydroxy-7-phenoxy-isoquinoline-3-carbonyl)-amino]-cyclopentanecarboxylic acid;
3-(4-Chloro-phenyl)-4-[(1-cyano-4-hydroxy-7-phenoxy-isoquinoline-3-carbonyl)-amino]-butyric acid;
(S)-4-(1-Cyano-4-hydroxy-7-phenoxyisoquinoline-3-carboxamido)-3-hydroxybutanoic acid
(1-{[(1-Cyano-4-hydroxy-7-phenoxy-isoquinoline-3-carbonyl)-amino]-methyl}-cyclohexyl)-acetic acid;
(R)-3-(1-Cyano-4-hydroxy-7-phenoxyisoquinoline-3-carboxamido)-4-hydroxybutanoic acid;
3-(7-(2-Chlorophenoxy)-1-cyano-4-hydroxyisoquinoline-3-carboxamido)-2,2-dimethylpropanoic acid;
3-{[7-(3-Chloro-phenoxy)-1-cyano-4-hydroxy-isoquinoline-3-carbonyl]-amino}-2,2-dimethyl-propionic acid;
3-{[7-(4-Chloro-phenoxy)-1-cyano-4-hydroxy-isoquinoline-3-carbonyl]-amino}-2,2-dimethyl-propionic acid;
3-{[1-Cyano-7-(2-fluoro-phenoxy)-4-hydroxy-isoquinoline-3-carbonyl]-amino}-2,2-dimethyl-propionic acid;
3-(1-Cyano-7-(3-fluorophenoxy)-4-hydroxyisoquinoline-3-carboxamido)-2,2-dimethylpropanoic acid;
3-(1-Cyano-4-hydroxy-7-(naphthalen-1-yloxy)isoquinoline-3-carboxamido)-2,2-dimethylpropanoic acid;
3-[(1-Cyano-4-hydroxy-7-p-tolyloxy-isoquinoline-3-carbonyl)-amino]-2,2-dimethyl-propionic acid;
(S)-2-Amino-4-(1-cyano-4-hydroxy-7-phenoxyisoquinoline-3-carboxamido)butanoic acid;
4-(1-Cyano-4-hydroxy-7-phenoxyisoquinoline-3-carboxamido)-4-methylpentanoic acid;
(S)-3-[(1-Cyano-4-hydroxy-7-phenoxy-isoquinoline-3-carbonyl)-amino]-3-phenyl-propionic acid;
(R)-3-[(1-Cyano-4-hydroxy-7-phenoxy-isoquinoline-3-carbonyl)-amino]-3-phenyl-propionic acid;
(S)-2-Benzyl-3-[(1-cyano-4-hydroxy-7-phenoxy-isoquinoline-3-carbonyl)-amino]-propionic acid;
(R)-2-Amino-4-(1-cyano-4-hydroxy-7-phenoxyisoquinoline-3-carboxamido)butanoic acid;
(R)-2-Acetylamino-4-[(1-cyano-4-hydroxy-7-phenoxy-isoquinoline-3-carbonyl)-amino]-butyric acid;
(R)-4-(1-Cyano-4-hydroxy-7-phenoxyisoquinoline-3-carboxamido)-2-(3-ethylureido)butanoic acid;

(R)-4-(1-Cyano-4-hydroxy-7-phenoxyisoquinoline-3-carboxamido)-2-(methoxycarbonylamino)butanoic acid;
(R)-4-(1-Cyano-4-hydroxy-7-phenoxyisoquinoline-3-carboxamido)-2-(3,3-dimethylureido)butanoic acid;
(R)-4-(1-Cyano-4-hydroxy-7-phenoxyisoquinoline-3-carboxamido)-2-ureidobutanoic acid;
4-(1-Cyano-4-hydroxy-7-phenoxyisoquinoline-3-carboxamido)-2-oxobutanoic acid;
2-((1-Cyano-4-hydroxy-7-phenoxyisoquinoline-3-carboxamido)methyl)butanoic acid;
2-{[(1-Cyano-4-hydroxy-7-phenoxy-isoquinoline-3-carbonyl)-amino]-methyl}-2-methyl-butyric acid;
3-{[1-Cyano-4-hydroxy-7-(naphthalen-2-yloxy)-isoquinoline-3-carbonyl]-amino}-2,2-dimethyl-propionic acid;
3-{[1-Cyano-4-hydroxy-7-(2-methoxy-phenoxy)-isoquinoline-3-carbonyl]-amino}-2,2-dimethyl-propionic acid;
3-[(1-Cyano-4-hydroxy-7-phenoxy-isoquinoline-3-carbonyl)-amino]-4-methyl-pentanoic acid;
3-{[1-Cyano-7-(2-ethyl-phenoxy)-4-hydroxy-isoquinoline-3-carbonyl]-amino}-2,2-dimethyl-propionic acid;
3-(R)-[(1-Cyano-4-hydroxy-7-phenoxy-isoquinoline-3-carbonyl)-amino]-pentanoic acid;
3-(R)-[(1-Cyano-4-hydroxy-7-phenoxy-isoquinoline-3-carbonyl)-amino]-butyric acid;
3-[(1-Cyano-4-hydroxy-7-phenoxy-isoquinoline-3-carbonyl)-amino]-2,2-difluoro-propionic acid;
3-[(1-Cyano-4-hydroxy-7-phenoxy-isoquinoline-3-carbonyl)-amino]-5-methyl-hexanoic acid;
(S)-3-[(1-Cyano-4-hydroxy-7-phenoxy-isoquinoline-3-carbonyl)-amino]-4-phenyl-butyric acid;
(R)-3-[(1-Cyano-4-hydroxy-7-phenoxy-isoquinoline-3-carbonyl)-amino]-4-phenyl-butyric acid;
(2R,3R)-3-[(1-Cyano-4-hydroxy-7-phenoxy-isoquinoline-3-carbonyl)-amino]-2-methyl-butyric acid;
(2S,3R)-3-[(1-Cyano-4-hydroxy-7-phenoxy-isoquinoline-3-carbonyl)-amino]-2-methyl-butyric acid;
(2S,3S)-3-[(1-Cyano-4-hydroxy-7-phenoxy-isoquinoline-3-carbonyl)-amino]-2-methyl-butyric acid;
(2R,3S)-3-[(1-Cyano-4-hydroxy-7-phenoxy-isoquinoline-3-carbonyl)-amino]-2-methyl-butyric acid;
(S)-3-(1-Cyano-4-hydroxy-7-phenoxyisoquinoline-3-carboxamido)-2-hydroxy-2-methylpropanoic acid;
(2S,3R)-3-(1-Cyano-4-hydroxy-7-phenoxyisoquinoline-3-carboxamido)-2-hydroxy-4-phenylbutanoic acid;
(2R,3R)-3-(1-Cyano-4-hydroxy-7-phenoxyisoquinoline-3-carboxamido)-2-hydroxy-4-phenylbutanoic acid;
3-[(1-Cyano-4-hydroxy-7-phenoxy-isoquinoline-3-carbonyl)-amino]-2-hydroxy-propionic acid;
3-[(1-Cyano-4-hydroxy-7-phenoxy-isoquinoline-3-carbonyl)-amino]-2,2-dimethyl-propionic acid;
3-(S)-[(1-Cyano-4-hydroxy-7-phenoxy-isoquinoline-3-carbonyl)-amino]-butyric acid;
3-[(1-Cyano-4-hydroxy-7-phenoxy-isoquinoline-3-carbonyl)-amino]-2-(S)-hydroxy-propionic acid;
4-[(1-Cyano-4-hydroxy-7-phenoxy-isoquinoline-3-carbonyl)-amino]-butyric acid;
5-[(1-Cyano-4-hydroxy-7-phenoxy-isoquinoline-3-carbonyl)-amino]-pentanoic acid;
3-[(1-Cyano-4-hydroxy-7-phenoxy-isoquinoline-3-carbonyl)-amino]-3-methyl-butyric acid;
4-[(1-Cyano-4-hydroxy-7-phenoxy-isoquinoline-3-carbonyl)-amino]-2-(S)-hydroxy-butyric acid;
4-[(1-Cyano-4-hydroxy-7-phenoxy-isoquinoline-3-carbonyl)-amino]-2,2-dimethyl-butyric acid;
2-(S)-tert-Butoxycarbonylamino-3-[(1-cyano-4-hydroxy-7-phenoxy-isoquinoline-3-carbonyl)-amino]-propionic acid;
2-(S)-Amino-3-[(1-cyano-4-hydroxy-7-phenoxy-isoquinoline-3-carbonyl)-amino]-propionic acid;
2-(S)-Benzyloxycarbonylamino-3-[(1-cyano-4-hydroxy-7-phenoxy-isoquinoline-3-carbonyl)-amino]-propionic acid;
trans-4-[(1-Cyano-4-hydroxy-7-phenoxy-isoquinoline-3-carbonyl)-amino]-cyclohexanecarboxylic acid;
4-[(1-Cyano-4-hydroxy-7-phenoxy-isoquinoline-3-carbonyl)-amino]-3,3-dimethyl-butyric acid;
{1-[(1-Cyano-4-hydroxy-7-phenoxy-isoquinoline-3-carbonyl)-amino]-cyclohexyl}-acetic acid;
3-[(1-Cyano-4-hydroxy-7-phenoxy-isoquinoline-3-carbonyl)-amino]-3-phenyl-propionic acid;
3-[(1-Cyano-4-hydroxy-7-phenoxy-isoquinoline-3-carbonyl)-amino]-2-(R)-methyl-propionic acid;
3-[(1-Cyano-4-hydroxy-7-phenoxy-isoquinoline-3-carbonyl)-amino]-2-(S)-methyl-propionic acid;
4-[(1-Cyano-4-hydroxy-7-phenoxy-isoquinoline-3-carbonyl)-amino]-2-(S)-methoxy-butyric acid;
5-[(1-Cyano-4-hydroxy-7-phenoxy-isoquinoline-3-carbonyl)-amino]-2,2-dimethyl-pentanoic acid;
4-Carboxymethyl-4-[(1-cyano-4-hydroxy-7-phenoxy-isoquinoline-3-carbonyl)-amino]-piperidine-1-carboxylic acid tert-butyl ester;
3-{[7-(2-Chloro-4-fluoro-phenoxy)-1-cyano-4-hydroxy-isoquinoline-3-carbonyl]-amino}-propionic acid;
5-{[7-(2-Chloro-4-fluoro-phenoxy)-1-cyano-4-hydroxy-isoquinoline-3-carbonyl]-amino}-pentanoic acid;
3-{[7-(2-Chloro-4-fluoro-phenoxy)-1-cyano-4-hydroxy-isoquinoline-3-carbonyl]-amino}-2,2-dimethyl-propionic acid;
5-{[7-(2,6-Difluoro-phenoxy)-4-hydroxy-isoquinoline-3-carbonyl]-amino}-pentanoic acid;
3-{[1-Cyano-7-(4-fluoro-phenoxy)-4-hydroxy-isoquinoline-3-carbonyl]-amino}-2,2-dimethyl-propionic acid;
3-{[1-Cyano-7-(4-fluoro-phenoxy)-4-hydroxy-isoquinoline-3-carbonyl]-amino}-3-methyl-butyric acid;
2-(S)-Hydroxy-3-{[4-hydroxy-7-(4-methoxy-phenoxy)-isoquinoline-3-carbonyl]-amino}-propionic acid;
3-{[4-Hydroxy-7-(4-methoxy-phenoxy)-isoquinoline-3-carbonyl]-amino}-2,2-dimethyl-propionic acid;
5-{[4-Hydroxy-7-(4-methoxy-phenoxy)-isoquinoline-3-carbonyl]-amino}-pentanoic acid;
{1-[(1-Cyano-4-hydroxy-7-phenoxy-isoquinoline-3-carbonyl)-amino]-cyclobutyl}-acetic acid;
(R)-3-[(1-Cyano-4-hydroxy-7-phenoxy-isoquinoline-3-carbonyl)-amino-]5-phenylpentanoic acid;
3-[(4-Hydroxy-1-methyl-7-phenoxy-isoquinoline-3-carbonyl)-amino]-propionic acid;
3-{[1-Cyano-6-(2,6-dimethyl-phenoxy)-4-hydroxy-isoquinoline-3-carbonyl]-amino}-propionic acid;
4-{[1-Cyano-6-(2,6-dimethyl-phenoxy)-4-hydroxy-isoquinoline-3-carbonyl]-amino}-butyric acid;
5-{[1-Cyano-6-(2,6-dimethyl-phenoxy)-4-hydroxy-isoquinoline-3-carbonyl]-amino}-pentanoic acid;
3-[(4-Hydroxy-6-phenoxy-isoquinoline-3-carbonyl)-amino]-propionic acid;
4-[(4-Hydroxy-6-phenoxy-isoquinoline-3-carbonyl)-amino]-butyric acid;
5-[(4-Hydroxy-7-phenylsulfanyl-isoquinoline-3-carbonyl)-amino]-pentanoic acid;
4-[(4-Hydroxy-7-phenylsulfanyl-isoquinoline-3-carbonyl)-amino]-butyric acid;
3-{[4-Hydroxy-7-(3-phenyl-ureido)-isoquinoline-3-carbonyl]-amino}-propionic acid;
(S)-2-Hydroxy-3-{[4-hydroxy-7-(3-phenyl-ureido)-isoquinoline-3-carbonyl]-amino}-propionic acid;

3-{[7-(4-Fluoro-benzoylamino)-4-hydroxy-isoquinoline-3-carbonyl]-amino}-propionic acid;
4-{[4-Hydroxy-7-(3-phenyl-ureido)-isoquinoline-3-carbonyl]-amino}-butyric acid;
4-{[7-(4-Fluoro-benzoylamino)-4-hydroxy-isoquinoline-3-carbonyl]-amino}-butyric acid;
3-[(1-Cyano-4-hydroxy-7-phenylsulfanyl-isoquinoline-3-carbonyl)-amino]-2,2-dimethyl-propionic acid;
3-[(1-Cyano-4-hydroxy-7-phenethyl-isoquinoline-3-carbonyl)-amino]-2,2-dimethyl-propionic acid;
3-[(1-Cyano-4-hydroxy-6-phenoxy-isoquinoline-3-carbonyl)-amino]-2,2-dimethyl-propionic acid;
5-[(4-Hydroxy-7-phenylamino-isoquinoline-3-carbonyl)-amino]-pentanoic acid;
5-{[4-Hydroxy-7-(4-methoxy-benzylamino)-isoquinoline-3-carbonyl]-amino}-pentanoic acid;
3-{[4-Hydroxy-7-(4-methoxy-benzylamino)-isoquinoline-3-carbonyl]-amino}-2,2-dimethyl-propionic acid;
3-[(4-Hydroxy-7-phenylsulfanyl-isoquinoline-3-carbonyl)-amino]-2,2-dimethyl-propionic acid;
5-[(1-Cyano-4-hydroxy-6-phenoxy-isoquinoline-3-carbonyl)-amino]-pentanoic acid;
3-[(4-Hydroxy-7-phenyl-isoquinoline-3-carbonyl)-amino]-2,2-dimethyl-propionic acid;
3-{[7-(3-Cyclohexyl-ureido)-4-hydroxy-isoquinoline-3-carbonyl]-amino}-propionic acid;
4-{[7-(3-Cyclohexyl-ureido)-4-hydroxy-isoquinoline-3-carbonyl]-amino}-butyric acid;
3-{[7-(4-Fluoro-phenyl)-4-hydroxy-isoquinoline-3-carbonyl]-amino}-propionic acid;
3-{[7-(3-Benzyl-ureido)-4-hydroxy-isoquinoline-3-carbonyl]-amino}-propionic acid;
4-{[7-(3-Benzyl-ureido)-4-hydroxy-isoquinoline-3-carbonyl]-amino}-butyric acid;
3-[(7-Cyclohexanesulfonyl-4-hydroxy-isoquinoline-3-carbonyl)-amino]-propionic acid;
3-{[1-(5-Fluoro-pyridin-3-yl)-4-hydroxy-7-phenoxy-isoquinoline-3-carbonyl]-amino}-2,2-dimethyl-propionic acid;
3-[(1-Cyano-4-hydroxy-7-phenyl-isoquinoline-3-carbonyl)-amino]-propionic acid;
3-[(1-Cyano-4-hydroxy-7-phenyl-isoquinoline-3-carbonyl)-amino]-2,2-dimethyl-propionic acid;
3-{[7-(4-Fluoro-benzoylamino)-4-hydroxy-isoquinoline-3-carbonyl]-amino}-2,2-dimethyl-propionic acid;
3-{[1-Cyano-4-hydroxy-7-(3-phenyl-ureido)-isoquinoline-3-carbonyl]-amino}-2,2-dimethyl-propionic acid;
3-({7-[3-(4-Fluoro-phenyl)-ureido]-4-hydroxy-isoquinoline-3-carbonyl}-amino)-propionic acid;
4-({7-[3-(4-Fluoro-phenyl)-ureido]-4-hydroxy-isoquinoline-3-carbonyl}-amino)-butyric acid;
3-[(4-Hydroxy-7-phenoxy-1-phenyl-isoquinoline-3-carbonyl)-amino]-2,2-dimethyl-propionic acid;
3-[(4-Hydroxy-7-phenoxy-1-phenyl-isoquinoline-3-carbonyl)-amino]-propionic acid;
3-[(4-Hydroxy-7-phenoxy-1-trifluoromethyl-isoquinoline-3-carbonyl)-amino]-propionic acid;
3-[(7-Benzyl-4-hydroxy-isoquinoline-3-carbonyl)-amino]-2,2-dimethyl-propionic acid;
5-{[1-(5-Fluoro-pyridin-3-yl)-4-hydroxy-7-phenoxy-isoquinoline-3-carbonyl]-amino}-pentanoic acid;
4-{[7-(4-Fluoro-phenyl)-4-hydroxy-isoquinoline-3-carbonyl]-amino}-butyric acid;
5-{[7-(4-Fluoro-phenyl)-4-hydroxy-isoquinoline-3-carbonyl]-amino}-pentanoic acid;
3-{[7-(4-Fluoro-phenyl)-4-hydroxy-isoquinoline-3-carbonyl]-amino}-2,2-dimethyl-propionic acid;
3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid;
3-[(7-Benzyloxy-1-cyano-4-hydroxy-isoquinoline-3-carbonyl)-amino]-3-methyl-butyric acid;
3-[(7-Benzyloxy-1-cyano-4-hydroxy-isoquinoline-3-carbonyl)-amino]-2,2-dimethyl-propionic acid;
1-{[(1-Cyano-4-hydroxy-7-phenylsulfanyl-isoquinoline-3-carbonyl)-amino]-methyl}-cyclobutanecarboxylic acid;
3-[(1-Cyano-4-hydroxy-6-o-tolyloxy-isoquinoline-3-carbonyl)-amino]-2,2-dimethyl-propionic acid;
3-[(1-Cyano-7-cyclohexyloxy-4-hydroxy-isoquinoline-3-carbonyl)-amino]-2,2-dimethyl-propionic acid;
3-(2-Carboxy-2-methylpropylcarbamoyl)-1-cyano-4-hydroxy-7-phenoxyisoquinoline 2-oxide;
3-(3-Carboxypropylcarbamoyl)-1-cyano-4-hydroxy-7-phenoxyisoquinoline 2-oxide;
1-{[(1-Cyano-7-cyclohexyloxy-4-hydroxy-isoquinoline-3-carbonyl)-amino]-methyl}-cyclobutanecarboxylic acid;
3-[(1-Cyano-7-cyclohexanesulfonyl-4-hydroxy-isoquinoline-3-carbonyl)-amino]-2,2-dimethyl-propionic acid;
1-{[(1-Cyano-7-cyclohexanesulfonyl-4-hydroxy-isoquinoline-3-carbonyl)-amino]-methyl}-cyclobutanecarboxylic acid;
3-{[7-(3-Benzyl-ureido)-1-cyano-4-hydroxy-isoquinoline-3-carbonyl]-amino}-2,2-dimethyl-propionic acid;
(S)-2-[Amino-5-(1-cyano-4-hydroxy-7-phenoxy-isoquinoline-3-carbonyl)-amino]-pentanoic acid 2,2,2-trifluoro-acetic acid (1:1);
3-[(7-Benzyl-1-cyano-4-hydroxy-isoquinoline-3-carbonyl)-amino]-2,2-dimethyl-propionic acid;
3-(3-Chloro-phenyl)-3-[(1-cyano-4-hydroxy-7-phenoxy-isoquinoline-3-carbonyl)-amino]-propionic acid;
3-[(1-Cyano-4-hydroxy-7-phenoxy-isoquinoline-3-carbonyl)-amino]-2-cyclopropyl-propionic acid;
2-Cyclopropyl-3-[(4-hydroxy-7-phenoxy-isoquinoline-3-carbonyl)-amino]-propionic acid;
3-[(1-Cyano-4-hydroxy-7-phenoxy-isoquinoline-3-carbonyl)-amino]-2-phenyl-propionic acid;
3-[(4-Hydroxy-7-phenoxy-isoquinoline-3-carbonyl)-amino]-2-phenyl-propionic acid;
3-(S)-[(1-Cyano-4-hydroxy-7-phenoxy-isoquinoline-3-carbonyl)-amino]-3-(2-fluoro-phenyl)-propionic acid;
3-(S)-[(1-Cyano-4-hydroxy-7-phenoxy-isoquinoline-3-carbonyl)-amino]-3-o-tolyl-propionic acid;
3-(S)-[(1-Cyano-4-hydroxy-7-phenoxy-isoquinoline-3-carbonyl)-amino]-3-(4-cyano-phenyl)-propionic acid;
3-(4-Chloro-phenyl)-3-[(1-cyano-4-hydroxy-7-phenoxy-isoquinoline-3-carbonyl)-amino]-propionic acid;
3-[(1-Cyano-4-hydroxy-7-phenoxy-isoquinoline-3-carbonyl)-amino]-3-pyridin-3-yl-propionic acid;
3-(S)-[(1-Cyano-4-hydroxy-7-phenoxy-isoquinoline-3-carbonyl)-amino]-3-pyridin-3-yl-propionic acid;
3-(R)-[(1-Cyano-4-hydroxy-7-phenoxy-isoquinoline-3-carbonyl)-amino]-3-pyridin-3-yl-propionic acid;
3-{[1-Cyano-7-(2-fluoro-phenoxy)-4-hydroxy-isoquinoline-3-carbonyl]-amino}-2-cyclopropyl-propionic acid;
3-{[1-Cyano-4-hydroxy-7-(pyridin-3-yloxy)-isoquinoline-3-carbonyl]-amino}-2-cyclopropyl-propionic acid tert-butyl ester, trifluoro-acetic acid salt;
3-{[1-Cyano-7-(4-fluoro-phenoxy)-4-hydroxy-isoquinoline-3-carbonyl]-amino}-2-cyclopropyl-propionic acid;
3-{[1-Cyano-7-(2,6-difluoro-phenoxy)-4-hydroxy-isoquinoline-3-carbonyl]-amino}-2-cyclopropyl-propionic acid;
3-[(1-Cyano-4-hydroxy-7-phenoxy-isoquinoline-3-carbonyl)-amino]-2-(4-fluoro-phenyl)-propionic acid;

3-[(1-Cyano-4-hydroxy-7-phenoxy-isoquinoline-3-carbonyl)-amino]-2-(2-fluoro-phenyl)-propionic acid;

3-{[(1-Cyano-4-hydroxy-7-phenoxy-isoquinoline-3-carbonyl)-amino]-methyl}-5-methyl-hexanoic acid; or 4-[(1-Cyano-4-hydroxy-7-phenoxy-isoquinoline-3-carbonyl)-amino]-pentanoic acid;

or a pharmaceutically acceptable salt, single stereoisomer, mixture of stereoisomers, ester, tautomer or prodrug thereof.

2. Compositions and Methods

The invention provides for use of a compound of Formula I, II or III for the manufacture of a medicament for use in treating various conditions or disorders as described herein. In one embodiment, a pharmaceutical composition is provided comprising at least one compound of Formula I, II or III and a pharmaceutically acceptable excipient or carrier.

In various embodiments, the medicament or pharmaceutical composition can further comprise or be used in combination with at least one additional therapeutic agent.

The compounds of the present invention, or medicaments or compositions comprising the compounds, can be used to inhibit PHD1 activity selectively over other isoforms, for example, PHD2 and/or PHD3 enzymes. Selective inhibition of PHD1 may be of particular benefit in treating skeletal muscle cell degeneration, colitis and other forms of inflammatory bowel disease, and heart failure in patients with concomitant cardiac and renal disease. In one embodiment, the method of the invention comprises administering to a patient in need a therapeutically effective amount of a compound of Formula I, II or III, or a pharmaceutical composition comprising one or more compounds of Formula I, II or III.

The invention is also directed to a method of inhibiting the activity of PHD1. The PHD1 enzyme is selectively inhibited over other PHD isoforms, for example, PHD2 and/or PHD3 enzymes. In one embodiment, the method comprises contacting PHD1 with an effective amount of one or more compounds selected from the group comprising compounds of Formula I, II or III.

3. Definitions

It must be noted that as used herein, and in the appended claims, the singular forms "a," "an," and "the" include plural references unless the context clearly dictates otherwise.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the invention. Nothing herein is to be construed as an admission that the invention is not entitled to antedate such disclosure by virtue of prior invention.

The practice of the present invention will employ, unless otherwise indicated, conventional methods of chemistry, biochemistry, molecular biology, cell biology, genetics, immunology, and pharmacology, within the skill of the art. Such techniques are explained fully in the literature. (See, e.g., Gennaro, A. R., ed. (1990) Remington's Pharmaceutical Sciences, 18$^{th}$ ed., Mack Publishing Co.; Colowick, S. et al., eds., Methods In Enzymology, Academic Press, Inc.; D. M. Weir, and C. C. Blackwell, eds. (1986) Handbook of Experimental Immunology, Vols. I-IV, Blackwell Scientific Publications; Maniatis, T. et al., eds. (1989) Molecular Cloning: A Laboratory Manual, 2$^{nd}$ edition, Vols. I-III, Cold Spring Harbor Laboratory Press; Ausubel, F. M. et al., eds. (1999) Short Protocols in Molecular Biology, 4$^{th}$ edition, John Wiley & Sons; Ream et al., eds. (1998) Molecular Biology Techniques: An Intensive Laboratory Course, Academic Press; Newton & Graham eds. (1997) PCR (Introduction to Biotechniques Series), 2nd ed., Springer Verlag).

The terms "PHD", "prolyl hydroxylase domain-containing protein", "HIF prolyl hydroxylase," "HpH," and "HIF pH" refer to members of the Egl-Nine (EGLN) gene family described by Taylor (2001, *Gene* 275:125-132), and characterized by Aravind and Koonin (2001, Genome Biol 2: RESEARCH 0007), Epstein et al. (2001, *Cell* 107:43-54), and Bruick and McKnight (2001, *Science* 294:1337-1340). The term "PHD1" refers to prolyl hydroxylase domain-containing protein-1. This protein is also sometimes referred to as EIT6, HIF-pH1, HIFpH1, HpH-1, EGLN2 and HpH-3. PHD1 proteins include, but are not limited to, human PHD1 (GenBank Accession No. NP_444274.1), human EGLN2 isoform 1 (GenBank Accession No. CAC42510; Taylor, supra), human EGLN2 isoform 3 (GenBank Accession No. NP_542770), mouse EGLN2 (GenBank Accession No. CAC42516), and rat EGLN2 (GenBank Accession No. AAO46039). PHD2 (also known as EGLN-1) include, but are not limited to, human EGLN1 (GenBank Accession No. AAG33965; Dupuy et al. (2000) *Genomics* 69:348-54), mouse EGLN1 (GenBank Accession No. CAC42515), and rat EGLN1 (GenBank Accession No. P59722). PHD3 (also known as EGLN-3) include, but are not limited to, human EGLN3 (GenBank Accession No. CAC42511; Taylor, supra), mouse EGLN3 (GenBank Accession No. CAC42517), and rat EGLN3 (SM-20) (GenBank Accession No. AAA19321). In other embodiments of the present invention, EGLN may include *Caenorhabditis elegans* EGL-9 (GenBank Accession No. AAD56365) and *Drosophila melanogaster* CG1114 gene product (GenBank Accession No. AAF52050). All GenBank sequences associated with the provided accession Nos. are herein incorporated by reference in their entirety.

In addition to those provided above for PHD1 protein, a further GenBank Accession No. associated with the human PHD1 gene is NM_053046.3 (mRNA), which is herein incorporated by reference in its entirety.

The terms "disorders," "diseases," and "conditions" are used inclusively herein and refer to any condition deviating from normal.

The terms "treating," "treatment" and the like, are used herein to mean administering a therapy to a patient in need thereof. The therapy may be administered thereby providing a prophylactic effect in terms of completely or partially preventing a disorder or sign or symptom thereof; and/or the therapy may be administered thereby providing a partial or complete cure for a disorder and/or adverse effect attributable to the disorder.

The term "alkyl" refers to saturated monovalent hydrocarbyl groups having from 1 to 10 carbon atoms, more particularly from 1 to 5 carbon atoms, and even more particularly 1 to 3 carbon atoms. This term is exemplified by groups such as methyl, ethyl, n-propyl, iso-propyl, n-butyl, t-butyl, n-pentyl, and the like. The term "$C_1$-$C_4$ alkyl" refers to an alkyl having from 1 to 4 carbon atoms and includes methyl, ethyl, n-propyl, iso-propyl, n-butyl, t-butyl, and the like.

The term "substituted alkyl" refers to an alkyl group of from 1 to 10 carbon atoms, more particularly 1 to 5 carbon atoms, and having from 1 to 5 substituents, preferably 1 to 3 substituents, each of which substituents is independently selected from the group consisting of alkoxy, substituted alkoxy, acyl, acylamino, acyloxy, amino, substituted amino, aminoacyl, aminocarbonylamino, aminothiocarbonylamino, aminocarbonyloxy, aryl, substituted aryl, aryloxy, substituted aryloxy, aryloxyaryl, substituted aryloxyaryl, cyano, halogen, hydroxyl, nitro, oxo, thioxo, carboxyl, carboxyl esters, cycloalkyl, substituted cycloalkyl, thio, alkylthio, substituted alkylthio, arylthio, substituted arylthio, cycloalkylthio, substituted cycloalkylthio, heteroarylthio, substituted heteroarylthio, heterocyclicthio, substituted heterocyclicthio, sulfonyl, substituted sulfonyl, heteroaryl, substituted heteroaryl, heterocyclic, substituted heterocyclic, cycloalkoxy, substituted cycloalkoxy, heteroaryloxy, substituted heteroaryloxy, heterocyclyloxy, substituted heterocyclyloxy, oxycarbonylamino, oxythiocarbonylamino, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{40}$R$^{40}$—NR$^{40}$S(O)$_2$—NR$^{40}$-alkyl, —NR$^{40}$S(O)$_2$—NR$^{40}$-substituted alkyl, —NR$^{40}$S(O)$_2$—NR$^{40}$-aryl, —NR$^{40}$S(O)$_2$—NR$^{40}$-substituted aryl, —NR$^{40}$S(O)$_2$—NR$^{40}$-heteroaryl, —NR$^{40}$S(O)$_2$—NR$^{40}$-substituted heteroaryl, —NR$^{40}$S(O)$_2$—NR$^{40}$-heterocyclic, and —NR$^{40}$S(O)$_2$—NR$^{40}$-substituted heterocyclic, where each R$^{40}$ is independently selected from hydrogen or alkyl. This group is exemplified by groups such as trifluoromethyl, benzyl, pyrazol-1-ylmethyl, etc.

The term "aralkyl" refers to an aryl group covalently linked to an alkylene group, where aryl and alkylene are defined herein. The term "substituted aralkyl" refers to an optionally substituted aryl group covalently linked to an optionally substituted alkylene group. Such aralkyl groups are exemplified by benzyl, phenylethyl, 3-(4-methoxyphenyl)propyl, and the like.

The term "alkylidene" or "alkylene" refers to divalent saturated aliphatic hydrocarbyl groups preferably having from 1 to 5 and more preferably 1 to 3 carbon atoms which are either straight-chained or branched. This term is exemplified by groups such as methylene (—CH$_2$—), ethylene (—CH$_2$CH$_2$—), n-propylene (—CH$_2$CH$_2$CH$_2$—), iso-propylene (—CH$_2$CH(CH$_3$)—) and the like. "(C$_{u-v}$)alkylene" refers to alkylene groups having from u to v carbon atoms. The alkylidene or alkylene groups include branched and straight chain hydrocarbyl groups. For example "(C$_{1-6}$)alkylene" is meant to include methylene, ethylene, propylene, 2-methypropylene, pentylene, and the like.

The term "alkyl alcohol" refers to the group "alkyl-OH". For example, alkyl alcohol is meant to include methanol, ethanol, 2-propanol, 2-butanol, butanol, etc.

The term "substituted alkyl alcohol" refers to the group "substituted alkyl-OH".

The term "alkoxy" refers to the group "alkyl-O—," which includes, by way of example, methoxy, ethoxy, n-propoxy, iso-propoxy, n-butoxy, t-butoxy, sec-butoxy, n-pentoxy, and the like.

The term "substituted alkoxy" refers to the group "substituted alkyl-O—".

The term "acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—, provided that a nitrogen atom of the heterocyclic or substituted heterocyclic is not bound to the —C(O)— group, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminoacyl" or "amide," or the prefix "carbamoyl," "carboxamide," "substituted carbamoyl" or "substituted carboxamide" refers to the group —C(O)NR$^{42}$R$^{42}$ where each R$^{42}$ is independently selected from the group consisting of hydrogen, alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, and substituted heterocyclic; or where each R$^{42}$ is joined to form together with the nitrogen atom a heterocyclic or substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "alkenyl" refers to a vinyl unsaturated monovalent hydrocarbyl group having from 2 to 6 carbon atoms, and preferably 2 to 4 carbon atoms, and having at least 1, and preferably from 1 to 2 sites of vinyl (>C=C<) unsaturation. Such groups are exemplified by vinyl (ethen-1-yl), allyl, but-3-enyl and the like.

The term "substituted alkenyl" refers to alkenyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This term includes both E (trans) and Z (cis) isomers as appropriate. It also includes mixtures of both E and Z components.

The term "alkynyl" refers to acetylenic unsaturated monovalent hydrocarbyl groups having from 2 to 6 carbon atoms, and preferably 2 to 3 carbon atoms, and having at least 1, and preferably from 1 to 2 sites of acetylenic (—C≡C—) unsaturation. This group is exemplified by ethyn-1-yl, propyn-1-yl, propyn-2-yl, and the like.

The term "substituted alkynyl" refers to alkynyl groups having from 1 to 3 substituents, and preferably 1 to 2 substituents, selected from the group consisting of alkoxy, substituted alkoxy, acyl, acylamino, acyloxy, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic. This group is exemplified by groups such as phenylethynyl, etc.

The term "amino" refers to the group —NH$_2$.

The term "substituted amino" refers to the group —NR$^{41}$R$^{41}$, where each R$^{41}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, substituted heterocyclic, sulfonyl, and substituted sulfonyl, provided that both R$^{41}$ groups are not hydrogen; or the R$^{41}$ groups can be joined together with the nitrogen atom to form a heterocyclic or substituted heterocyclic ring. This group is exemplified by phenylamino, methylphenylamino, and the like. This group is exemplified by groups such as (ethanic acid-2-yl)amino, etc.

The term "acylamino" refers to the groups —NR$^{45}$C(O)alkyl, —NR$^{45}$C(O)substituted alkyl, —NR$^{45}$C(O)cycloalkyl, —NR$^{45}$C(O)substituted cycloalkyl, —NR$^{45}$C(O)alkenyl, —NR$^{45}$C(O)substituted alkenyl, —NR$^{45}$C(O)alkynyl, —NR$^{45}$C(O)substituted alkynyl, —NR$^{45}$C(O)aryl, —NR$^{45}$C(O)substituted aryl, —NR$^{45}$C(O)heteroaryl, —NR$^{45}$C(O)substituted heteroaryl, —NR$^{45}$C(O)heterocyclic, and —NR$^{45}$C(O)substituted heterocyclic where R$^{45}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are defined herein.

The term "oxycarbonylamino" refers to the groups —NR$^{46}$C(O)O-alkyl, —NR$^{46}$C(O)O-substituted alkyl, —NR$^{46}$C(O)O-alkenyl, —NR$^{46}$C(O)O-substituted alkenyl, —NR$^{46}$C(O)O-alkynyl, —NR$^{46}$C(O)O-substituted alkynyl, —NR$^{46}$C(O)O-cycloalkyl, —NR$^{46}$C(O)O-substituted cycloalkyl, —NR$^{46}$C(O)O-aryl, —NR$^{46}$C(O)O-substituted aryl, —NR$^{46}$C(O)O-heteroaryl, —NR$^{46}$C(O)O-substituted heteroaryl, —NR$^{46}$C(O)O-heterocyclic, and —NR$^{46}$C(O)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "oxythiocarbonylamino" refers to the groups —NR$^{46}$C(S)O-alkyl, —NR$^{46}$C(S)O-substituted alkyl, —NR$^{46}$C(S)O-alkenyl, —NR$^{46}$C(S)O-substituted alkenyl, —NR$^{46}$C(S)O-alkynyl, —NR$^{46}$C(S)O-substituted alkynyl, —NR$^{46}$C(S)O-cycloalkyl, —NR$^{46}$C(S)O-substituted cycloalkyl, —NR$^{46}$C(S)O-aryl, —NR$^{46}$C(S)O-substituted aryl, —NR$^{46}$C(S)O-heteroaryl, —NR$^{46}$C(S)O-substituted heteroaryl, —NR$^{46}$C(S)O-heterocyclic, and —NR$^{46}$C(S)O-substituted heterocyclic where R$^{46}$ is hydrogen or alkyl, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonyloxy," or the prefix "carbamoyloxy" or "substituted carbamoyloxy," refers to the groups —OC(O)NR$^{47}$R$^{47}$ where each R$^{47}$ is independently selected from the group consisting of hydrogen, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic; or where each R$^{47}$ is joined to form, together with the nitrogen atom, a heterocyclic or substituted heterocyclic, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

The term "aminocarbonylamino" refers to the group —NR$^{49}$C(O)N(R$^{49}$)$_2$ where each R$^{49}$ is independently selected from the group consisting of hydrogen and alkyl.

The term "aminothiocarbonylamino" refers to the group —NR$^{49}$C(S)N(R$^{49}$)$_2$ where each R$^{49}$ is independently selected from the group consisting of hydrogen and alkyl.

The term "aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3 (4H)-one-7-yl, and the like) provided that the point of attachment is the aryl group. Preferred aryls include phenyl and naphthyl.

The term "substituted aryl" refers to aryl groups, as defined herein, which are substituted with from 1 to 4, particularly 1 to 3, substituents selected from the group consisting of hydroxy, acyl, acylamino, acyloxy, alkyl, substituted alkyl, alkoxy, substituted alkoxy, alkenyl, substituted alkenyl, alkynyl, substituted alkynyl, amidino (—C(=NH)-amino or substituted amino), amino, substituted amino, aminoacyl, aminocarbonyloxy, aminocarbonylamino, aminothiocarbonylamino, aryl, substituted aryl, aryloxy, substituted aryloxy, cycloalkoxy, substituted cycloalkoxy, heteroaryloxy, substituted heteroaryloxy, heterocyclyloxy, substituted heterocyclyloxy, carboxyl, carboxyl esters, cyano, thio, alkylthio, substituted alkylthio, arylthio, substituted arylthio, heteroarylthio, substituted heteroarylthio, cycloalkylthio, substituted cycloalkylthio, heterocyclicthio, substituted heterocyclicthio, cycloalkyl, substituted cycloalkyl, guanidino (—NH—C(=NH)-amino or substituted amino), halo, nitro, heteroaryl, substituted heteroaryl, heterocyclic, substituted heterocyclic, oxycarbonylamino, oxythiocarbonylamino, sulfonyl, substituted sulfonyl, —OS(O)$_2$-alkyl, —OS(O)$_2$-substituted alkyl, —OS(O)$_2$-aryl, —OS(O)$_2$-substituted aryl, —OS(O)$_2$-heteroaryl, —OS(O)$_2$-substituted heteroaryl, —OS(O)$_2$-heterocyclic, —OS(O)$_2$-substituted heterocyclic, and —OSO$_2$—NR$^{51}$R$^{51}$, —NR$^{51}$S(O)$_2$—NR$^{51}$-alkyl, —NR$^{51}$S(O)$_2$—NR$^{51}$-substituted alkyl, —NR$^{51}$S(O)$_2$—NR$^{51}$-aryl, —NR$^{51}$S(O)$_2$—NR$^{51}$-substituted aryl, —NR$^{51}$S(O)$_2$—NR$^{51}$-heteroaryl, —NR$^{51}$S(O)$_2$—NR$^{51}$-substituted heteroaryl, —NR$^{51}$S(O)$_2$—NR$^{51}$-heterocyclic, —NR$^{51}$S(O)$_2$—NR$^{51}$-substituted heterocyclic, where each R$^{51}$ is independently selected from hydrogen or alkyl, wherein each of the terms is as defined herein. This group is exemplified by groups such as 4-fluorophenyl, 3-methoxyphenyl, 4-t-butylphenyl, 4-trifluoromethylphenyl, 2-trifluoromethoxyphenyl, 3-trifluoromethoxyphenyl, 4-trifluoromethoxyphenyl, 2-chlorophenyl, 3-chlorophenyl, 4-chlorophenyl, 2-chloro-6-fluorophenyl, 2,4-dichlorophenyl, 4-methoxyphenyl, 3-cyanophenyl, 4-cyanophenyl, 4-phenoxyphenyl, 4-methanesulfonylphenyl, biphenyl-4-yl, etc.

The term "aryloxy" refers to the group aryl-O— that includes, by way of example, phenoxy, naphthoxy, and the like.

The term "substituted aryloxy" refers to substituted aryl-O— groups.

The term "aryloxyaryl" refers to the group -aryl-O-aryl.

The term "substituted aryloxyaryl" refers to aryloxyaryl groups substituted with from 1 to 3 substituents on either or both aryl rings as defined above for substituted aryl.

The term "carboxyl" refers to —COOH or salts thereof.

The term "carboxyl ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-cycloalkyl, —C(O)O-substituted cycloalkyl, —C(O)O-aryl, —C(O)O-substituted aryl, —C(O)O-heteroaryl, —C(O)O-substituted heteroaryl, —C(O)O-heterocyclic, and —C(O)O-substituted heterocyclic.

The term "cyano" refers to the group —CN.

The term "cycloalkyl" refers to a saturated or an unsaturated but nonaromatic cyclic alkyl groups of from 3 to 10, 3 to 8 or 3 to 6 carbon atoms having single or multiple cyclic rings including, by way of example, adamantyl, cyclopropyl, cyclobutyl, cyclopentyl, cyclooctyl, cyclohexenyl, and the like.

The term "substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, acyloxy, amino, substituted amino, aminoacyl, aryl, substituted aryl, aryloxy, substituted aryloxy, cyano, halogen, hydroxy, nitro, carboxyl, carboxyl esters, cycloalkyl, substituted cycloalkyl, heteroaryl, substituted heteroaryl, heterocyclic, and substituted heterocyclic.

The term "cycloalkylene" and "substituted cycloalkylene" refer to divalent cycloalkyl and substituted cycloalkyl groups as defined above.

The term "cycloalkoxy" refers to —O-cycloalkyl groups.

The term "substituted cycloalkoxy" refers to —O-substituted cycloalkyl groups.

The term "halo" or "halogen" refers to fluoro, chloro, bromo, and iodo.

The term "hydroxy" or "hydroxyl" refers to the group —OH.

The term "heteroaryl" refers to an aromatic ring of from 1 to 15 carbon atoms, preferably from 1 to 10 carbon atoms, and 1 to 4 heteroatoms within the ring selected from the group consisting of oxygen, nitrogen, and sulfur. Such heteroaryl groups can have a single ring (e.g., pyridinyl, furyl, or thienyl) or multiple condensed rings (e.g., indolizinyl or benzothienyl) provided the point of attachment is through a ring containing the heteroatom and that ring is aromatic. The nitrogen and/or sulfur ring atoms can optionally be oxidized to provide for the N-oxide or the sulfoxide, and sulfone derivatives. Examples of heteroaryls include but are not limited to, pyridinyl, pyrimidinyl, pyrrolyl, pyrazolyl, indolyl, thiophenyl, thienyl, and furyl.

The term "substituted heteroaryl" refers to heteroaryl groups that are substituted with from 1 to 3 substituents selected from the same group of substituents defined for substituted aryl. This group is exemplified by groups such as 5-fluoro-pyridin-3-yl, 1-benzyl-1H-[1,2,3]triazol-4-yl, 5-bromo-furan-2-yl, trifluoromethyl-2H-pyrazol-3-yl, etc.

The term "heteroaryloxy" refers to the group —O-heteroaryl, and "substituted heteroaryloxy" refers to the group —O-substituted heteroaryl.

The term "heterocyclyl" or "heterocyclic" refers to a saturated or unsaturated (but not aromatic) group having a single ring or multiple condensed rings, from 1 to 10 carbon atoms, and from 1 to 4 hetero atoms selected from the group consisting of nitrogen, sulfur or oxygen within the ring wherein, in fused ring systems, one or more of the rings can be aryl or heteroaryl provided that the point of attachment is at the heterocycle. The nitrogen and/or sulfur ring atoms can optionally be oxidized to provide for the N-oxide or the sulfoxide, and sulfone derivatives.

The term "substituted heterocyclyl" or "substituted heterocyclic" refers to heterocycle groups that are substituted with from 1 to 3 of the same substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

The term "nitro" refers to the group —NO$_2$.

The term "oxo" refers to the atom (=O) or to the atom (—O$^-$).

The term "carbonyl" refers to the group —C(O)—.

The term "sulfonyl" refers to the group —S(O)$_2$H. The term "substituted sulfonyl" refers to the group —SO$_2$-alkyl, —SO$_2$-substituted alkyl, —SO$_2$-alkenyl, —SO$_2$-substituted alkenyl, —SO$_2$-alkynyl, —SO$_2$-substituted alkynyl, —SO$_2$-cycloalkyl, —SO$_2$-substituted cycloalkyl, —SO$_2$-cycloalkenyl, —SO$_2$-substituted cycloalkenyl, —SO$_2$-aryl, —SO$_2$-substituted aryl, —SO$_2$-heteroaryl, —SO$_2$-substituted heteroaryl, —SO$_2$-heterocyclic, —SO$_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein. Substituted sulfonyl includes groups such as methyl-SO$_2$—, phenyl-SO$_2$—, and 4-methylphenyl-SO$_2$—.

The term "heterocyclyloxy" refers to the group —O-heterocyclic, and "substituted heterocyclyloxy" refers to the group —O-substituted heterocyclic.

The term "thio" or "mercapto" refers to the group —SH.

The term "alkylsulfanyl," "alkylthio," or "thioether" refers to the groups —S-alkyl where alkyl is as defined above.

The term "substituted alkylthio," "substituted alkylsulfanyl," or "substituted alkylthio" refers to the group —S-substituted alkyl where substituted alkyl is as defined above.

The term "cycloalkylthio" or "cycloalkylsulfanyl" refers to the groups —S-cycloalkyl where cycloalkyl is as defined above.

The term "substituted cycloalkylthio" refers to the group —S-substituted cycloalkyl where substituted cycloalkyl is as defined above.

The term "arylthio" or "arylsulfanyl" refers to the group —S-aryl, and "substituted arylthio" refers to the group —S-substituted aryl where aryl and substituted aryl are as defined above.

The term "heteroarylthio" or "heteroarylsulfanyl" refers to the group —S-heteroaryl, and "substituted heteroarylthio" refers to the group —S-substituted heteroaryl where heteroaryl and substituted heteroaryl are as defined above.

The term "heterocyclicthio" or "heterocyclicsulfanyl" refers to the group —S-heterocyclic, and "substituted heterocyclicthio" refers to the group —S-substituted heterocyclic where heterocyclic, and substituted heterocyclic are as defined above.

The term "ester" refers to compounds of Formula I, II or III that include the group —COOR$^{54}$ where R$^{54}$ is alkyl, substituted alkyl, aryl, or substituted aryl. For example, esters of the invention include compounds of Formula I, II or III wherein $R^9$ is alkyl. Esters of Formula I, II or III can be provided, for example, via esterification of the hydroxyl group at the C4 position of the isoquinoline ring using a suitable reagent such as an acylhalide or an anhydride and/or via esterification of the carboxylic acid moiety when $R^9$ is hydrogen. Such methods are well known in the art.

The term "pharmaceutically acceptable salt" refers to pharmaceutically acceptable salts of a compound, which salts are derived from a variety of organic and inorganic counter ions well known in the art, and include, by way of example only, sodium, potassium, calcium, magnesium, ammonium, tetraalkylammonium, and the like; and, when the molecule contains a basic functionality such as —$NH_2$, salts of organic or inorganic acids, such as hydrochloride, hydrobromide, tartrate, mesylate, acetate, trifluoroacetate, maleate, oxalate, and the like. For example, pharmaceutically acceptable salts of the invention can be provided by compounds of Formula I, II or III when $R^9$ is a cation. Similarly, pharmaceutically acceptable salts of the invention can be provided by compounds of Formula I, II or III at the hydroxyl group at the C4 position of the isoquinoline, and/or at the carboxylic acid moiety when $R^9$ is hydrogen by methods well known in the art. The term "cation" refers to a positively charged organic and inorganic counter ion, and includes, by way of example only, sodium, potassium, calcium, magnesium, ammonium, tetraalkylammonium, and the like.

The terms "stereoisomer" or "stereoisomers" refer to compounds that differ in the chirality of one or more stereocenters. Stereoisomers include enantiomers (compounds are non-superimposable mirror images) and diastereomers (compounds having more than one stereogenic center that are non-mirror images of each other and wherein one or more stereogenic center differs between the two stereoisomers). The compounds of the invention can be present as a mixture of stereoisomers or as a single stereoisomer.

The term "tautomer" refers to alternate forms of a compound that differ in the position of a proton, such as enol, keto, and imine enamine tautomers, or the tautomeric forms of heteroaryl groups containing a ring atom attached to both a ring NH moiety and a ring=N moiety such as pyrazoles, imidazoles, benzimidazoles, triazoles, and tetrazoles.

The term "prodrug" as used herein, refers to compounds of Formula I, II or III that include chemical groups which, in vivo, can be converted into the carboxylate group when $R^9$ is hydrogen in compounds of Formula I and II, and/or can be split off from the amide N-atom and/or can be split off from the C4 hydroxy to provide for the active drug, a pharmaceutically acceptable salt thereof, or a biologically active metabolite thereof. Suitable groups are well known in the art and particularly include: for the carboxylic acid moiety, a prodrug selected from, e.g., esters including, but not limited to, those derived from alkyl alcohols, substituted alkyl alcohols, hydroxy substituted aryls and heteroaryls and the like; amides, particularly amides derived from amines of the Formula $HNR^{200}R^{210}$ where $R^{200}$ and $R^{210}$ are independently hydrogen, alkyl, substituted alkyl, aryl, substituted aryl, and the like; hydroxymethyl, aldehyde and derivatives thereof.

The term "excipient" as used herein means an inert or inactive substance used in the production of pharmaceutical products or other tablets, including without limitation any substance used as a binder, disintegrant, coating, compression/encapsulation aid, cream or lotion, lubricant, parenteral, sweetener or flavoring, suspending/gelling agent, or wet granulation agent. Binders include, e.g., carbopol, povidone, xanthan gum, etc.; coatings include, e.g., cellulose acetate phthalate, ethylcellulose, gellan gum, maltodextrin, etc.; compression/encapsulation aids include, e.g., calcium carbonate, dextrose, fructose dc, honey dc, lactose (anhydrate or monohydrate; optionally in combination with aspartame, cellulose, or microcrystalline cellulose), starch dc, sucrose, etc.; disintegrants include, e.g., croscarmellose sodium, gellan gum, sodium starch glycolate, etc.; creams and lotions include, e.g., maltodextrin, carrageenans, etc.; lubricants include, e.g., magnesium stearate, stearic acid, sodium stearyl fumarate, etc.; materials for chewable tablets include, e.g., dextrose, fructose dc, lactose (monohydrate, optionally in combination with aspartame or cellulose), etc.; parenterals include, e.g., mannitol, povidone, etc.; plasticizers include, e.g., dibutyl sebacate, polyvinylacetate phthalate, etc.; suspending/gelling agents include, e.g., carrageenan, sodium starch glycolate, xanthan gum, etc.; sweeteners include, e.g., aspartame, dextrose, fructose dc, sorbitol, sucrose dc, etc.; and wet granulation agents include, e.g., calcium carbonate, maltodextrin, microcrystalline cellulose, etc.

The term "selectively" as used herein with respect to the ability of compound to inhibit the activity of a PHD1 enzyme is intended to refer to a compound exhibiting a lower $IC_{50}$ for PHD1 than PHD2 and/or PHD3. In certain embodiments, being selective indicates that the compound is at least five times more active in inhibiting PHD1 enzyme over PHD2 and/or PHD3 enzyme; namely, the ratio of the $IC_{50}$ for PHD2 and/or PHD3 over the $IC_{50}$ for PHD1 (i.e., $IC_{50}$ PHD2 and/or PHD3/$IC_{50}$ PHD1) is equal to or greater than five.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

Similarly, it is understood that the above definitions are not intended to include impermissible substitution patterns (e.g., methyl substituted with 5 fluoro groups or a hydroxyl group alpha to ethenylic or acetylenic unsaturation). Such impermissible substitution patterns are well known to the skilled artisan.

4. Compound Preparation

The compounds of this invention can be prepared from readily available starting materials using, for example, the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis,* 3rd Edition, Wiley, New York, and references cited therein.

Furthermore, the compounds of this invention may contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

5. Synthesis of Compounds

The substituted isoquinolines 300 of this disclosure can be prepared by the synthetic protocols illustrated in Scheme 1, where $R^1$, $R^2$, $R^3$, $R^4$, $R^5$, $R^6$, $R^7$, n, and $R^9$ are as defined herein.

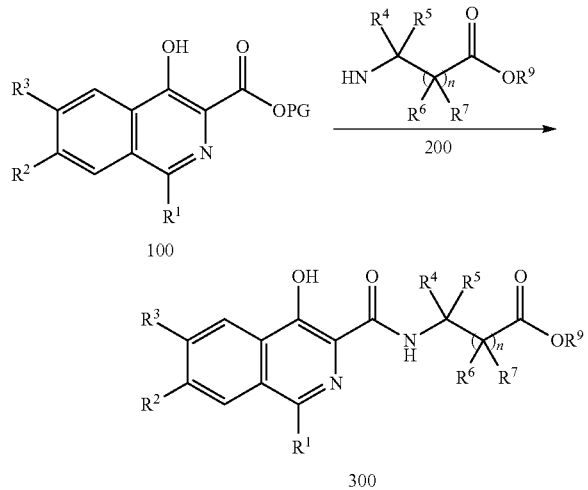

Scheme 1

Compound 100 (wherein PG refers to a suitable protecting group such as methyl, ethyl, butyl, etc.) is reacted with at least a stoichiometric amount and preferably an excess of a suitable amine compound 200. The reaction is typically conducted under conventional coupling conditions well known in the art.

In one embodiment, the reaction is conducted in the presence of sodium methoxide, or another suitable base in methanol, or other suitable solvent, under elevated reaction temperatures and typically at reflux. The reaction is continued until substantially complete which typically occurs within about 1 to 72 hours. Alternatively, the reaction can be performed at elevated temperatures in a microwave oven. Upon reaction completion, compound 300 can be recovered by conventional techniques such as neutralization, extraction, precipitation, chromatography, filtration and the like.

Alternatively, coupling of compound 100 (typically as the corresponding free acid) with compound 200 (typically as an ester derivative) can proceed via conventional peptide coupling procedures well known in the art. This coupling reaction is typically conducted using well-known coupling reagents such as carbodiimides, BOP reagent (benzotriazol-1-yloxy-tris(dimethylamino)-phosphonium hexafluorophosphonate), and the like. Suitable carbodiimides include, by way of example, dicyclohexylcarbodiimide (DCC), 1-(3-dimethylamino-propyl)-3-ethylcarbodiimide (DECI) and the like. If desired, polymer supported forms of carbodiimide coupling reagents may also be used including, for example, those described in *Tetrahedron Letters,* 34(48), 7685 (1993). Additionally, well-known coupling promoters, such as N-hydroxysuccinimide, 1-hydroxybenzotriazole and the like, may be used to facilitate the coupling reaction. This coupling reaction is typically conducted by contacting the corresponding free acids of compound 100 with about 1 to about 2 equivalents of the coupling reagent and at least one equivalent, preferably about 1 to about 1.2 equivalents, of an ester of compound 200, in an inert diluent such as dichloromethane, chloroform, acetonitrile, tetrahydrofuran, N,N-dimethylformamide and the like. Generally, this reaction is conducted at a temperature ranging from about 0° C. to about 37° C. for about 12 to about 24 hours. Upon completion of the reaction, the corresponding ester of compound 300 is recovered by conventional methods including neutralization, extraction, precipitation, chromatography, filtration, and the like, and is then transformed into compound 300 by hydrolysis.

Alternatively, compound 100 (typically as the corresponding free acid, not shown) can be converted into an acid halide and the acid halide coupled with compound 200 to provide for compound 300. The acid halide of compound 100 can be prepared by contacting the free acid of compound 100 (typically as the corresponding free acid) with an inorganic acid halide such as thionyl chloride, phosphorous trichloride, phosphorous tribromide, or phosphorous pentachloride, or, particularly, with oxalyl chloride under conventional conditions. Generally, this reaction is conducted using about 1 to 5 molar equivalents of the inorganic acid halide or oxalyl chloride, either neat or in an inert solvent such as dichloromethane or carbon tetrachloride, at temperature in the range of about 0° C. to about 80° C. for about 1 to about 48 hours. A catalyst, such as DMF, may also be used in this reaction.

The acid halide (not shown) is then contacted with at least one equivalent, preferably about 1.1 to about 1.5 equivalents, of compound 200, in an inert diluent such as dichloromethane, at a temperature ranging from about −70° C. to about 40° C. for about 1 to about 24 hours. Preferably, this reaction is conducted in the presence of a suitable base to scavenge the acid generated during the reaction. Suitable bases include, by way of example, tertiary amines such as triethylamine, diisopropylethylamine, N-methyl-morpholine, and the like. Alternatively, the reaction can be conducted under Schotten-Baumann-type conditions using aqueous alkali such as sodium hydroxide and the like. Upon completion of the reaction, the ester of compound 300 is recovered by conventional methods including neutralization, extraction, precipitation, chromatography, filtration, and the like.

Compound 100, for use in Scheme 1 above, can be prepared according to Scheme 2, where PG, $R^1$, $R^2$ and $R^3$ are as defined herein.

Other modifications to arrive at compounds of this invention are well within the skill of the art. For example, modification of the C-4 hydroxy group may be done by conventional means to corresponding ethers, acyloxy, and the like. In addition, the nitrogen of the isoquinoline moiety can be oxidized

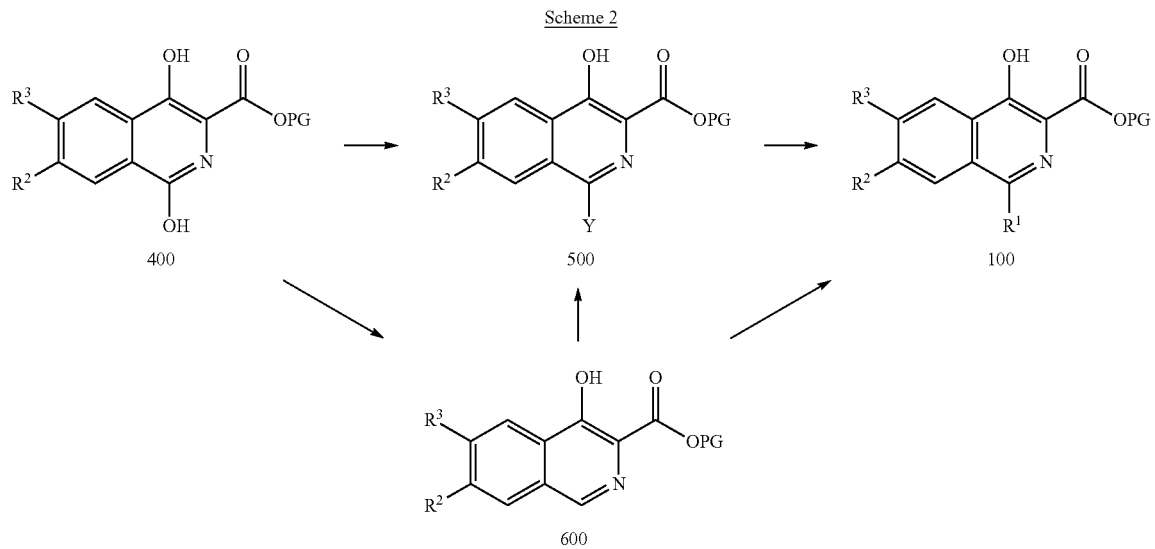

Treatment of compound 400 with phosphorous oxychloride or phosphorous oxybromide using a suitable solvent such as acetonitrile or toluene particularly at reflux temperature gives compound 500 wherein Y is Cl or Br, respectively. The reaction typically occurs within about 1 to 72 h. Alternatively, the reaction can be performed at elevated temperatures in a microwave oven. Upon reaction completion, compound 500 can be recovered by conventional techniques such as neutralization, extraction, precipitation, chromatography, filtration and the like; or, alternatively, used in the next step without purification and/or isolation.

Alternatively, compound 600 can be halogenated using conventional methods to give compound 500 wherein Y is Cl, Br, or I. The halogenation of compound 600 can be performed with a stoichiometric amount or slight excess of, e.g., N-bromosuccinimide in the presence of a catalytic amount of benzoylperoxide, azobisisobutyronitrile, or another suitable free radical initiator, in $CCl_4$, benzene, or another suitable solvent known to one skilled in the art typically at reflux temperature or higher temperatures using a microwave oven. Upon reaction completion, compounds 500 can be recovered by conventional techniques such as neutralization, extraction, precipitation, chromatography, filtration and the like; or, alternatively, used in the next step without purification and/or isolation. Alternatively, compound 500 can be obtained by halogenating compound 400 as described above followed by reduction using conventional methods such as hydrogenation catalyzed by palladium on carbon, etc.

The synthesis of substituted isoquinoline carboxylic acids and esters thereof (i.e., compounds 100, 400, 500, and 600) for use in the schemes above are generally known in the art and are described by, for example, Weidmann, et al., U.S. Pat. No. 6,093,730, Arend, et al., U.S. Pat. No. 7,323,475, and Arend, et al., U.S. Pat. No. 7,928,120, each of which are incorporated herein by reference in their entirety. Compound 200, for use in the reactions above, can be obtained from commercial sources or by conventional methods known in the art.

to provide the corresponding N-oxide compounds of Formula I, II or III using methods well known to those of skill in the art.

6. Use of Compounds

The specific in vivo roles of the PHD isoforms may, in part, be due to many different factors. These include: differing hydroxylase activities toward HIF-1α, structural divergence of the PHD proteins, differences in spacial and temporal expression of the PHD proteins, and differences in the expression patterns of the HIFα subunits in vivo. PHD1, PHD2, and PHD3 all hydroxylate human HIF-1α at Pro 564, but only PHD1 and PHD2 hydroxylate human HIF-1α at Pro 402. Hydroxylase activities to HIF-2α and HIF-3α have yet to be determined Structural divergence of the PHD proteins may account for the different in vitro specificities for the two proline residues of the HIF-1α protein as well as the nonredundant in vivo roles of the different PHD isoforms. All three of the PHD proteins share a well-conserved hydroxylase domain at the C-terminal portion of the protein. PHD1 and PHD2 are both over 400 amino acids (407 and 426 respectively) and have a large N-terminal portion that lacks sequence homology. PHD3 is 239 amino acids and only has a short stretch of the divergent N-terminal portion. Differential functions of the divergent N-terminal sequences may provide one hypothesis as to why the different PHD proteins are not functionally redundant in vivo. The PHD proteins are also differentially expressed in distinct tissue types. For example, RNA expression analysis of the PHD proteins revealed that PHD1 is the predominant isoform expressed in the testes and PHD3 is the predominant isoform in the heart.

However, protein expression analysis showed that the PHD2 protein is most abundant in all mouse organs. These studies indicate that many factors contribute to the in vivo specificity of the PHD proteins. (Fong and Takeda. (2008) Cell Death and Differentiation. 15:635-641; Bernhardt et al. (2007). Methods in Enzymology. 435:221-245; William et al.

(2006) J. Mol. Cell. Cardiol. 17:503-512; Takeda et al. (2008) Blood. Vol. 111 No. 6:3229-3235; Epstein et al. (2001) Cell. 107:43-54.)

Inhibitors that are selective for PHD1 would be preferable for the therapeutic uses described above in order to minimize unwanted side effects that could occur from significant inhibition of PHD2 and PHD3.

7. Biological Testing

The biological activity of the compounds of the invention may be assessed using any conventionally known methods. Suitable assay methods are well known in the art. The following assay is presented only as an example and is not intended to be limiting.

HIF-PH Assay

Ketoglutaric acid α-[1-$^{14}$C]-sodium salt, alpha-ketoglutaric acid sodium salt, and HPLC purified peptide may be obtained from commercial sources, e.g., Perkin-Elmer (Wellesley Mass.), Sigma-Aldrich, and SynPep Corp. (Dublin Calif.), respectively. Peptides for use in the assay may be fragments of HIFα as described above or as disclosed in International Publication WO 2005/118836, incorporated by reference herein. HIF-pH, e.g., PHD1 (EGLN2) or PHD2 (EGLN1), can be expressed in, e.g., insect Hi5 cells, and partially purified, e.g., through a SP ion exchange chromatography column. Enzyme activity is determined by capturing $^{14}CO_2$ using an assay described by Kivirikko and Myllyla (1982, *Methods Enzymol.* 82:245-304). Assay reactions contain 50 mM HEPES (pH 7.4), 100 μM α-ketoglutaric acid sodium salt, 0.30 mCi/mL ketoglutaric acid α-[1-$^{14}$C]-sodium salt, 40 μM $FeSO_4$, 1 mM ascorbate, 1541.8 units/mL Catalase, with or without 50 μM peptide substrate and various concentrations of compound of the invention. Reactions are initiated by addition of HIF-PH enzyme. $IC_{50}$ (compound concentration for 50% inhibition of enzyme activity) of the compounds for each enzyme can be determined.

The peptide-dependent percent turnover is calculated by subtracting percent turnover in the absence of peptide from percent turnover in the presence of substrate peptide. Percent inhibition and $IC_{50}$ are calculated using peptide-dependent percent turnover at given inhibitor concentrations. Calculation of $IC_{50}$ values for each inhibitor is conducted using GraFit software (Erithacus Software Ltd., Surrey UK).

Compounds of the invention are selective PHD1 inhibitors, and exhibit a greater potency for inhibition of PHD1 over PHD2 inhibition. Compounds of the invention were analyzed using the assay described above and Table 1 presents PHD1 and PHD2 enzyme inhibition data ($IC_{50}$) for exemplary compounds. The PHD2/PHD1 is the ratio of the $IC_{50}$ of the compound for each enzyme.

TABLE 1

| Compound No. | $IC_{50}$ (μM) PHD1 | $IC_{50}$ (μM) PHD2 | PHD2/PHD1 |
|---|---|---|---|
| 1 | 0.92 | 10.35 | 11 |
| 2 | 5.50 | 46.67 | 8 |
| 3 | 1.08 | 15.60 | 14 |
| 4 | 1.17 | 7.00 | 6 |
| 5 | 2.75 | 61.69 | 22 |
| 6 | 8.19 | 191.92 | 23 |
| 7 | 3.02 | 52.74 | 17 |
| 8 | 11.58 | 118.55 | 10 |
| 9 | 33.92 | >200 | 6 |
| 10 | 0.24 | 1.33 | 5 |
| 11 | 1.37 | 56.64 | 41 |
| 12 | 0.17 | 1.62 | 9 |
| 13 | 5.51 | 40.80 | 7 |
| 14 | 0.31 | 3.52 | 11 |
| 15 | 9.71 | 51.52 | 5 |
| 16 | 1.89 | 24.26 | 13 |
| 17 | 3.39 | 47.94 | 14 |
| 18 | 4.43 | 29.89 | 7 |
| 19 | 1.73 | 22.83 | 13 |
| 20 | 0.35 | 5.22 | 15 |
| 21 | 0.24 | 9.40 | 39 |
| 22 | 0.93 | 15.10 | 16 |
| 23 | 2.77 | 12.67 | 5 |
| 24 | 2.31 | 23.31 | 10 |
| 25 | 4.57 | 44.60 | 10 |
| 26 | 0.70 | 5.43 | 8 |
| 27 | 3.27 | 33.27 | 10 |
| 28 | 1.30 | 7.15 | 5 |
| 29 | 3.76 | 37.28 | 9.9 |
| 30 | 25.05 | 200 | 8 |
| 31 | 0.53 | 4.2 | 8 |
| 32 | 27.95 | 181.55 | 6 |
| 33 | 16.87 | 94.81 | 6 |
| 34 | 2.55 | 30.88 | 12 |
| 35 | 0.23 | 2.83 | 12 |
| 36 | 5.93 | 56.55 | 10 |
| 37 | 6.67 | 158.64 | 24 |
| 38 | 0.24 | 4.79 | 20 |
| 39 | 0.18 | 1.97 | 11 |
| 40 | 0.30 | 4.01 | 13 |
| 41 | 0.55 | 9.56 | 17 |
| 42 | 0.36 | 3.95 | 11 |
| 43 | 0.22 | 1.73 | 8 |
| 44 | 0.28 | 3.90 | 14 |
| 45 | 1.41 | 36.70 | 26 |
| 46 | 0.94 | 20.76 | 22 |
| 47 | 1.28 | 30.15 | 24 |
| 48 | 5.42 | 50.15 | 9 |
| 49 | 1.66 | 23.92 | 14 |
| 50 | 5.19 | 45.40 | 9 |
| 51 | 0.28 | 2.1 | 7.5 |
| 52 | 1.33 | 24.7 | 18.6 |
| 53 | 0.24 | 1.4 | 5.8 |
| 54 | 1.81 | 11 | 6.1 |
| 55 | 1.1 | 9.1 | 8 |
| 56 | 0.26 | 1.8 | 7 |
| 57 | 0.54 | 5.1 | 9 |
| 58 | 1.1 | 12.3 | 11 |
| 59 | 0.13 | 0.86 | 6.5 |
| 60 | (1, 1.08)* 1.04 avg. | (3.65, 10.8)* 7.23 avg. | (3.6, 10)* 6.8 avg |
| 61 | 33.32 | >200 | 6 |
| 62 | 0.48 | 3.06 | 6 |
| 63 | 2.82 | 26.85 | 10 |
| 64 | 0.93 | 12.59 | 14 |
| 65 | 0.73 | 5.99 | 8 |
| 66 | (6.23, 4.8)* 5.52 avg. | (26.54, 80.5)* 53.52 avg. | (4, 17)* 10.5 avg. |
| 67 | 3.43 | 32.06 | 9 |
| 68 | 2.27 | 48.09 | 21 |
| 69 | 2.43 | 64.08 | 26 |
| 70 | 1.86 | 65.81 | 35 |
| 71 | 2.77 | 107.22 | 39 |
| 72 | 11.78 | 200 | 17 |
| 73 | 0.74 | 3.38 | 5 |
| 74 | 1.55 | 7.64 | 5 |
| 75 | 1.17 | 18.91 | 16 |
| 76 | 0.16 | 2.86 | 18 |
| 77 | 0.41 | 9.12 | 22 |
| 78 | 3.27 | 96.75 | 30 |
| 79 | 0.11 | 1.69 | 15 |
| 80 | 0.14 | 0.71 | 5 |
| 81 | 0.42 | 4.95 | 12 |
| 82 | 0.91 | 20.41 | 23 |
| 83 | 0.24 | 2.75 | 12 |
| 84 | 0.34 | 2.11 | 6 |
| 85 | 19.11 | 112.25 | 6 |
| 86 | 2.51 | 51.92 | 21 |
| 87 | 3.56 | 27.48 | 8 |
| 88 | 14.08 | 93.29 | 7 |
| 89 | 2.86 | 13.60 | 5 |

TABLE 1-continued

| Compound No. | IC$_{50}$ (µM) PHD1 | IC$_{50}$ (µM) PHD2 | PHD2/PHD1 |
|---|---|---|---|
| 90 | 7.32 | 56.31 | 8 |
| 91 | 1.91 | 11.34 | 6 |
| 92 | 0.28 | 3.88 | 14 |
| 93 | 0.16 | 2.40 | 15 |
| 94 | 0.31 | 2.18 | 7 |
| 95 | 0.74 | 3.50 | 5 |
| 96 | 11.28 | 157.72 | 14 |
| 97 | 1.30 | 7.43 | 6 |
| 98 | 0.27 | 3.73 | 14 |
| 99 | 0.29 | 5.55 | 19 |
| 100 | 23.1 | 200 | 9 |
| 101 | 0.41 | 4.65 | 11 |
| 102 | 0.53 | 8.50 | 16 |
| 103 | 0.79 | 4.78 | 6 |
| 104 | 3.30 | 19.52 | 6 |
| 105 | 2.3 | 13.4 | 6 |
| 106 | 7.79 | 74.45 | 10 |
| 107 | (2.46, 2.28)* 2.37 avg. | (9.28, 14.4)* 11.84 avg. | (4, 6)* 5 avg. |
| 108 | 29.03 | 200.00 | 7 |
| 109 | 6.40 | 30.39 | 5 |
| 110 | 3.63 | 21.32 | 6 |
| 111 | 10.52 | 111.99 | 11 |
| 112 | 23.71 | 200 | 8 |
| 113 | 21.21 | 200 | 9 |
| 114 | 13.51 | 86.62 | 6 |
| 115 | 1.41 | 14.79 | 11 |
| 116 | 3.34 | 29.17 | 9 |
| 117 | 4.66 | 51.44 | 11 |
| 118 | 6.45 | 112.94 | 18 |
| 119 | 12.56 | 72.27 | 6 |
| 120 | 12.43 | 200.00 | 16 |
| 121 | 0.84 | 8.18 | 10 |
| 122 | 2.57 | 29.30 | 11 |
| 123 | 6.11 | 183.24 | 30 |
| 124 | 25.44 | 200.00 | 8 |
| 125 | 7.92 | 158.18 | 20 |
| 126 | 33.97 | 200.00 | 6 |
| 127 | 7.69 | 63.12 | 8 |
| 128 | 8.99 | 65.15 | 7 |
| 129 | 25.26 | 179.68 | 7 |
| 130 | 4.91 | 39.62 | 8 |
| 131 | 3.16 | 77.60 | 25 |
| 132 | 2.38 | 27.55 | 12 |
| 133 | 0.85 | 6.06 | 7 |
| 134 | 2.15 | 13.38 | 6 |
| 135 | 0.35 | 2.88 | 8 |
| 136 | 7.21 | 200.00 | 28 |
| 137 | 0.61 | 3.67 | 6 |
| 138 | 1.13 | 24.11 | 21 |
| 139 | 5.65 | 200.00 | 35 |
| 140 | 2.81 | 33.51 | 12 |
| 141 | 3.00 | 37.80 | 13 |
| 142 | 4.12 | 56.35 | 14 |
| 143 | 11.07 | 88.42 | 8 |
| 144 | 6.40 | 31.74 | 5 |
| 145 | 18.58 | 101.24 | 5 |
| 146 | 23.73 | 180.77 | 8 |
| 147 | 5.09 | 76.96 | 15 |
| 148 | 2.88 | 24.48 | 9 |
| 149 | 18.48 | 86.95 | 5 |
| 150 | 22.87 | 113.83 | 5 |
| 151 | 12.76 | 111.45 | 9 |
| 152 | 4.35 | 55.05 | 13 |
| 153 | 2.58 | 30.52 | 12 |
| 154 | 0.11 | 1.90 | 18 |
| 155 | 5.25 | 42.11 | 8 |
| 156 | 1.49 | 23.46 | 16 |
| 157 | 13.60 | 200.00 | 15 |
| 158 | 1.66 | 20.99 | 13 |
| 159 | 0.91 | 7.90 | 9 |
| 160 | 17.39 | 200.00 | 12 |
| 161 | 19.84 | 200.00 | 10 |
| 162 | 2.35 | 24.11 | 10 |
| 163 | 43.58 | >200 | 5 |
| 164 | 1.35 | 18.56 | 14 |
| 165 | 1.51 | 28.09 | 19 |
| 166 | 0.42 | 12.15 | 29 |
| 167 | 9.57 | 99.98 | 10 |
| 168 | 1.79 | 26.62 | 15 |
| 169 | 26.55 | 152.70 | 6 |
| 170 | 2.76 | 32.23 | 12 |
| 171 | 5.26 | 45.74 | 9 |
| 172 | 2.83 | 27.58 | 10 |
| 173 | 3.97 | 20.86 | 5 |
| 174 | 6.75 | 39.43 | 6 |
| 175 | 4.51 | 25.13 | 6 |
| 176 | 4.08 | 24.63 | 6 |
| 177 | 0.75 | 10.47 | 14 |
| 178 | 2.65 | 23.26 | 9 |
| 179 | 0.95 | 8.54 | 9 |
| 180 | 4.57 | 28.86 | 6 |
| 181 | 1.45 | 9.45 | 7 |
| 182 | 1.81 | 11.93 | 7 |
| 183 | 1.63 | 12.57 | 8 |
| 184 | 1.38 | 12.60 | 9 |

*For some compounds, multiple independent measurements of the IC$_{50}$ were made. The individual measurements as well as the average of these are reported in the table.

8. Pharmaceutical Formulations and Routes of Administration

The compositions of the present invention can be delivered directly or in pharmaceutical compositions or medicaments along with suitable carriers or excipients, as is well known in the art. Present methods of treatment can comprise administration of an effective amount of a compound of the invention to a subject in need. In a preferred embodiment, the subject is a mammalian subject, and in a most preferred embodiment, the subject is a human subject.

An effective amount of such compound, composition, or medicament can readily be determined by routine experimentation, as can the most effective and convenient route of administration, and the most appropriate formulation. Various formulations and drug delivery systems are available in the art. See, e.g., Gennaro, A. R., ed. (1995) Remington's Pharmaceutical Sciences, supra.

Suitable routes of administration may, for example, include oral, rectal, topical, nasal, pulmonary, ocular, intestinal, and parenteral administration. Primary routes for parenteral administration include intravenous, intramuscular, and subcutaneous administration. Secondary routes of administration include intraperitoneal, intra-arterial, intra-articular, intracardiac, intracisternal, intradermal, intralesional, intraocular, intrapleural, intrathecal, intrauterine, and intraventricular administration. The indication to be treated, along with the physical, chemical, and biological properties of the drug, dictate the type of formulation and the route of administration to be used, as well as whether local or systemic delivery would be preferred.

Pharmaceutical dosage forms of a compound of the invention may be provided in an instant release, controlled release, sustained release, or target drug-delivery system. Commonly used dosage forms include, for example, solutions and suspensions, (micro-) emulsions, ointments, gels and patches, liposomes, tablets, dragees, soft or hard shell capsules, suppositories, ovules, implants, amorphous or crystalline powders, aerosols, and lyophilized formulations. Depending on route of administration used, special devices may be required for application or administration of the drug, such as, for example, syringes and needles, inhalers, pumps, injection pens, applicators, or special flasks. Pharmaceutical dosage forms are often composed of the drug, an excipient(s), and a container/closure system. One or multiple excipients, also referred to as inactive ingredients, can be added to a compound of the invention to improve or facilitate manufacturing, stability, administration, and safety of the drug, and can provide a means to achieve a desired drug release profile. Therefore, the type of excipient(s) to be added to the drug can depend on various factors, such as, for example, the physical and chemical properties of the drug, the route of administration, and the manufacturing procedure. Pharmaceutically acceptable excipients are available in the art and include those listed in various pharmacopoeias. (See, e.g., the U.S. Pharmacopeia (USP), Japanese Pharmacopoeia (JP), European Pharmacopoeia (EP), and British pharmacopeia (BP); the U.S. Food and Drug Administration (www.fda.gov) Center for Drug Evaluation and Research (CEDR) publications, e.g., Inactive Ingredient Guide (1996); Ash and Ash, Eds. (2002) Handbook of Pharmaceutical Additives, Synapse Information Resources, Inc., Endicott N.Y.; etc.)

Pharmaceutical dosage forms of a compound of the present invention may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present invention can include one or more physiologically acceptable inactive ingredients that facilitate processing of active molecules into preparations for pharmaceutical use.

Proper formulation is dependent upon the desired route of administration. For intravenous injection, for example, the composition may be formulated in aqueous solution, if necessary using physiologically compatible buffers, including, for example, phosphate, histidine, or citrate for adjustment of the formulation pH, and a tonicity agent, such as, for example, sodium chloride or dextrose. For transmucosal or nasal administration, semisolid, liquid formulations, or patches may be preferred, possibly containing penetration enhancers. Such penetrants are generally known in the art. For oral administration, the compounds can be formulated in liquid or solid dosage forms, and as instant or controlled/sustained release formulations. Suitable dosage forms for oral ingestion by a subject include tablets, pills, dragees, hard and soft shell capsules, liquids, gels, syrups, slurries, suspensions, and emulsions. The compounds may also be formulated in rectal compositions, such as suppositories or retention enemas, e.g., containing conventional suppository bases such as cocoa butter or other glycerides.

Solid oral dosage forms can be obtained using excipients, which may include fillers, disintegrants, binders (dry and wet), dissolution retardants, lubricants, glidants, antiadherants, cationic exchange resins, wetting agents, antioxidants, preservatives, coloring, and flavoring agents. These excipients can be of synthetic or natural source. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (i.e. dextrose, sucrose, lactose, etc.), talc, tragacanth mucilage, vegetable oils (hydrogenated), and waxes. Ethanol and water may serve as granulation aides. In certain instances, coating of tablets with, for example, a taste-masking film, a stomach acid resistant film, or a release-retarding film is desirable. Natural and synthetic polymers, in combination with colorants, sugars, and organic solvents or water, are often used to coat tablets, resulting in dragees. When a capsule is preferred over a tablet, the drug powder, suspension, or solution thereof can be delivered in a compatible hard or soft shell capsule.

In one embodiment, the compounds of the present invention can be administered topically, such as through a skin patch, a semi-solid, or a liquid formulation, for example a gel, a (micro-) emulsion, an ointment, a solution, a (nano/micro)-suspension, or a foam. The penetration of the drug into the skin and underlying tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and use of complexing agents. Other techniques, such as iontophoresis, may be used to regulate skin penetration of a compound of the invention. Transdermal or topical administration would be preferred, for example, in situations in which local delivery with minimal systemic exposure is desired.

For administration by inhalation, or administration to the nose, the compounds for use according to the present invention are conveniently delivered in the form of a solution, suspension, emulsion, or semisolid aerosol from pressurized packs, or a nebuliser, usually with the use of a propellant, e.g., halogenated carbons derived from methane and ethane, carbon dioxide, or any other suitable gas. For topical aerosols, hydrocarbons like butane, isobutene, and pentane are useful. In the case of a pressurized aerosol, the appropriate dosage unit may be determined by providing a valve to deliver a metered amount. Capsules and cartridges of, for example, gelatin, for use in an inhaler or insufflator, may be formulated. These typically contain a powder mix of the compound and a suitable powder base such as lactose or starch.

Compositions formulated for parenteral administration by injection are usually sterile and can be presented in unit dosage forms, e.g., in ampoules, syringes, injection pens, or in multi-dose containers, the latter usually containing a preservative. The compositions may take such forms as suspensions, solutions, or emulsions in oily or aqueous vehicles, and may contain formulatory agents, such as buffers, tonicity agents, viscosity enhancing agents, surfactants, suspending and dispersing agents, antioxidants, biocompatible polymers, chelating agents, and preservatives. Depending on the injection site, the vehicle may contain water, a synthetic or vegetable oil, and/or organic co-solvents. In certain instances, such as with a lyophilized product or a concentrate, the parenteral formulation would be reconstituted or diluted prior to administration. Depot formulations, providing controlled or sustained release of a compound of the invention, may include injectable suspensions of nano/micro particles or nano/micro or non-micronized crystals. Polymers such as poly(lactic acid), poly(glycolic acid), or copolymers thereof, can serve as controlled/sustained release matrices, in addition to others well known in the art. Other depot delivery systems may be presented in form of implants and pumps requiring incision.

Suitable carriers for intravenous injection for the compounds of the invention are well-known in the art and include water-based solutions containing a base, such as, for example, sodium hydroxide, to form an ionized compound; sucrose or sodium chloride as a tonicity agent; and a buffer, for example, a buffer that contains phosphate or histidine. Co-solvents, such as, for example, polyethylene glycols, may be added. These water-based systems are effective at dissolving compounds of the invention and produce low toxicity upon systemic administration. The proportions of the components of a solution system may be varied considerably, without destroying solubility and toxicity characteristics.

Furthermore, the identity of the components may be varied. For example, low-toxicity surfactants, such as polysorbates or poloxamers, may be used, as can polyethylene glycol or other co-solvents, biocompatible polymers such as polyvinyl pyrrolidone may be added, and other sugars and polyols may substitute for dextrose.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays. In certain embodiments, a compound of the disclosure is formulated for oral administration. An exemplary dose of a compound of the disclosure in a pharmaceutical formulation for oral administration is from about 0.5 to about 10 mg/kg body weight of subject. In some embodiments, a pharmaceutical formulation comprises from about 0.7 to about 5.0 mg/kg body weight of subject, or alternatively, from about 1.0 to about 2.5 mg/kg body weight of subject. A typical dosing regimen for oral administration would be administration of the pharmaceutical formulation for oral administration three times per week, two times per week, once per week or daily.

An effective amount or a therapeutically effective amount or dose of an agent, e.g., a compound of the invention, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of compound or composition administered may be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack; or glass and rubber stoppers such as in vials. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

These and other embodiments of the present invention will readily occur to those of ordinary skill in the art in view of the disclosure herein and are specifically contemplated.

EXAMPLES

The invention is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Unless otherwise stated all temperatures are in degrees Celsius (° C.). Also, in these examples and elsewhere, abbreviations have the following meanings:

° C.=Degree Celcius
μL=Microliter
μM=Micromolar
Å=Angstrom
Ac=Acetate
Aq=Aqueous
aq.=Aqueous
atm=Atmosphere
BOC=tert-butoxycarbonyl
Boc-L-=N-alpha-t-Butyloxycarbonyl-N-gamma-(9-Dab (Fmoc)-fluorenylmethyloxycarbonyl)-L-2,4-diaminobutyric
OH acid
br=Broad
bu=Butyl
ca.=About
d=Doublet
DABCO=1,4-diazabicyclo[2.2.2]octane
DBU=1,8-Diazabicyclo[5.4.0]undec-7-ene
DCC=Dicyclohexylcarbodiimide
DCM=Dichloromethane
dd=Doublet of doublets
dil.=Dilute
DIPEA=N,N-Diisopropylethylamine
DMA=Dimethylacetamide
DMF=Dimethylformamide
DMSO=Dimethylsulfoxide
EDC=1-Ethyl-3-(3-dimethylaminopropyl)carbodiimide
EDTA=Ethylenediamine tetraacetic acid
ESI MS=Electrospray Ionization Mass Spectrometry
Et=Ethyl
EtOAc=Ethyl acetate
g=Gram
Gly=Glycine
h=Hour
HEPES=4-(2-Hydroxyethyl)-1-piperazineethanesulfonic acid
HOBT=1-Hydroxybenzotriazole
Hz=Hertz
J=Coupling constant L=Liter
LC=Liquid chromatography
LDA=Lithium diisopropylamide
M=Molar
m=Multiplet
m/e=Mass peak
m/z=Mass to charge ratio
M+1=Mass plus 1
M−1=Mass minus 1
mCPBA=meta-Chloroperoxybenzoic acid
Me=Methyl
mg=Milligram
MHz=Mega Hertz
min=Minute
mL=Milliliter
mM=Millimolar
mmol=Millimole
mol=Mole
MPLC=Medium Pressure Liquid Chromatography
MS=Mass spectroscopy
N=Normal
NBS=N-Bromosuccinimide
NIS=N-Iodosuccinimide
NMP=N-methylpyrrolidone
NMR=Nuclear magnetic resonance
$Pd_2(dpa)_3$=Tris(dibenzylideneacetone)dipalladium(0)
Ph=phenyl
ppm=Parts per million
q=Quartet
rt/r.t.=Room temperature
s=Singlet
sat'd=Saturated
t=Triplet
TFA=Trifluoroacetic acid
THF=Tetrahydrofuran
TLC=Thin Layer Chromatography
TMHD=2,2,6,6-tetramethyl-heptane-3,5-dione
ts=Tosyl
xantphos=4,5-Bis(diphenylphosphino)-9,9-dimethylxanthene
δ=Chemical shift (ppm)

The compound numbers refer to the example number describing the synthesis, i.e., Compound 1 is described in Example 1.

Example 1

3-[(4-Hydroxy-7-phenoxy-isoquinoline-3-carbonyl)-amino]propionic acid

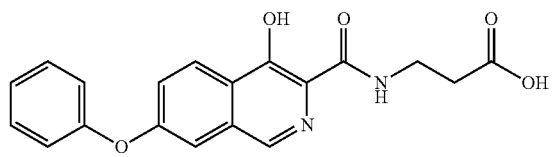 [SMILES: O=C(O)CCNC(=O)c1ncc2cc(Oc3ccccc3)ccc2c1O]

a) 5-phenoxy-3H-isobenzofuran-1-one

A mixture of 5-bromo-3H-isobenzofuran-1-one (75.9 g, 0.36 mol) (Sigma-Aldrich), phenol (67.1 g, 0.713 mol), CuCl (17.6 g, 0.178 mol), 2,2,6,6-tetramethyl-heptane-3,5-dione (TMHD, 7.33 mL) and cesium carbonate (232.3 g, 0.713 mol) in NMP (200 mL) was heated at 130° C. for 64 h. After cooled, reaction mixture was poured into ice/2M HCl mixture (1 L). The mixture was then refluxed for 1 h. After cooled, the solid was collected, rinsed with water and dried in vacuo to provide the title compound (72.22 g, 0.32 mol). $^1$H NMR in DMSO-d6, δ in ppm: 7.82 (dd, 1H, J=1.6 Hz, 7.6 Hz), 7.51-7.40 (m, 2H), 7.3-7.1 (m, 5H), 5.31 (s, 2H).

b) 2-Chloromethyl-4-phenoxy-benzoic acid methyl ester

To a solid mixture of 5-phenoxy-3H-isobenzofuran-1-one (65.54 g, 0.29 mol), boric acid (538 mg, 8.7 mmol) and triphenylphosphine oxide (2.42 g, 8.7 mmol) was added thionyl chloride (42.3 mL). The resulting mixture was refluxed overnight. After cooled, methanol (300 mL) was slowly added to the reaction mixture. It was then refluxed for 1 h and concentrated. Residue was partitioned between EtOAc and saturated $NaHCO_3$ solution. The organic layer was washed with brine, dried over $Na_2SO_4$, filtered and concentrated to provide the title compound (87.02 g, 0.31 mol) as an oil. It was used directly to the next reaction without further purification. $^1$H NMR in $CDCl_3$, δ in ppm: 7.91 (d, 1H, 8.6 Hz), 7.5-6.9 (m, 7H), 5.06 (s, 2H), 3.83 (s, 3H).

c) 2-{[Methoxycarbonylmethyl-(toluene-4-sulfonyl)-amino]-methyl}-4-phenoxy-benzoic acid methyl ester To a mixture of 2-chloromethyl-4-phenoxy-benzoic acid methyl ester (17.8 g, 64.3 mmol) in DMF (100 mL) was added (toluene-4-sulfonylamino)-acetic acid methyl ester (15.65 g, 64.3 mmol), $K_2CO_3$ (17.78 g, 128.6 mmol) and then NaI (964 mg, 6.43 mmol). The resulting mixture was stirred at 50° C. overnight. After cooled, reaction mixture was partitioned between EtOAc and water. The organic layer was washed with water (2×) and brine. It was dried over $Na_2SO_4$, filtered and concentrated. Crude residue was purified by silica gel chromatography to provide the title compound (14.34 g, 29.8 mmol). $^1$H NMR in $CDCl_3$, δ in ppm: 7.86 (d, 1H, 8.8 Hz), 7.70 (d, 2H, J=8.4 Hz), 7.38-6.8 (m, 9H), 4.88 (s, 2H), 3.99 (s, 2H), 3.82 (s, 3H), 3.53 (s, 3H), 2.41 (s, 3H).

d) 4-hydroxy-7-phenoxy-isoquinoline-3-carboxylic acid methyl ester

To a mixture of 2-{[Methoxycarbonylmethyl-(toluene-4-sulfonyl)-amino]-methyl}-4-phenoxy-benzoic acid methyl ester (14.0 g, 28.1 mmol) in DMSO (56 mL) was slowly added 30% NaOMe in MeOH (15.3 mL, 84.3 mmol). The resultant mixture was stirred at room temperature for 30 min and poured into 200 mL of ice and water. It was slowly acidified by conc. HCl aq. solution (10 mL) and then extracted with EtOAc. Organic layer was washed with 3% $NaHCO_3$ solution, water and brine, and was dried over $Na_2SO_4$, filtered and concentrated. Crude produce was purified by silica gel chromatography to provide the title compound 6.05 g (20.5 mmol) in 72.9% yield. $^1$H NMR in $CDCl_3$, δ in ppm: 11.7 (s, 1H), 8.59 (s, 1H), 8.36 (d, 1H, J=9.2 Hz), 7.55-7.1 (m, 7H), 4.07 (s, 3H).

e) 3-[(4-Hydroxy-7-phenoxy-isoquinoline-3-carbonyl)-amino]propionic acid

A mixture of 4-hydroxy-7-phenoxy-isoquinoline-3-carboxylic acid methyl ester (185 mg, 0.55 mmol), beta-alanine (489 mg, 5.5 mmol) in 0.5 M NaOMe in MeOH solution (8.8 mL, 4.4 mmol) was refluxed overnight. After cooled, the reaction mixture was concentrated and residue was dissolved in water (80 mL). It was acidified by 1 N HCl solution to pH ca. 3-4. Resulting gummy solid was collected by filtration, rinsed with water and then dissolved in EtOAc. The organic solution was dried over MgSO₄, filtered and concentrated to provide the title compound (173 mg, 0.49 mmol) as an off-white solid in 89% yield. LC-MS ESI−: 351.14 (M−1)⁻.

Example 2

3-[(4-Hydroxy-7-phenoxy-isoquinoline-3-carbonyl)-amino]-2,2-dimethyl-propionic acid

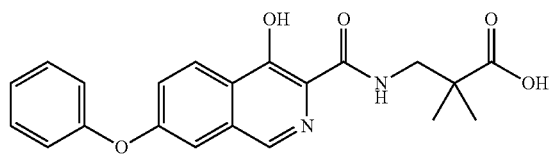 [SMILES: CC(C)(CNC(=O)c1ncc2cc(Oc3ccccc3)ccc2c1O)C(=O)O]

A mixture of 4-hydroxy-7-phenoxy-isoquinoline-3-carboxylic acid methyl ester (68 mg, 0.23 mmol) and 3-amino-2,2-dimethyl-propionic acid (81 mg, 0.69 mmol) (ChemBridge) in 0.5 N NaOMe in MeOH solution (0.92 mL, 0.46 mmol) was microwaved at 120° C. for 1 h. Reaction mixture was diluted with water (50 mL) and acidified by 1 N HCl solution to pH=3-4. Precipitate was collected and rinsed with water and dried in vacuo to provide the title compound (71 mg, 0.19 mmol) as an off-white solid in 81% yield. LC-MS ESI−: 379.04 (M−1)⁻.

Example 3

2-(S)-Hydroxy-3-[(4-hydroxy-7-phenoxy-isoquinoline-3-carbonyl)-amino]propionic acid

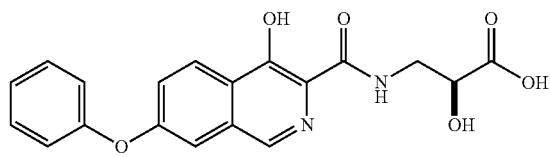 [SMILES: O=C(NC[C@H](O)C(=O)O)c1ncc2cc(Oc3ccccc3)ccc2c1O]

A mixture of 4-hydroxy-7-phenoxy-isoquinoline-3-carboxylic acid methyl ester (90 mg, 0.31 mmol) and 2-(S)-hydroxy-3-amino-propionic acid (Sigma-Aldrich) (96 mg, 0.92 mmol) in 0.5 N NaOMe in MeOH solution (1.22 mL, 0.61 mmol) was microwaved at 120° C. for 1 h and concentrated. Residue was dissolved in water (70 mL) and acidified by 1 N HCl solution to pH=3-4. It was extracted with EtOAc, Organic layer was washed with brine, dried over MgSO₄, filtered and concentrated to give the title compound (105 mg, 0.29 mmol) in 92% yield. LC-MS ESI−: 366.99 (M−1)⁻.

Example 4

4-[(4-Hydroxy-7-phenoxy-isoquinoline-3-carbonyl)-amino]-butyric acid

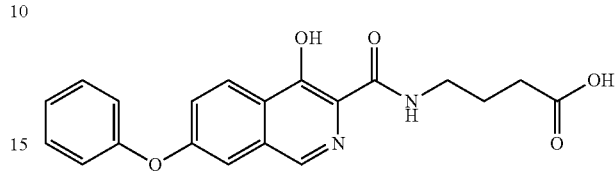

A mixture of 4-hydroxy-7-phenoxy-isoquinoline-3-carboxylic acid methyl ester (100 mg, 0.34 mmol) and 4-aminobutyric acid (525 mg, 5.1 mmol) in 0.5 N NaOMe in MeOH solution (6.8 mL, 3.4 mmol) was heated to reflux overnight. Reaction mixture was diluted with water (100 mL) and acidified by 1 N HCl solution to pH=3-4. Precipitate was collected and rinsed with water. It was dried in vacuo to provide the title compound (117 mg, 0.32 mmol) in 94% yield. LC-MS ESI−: 365.05 (M−1)⁻.

Example 5

5-[(4-Hydroxy-7-phenoxy-isoquinoline-3-carbonyl)-amino]-pentanoic acid

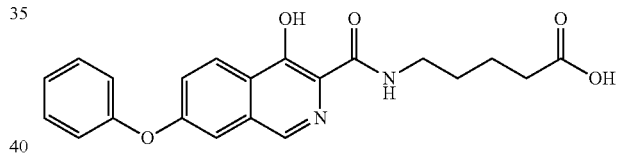

A mixture of 4-hydroxy-7-phenoxy-isoquinoline-3-carboxylic acid methyl ester (100 mg, 0.34 mmol) and 5-aminovaleric acid (597 mg, 5.1 mmol) in 0.5 N NaOMe in MeOH solution (6.8 mL, 3.4 mmol) was heated to reflux overnight. Reaction mixture was diluted with water (100 mL) and acidified by 1 N HCl solution to pH=3-4. Precipitate was collected and rinsed with water. It was dried in vacuo to provide the title compound (102 mg, 0.27 mmol) in 80% yield. LC-MS ESI−: 379.07 (M−1)⁻.

Example 6

3-[(4-Hydroxy-7-phenoxy-isoquinoline-3-carbonyl)-amino]-3-methyl-butyric acid

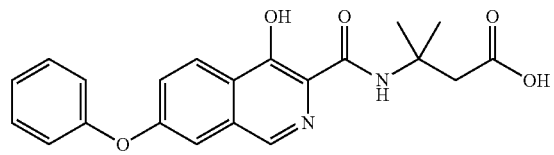 [SMILES: CC(C)(CC(=O)O)NC(=O)c1ncc2cc(Oc3ccccc3)ccc2c1O]

To a mixture of 4-hydroxy-7-phenoxy-isoquinoline-3-carboxylic acid methyl ester (100 mg, 0.34 mmol) and 3-amino- 3-methyl-butyric acid (Oakwood) (199 mg, 1.7 mmol) in DMF (3 mL) was added sodium methoxide solid (73 mg, 1.36 mmoL). The mixture was gently refluxed for 2 h. After cooled, it was diluted with water (100 mL) and acidified by 1 N HCl aqueous solution to pH=3-4. Precipitate was collected and dried in vacuo. The crude product was purified by silica gel chromatography, eluting with 20%-100% EtOAc-hexanes, to provide the title compound (42 mg, 0.11 mmol) in 33% yield. LC-MS ESI–: 379.04 (M–1)–.

Example 7

2-(S)-Hydroxy-4-[(4-hydroxy-7-phenoxy-isoquinoline-3-carbonyl)-amino]-butyric acid

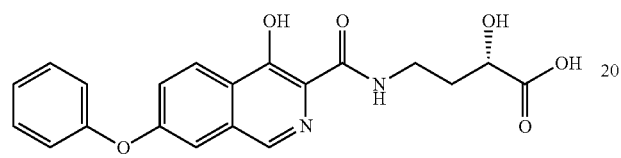

A mixture of 4-hydroxy-7-phenoxy-isoquinoline-3-carboxylic acid methyl ester (100 mg, 0.34 mmol) and (S)-(–)-4-amino-2-hydroxybutyric acid (122 mg, 1.02 mmol) in 0.5 N NaOMe in MeOH solution (1.4 mL, 0.7 mmol) was microwaved at 120° C. for 1 h. Reaction mixture was diluted with water (100 mL), acidified by 1 N HCl aqueous solution to pH=3-4 and extracted with EtOAc. Organic layer was washed with brine, dried over $Mg_2SO_4$, filtered and concentrated to provide the title compound (120 mg, 0.31 mmol) in 92.4% yield. LC-MS ESI–: 381.05 (M–1)–.

Example 8

4-[(4-Hydroxy-7-phenoxy-isoquinoline-3-carbonyl)-amino]-2,2-dimethyl-butyric acid

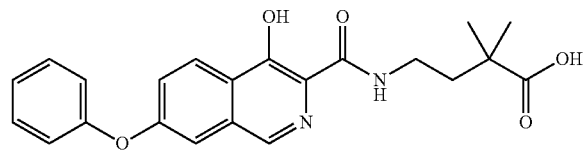 [SMILES: CC(C)(CCNC(=O)c1ncc2cc(Oc3ccccc3)ccc2c1O)C(=O)O]

a) 2,2-Dimethyl-4-(trityl-amino)-butyric acid methyl ester

To a cold mixture of 4-(trityl-amino)-butyric acid methyl ester (2.0 g, 5.57 mmol) (prepared following the procedures described in J. Org. Chem. 1969, 34(3), 576-580) in THF (11 mL) at –78° C. was slowly added LDA (1.8 M in heptane/THF/ethylbenzene) (6.8 mL, 12.25 mL). The mixture was stirred at –78° C. for 30 min, and then added iodomethane (3.16 g, 22.28 mmol). The resultant mixture was stirred at –78° C. for 30 min, and then allowed to be warmed up to room temperature. It was quenched with saturated $NH_4Cl$ aqueous solution (60 mL) and was extracted with EtOAc (150 mL). Organic layer was washed with saturated $NaHCO_3$ solution, brine and dried over $MgSO_4$. It was filtered and concentrated. To ensure the completion of the reaction of di-methylation, the above procedure was repeated again on the isolated residue. The resultant crude product was purified by silica gel chromatography, eluting with 5-50% EtOAc in hexanes to provide the title compound 0.91 g (2.35 mmol) in 42% yield as a colorless oil. $^1$H NMR in $CDCl_3$, δ ppm: 7.44-7.15 (m, 15H), 3.56 (s, 3H), 2.09 (m, 2H), 1.73 (m, 2H), 1.09 (s, 6H).

b) 4-Amino-2,2-dimethyl-butyric acid methyl ester, trifluoroacetic acid salt

A mixture of 2,2-Dimethyl-4-(trityl-amino)-butyric acid methyl ester (0.9 g, 2.32 mmol) in $TFA/CH_2Cl_2$ (½) (9 mL) was stirred at room temperature for 2 h. Reaction mixture was concentrated and was treated with water (120 mL). Insoluble solid was filtered off and the aqueous filtrate was concentrated to provide the title compound 534 mg (2.06 mmol) in 88.8% yield. $^1$H NMR in DMSO-d6, δ ppm: 7.71 (br s, 3H), 3.61 (s, 3H), 2.75 (m, 2H), 1.75 (m, 2H), 1.14 (s, 6H).

c) 4-[(4-Hydroxy-7-phenoxy-isoquinoline-3-carbonyl)-amino]-2,2-dimethyl-butyric acid methyl ester A mixture of 4-hydroxy-7-phenoxy-isoquinoline-3-carboxylic acid methyl ester (80 mg, 0.27 mmol) and 4-amino-2,2-dimethyl-butyric acid methyl ester, trifluoroacetic acid salt (210 mg, 0.81 mmol) in 0.5 M NaOMe/MeOH solution (1.62 mL, 0.81 mmol) was microwaved at 130° C. for 3 h. The reaction mixture was diluted with water (50 mL), acidified by 1 N HCl to pH=3-4 and then extracted with EtOAc. Organic layer was washed with water, brine, dried over $MgSO_4$, filtered and concentrated. Residue was purified by silica gel chromatography, eluting with 5-50% EtOAc/hexanes, to provide the title compound 26 mg (0.063 mmol) in 23.6% yield. $^1$H NMR in $CDCl_3$, δ ppm: 13.23 (s, 1H), 8.40 (s, 1H), 8.32 (d, J=8.8 Hz, 1H), 7.97 (br t, 1H), 7.42 (m, 4H), 7.12 (m, 3H), 3.64 (s, 3H), 3.52 (m, 2H), 1.95 (dd, J=9.1, 5.9 Hz, 2H), 1.27 (s, 6H).

d) 4-[(4-Hydroxy-7-phenoxy-isoquinoline-3-carbonyl)-amino]-2,2-dimethyl-butyric acid A mixture of 4-[(4-Hydroxy-7-phenoxy-isoquinoline-3-carbonyl)-amino]-2,2-dimethyl-butyric acid methyl ester (25 mg, 0.064 mmol) and (1/1) 1 N NaOH aqueous solution/MeOH (2 mL) was stirred at room temperature for 2 days. It was diluted with water (50 mL), acidified by 1 N HCl to pH=3-4. Precipitate was collected and dried in vacuo to provide the title product 6.5 mg (0.016 mmol) in 26% yield. LC-MS ESI–: 393.10 (M–1)–.

Example 9

2-(S)-Amino-3-[(4-hydroxy-7-phenoxy-isoquinoline-3-carbonyl)-amino]-propionic acid

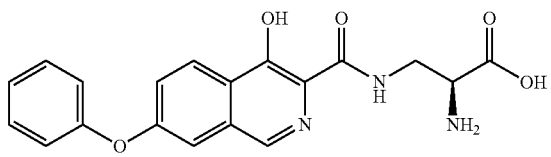

a) 2-(S)-tert-Butoxycarbonylamino-3-[(4-hydroxy-7-phenoxy-isoquinoline-3-carbonyl)-amino]-propionic acid A mixture of 4-hydroxy-7-phenoxy-isoquinoline-3-carboxylic acid methyl ester (100 mg, 0.34 mmol) and 3-(S)- amino-2-tert-butoxycarbonylamino-propionic acid (346 mg, 1.69 mmol) (Bachem Americas, Torrance Calif.) in 0.5 M NaOMe/MeOH solution (2.7 mL, 1.36 mmol) was refluxed for 30 h. It was diluted with water (75 mL), acidified by 1 N HCl to pH=5. Precipitate was collected, rinsed with water and dried in vacuo to provide the title compound 140 mg (0.30 mmol) in 88% yield. LC-MS ESI−: 466.10 (M−1)−.

b) 2-(S)-Amino-3-[(4-hydroxy-7-phenoxy-isoquinoline-3-carbonyl)-amino]propionic acid TFA (0.4 mL) was added to a mixture of 2-(S)-tert-Butoxycarbonylamino-3-[(4-hydroxy-7-phenoxy-isoquinoline-3-carbonyl)-amino]-propionic acid (99 mg, 0.21 mmol) in CH$_2$Cl$_2$ (2 mL). The resultant mixture was stirred at room temperature for 3 h and concentrated. Residue was taken up with water (100 mL) and the pH was adjusted by 1 N NaOH aq. Solution to 9-10, then acidified by 1 N HCl to pH=5. Precipitate was collected, rinsed with water and dried in vacuo to provide the title compound 58 mg (0.158 mmol) in 75% yield. LC-MS ESI−: 366.10 (M−1)−.

Example 10

3-[(1-Cyano-4-hydroxy-7-phenoxy-isoquinoline-3-carbonyl)-amino]-propionic acid

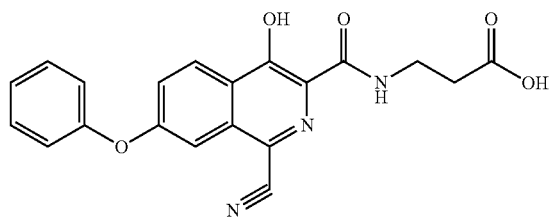 [SMILES: N#Cc1nc(C(=O)NCCC(=O)O)c(O)c2ccc(Oc3ccccc3)cc12]

a) 1-Bromo-4-hydroxy-7-phenoxy-isoquinoline-3-carboxylic acid methyl ester

A mixture of 4-hydroxy-7-phenoxy-isoquinoline-3-carboxylic acid methyl ester (6.0 g, 20.32 mmol), N-bromosuccinimide (3.80 g, 21.33 mmol) and benzoyl peroxide (246 mg, 1.01 mmol) in CCl$_4$ was refluxed for 1 h. Solid was filtered off through a plug of silica gel. Filtrate was concentrated and purified by silica chromatography, eluting with EtOAc. All fractions contain the desired product was combined and concentrated. Residue was suspended in 150 mL of (3/1) MeOH/EtOAc and was refluxed for 1 h. After cooled, solid was collected, rinsed with MeOH and dried on vacuo to provide the title compound 4.42 g (11.8 mmol) in 58% yield as a white solid. $^1$H NMR in CDCl$_3$, δ ppm: 11.7 (s, 1H), 8.36 (d, 1H, J=9.2 Hz), 7.63 (d, 1H, J=2.4 Hz), 7.55-7.10 (m, 6H), 4.06 (s, 3H).

b) 1-Cyano-4-hydroxy-7-phenoxy-isoquinoline-3-carboxylic acid methyl ester

To a mixture of 1-bromo-4-hydroxy-7-phenoxy-isoquinoline-3-carboxylic acid methyl ester (2.0 g, 5.34 mmol) in 16.2 mL of N-methylpyrrolidone was heated in a 130° C. oil bath for 2 h. After cooled, the reaction mixture was poured into a mixture of 100 mL of water (containing 5% conc. NH4OH) and EtOAc (100 mL). It was vigorously stirred at room temperature for 30 min, then was acidified by conc. HCl solution until two phases became clear. Organic layer was washed with water, brine and dried over MgSO4. It was filtered and concentrated. Crude product was triturated with MeOH and white solid was collected to provide the title compound 1.20 g (3.75 mmol) in 70% yield. LC-MS ESI+: 321.31 (M+1)+.

c) 3-[(1-Cyano-4-hydroxy-7 phenoxy-isoquinoline-3-carbonyl)-amino]-propionic acid A mixture of 1-cyano-4-hydroxy-7-phenoxy-isoquinoline-3-carboxylic acid methyl ester (88 mg, 0.27 mmol) and beta-alanine (122 mg, 1.38 mmol) in 2.2 ml of 0.5 M NaOMe/MeOH solution was microwaved at 120° C. for 10 min. Reaction mixture was concentrated. The residue was dissolved in water (80 ml) and extracted with EtOAc, which was discarded. The aqueous layer was acidified by 1 N HCl to pH=3-4 and extracted with EtOAc. Organic layer was dried over MgSO4, filtered and concentrated. The crude product was triturated with hot MeOH and then CH$_2$Cl$_2$. Solid was collected and dried to provide the title compound 24 mg (0.064 mmol) in 24% yield.

Example 11

3-[(1-Cyano-4-hydroxy-7-phenoxy-isoquinoline-3-carbonyl)-amino]butyric acid

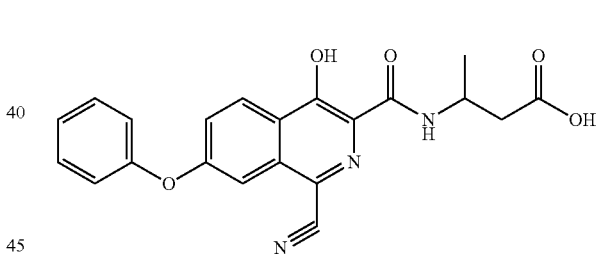

A mixture of 1-cyano-4-hydroxy-7-phenoxy-isoquinoline-3-carboxylic acid methyl ester (110 mg, 0.34 mmol) and 3-amino-butyric acid (354 mg, 3.4 mmol) (Sigma-Aldrich Corp., St. Louis Mo.) in 0.5 M NaOMe/MeOH solution (5.4 mL<2.72 mmol) was refluxed overnight and then microwaved at 120° C. for 2 h. Reaction mixture was concentrated and residue was dissolved in water (60 mL). It was acidified by 1 N HCl to pH=3-4. Precipitate was collected, rinsed with water and dried. The crude product was purified by silica gel chromatography, eluting with 5-100% EtOAc (with 0.075% acetic acid)/hexane (with 0.1% acetic acid). White solid was crystallized from fractions containing the desired produce. Solid was collected and rinsed with EtOAc and dried in vacuo

Example 12

1-{[(1-Cyano-4-hydroxy-7-phenoxy-isoquinoline-3-carbonyl)-amino]-methyl}-cyclopropanecarboxylic acid

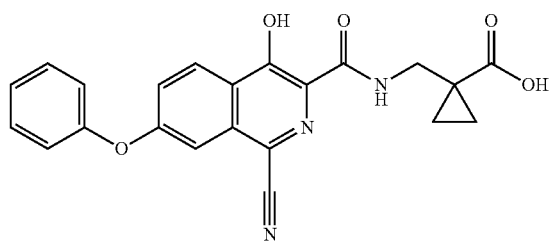 [SMILES: N#Cc1nc(C(=O)NCC2(C(=O)O)CC2)c(O)c2ccc(Oc3ccccc3)cc12]

After a mixture of 1-cyano-4-hydroxy-7-phenoxy-isoquinoline-3-carboxylic acid methyl ester (101 mg, 0.318 mmol), 1-aminomethyl-cyclopropanecarboxylic acid (110 mg, 0.955 mmol, prepared according to literature: Ohno, Mitsuru et al *Synlett* 1991, 919-920), and NaOMe in MeOH (1.6 mL, 0.5 M solution) was microwaved at 120° C. for 1 h, the reaction mixture was cooled, diluted with water and acidified with 2 M HCl aqueous solution, the resulted solids were collected via filtration, water-washed and air-dried to give solids, which were further column purified to give the desired product (33 mg). LC MS ESI+: 404 (M+1)$^+$.

Example 13

1-{[(4-Hydroxy-7-phenoxy-isoquinoline-3-carbonyl)-amino]-methyl}-cyclobutanecarboxylic acid

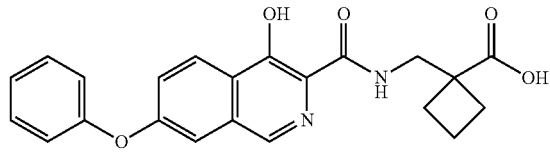 [SMILES: O=C(NCC1(C(=O)O)CCC1)c1ncc2cc(Oc3ccccc3)ccc2c1O]

a) 1-{[(4-Hydroxy-7-phenoxy-isoquinoline-3-carbonyl)-amino]-methyl}-cyclobutanecarboxylic acid methyl ester A mixture of 4-hydroxy-7-phenoxy-isoquinoline-3-carboxylic acid methyl ester (110 mg, 0.37 mmol) and 1-aminomethyl-cyclobutanecarboxylic acid methyl ester (159 mg, 1.11 mmol, available from Ukrorgsyntez Ltd) in MeOH (2 mL) was microwaved at 150° C. for 500 min; cooled, concentrated, the residue was partitioned between EtOAc and diluted HCl solution, EtOAc phase was washed with water and diluted NaCl solution, dried over anhydrous sodium sulfate, filtered, concentrated and column purified to give product (76 mg). LC MS ESI+: 407 (M+1)$^+$.

b) 1-{[(4-Hydroxy-7-phenoxy-isoquinoline-3-carbonyl)-amino]-methyl}-cyclobutanecarboxylic acid The product from previous step (76 mg) was dissolved in a mixture of THF/MeOH/water (9 mL, 1:1:1 by volume), then stirred with a solution of LiOH (0.75 mL, 1 M solution) at rt overnight. The mixture was concentrated, residue was re-dissolved in water, acidified with 2 M HCl, solids were collected via filtration and water washed, air dried to give the desired product (67 mg). LC MS ESI+: 393 (M+1)$^+$.

Example 14

1-{[(1-Cyano-4-hydroxy-7-phenoxy-isoquinoline-3-carbonyl)-amino]-methyl}-cyclobutanecarboxylic acid

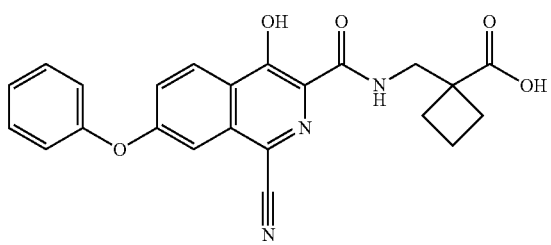

a) 1-{[(1-Cyano-4-hydroxy-7-phenoxy-isoquinoline-3-carbonyl)-amino]-methyl}-cyclobutanecarboxylic acid methyl ester After a mixture of 1-cyano-4-hydroxy-7-phenoxy-isoquinoline-3-carboxylic acid methyl ester (129 mg, 0.401 mmol), 1-aminomethyl-cyclobutanecarboxylic acid methyl ester (115 mg, 0.803 mmol in MeOH was microwaved at 150° C. for 500 min; cooled, concentrated, the residue was partitioned between EtOAc and diluted HCl solution, EtOAc phase was washed with water and diluted NaCl solution, dried over anhydrous sodium sulfate, filtered, concentrated and column purified to give product (172 mg). LC MS ESI+: 432 (M+1)$^+$.

b) 1-{[(1-Cyano-4-hydroxy-7-phenoxy-isoquinoline-3-carbonyl)-amino]-methyl}-cyclobutanecarboxylic acid The product from previous step (172 mg) was dissolved in a mixture of THF/MeOH/water (9 mL, 1:1:1 by volume), then stirred with a solution of LiOH (1.6 mL, 1 M solution) at rt overnight. The mixture was concentrated, residue was re-dissolved in water, acidified with 2 M HCl, solids were collected via filtration and water washed, air dried to give the desired product (130 mg). LC MS ESI+: 418 (M+1)+.

Example 15

4-{[(4-Hydroxy-7-phenoxy-isoquinoline-3-carbonyl)-amino]-methyl}-tetrahydro-pyran-4-carboxylic acid

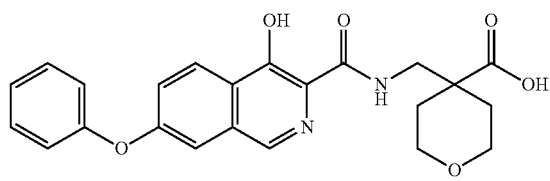 [SMILES: O=C(NCC1(C(=O)O)CCOCC1)c1ncc2cc(Oc3ccccc3)ccc2c1O]

a) 4-{[(4-Hydroxy-7-phenoxy-isoquinoline-3-carbonyl)-amino]-methyl}-tetrahydro-pyran-4-carboxylic acid methyl ester After a mixture of 4-hydroxy-7-phenoxy-isoquinoline-3-carboxylic acid methyl ester (121 mg), 4-aminomethyl-tetrahydro-pyran-4-carboxylic acid methyl ester (177 mg; commercially available) in MeOH (3 mL) was microwaved at 150° C. for 650 min; cooled, concentrated, the residue was partitioned between EtOAc and diluted HCl solution, EtOAc phase was washed with water and diluted NaCl solution, dried over anhydrous sodium sulfate, filtered, concentrated and column purified to give product (48 mg). LC MS ESI+: 437 (M+1)+.

b) 4-{[(4-Hydroxy-7-phenoxy-isoquinoline-3-carbonyl)-amino]-methyl}-tetrahydro-pyran-4-carboxylic acid The product from previous step (48 mg) was dissolved in a mixture of THF/MeOH/water (9 mL, 1:1:1 by volume), then stirred with a solution of LiOH (0.44 mL, 1 M solution) at rt overnight. The mixture was concentrated, residue was re-dissolved in water, acidified with 2 M HCl, solids were collected via filtration and water-washed, air-dried to give the desired product (13 mg). LC MS ESI+: 423 (M+1)+.

Example 16

4-{[(1-Cyano-4-hydroxy-7-phenoxy-isoquinoline-3-carbonyl)-amino]-methyl}-tetrahydro-pyran-4-carboxylic acid

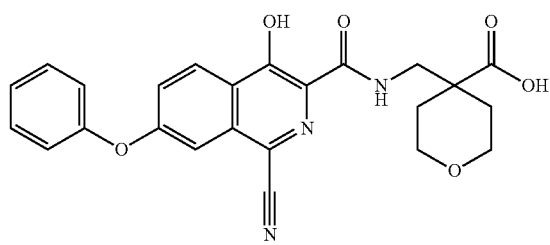 [SMILES: N#Cc1nc(C(=O)NCC2(C(=O)O)CCOCC2)c(O)c2ccc(Oc3ccccc3)cc12]

a) 4-{[(1-Cyano-4-hydroxy-7-phenoxy-isoquinoline-3-carbonyl)-amino]-methyl}-tetrahydro-pyran-4-carboxylic acid methyl ester After a mixture of 1-cyano-4-hydroxy-7-phenoxy-isoquinoline-3-carboxylic acid methyl ester (151 mg), 4-aminomethyl-tetrahydro-pyran-4-carboxylic acid methyl ester (205 mg; commercially available) in MeOH (2 mL) was microwaved at 150° C. for 500 min; cooled, concentrated, the residue was partitioned between EtOAc and diluted HCl solution, EtOAc phase was washed with water and diluted NaCl solution, dried over anhydrous sodium sulfate, filtered, concentrated and column purified to give product (154 mg). LC MS ESI+: 462 (M+1)+.

b) 4-{[(1-Cyano-4-hydroxy-7-phenoxy-isoquinoline-3-carbonyl)-amino]-methyl}-tetrahydro-pyran-4-carboxylic acid The product from previous step (154 mg) was dissolved in a mixture of THF/MeOH/water (9 mL, 1:1:1 by volume), then stirred with a solution of LiOH (1 mL, 1 M solution) at rt overnight. The mixture was concentrated, residue was re-dissolved in water, acidified with 2 M HCl, solids were collected via filtration and water washed, air dried to give the desired product (119 mg). LC MS ESI+: 448 (M+1)+.

Example 17

2-{[(1-Cyano-4-hydroxy-7-phenoxy-isoquinoline-3-carbonyl)-amino]-methyl}-pentanoic acid

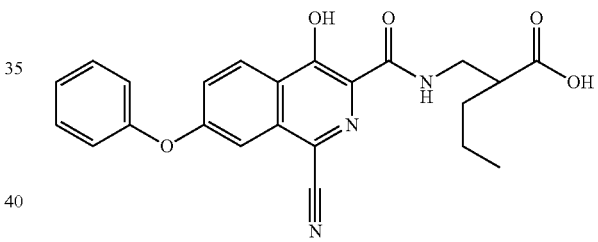

a) 2-Cyano-2-propyl-pentanoic acid tert-butyl ester and 2-Cyano-pentanoic acid tert-butyl ester DBU was added slowly to a solution of cyano-acetic acid tert-butyl ester (6.03 g) in DMF (100 mL) at rt, followed by addition of 1-iodopropane (9.58 mL); the reaction mixture was stirred in an oil bath (bath temperature=80° C.) overnight subsequently. The reaction was cooled, diluted with EtOAc, then washed with cold water, dil. NaCl solution; EtOAc phase was dried over anhydrous sodium sulfate, filtered, concentrated, the residue was column purified to give 2-cyano-2-propyl-pentanoic acid tert-butyl ester (6.87 g) and 2-cyano-pentanoic acid tert-butyl ester (420 mg). 2-Cyano-2-propyl-pentanoic acid tert-butyl ester (¹H NMR in CDCl₃, δ in ppm) 1.502 (s, 9H), 1.9-1.2 (m, 8H), 0.96 (t, 6H, J=7.0 Hz). 2-Cyano-pentanoic acid tert-butyl ester (¹H NMR in CDCl₃, δ in ppm) 3.39 (t, 1H, J=7.0 Hz), 1.95-1.83 (m, 2H), 1.6-1.55 (m, 2H), 1.51 (s, 9H), 0.98 (t, 3H, J=7.2 Hz).

b) 2-Aminomethyl-pentanoic acid tert-butyl ester HCl salt

A mixture of 2-cyano-pentanoic acid tert-butyl ester (420 mg) and Raney Ni (0.5 mL in water) in MeOH (10 mL) was stirred at rt under H$_2$ atmosphere (balloon) overnight. Then the reaction mixture was filtered over Celite pad, filtrate was concentrated; residue was redissolved in ether then 2 mL 2 M HCl in dioxane was added; the mixture was then concentrated, triturated with ether, the white solids were collected via filtration and washed with ether and air dried to give the title compound (222 mg). 2-Aminomethyl-pentanoic acid tert-butyl ester HCl salt ($^1$H NMR in DMSO-d$_6$, δ in ppm) 8.0 (br, 3H), 3.0-2.6 (m, 3H), 1.42 (s, 9H), 1.6-1.2 (m, 4H), 0.88 (t, 3H, J=7.0 Hz).

c) 2-{[(1-Cyano-4-hydroxy-7-phenoxy-isoquinoline-3-carbonyl)-amino]-methyl}-pentanoic acid tert-butyl ester A mixture of 1-cyano-4-hydroxy-7-phenoxy-isoquinoline-3-carboxylic acid methyl ester (138 mg), 2-aminomethyl-pentanoic acid tert-butyl ester HCl salt (96 mg) and NaOMe in MeOH (0.85 mL, 0.5 M solution) in MeOH (1 mL) was microwaved at 150° C. for 2 h. The mixture was cooled, concentrated with HOAc (0.1 mL), the residue was directly column purified to give the desired product (44 mg). LC MS ESI+: 476 (M+1)$^+$.

d) 2-{[(1-Cyano-4-hydroxy-7-phenoxy-isoquinoline-3-carbonyl)-amino]-methyl}-pentanoic acid A mixture of 2-{[(1-cyano-4-hydroxy-7-phenoxy-isoquinoline-3-carbonyl)-amino]-methyl}-pentanoic acid tert-butyl ester (44 mg), TFA (2 mL) and DCM (2 mL) was stirred at rt overnight; then concentrated, the residue was dissolved in water and added 2 M HCl solution, solids were collected via filtration, washed with water and air dried to give the desired product (27 mg). LC MS ESI+: 420 (M+1)$^+$.

Example 18

2-{[(1-Cyano-4-hydroxy-7-phenoxy-isoquinoline-3-carbonyl)-amino]-methyl}-2-propyl-pentanoic acid

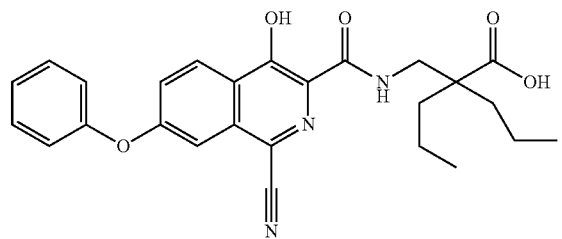 [SMILES: CCCC(CCC)(CNC(=O)c1nc(C#N)c2cc(Oc3ccccc3)ccc2c1O)C(=O)O]

a) 2-Aminomethyl-2-propyl-pentanoic acid tert-butyl ester

A mixture of 2-cyano-2-propyl-pentanoic acid tert-butyl ester (6.87 g) and Raney Ni (4 mL in water) in MeOH (200 mL) was stirred at rt under H$_2$ atmosphere (balloon) overnight. Then the reaction mixture was filtered over Celite pad, filtrate was concentrated to give the desired product (4.92 g). $^1$H NMR in CDCl$_3$, δ in ppm: 2.76 (s, 2H), 1.44 (s, 9H), 1.5-1.1 (m, 8H), 0.91 (t, 6H, J=7.0 Hz).

b) 2-{[(1-Cyano-4-hydroxy-7-phenoxy-isoquinoline-3-carbonyl)-amino]-methyl}-2-propyl-pentanoic acid tert-butyl ester A mixture of 1-cyano-4-hydroxy-7-phenoxy-isoquinoline-3-carboxylic acid methyl ester (135 mg) and 2-aminomethyl-2-propyl-pentanoic acid tert-butyl ester (193 mg) in MeOH (2 mL) was microwaved at 120° C. for 2 h. The mixture was cooled, concentrated with HOAc (0.02 mL), the residue was directly column purified to give the desired product (180 mg). LC MS ESI+: 518 (M+1)$^+$.

c) 2-{[(1-Cyano-4-hydroxy-7-phenoxy-isoquinoline-3-carbonyl)-amino]-methyl}-2-propyl-pentanoic acid A mixture of 2-{[(1-cyano-4-hydroxy-7-phenoxy-isoquinoline-3-carbonyl)-amino]-methyl}-2-propyl-pentanoic acid tert-butyl ester (180 mg), TFA (5 mL) and DCM (5 mL) was stirred at rt overnight; then concentrated, the residue was dissolved in water and added 2 M HCl solution, solids were collected via filtration, washed with water and air dried to give the desired product (150 mg). LC MS ESI+: 462 (M+1)$^+$.

Example 19

1-{[(1-Cyano-4-hydroxy-7-phenoxy-isoquinoline-3-carbonyl)-amino]-methyl}-cyclopentanecarboxylic acid

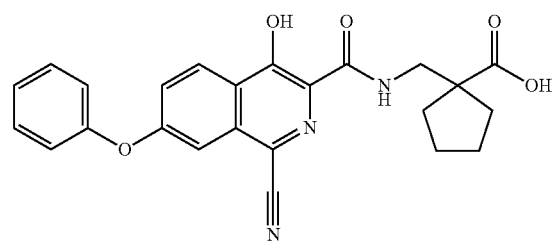 [SMILES: N#Cc1nc(C(=O)NCC2(C(=O)O)CCCC2)c(O)c2ccc(Oc3ccccc3)cc12]

a) 1-{[(1-Cyano-4-hydroxy-7-phenoxy-isoquinoline-3-carbonyl)-amino]-methyl}-cyclopentanecarboxylic acid tert-butyl ester A mixture of 1-cyano-4-hydroxy-7-phenoxy-isoquinoline-3-carboxylic acid methyl ester (200 mg) and 1-aminomethyl-cyclopentanecarboxylic acid tert-butyl ester (250 mg, commercially available from J & W PharmLab LLC, Levittown Pa.) in MeOH (3 mL) was heated at 100° C. in an oil bath for 24 h. The mixture was cooled, concentrated and the residue was column purified to give the desired product (164 mg). LC MS ESI+: 488 (M+1)$^+$.

b) 1-{[(1-Cyano-4-hydroxy-7-phenoxy-isoquinoline-3-carbonyl)-amino]-methyl}-cyclopentanecarboxylic acid A mixture of 1-{[(1-Cyano-4-hydroxy-7-phenoxy-isoquinoline-3-carbonyl)-amino]-methyl}-cyclopentanecarboxylic acid tert-butyl ester (164 mg), TFA (5 mL) and DCM (5 mL) was stirred at rt overnight; then concentrated, the residue was dissolved in water and added 2 M HCl solution, solids were collected via filtration, washed with water and air dried to give the desired product (143 mg). LC MS ESI+: 432 (M+1)+.

Example 20

3{-[1-Cyano-4-hydroxy-7-(4-methoxy-phenoxy)-isoquinoline-3-carbonyl]-amino}-2,2-dimethyl-propionic acid

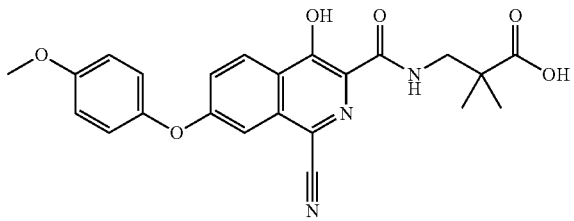 [SMILES: COc1ccc(Oc2ccc3c(O)c(C(=O)NCC(C)(C)C(=O)O)nc(C#N)c3c2)cc1]

a) Cyano-dimethyl-acetic acid tert-butyl ester

DBU (22.2 mL) was added slowly to a solution of cyano-acetic acid tert-butyl ester (9.1 g) in DMF (150 mL) at rt, followed by addition of iodomethane (10.03 mL); then the reaction mixture was stirred in an oil bath (bath temperature=100° C.) overnight. The reaction was cooled, diluted with EtOAc, then washed with cold water, dil. NaCl solution; EtOAc phase was dried over anhydrous sodium sulfate, filtered, concentrated; the residue was column purified to give title compound (5.328 g). $^1$H NMR in CDCl$_3$, δ in ppm: 1.56 (s, 6H), 1.50 (s, 9H).

b) 3-Amino-2,2-dimethyl-propionic acid tert-butyl ester

A mixture of cyano-dimethyl-acetic acid tert-butyl ester (5.3 g) and Raney Ni (2 mL in water) in MeOH (400 mL) was stirred at rt under H$_2$ atmosphere (balloon) overnight. Then the reaction mixture was filtered over Celite pad, filtrate was concentrated to give the desired product (5 g). $^1$H NMR in CDCl$_3$, δ in ppm: 2.8 (br, 2H), 1.45 (s, 9H), 1.17 (s, 6H).

c) 3-{[1-Cyano-4-hydroxy-7-(4-methoxy-phenoxy)-isoquinoline-3-carbonyl]amino}-2,2-dimethyl-propionic acid tert-butyl ester A mixture of 1-cyano-4-hydroxy-7-(4-methoxy-phenoxy)-isoquinoline-3-carboxylic acid methyl ester (91 mg) and 3-amino-2,2-dimethyl-propionic acid tert-butyl ester (90 mg) in MeOH (3 mL) was heated at 100° C. in an oil bath for 48 h. The mixture was cooled, concentrated and the residue was column purified to give the desired product (84 mg). LC MS ESI+: 492 (M+1)+.

d) 3-{[7-Cyano-4-hydroxy-7-(4-methoxy-phenoxy)-isoquinoline-3-carbonyl]amino}-2,2-dimethyl-propionic acid A mixture of 3-{[1-cyano-4-hydroxy-7-(4-methoxy-phenoxy)-isoquinoline-3-carbonyl]-amino}-2,2-dimethyl-propionic acid tert-butyl ester (84 mg), TFA (5 mL) and DCM (5 mL) was stirred at rt overnight; then concentrated, the residue was dissolved in water and added 2 M HCl solution, solids were collected via filtration, washed with water and air dried to give the desired product. LC MS ESI+: 436 (M+1)+.

Example 21

3{-[1-Cyano-4-hydroxy-7-(4-methoxy-phenoxy)-isoquinoline-3-carbonyl]-amino}-3-methyl-butyric acid

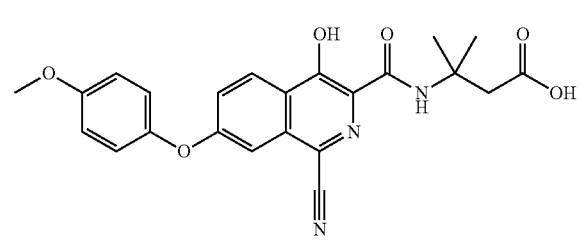 [SMILES: COc1ccc(Oc2ccc3c(O)c(C(=O)NC(C)(C)CC(=O)O)nc(C#N)c3c2)cc1]

A mixture of 1-cyano-4-hydroxy-7-(4-methoxy-phenoxy)-isoquinoline-3-carboxylic acid methyl ester (100 mg) and 3-amino-3-methyl-butyric acid (100 mg) and NaOMe (45 mg) in DMA (1.5 mL) was microwaved at 150° C. for 3 h. The mixture was cooled, diluted with water, acidified with 2 M HCl solution, solids were collected with filtration, washed with water, air dried then the residue was further column purified to give the desired product (27 mg). LC MS ESI+: 436 (M+1)+.

Example 22

3-{[1-Cyano-7-(2,6-difluoro-phenoxy)-4-hydroxy-isoquinoline-3-carbonyl]-amino}-2,2-dimethyl-propionic acid

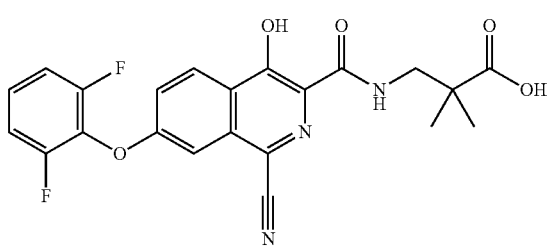 [SMILES: CC(C)(CNC(=O)c1nc(C#N)c2cc(Oc3c(F)cccc3F)ccc2c1O)C(=O)O]

a) 4-Bromo-2-{[(2,4-dimethoxy-benzyl)-ethoxycarbonylmethyl-amino]-methyl}-benzoic acid ethyl ester A mixture of 4-bromo-2-bromomethyl-benzoic acid ethyl ester (34.3 g, prepared according to Zhong, Min and Li, Leping PCT Int. Appl., 2010065674, 10 Jun. 2010), (2,4-dimethoxy-benzylamino)-acetic acid ethyl ester (32.4 g), NaI (1.6 g), DIPEA (27.8 mL) in DMF was stirred at rt overnight. Then the reaction mixture was diluted with EtOAc, washed with water, diluted NaCl, dried over sodium sulfate, filtered, concentrated and column purified to give the desired product (36.14 g). LC MS ESI+: 495 (M+1)+.

b) 4-(2,6-Difluoro-phenoxy)-2-{[(2,4-dimethoxy-benzyl)-ethoxycarbonylmethyl-amino]-methyl}-benzoic acid ethyl ester A mixture of 4-bromo-2-{[(2,4-dimethoxy-phenoxy)-ethoxycarbonylmethyl-amino]-methyl}-benzoic acid ethyl ester (3.144 g), 2,6-difluorophenol (1.24 g), CuCl (252 mg), 2,2,6,6-tetramethyl-heptane-3,5-dione (TMHD, 0.19 mL), cesium carbonate (3.11 g) in NMP (6 mL) was heated at 130° C. for 24 h. The cooled, diluted with EtOAc, solids were filtered off, filtrate was washed with water, diluted NaCl solution, dried over sodium sulfate, filtered off, concentrated, the residue was column purified to give the desired product (1.093 g). LC MS ESI+: 544 (M+1)+.

c) 7-(2,6-Difluoro-phenoxy)-4-hydroxy-isoquinoline-3-carboxylic acid ethyl ester To an ice-water bath cooled solution of 4-(2,6-difluoro-phenoxy)-2-{[(2,4-dimethoxy-benzyl)-ethoxycarbonylmethyl-amino]-methyl}-benzoic acid ethyl ester (1.09 g) in THF (10 mL) was added a solution of potassium tert-pentoxide (1.77 mL, 1.7 M in toluene); the mixture was stirred for 30 min at rt after addition; then the mixture was quenched with 2 M HCl (0.9 mL) diluted with EtOAc and water, EtOAc phase was separated and washed with water, diluted NaCl solution and dried over anhydrous sodium sulphate, filtered off, concentrated to give the desired cyclized intermediate. This intermediate was then dissolved in DCM (20 mL) and treated with thionyl chloride (0.15 mL) overnight. Then the reaction mixture was concentrated; the residue was dissolved in EtOAc, washed with water, diluted NaCl solution, then dried over sodium sulphate, filtered, concentrated and the residue was column purified to give the desired product (449 mg). LC MS ESI: 346 (M+1)+.

d) 1-Bromo-7-(2,6-difluoro-phenoxy)-4-hydroxy-isoquinoline-3-carboxylic acid ethyl ester A mixture of 7-(2,6-difluoro-phenoxy)-4-hydroxy-isoquinoline-3-carboxylic acid ethyl ester (210 mg) and NBS (133 mg) in MeCN (5 mL) was stirred in an ice/water bath for 2 h; then concentrated, the residue was column purified to give the desired product (156 mg). LC MS ESI: 424 (M+1)+.

e) 1-Cyano-7-(2,6-difluoro-phenoxy)-4-hydroxy-isoquinoline-3-carboxylic acid ethyl ester A mixture of 1-bromo-7-(2,6-difluoro-phenoxy)-4-hydroxy-isoquinoline-3-carboxylic acid ethyl ester (156 mg) and CuCN (66 mg) in NMP was stirred at 150° C. for 1 h; then cooled, diluted with DCM, filtered, then washed with water, dil. NaCl solution, dried over sodium sulphate, filtered, concentrated, the residue was column purified to give the desired product (100 mg). LC MS ESI: 371 (M+1)+.

f) 3-{[1-Cyano-7-(2,6-difluoro-phenoxy)-4-hydroxy-isoquinoline-3-carbonyl]-amino}-2,2-dimethyl-propionic acid tert-butyl ester A mixture of 1-cyano-7-(2,6-difluoro-phenoxy)-4-hydroxy-isoquinoline-3-carboxylic acid ethyl ester (26 mg) and 3-amino-2,2-dimethyl-propionic acid tert-butyl ester (26 mg) in EtOH (0.5 mL) was microwaved at 140° C. for 1 h. The mixture was cooled, concentrated and the residue was column purified to give the desired product (36 mg). LC MS ESI+: 498 (M+1)+.

g) 3-{[1-Cyano-7-(2,6-difluoro-phenoxy)-4-hydroxy-isoquinoline-3-carbonyl]-amino}-2,2-dimethyl-propionic acid A mixture of 3-{[1-Cyano-7-(2,6-difluoro-phenoxy)-4-hydroxy-isoquinoline-3-carbonyl]-amino}-2,2-dimethyl-propionic acid tert-butyl ester (36 mg), TFA (1 mL) and DCM (2 mL) was stirred at rt overnight; then concentrated, the residue was dissolved in water and added 2 M HCl solution, solids were collected via filtration, washed with water and air dried to give the desired product (21 mg). LC MS ESI+: 442 (M+1)+.

Example 23

3-{[7-(4-Chloro-3-fluoro-phenoxy)-4-hydroxy-isoquinoline-3-carbonyl]-amino}-2,2-dimethyl-propionic acid

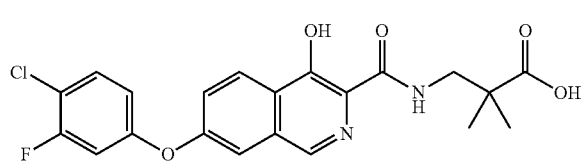 [SMILES: CC(C)(CNC(=O)c1ncc2cc(Oc3ccc(Cl)c(F)c3)ccc2c1O)C(=O)O]

a) 4-(4-Chloro-3-fluoro-phenoxy)-2-{[(2,4-dimethoxy-benzyl)-ethoxycarbonylmethyl-amino]-methyl}-benzoic acid ethyl ester A mixture of 4-bromo-2-{[(2,4-dimethoxy-phenoxy)-ethoxycarbonylmethyl-amino]-methyl}-benzoic acid ethyl ester (3.271 g), 4-chloro-3-fluoro-phenol (1.94 g), CuCl (328 mg), 2,2,6,6-tetramethyl-heptane-3,5-dione (TMHD, 0.26 mL), cesium carbonate (4.31 g) in NMP (6 mL) was heated at 130° C. for 24 h. The cooled, diluted with EtOAc, solids were filtered off, filtrate was washed with water, diluted NaCl solution, dried over sodium sulfate, filtered off, concentrated, the residue was column purified to give the desired product (2.529 g). LC MS ESI+: 561 (M+1)+.

b) 7-(4-Chloro-3-fluoro-phenoxy)-4-hydroxy-isoquinoline-3-carboxylic acid ethyl ester To an ice-water bath cooled solution of 4-(4-chloro-3-fluoro-phenoxy)-2-{[(2,4-dimethoxy-benzyl)-ethoxycarbonylmethyl-amino]-methyl}-benzoic acid ethyl ester (2.529 g) in THF (20 mL) was added a solution of potassium tert-pentoxide (4.5 mL, 1.7 M in toluene); the mixture was stirred at rt for 60 min after addition; then the mixture was quenched with 2 M HCl, diluted with EtOAc and water, EtOAc phase was separated and washed with water, diluted NaCl solution and dried over anhydrous sodium sulphate, filtered off, concentrated to give the desired cyclized intermediate. This intermediate was then dissolved in DCM (30 mL) and treated with thionyl chloride (0.63 mL) overnight. Then concentrated, the residue was dissolved in EtOAc, washed with water, diluted NaCl solution, then dried over sodium sulphate, filtered, concentrated and the residue was column purified to give the desired product (580 mg). LC MS ESI: 362 (M+1)+.

c) 3-{[7-(4-Chloro-3-fluoro-phenoxy)-4-hydroxy-isoquinoline-3-carbonyl]amino}-2,2-dimethyl-propionic acid tert-butyl ester A mixture of 7-(4-chloro-3-fluoro-phenoxy)-4-hydroxy-isoquinoline-3-carboxylic acid ethyl ester (45 mg) and 3-amino-2,2-dimethyl-propionic acid tert-butyl ester (65 mg) in EtOH (0.5 mL) was microwaved at 145° C. for 3 h. The mixture was cooled, concentrated and the residue was column purified to give the desired product (36 mg). LC MS ESI+: 489 (M+1)+.

d) 3-{[7-(4-Chloro-3-fluoro-phenoxy)-4-hydroxy-isoquinoline-3-carbonyl]amino}-2,2-dimethyl-propionic acid A mixture of 3-{[7-(4-chloro-3-fluoro-phenoxy)-4-hydroxy-isoquinoline-3-carbonyl]-amino}-2,2-dimethyl-propionic acid tert-butyl ester (36 mg), TFA (1 mL) and DCM (3 mL) was stirred at rt overnight; then concentrated, the residue was dissolved in water and added 2 M HCl solution, solids were collected via filtration, washed with water and air dried to give the desired product (20 mg). LC MS ESI+: 433 (M+1)+.

Example 24

3-{[4-Hydroxy-7-(pyridin-3-yloxy)-isoquinoline-3-carbonyl]-amino}-propionic acid

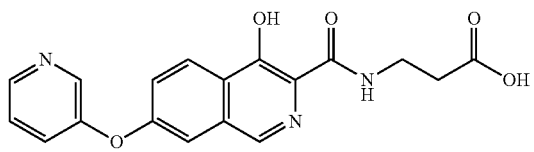 [SMILES: O=C(O)CCNC(=O)c1ncc2cc(Oc3cccnc3)ccc2c1O]

a) 2-{[(2,4-Dimethoxy-benzyl)-ethoxycarbonylmethyl-amino]-methyl}-4-(pyridin-3-yloxy)-benzoic acid ethyl ester A mixture of 4-bromo-2-{[(2,4-dimethoxy-phenoxy)-ethoxycarbonylmethyl-amino]-methyl}-benzoic acid ethyl ester (3.292 g), pyridin-3-ol (887 mg), CuCl (330 mg), 2,2,6,6-tetramethyl-heptane-3,5-dione (TMHD, 0.26 mL), cesium carbonate (3.26 g) in NMP (6 mL) was heated at 130° C. for 24 h. Then the reaction was cooled, diluted with EtOAc, solids were filtered off, filtrate was washed with water, diluted NaCl solution, dried over sodium sulfate, filtered off, concentrated; the residue was column purified to give the desired product (1.71 g). LC MS ESI+: 509 (M+1)+.

b) 4-Hydroxy-7-(pyridin-3-yloxy)-isoquinoline-3-carboxylic acid ethyl ester To an ice-water bath cooled solution of 2-{[(2,4-dimethoxy-benzyl)-ethoxycarbonylmethyl-amino]-methyl}-4-(pyridin-3-yloxy)-benzoic acid ethyl ester (1.71 g) in THF (30 mL) was added a solution of potassium tert-pentoxide (3.36 mL, 1.7 M in toluene); the mixture was stirred for 60 min at rt after addition; then the mixture was quenched with 2 M HCl, diluted with EtOAc and water, EtOAc phase was separated and washed with water, diluted NaCl solution and dried over anhydrous sodium sulphate, filtered off, concentrated to give the desired cyclized intermediate. This intermediate was then dissolved in DCM (30 mL) and treated with thionyl chloride (0.47 mL) overnight. Then concentrated, the residue was dissolved in EtOAc, washed with water, diluted NaCl solution, then dried over sodium sulphate, filtered, concentrated and the residue was column purified to give the desired product (673 mg). LC MS ESI: 311 (M+1)+.

c) 3-{[4-Hydroxy-7-(pyridin-3-yloxy)-isoquinoline-3-carbonyl]amino}-propionic acid A mixture of 4-hydroxy-7-(pyridin-3-yloxy)-isoquinoline-3-carboxylic acid ethyl ester (26 mg), 3-amino-propionic acid (30 mg) and NaOMe (0.50 mL, 0.5 M solution in MeOH) was microwaved at 130° C. for 1 h; then cooled, concentrated, residue was dissolved in water, acidified with 2 M HCl; solids were collected via filtration, washed with water and air dried to give the desired product (25 mg). LC MS ESI: 354 (M+1)+.

Example 25

3-{[4-Hydroxy-7-(pyridin-2-yloxy)-isoquinoline-3-carbonyl]-amino}-propionic acid

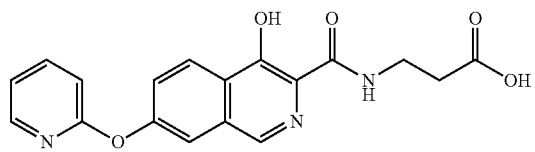 [SMILES: O=C(O)CCNC(=O)c1ncc2cc(Oc3ccccn3)ccc2c1O]

a) 2-Methyl-4-(pyridin-2-yloxy)-benzoic acid ethyl ester

A mixture of 4-hydroxy-2-methyl-benzoic acid ethyl ester (400 mg), 2-iodo-pyridine (0.29 mL), CuCl (110 mg), 2,2,6,6-tetramethyl-heptane-3,5-dione (TMHD, 0.087 mL), cesium carbonate (940 mg) in NMP (2 mL) was heated at 120° C. for 20 h. Then the reaction was cooled, diluted with EtOAc, solids were filtered off, filtrate was washed with water, diluted NaCl solution, dried over sodium sulfate, filtered off, concentrated, the residue was column purified to give the desired product (531 mg). LC MS ESI+: 258 (M+1)+.

b) 2-Bromomethyl-4-(pyridin-2-yloxy)-benzoic acid ethyl ester

A mixture of 2-methyl-4-(pyridin-2-yloxy)-benzoic acid ethyl ester (529 mg), NBS (440 mg), and BzOOBz (25 mg) in CCl$_4$ (10 mL) was refluxed for 6 h; then cooled, solids were filtered off, filtrate was concentrated to give crude product (855 mg). $^1$H NMR in CDCl$_3$, δ in ppm: 8.2-7.6 (m, 4H), 7.1-6.95 (m, 3H), 4.94 (s, 2H), 4.39 (q, 2H, J=7.0 Hz), 1.41 (t, 3H, J=7.0 Hz).

c) 2-{[Methoxycarbonylmethyl-(toluene-4-sulfonyl)-amino]-methyl}-4-(pyridin-2-yloxy)-benzoic acid ethyl ester A mixture of 2-bromomethyl-4-(pyridin-2-yloxy)-benzoic acid ethyl ester (855 mg, crude from previous step), Ts-Gly-OMe (502 mg), potassium carbonate (425 mg) and KI (32 mg) in DMF (10 mL) was stirred at rt overnight. Then the reaction mixture was diluted with EtOAc, washed with water, diluted NaCl sol and dried over anhydrous sodium sulfate, filtered, concentrated and the residue was column purified to give product (745 mg). LC MS ESI+: 499 (M+1)+.

d) 4-Hydroxy-7-(pyridin-2-yloxy)-isoquinoline-3-carboxylic acid methyl ester A mixture of 2-{[methoxycarbonylmethyl-(toluene-4-sulfonyl)-amino]-methyl}-4-(pyridin-2-yloxy)-benzoic acid ethyl ester (745 mg), and NaOMe (0.702 mL, 0.5 M solution in HOMe) in DMF (5 mL) was stirred with ice/water bath cooling for 4 h. HOAc (2.5 eq relative to NaOMe) was added, diluted with ice/water; then the solids were collected via filtration and washed with water to give product (247 mg). Filtrate was back extracted with EtOAc; EtOAc phase was washed with water, diluted NaCl solution and dried over anhydrous sodium sulphate, filtered, concentrated and column purified to give more product (135 mg). LC MS ESI+: 297 (M+1)+.

e) 3-{[4-Hydroxy-7-(pyridin-2-yloxy)-isoquinoline-3-carbonyl]amino}-propionic acid A mixture of 4-hydroxy-7-(pyridin-2-yloxy)-isoquinoline-3-carboxylic acid methyl ester (24 mg), 3-amino-propionic acid (29 mg) and NaOMe (0.48 mL, 0.5 M solution in MeOH) was microwaved at 130° C. for 1 h; then cooled, concentrated, residue was dissolved in water, acidified with 2 M HCl; solids were collected via filtration, washed with water and air dried to give the desired product (22 mg). LC MS ESI: 354 (M+1)+.

Example 26

1-({[1-Cyano-7-(2,6-difluoro-phenoxy)-4-hydroxy-isoquinoline-3-carbonyl]-amino}-methyl)-cyclobutanecarboxylic acid

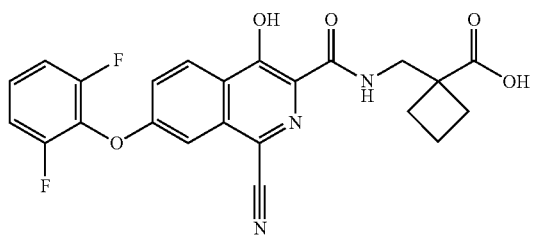 [SMILES: N#Cc1nc(C(=O)NCC2(C(=O)O)CCC2)c(O)c2ccc(Oc3c(F)cccc3F)cc12]

a) 1-Cyano-cyclobutanecarboxylic acid tert-butyl ester

DBU (23.5 mL) was added slowly to a solution of cyanoacetic acid tert-butyl ester (8.84 g) in DMF (100 mL) at rt, followed by addition of 1,3-dibromopropane (13.9 g); then the reaction mixture was stirred in an oil bath (bath temperature=80° C.) overnight. The reaction was cooled, diluted with EtOAc, then washed with cold water, dil. NaCl solution; EtOAc phase was dried over anhydrous sodium sulfate, filtered, concentrated, the residue was column purified to give title compound (6.58 g). $^1$H NMR in CDCl$_3$, δ in ppm: 2.8-2.5 (m, 4H), 2.4-2.2 (m, 2H), 1.51 (s, 9H).

b) 1-Aminomethyl-cyclobutanecarboxylic acid tert-butyl ester

A mixture of 1-cyano-cyclobutanecarboxylic acid tert-butyl ester (6.58 g) and Raney Ni (10 mL in water) in MeOH (250 mL) was stirred at rt under H$_2$ atmosphere (balloon) overnight. Then the reaction mixture was filtered over Celite pad, filtrate was concentrated to give the desired product (5.59 g). $^1$H NMR in CDCl$_3$, δ in ppm: 2.94 (s, 2H), 2.4-2.2 (m, 2H), 2.0-1.8 (m, 4H), 1.46 (s, 9H).

c) 1-({[7-Cyano-7-(2,6-difluoro-phenoxy)-4-hydroxy-isoquinoline-3-carbonyl]amino}-methyl)-cyclobutanecarboxylic acid tert-butyl ester A mixture of 1-cyano-7-(2,6-difluoro-phenoxy)-4-hydroxy-isoquinoline-3-carboxylic acid ethyl ester (11 mg) and 1-aminomethyl-cyclobutanecarboxylic acid tert-butyl ester (11 mg) in EtOH (0.3 mL) was microwaved at 140° C. for 1 h. The mixture was cooled, concentrated and the residue was column purified to give the desired product (13 mg). LC MS ESI+: 510 (M+1)+.

d) 1-({[1-Cyano-7-(2,6-difluoro-phenoxy)-4-hydroxy-isoquinoline-3-carbonyl]amino}-methyl)-cyclobutanecarboxylic acid A mixture of 1-({[1-cyano-7-(2,6-difluoro-phenoxy)-4-hydroxy-isoquinoline-3-carbonyl]-amino}-methyl)-cyclobutanecarboxylic acid tert-butyl ester (13 mg), TFA (0.3 mL) and DCM (1 mL) was stirred at rt for 1 h; then concentrated, the residue was treated with water and added 2 M HCl solution, solids were collected via filtration, washed with water and air dried to give the desired product (10 mg). LC MS ESI+: 454 (M+1)+.

Example 27

3{-[1-Cyano-4-hydroxy-7-(pyridin-3-yloxy)-isoquinoline-3-carbonyl]-amino}-2,2-dimethyl-propionic acid

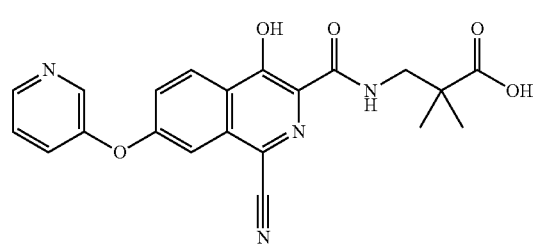 [SMILES: CC(C)(CNC(=O)c1nc(C#N)c2cc(Oc3cccnc3)ccc2c1O)C(=O)O]

a) 4-Hydroxy-1-iodo-7-(pyridin-3-yloxy)-isoquinoline-3-carboxylic acid ethyl ester A mixture of 4-hydroxy-7-(pyridin-2-yloxy)-isoquinoline-3-carboxylic acid methyl ester (204 mg) and NIS (177 mg) in DCM was refluxed for 24 h; then concentrated, the resulting residue was column purified to give product (215 mg). LCMS ESI+: 437 (M+1)+.

b) 1-Cyano-4-hydroxy-7-(pyridin-3-yloxy)-isoquinoline-3-carboxylic acid ethyl ester A mixture of 4-hydroxy-1-iodo-7-(pyridin-3-yloxy)-isoquinoline-3-carboxylic acid ethyl ester (215 mg) and CuCN (89 mg) in NMP (2 mL) was heated at 120° C. for 2 h; the reaction was then cooled, diluted with DCM, and stirred at rt overnight; then diluted HCl solution was added and stirred for 1 h; the solids were filtered off, and DCM phase was separated, washed with water, and dil. NaCl solution, dried over anhydrous sodium sulphate, filtered, concentrated and the residue was column purified to give product (53 mg). LCMS ESI+: 336 (M+1)+.

c) 3-{[1-Cyano-4-hydroxy-7-(pyridin-3-yloxy)-isoquinoline-3-carbonyl]amino}-2,2-dimethyl-propionic acid tert-butyl ester A mixture of 1-cyano-4-hydroxy-7-(pyridin-3-yloxy)-isoquinoline-3-carboxylic acid ethyl ester (19 mg) and 3-amino-2,2-dimethyl-propionic acid tert-butyl ester (25 mg) in EtOH (0.3 mL) was microwaved at 140° C. for 1 h. The mixture was cooled, concentrated and the residue was column purified to give the desired product (21 mg). LC MS ESI+: 463 (M+1)+.

d) 3-{[7-Cyano-4-hydroxy-7-(pyridin-3-yloxy)-isoquinoline-3-carbonyl]amino}-2,2-dimethyl-propionic acid A mixture of 3-{[1-cyano-4-hydroxy-7-(pyridin-3-yloxy)-isoquinoline-3-carbonyl]-amino}-2,2-dimethyl-propionic acid tert-butyl ester (21 mg), TFA (1.6 mL) and DCM (5 mL) was stirred at rt overnight; then concentrated, the residue was dissolved in water and added 2 M HCl solution, solids were collected via filtration, washed with water and air dried to give the desired product (14 mg). LC MS ESI+: 407 (M+1)+.

Example 28

1-({[1-Cyano-4-hydroxy-7-(pyridin-3-yloxy)-isoquinoline-3-carbonyl]-amino}-methyl)-cyclobutanecarboxylic acid

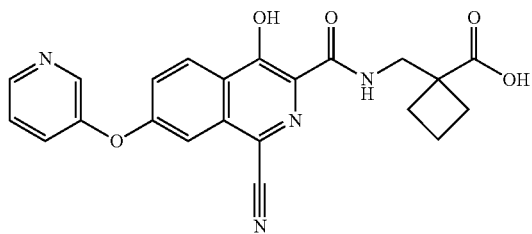 [SMILES: N#Cc1nc(C(=O)NCC2(C(=O)O)CCC2)c(O)c2ccc(Oc3cccnc3)cc12]

a) 1-({[7-Cyano-4-hydroxy-7-(pyridin-3-yloxy)-isoquinoline-3-carbonyl]amino}-methyl)-cyclobutanecarboxylic acid tert-butyl ester A mixture of 1-cyano-4-hydroxy-7-(pyridin-3-yloxy)-isoquinoline-3-carboxylic acid ethyl ester (12 mg) and 1-aminomethyl-cyclobutanecarboxylic acid tert-butyl ester (17 mg) in EtOH (0.3 mL) was microwaved at 140° C. for 1 h. The mixture was cooled, concentrated and the residue was column purified to give the desired product (14 mg). LC MS ESI+: 475 (M+1)+.

b) 1-({[7-Cyano-4-hydroxy-7-(pyridin-3-yloxy)-isoquinoline-3-carbonyl]amino}-methyl)-cyclobutanecarboxylic acid A mixture of 1-({[1-Cyano-4-hydroxy-7-(pyridin-3-yloxy)-isoquinoline-3-carbonyl]-amino}-methyl)-cyclobutanecarboxylic acid tert-butyl ester (14 mg), TFA (1 mL) and DCM (2 mL) was stirred at rt for 3 h; then concentrated, the residue was treated with water and added 2 M HCl solution, solids were collected via filtration, washed with water and air dried to give the desired product (6.6 mg). LC MS ESI+: 419 (M+1)+.

Example 29

4-{[(1-Cyano-4-hydroxy-7-phenoxy-isoquinoline-3-carbonyl)-amino]-methyl}-1,1-dioxo-hexahydro-1$\lambda^6$-thiopyran-4-carboxylic acid

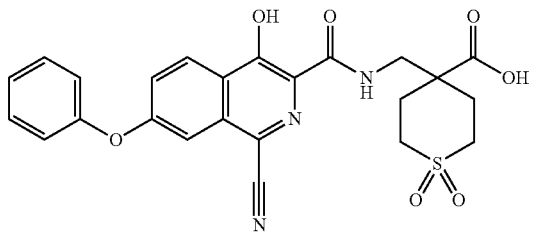 [SMILES: N#Cc1nc(C(=O)NCC2(C(=O)O)CCS(=O)(=O)CC2)c(O)c2ccc(Oc3ccccc3)cc12]

a) 4-Cyano-tetrahydro-thiopyran-4-carboxylic acid tert-butyl ester

A mixture of 2-(2-hydroxy-ethylsulfanyl)-ethanol (13.17 g), thionyl chloride (24 mL) in DCM (250 mL) was stirred in an ice/water bath overnight. Then the reaction mixture was concentrated to give crude product 1-chloro-2-(2-chloro-ethylsulfanyl)-ethane (100%), which was used directly in the next step. DBU (42.04 mL) was added slowly to a solution of cyano-acetic acid tert-butyl ester (13.23 g) and 1-chloro-2-(2-chloro-ethylsulfanyl)-ethane (all the crude from previous step) in DMF (200 mL) at rt and then the reaction mixture was stirred in an oil bath (bath temperature=80° C.) overnight. The reaction was cooled, diluted with EtOAc, then washed with cold water, dil. NaCl solution; EtOAc phase was dried over anhydrous sodium sulfate, filtered, concentrated; the residue was column purified to give title compound (7.961 g). $^1$H NMR in CDCl$_3$, δ in ppm: 3.1-2.9 (m, 2H), 2.7-2.5 (m, 2H), 2.45-2.35 (m, 2H), 2.2-2.1 (m, 2H), 1.51 (s, 9H).

b) 4-Cyano-1,1-dioxo-hexahydro-1$\lambda^6$-thiopyran-4-carboxylic acid tert-butyl ester A mixture of 4-cyano-tetrahydro-thiopyran-4-carboxylic acid tert-butyl ester (192 mg) and mCPBA (578 mg) in DCM (5 mL) was stirred at rt overnight; then the reaction was diluted with DCM, washed with dil. Na$_2$SO$_3$ solution, dil. NaHCO$_3$ and dil. NaCl solution respectively; DCM phase was dried over anhydrous sodium sulphate, filtered, concentrated and column-purified to give the desired product (208 mg). $^1$H NMR in CDCl$_3$, δ in ppm: 3.4-2.1 (m, 4H), 2.75-2.45 (m, 4H), 1.54 (s, 9H).

c) 4-{[(1-Cyano-4-hydroxy-7-phenoxy-isoquinoline-3-carbonyl)-amino]-methyl}-1,1-dioxo-hexahydro-1$\lambda^6$-thiopyran-4-carboxylic acid tert-butyl ester A mixture of 4-cyano-1,1-dioxo-hexahydro-1$\lambda^6$-thiopyran-4-carboxylic acid tert-butyl ester (208 mg) and Raney Ni (0.5 mL in water) in MeOH (20 mL) was stirred at rt under H$_2$ atmosphere (balloon) overnight. Then the reaction mixture was filtered over Celite pad, filtrate was concentrated to give the desired product 4-aminomethyl-1,1-dioxo-hexahydro-1$\lambda^6$-thiopyran-4-carboxylic acid tert-butyl ester (212 mg), which was used in the next step. A mixture of 1-cyano-4-hydroxy-7-phenoxy-isoquinoline-3-carboxylic acid methyl ester (24 mg) and 4-aminomethyl-1,1-dioxo-hexahydro-1$\lambda^6$-thiopyran-4-carboxylic acid tert-butyl ester (45 mg) in EtOH (1 mL) was microwaved at 140° C. for 2 h. The mixture was cooled, concentrated and the residue was column purified to give the desired product (5 mg). LC MS ESI+: 552 (M+1)$^+$.

d) 4-{[(1-Cyano-4-hydroxy-7-phenoxy-isoquinoline-3-carbonyl)-amino]-methyl}-1,1-dioxo-hexahydro-1$\lambda^6$-thiopyran-4-carboxylic acid A mixture of 4-{[(1-cyano-4-hydroxy-7-phenoxy-isoquinoline-3-carbonyl)-amino]-methyl}-1,1-dioxo-hexahydro-1%$^6$-thiopyran-4-carboxylic acid tert-butyl ester (5 mg), TFA (5 mL) and DCM (5 mL) was stirred at rt for 3 h; then concentrated, the residue was treated with water and added 2 M HCl solution, solids were collected via filtration, washed with water and air dried to give the desired product (5 mg). LC MS ESI+: 496 (M+1)$^+$.

Example 30

4-{[(1-Cyano-4-hydroxy-7-phenoxy-isoquinoline-3-carbonyl)-amino]-methyl}-1-oxo-hexahydro-1$\lambda^4$-thiopyran-4-carboxylic acid

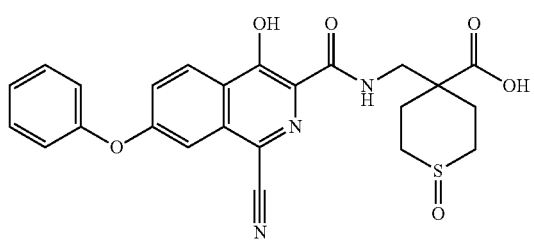 [SMILES: N#Cc1nc(C(=O)NCC2(C(=O)O)CCS(=O)CC2)c(O)c2ccc(Oc3ccccc3)cc12]

a) 4-Cyano-1-oxo-hexahydro-1$\lambda^4$-thiopyran-4-carboxylic acid tert-butyl ester A mixture of 4-cyano-tetrahydro-thiopyran-4-carboxylic acid tert-butyl ester (206 mg) and NaIO4 (217 mg) in MeCN/water (3 mL/3 mL) was stirred between 0° C. and rt overnight; then the reaction was diluted with EtOAc, washed with dil. Na$_2$SO$_3$ solution, water and dil. NaCl solution respectively; EtOAc phase was dried over anhydrous sodium sulphate, filtered, concentrated and column-purified to give the desired product (193 mg). $^1$H NMR in CDCl$_3$, δ in ppm: 3.2-2.6 (m, 6H), 2.4-2.1 (m, 2H), and 1.52 (s, 9H).

b) 4-{[(1-Cyano-4-hydroxy-7-phenoxy-isoquinoline-3-carbonyl)-amino]-methyl}-1-oxo-hexahydro-1$\lambda^4$-thiopyran-4-carboxylic acid tert-butyl ester A mixture of 4-cyano-1-oxo-hexahydro-1$\lambda^4$-thiopyran-4-carboxylic acid tert-butyl ester (193 mg) and Raney Ni (0.5 mL in water) in MeOH (30 mL) was stirred at rt under H$_2$ atmosphere (balloon) overnight. Then the reaction mixture was filtered over Celite pad, filtrate was concentrated to give the desired product 4-aminomethyl-1-oxo-hexahydro-1$\lambda^4$-thiopyran-4-carboxylic acid tert-butyl ester (195 mg), which was used in the next step. A mixture of 1-cyano-4-hydroxy-7-phenoxy-isoquinoline-3-carboxylic acid methyl ester (35 mg) and 4-aminomethyl-1-oxo-hexahydro-1$\lambda^4$-thiopyran-4-carboxylic acid tert-butyl ester (52 mg) in EtOH (1.5 mL) was refluxed overnight. The mixture was cooled, concentrated and the residue was column purified to give the desired product (23 mg). LC MS ESI+: 536 (M+1)$^+$.

c) 4-{[(1-Cyano-4-hydroxy-7-phenoxy-isoquinoline-3-carbonyl)-amino]-methyl}-1-oxo-hexahydro-1$\lambda^4$-thiopyran-4-carboxylic acid A mixture of 4-{[(1-cyano-4-hydroxy-7-phenoxy-isoquinoline-3-carbonyl)-amino]-methyl}-1-oxo-hexahydro-1$\lambda^4$-thiopyran-4-carboxylic acid tert-butyl ester (23 mg), TFA (5 mL) and DCM (5 mL) was stirred at rt overnight; then concentrated, the residue was treated with water and added 2 M HCl solution, solids were collected via filtration, washed with water and air dried to give the desired product (20 mg). LC MS ESI+: 480 (M+1)$^+$.

Example 31

3-{[7-(2-Chloro-5-fluoro-phenoxy)-1-cyano-4-hydroxy-isoquinoline-3-carbonyl]-amino}-2,2-dimethyl-propionic acid

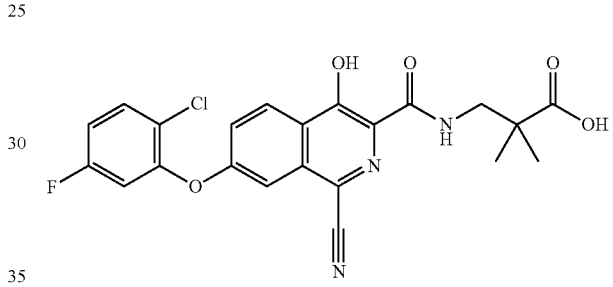

a) 4-(2-Chloro-5-fluoro-phenoxy)-2-{[(2,4-dimethoxy-benzyl)-ethoxycarbonylmethyl-amino]-methyl}-benzoic acid ethyl ester A mixture of 4-bromo-2-{[(2,4-dimethoxy-phenoxy)-ethoxycarbonylmethyl-amino]-methyl}-benzoic acid ethyl ester (3.37 g), 2-chloro-5-fluoro-phenol (1.5 g), CuCl (337 mg), 2,2,6,6-tetramethyl-heptane-3,5-dione (TMHD, 0.27 mL), cesium carbonate (3.33 g) in NMP (6 mL) was heated at 130° C. for 24 h. The reaction was cooled, diluted with EtOAc, solids were filtered off, filtrate was washed with water, diluted NaCl solution, dried over sodium sulfate, filtered off, concentrated, the residue was column purified to give the desired product (1.59 g). LC MS ESI+: 561 (M+1)$^+$.

b) 7-(2-Chloro-5-fluoro-phenoxy)-4-hydroxy-isoquinoline-3-carboxylic acid ethyl ester To an ice-water bath cooled solution of 4-(2-chloro-5-fluoro-phenoxy)-2-{[(2,4-dimethoxy-benzyl)-ethoxycarbonylmethyl-amino]-methyl}-benzoic acid ethyl ester (1.59 g) in THF (20 mL) was added a solution of potassium tert-pentoxide (2.83 mL, 1.7 M in toluene); the mixture was stirred for 2 h at rt after addition; then the mixture was quenched with 2 M HCl, diluted with EtOAc and water, EtOAc phase was separated and washed with water, diluted NaCl solution and dried over anhydrous sodium sulphate, filtered off, concentrated to give the desired cyclized intermediate. This intermediate was then dissolved in DCM (20 mL) and treated with thionyl chloride (0.42 mL) overnight. Then concentrated, the residue was dissolved in EtOAc, washed with water, diluted NaCl solution, then dried over sodium sulphate, filtered, concentrated and the residue was column purified to give the desired product (530 mg). LC MS ESI: 362 (M+1)+.

c) 7-(2-Chloro-5-fluoro-phenoxy)-4-hydroxy-1-iodo-isoquinoline-3-carboxylic acid ethyl ester A mixture of 7-(2-chloro-5-fluoro-phenoxy)-4-hydroxy-isoquinoline-3-carboxylic acid ethyl ester (459 mg) and NIS (343 mg) in DCM (13 mL) was refluxed overnight; then concentrated, the residue was column purified to give the desired product (184 mg). LC MS ESI: 488 (M+1)+.

d) 7-(2-Chloro-5-fluoro-phenoxy)-1-cyano-4-hydroxy-isoquinoline-3-carboxylic acid ethyl ester A mixture of 7-(2-chloro-5-fluoro-phenoxy)-4-hydroxy-1-iodo-isoquinoline-3-carboxylic acid ethyl ester (180 mg) and CuCN (66 mg) in NMP (2 mL) was stirred at 130° C. for 1 h; then cooled, diluted with DCM, filtered, then washed with water, dil. NaCl solution, dried over sodium sulphate, filtered, concentrated, the residue was column purified to give the desired product (120 mg). LC MS ESI: 387 (M+1)+.

e) 3-{[7-(2-Chloro-5-fluoro-phenoxy)-1-cyano-4-hydroxy-isoquinoline-3-carbonyl]amino}-2,2-dimethyl-propionic acid tert-butyl ester A mixture of 7-(2-chloro-5-fluoro-phenoxy)-1-cyano-4-hydroxy-isoquinoline-3-carboxylic acid ethyl ester (15 mg) and 3-amino-2,2-dimethyl-propionic acid tert-butyl ester (19 mg) in EtOH (0.7 mL) was microwaved at 150° C. for 2 h. The mixture was cooled, concentrated and the residue was column purified to give the desired product (19 mg). LC MS ESI+: 514 (M+1)+.

f) 3-{[7-(2-Chloro-5-fluoro-phenoxy)-1-cyano-4-hydroxy-isoquinoline-3-carbonyl]amino}-2,2-dimethyl-propionic acid A mixture of 3-{[7-(2-chloro-5-fluoro-phenoxy)-1-cyano-4-hydroxy-isoquinoline-3-carbonyl]-amino}-2,2-dimethyl-propionic acid tert-butyl ester (19 mg), TFA (1 mL) and DCM (2 mL) was stirred at rt overnight; then concentrated, the residue was dissolved in water and added 2 M HCl solution, solids were collected via filtration, washed with water and air dried to give the desired product (17 mg). LC MS ESI+: 458 (M+1)+.

Example 32 cis-2-(1-Cyano-4-hydroxy-7-phenoxyisoquinoline-3-carboxamido)cyclohexanecarboxylic acid

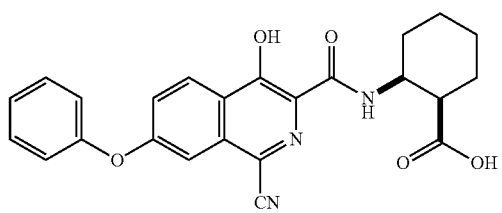

Methyl 1-cyano-4-hydroxy-7-phenoxyisoquinoline-3-carboxylate (30 mg, 0.09 mmol), cis-2-amino-cyclohexanecarboxylic acid (67 mg, 0.47 mmol, Acros) and sodium methoxide (20 mg, 0.37 mmol) were suspended in 2-methoxyethanol (3 mL). The resulting mixture was heated to reflux for 3 hours and then cooled to room temperature. The solvent was removed in vacuo and the residue was dissolved in H2O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO4, concentrated, and purified by flash chromatography (0-50% EtOAc/hexanes with 0.5% formic acid) to give the title compound in 34 mg. MS: (−) m/z 429.99 (M−1).

Example 33 cis-2-[(1-Cyano-4-hydroxy-7-phenoxy-isoquinoline-3-carbonyl)-amino]-cyclopentanecarboxylic acid

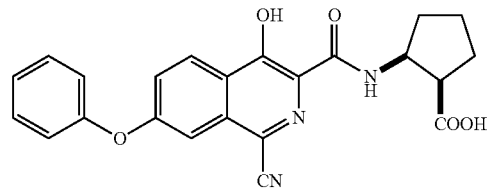

Methyl 1-cyano-4-hydroxy-7-phenoxyisoquinoline-3-carboxylate (30 mg, 0.09 mmol), cis-2-amino-cyclopentanecarboxylic acid hydrochloride hemihydrate (82 mg, 0.47 mmol, Acros) and sodium methoxide (48 mg, 0.89 mmol) were suspended in 2-methoxyethanol (3 mL). The resulting mixture was heated to reflux for 3 hours and then cooled to room temperature. The solvent was removed in vacuo and the residue was dissolved in H2O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO4, concentrated, and purified by flash chromatography (0-50% EtOAc/hexanes with 0.5% formic acid) to give the title compound in 14 mg. MS: (−) m/z 415.92 (M−1).

Example 34

3-(4-Chloro-phenyl)-4-[(1-cyano-4-hydroxy-7-phenoxy-isoquinoline-3-carbonyl)-amino]-butyric acid

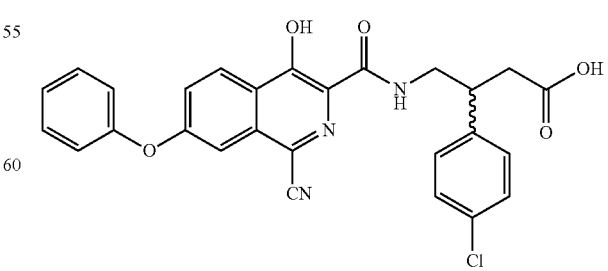

Methyl 1-cyano-4-hydroxy-7-phenoxyisoquinoline-3-carboxylate (70 mg, 0.22 mmol), (±)-baclofen (134 mg, 1.10 mmol, Sigma-Aldrich) and sodium methoxide (53 mg, 0.98 mmol) were suspended in 2-methoxyethanol (7 mL). The resulting mixture was heated to reflux for 3 hours and then cooled to room temperature. The solvent was removed in vacuo and the residue was dissolved in $H_2O$ (20 mL) and EtOAc (20 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/hexanes with 0.5% formic acid) to give the title compound in 28 mg. MS: (−) m/z 499.95 (M−1).

Example 35

(S)-4-(1-Cyano-4-hydroxy-7-phenoxyisoquinoline-3-carboxamido)-3-hydroxybutanoic acid

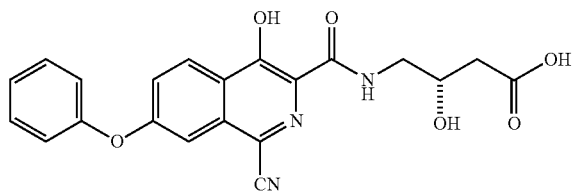 [SMILES: N#Cc1nc(C(=O)NC[C@@H](O)CC(=O)O)c(O)c2ccc(Oc3ccccc3)cc12]

Methyl 1-cyano-4-hydroxy-7-phenoxyisoquinoline-3-carboxylate (30 mg, 0.09 mmol), (S)-4-amino-3-hydroxybutanoic acid (67 mg, 0.56 mmol, Sigma-Aldrich) and sodium methoxide (28 mg, 0.53 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/hexanes with 0.5% formic acid) to give the title compound in 27 mg. MS: (−) m/z 406.00 (M−1).

Example 36

(1-{[(1-Cyano-4-hydroxy-7-phenoxy-isoquinoline-3-carbonyl)-amino]-methyl}-cyclohexyl)-acetic acid

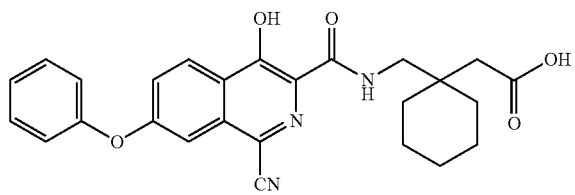 [SMILES: N#Cc1nc(C(=O)NCC2(CC(=O)O)CCCCC2)c(O)c2ccc(Oc3ccccc3)cc12]

Methyl 1-cyano-4-hydroxy-7-phenoxyisoquinoline-3-carboxylate (30 mg, 0.09 mmol), gabapentin (96 mg, 0.56 mmol, TCI) and sodium methoxide (28 mg, 0.53 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/hexanes with 0.5% formic acid) to give the title compound in 11 mg. MS: (−) m/z 458.00 (M−1).

Example 37

(R)-3-(1-Cyano-4-hydroxy-7-phenoxyisoquinoline-3-carboxamido)-4-hydroxybutanoic acid

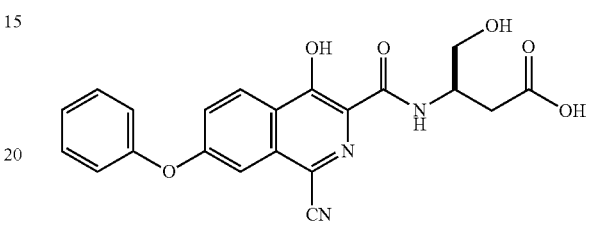

Methyl 1-cyano-4-hydroxy-7-phenoxyisoquinoline-3-carboxylate (30 mg, 0.09 mmol), (R)-3-amino-4-hydroxybutanoic acid (67 mg, 0.56 mmol, PepTech) and sodium methoxide (28 mg, 0.53 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/$CH_2Cl_2$ with 0.5% formic acid) to give the title compound in 12 mg. MS: (−) m/z 405.97 (M−1).

Example 38

3-(7-(2-Chlorophenoxy)-1-cyano-4-hydroxyisoquinoline-3-carboxamido)-2,2-dimethylpropanoic acid

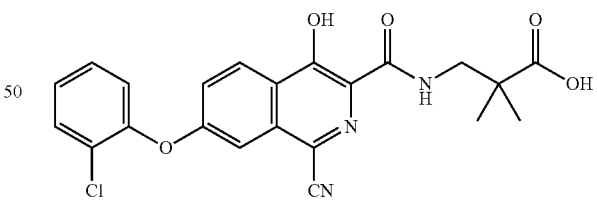

a) Ethyl 3-amino-2,2-dimethylpropanoate

To a slurry of Raney-Ni (1.6 g, 50% in $H_2O$, rinsed 3 times with EtOH before use) in EtOH (78 mL) was added ethyl 2-cyano-2-methylpropanoate (5 g, 35 mmol). The resulting mixture was stirred under a hydrogen atmosphere at room temperature for 20 hours. The liquid was then carefully decanted into another flask and the metal was washed twice with EtOH. The combined EtOH solution was concentrated in vacuo to give the title compound in 4.5 g, which was used in the subsequent step without further purification. $^1$H NMR (CDCl$_3$, 200 MHz): δ=4.13 (q, 2H, J=7.0 Hz), 2.74 (s, 2H), 1.26 (t, 3H, J=7.0 Hz), 1.17 (s, 6H).

b) Methyl 7-(2-chlorophenoxy)-1-cyano-4-hydroxy-isoquinoline-3-carboxylate

Methyl 7-(2-chlorophenoxy)-4-hydroxy-1-iodoisoquinoline-3-carboxylate (0.2 g, 0.44 mmol) and CuCN (79 mg, 0.88 mmol) were suspended in DMF (1.8 mL). The resulting mixture was heated at 120° C. for 7 minutes and then cooled to room temperature. The reaction crude was poured into CH$_2$Cl$_2$ (30 mL) and then stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-50% EtOAc/hexanes) to give the title compound in 150 mg. MS: (−) m/z 353.24 (M−1).

c) Ethyl 3-(7-(2-chlorophenoxy)-1-cyano-4-hydroxy-isoquinoline-3-carboxamido)-2,2-dimethylpropanoate Methyl 7-(2-chlorophenoxy)-1-cyano-4-hydroxyisoquinoline-3-carboxylate (20 mg, 0.06 mmol) and ethyl 3-amino-2,2-dimethylpropanoate (33 mg, 0.23 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 30 mg. $^1$H NMR (CDCl$_3$, 200 MHz): δ=8.41 (d, 1H, J=8.5 Hz), 8.30 (t, 1H, J=6.6 Hz), 7.57-7.48 (m, 2H), 7.42-7.17 (m, 4H), 4.23 (q, 2H, J=7.0 Hz), 3.60 (d, 2H, J=6.6 Hz), 1.35 (t, 3H, J=7.0 Hz), 1.28 (s, 6H).

d) 3-(7-(2-Chlorophenoxy)-1-cyano-4-hydroxyisoquinoline-3-carboxamido)-2,2-dimethylpropanoic acid Ethyl 3-(7-(2-chlorophenoxy)-1-cyano-4-hydroxyisoquinoline-3-carboxamido)-2,2-dimethylpropanoate (30 mg, 0.06 mmol) was dissolved in MeOH (4 mL) and 2 N NaOH (4 mL). After stirring for 5 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 19 mg. MS: (−) m/z 437.95 (M−1).

Example 39

3-{[7-(3-Chloro-phenoxy)-1-cyano-4-hydroxy-isoquinoline-3-carbonyl]-amino}-2,2-dimethyl-propionic acid

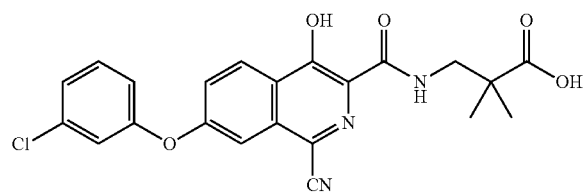 [SMILES: CC(C)(CNC(=O)c1nc(C#N)c2cc(Oc3cccc(Cl)c3)ccc2c1O)C(=O)O]

a) 7-(3-Chloro-phenoxy)-1-cyano-4-hydroxy-isoquinoline-3-carboxylic acid methyl ester 7-(3-Chloro-phenoxy)-4-hydroxy-1-iodo-isoquinoline-3-carboxylic acid methyl ester (120 mg, 0.26 mmol) and CuCN (47 mg, 0.53 mmol) were suspended in DMF (1.1 mL). The resulting mixture was heated at 120° C. for 7 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-50% EtOAc/hexanes) to give the title compound in 62 mg. MS: (−) m/z 353.25 (M−1).

b) 3-{[7-(3-Chloro-phenoxy)-1-cyano-4-hydroxy-isoquinoline-3-carbonyl]amino}-2,2-dimethyl-propionic acid ethyl ester 7-(3-Chloro-phenoxy)-1-cyano-4-hydroxy-isoquinoline-3-carboxylic acid methyl ester (25 mg, 0.07 mmol) and ethyl 3-amino-2,2-dimethylpropanoate (41 mg, 0.28 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 26 mg. MS: (−) m/z 466.42 (M−1).

c) 3-{[7-(3-Chloro-phenoxy)-1-cyano-4-hydroxy-isoquinoline-3-carbonyl]amino}-2,2-dimethyl-propionic acid 3-{[7-(3-Chloro-phenoxy)-1-cyano-4-hydroxy-isoquinoline-3-carbonyl]-amino}-2,2-dimethyl-propionic acid ethyl ester (26 mg, 0.06 mmol) was dissolved in MeOH (4 mL) and 2 N NaOH (4 mL). After stirring for 5 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 18 mg. MS: (−) m/z 437.93 (M−1).

Example 40

3-{[7-(4-Chloro-phenoxy)-1-cyano-4-hydroxy-isoquinoline-3-carbonyl]-amino}-2,2-dimethyl-propionic acid

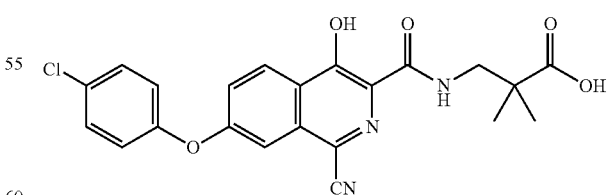

a) 7-(4-Chloro-phenoxy)-1-cyano-4-hydroxy-isoquinoline-3-carboxylic acid methyl ester 7-(4-Chloro-phenoxy)-4-hydroxy-1-iodo-isoquinoline-3-carboxylic acid methyl ester (100 mg, 0.22 mmol) and CuCN (39 mg, 0.44 mmol) were suspended in DMF (1.0 mL). The resulting mixture was heated at 120° C. for 7 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-30% EtOAc/CH$_2$Cl$_2$) to give the title compound in 65 mg. MS: (−) m/z 353.25 (M−1).

b) 3-{[7-(4-Chloro-phenoxy)-1-cyano-4-hydroxy-isoquinoline-3-carbonyl]amino}-2,2-dimethyl-propionic acid ethyl ester 7-(4-Chloro-phenoxy)-1-cyano-4-hydroxy-isoquinoline-3-carboxylic acid methyl ester (21 mg, 0.06 mmol) and ethyl 3-amino-2,2-dimethylpropanoate (34 mg, 0.24 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 20 mg. $^1$H NMR (CDCl$_3$, 200 MHz): δ=8.41 (d, 1H, J=9.0 Hz), 8.32 (t, 1H, J=6.6 Hz), 7.60-7.39 (m, 4H), 7.12-7.06 (m, 2H), 4.24 (q, 2H, J=7.0 Hz), 3.61 (d, 2H, J=6.6 Hz), 1.37 (t, 3H, J=7.0 Hz), 1.30 (s, 6H).

c) 3-{[7-(4-Chloro-phenoxy)-1-cyano-4-hydroxy-isoquinoline-3-carbonyl]amino}-2,2-dimethyl-propionic acid 3-{[7-(4-Chloro-phenoxy)-1-cyano-4-hydroxy-isoquinoline-3-carbonyl]-amino}-2,2-dimethyl-propionic acid ethyl ester (20 mg, 0.04 mmol) was dissolved in MeOH (4 mL) and 2 N NaOH (4 mL). After stirring for 5 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 11 mg. MS: (−) m/z 437.95 (M−1).

Example 41

3{-[1-Cyano-7-(2-fluoro-phenoxy)-4-hydroxy-isoquinoline-3-carbonyl]-amino}-2,2-dimethyl-propionic acid

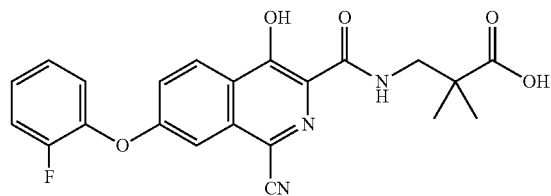 [SMILES: CC(C)(CNC(=O)c1nc(C#N)c2cc(Oc3ccccc3F)ccc2c1O)C(=O)O]

a) 3-Amino-2,2-dimethyl-propionic acid

Ethyl 3-amino-2,2-dimethylpropanoate (180 mg, 1.24 mmol) was dissolved in MeOH (3 mL) and 2 N NaOH (3 mL). The resulting mixture was then stirred at room temperature for 6 hours. To the reaction crude was added 1 N hydrochloric acid until pH was 6. The volatiles were removed in vacuo and the residue was used directly in the subsequent step without further purification.

b) 1-Cyano-7-(2-fluoro-phenoxy)-4-hydroxy-isoquinoline-3-carboxylic acid methyl ester 7-(2-Fluoro-phenoxy)-4-hydroxy-1-iodo-isoquinoline-3-carboxylic acid methyl ester (100 mg, 0.23 mmol) and CuCN (41 mg, 0.46 mmol) were suspended in DMF (1.0 mL). The resulting mixture was heated at 120° C. for 7 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-50% EtOAc/hexanes) to give the title compound in 75 mg. $^1$H NMR (CDCl$_3$, 200 MHz): δ=12.27 (s, 1H), 8.45 (d, 1H, J=9.0 Hz), 7.63-7.57 (m, 1H), 7.50-7.48 (m, 1H), 7.29-7.20 (m, 4H), 4.11 (s, 3H).

c) 3-{[7-Cyano-7-(2-fluoro-phenoxy)-4-hydroxy-isoquinoline-3-carbonyl]amino}-2,2-dimethyl-propionic acid 1-Cyano-7-(2-fluoro-phenoxy)-4-hydroxy-isoquinoline-3-carboxylic acid methyl ester (20 mg, 0.06 mmol), 3-amino-2,2-dimethyl-propionic acid (62 mg, 0.4 mmol) and NaOMe (19 mg, 0.36 mmol) in EtOH (3 mL) were heated at 150° C. in a microwave for 2 hours. The solvent was removed in vacuo and the residue was dissolved in H$_2$O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-25% MeOH/CH$_2$Cl$_2$) to give the title compound in 6 mg. MS: (−) m/z 421.98 (M−1).

Example 42

3-(1-Cyano-7-(3-fluorophenoxy)-4-hydroxyisoquinoline-3-carboxamido)-2,2-dimethylpropanoic acid

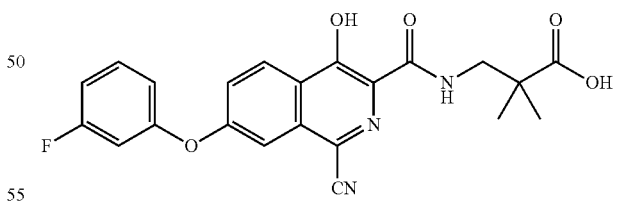

a) Methyl 1-cyano-7-(3-fluorophenoxy)-4-hydroxy-isoquinoline-3-carboxylate

Methyl 7-(3-fluorophenoxy)-4-hydroxy-1-iodoisoquinoline-3-carboxylate (100 mg, 0.23 mmol) and CuCN (41 mg, 0.46 mmol) were suspended in DMF (1.0 mL). The resulting mixture was heated at 120° C. for 7 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-50% EtOAc/hexanes) to give the title compound in 67 mg. MS: (−) m/z 337.25 (M−1).

b) Ethyl 3-(1-cyano-7-(3-fluorophenoxy)-4-hydroxy-isoquinoline-3-carboxamido)-2,2-dimethylpropanoate Methyl 1-cyano-7-(3-fluorophenoxy)-4-hydroxyisoquinoline-3-carboxylate (18 mg, 0.05 mmol) and ethyl 3-amino-2,2-dimethylpropanoate (31 mg, 0.21 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 22 mg. MS: (−) m/z 450.30 (M−1).

c) 3-(1-Cyano-7-(3-fluorophenoxy)-4-hydroxyisoquinoline-3-carboxamido)-2,2-dimethylpropanoic acid Ethyl 3-(1-cyano-7-(3-fluorophenoxy)-4-hydroxyisoquinoline-3-carboxamido)-2,2-dimethylpropanoate (22 mg, 0.05 mmol) was dissolved in MeOH (4 mL) and 2 N NaOH (4 mL). After stirring for 5 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 15 mg. MS: (−) m/z 421.91 (M−1).

Example 43

3-(1-Cyano-4-hydroxy-7-(naphthalen-1-yloxy)isoquinoline-3-carboxamido)-2,2-dimethylpropanoic acid

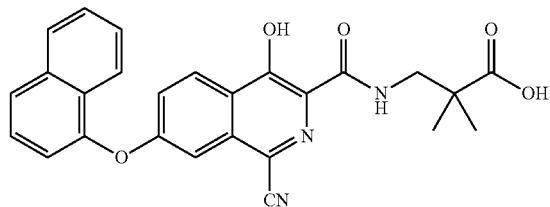 [SMILES: CC(C)(CNC(=O)c1nc(C#N)c2cc(Oc3cccc4ccccc34)ccc2c1O)C(=O)O]

a) Methyl 1-cyano-4-hydroxy-7-(naphthalen-1-yloxy)isoquinoline-3-carboxylate Methyl 4-hydroxy-1-iodo-7-(naphthalen-1-yloxy)isoquinoline-3-carboxylate (130 mg, 0.28 mmol) and CuCN (49 mg, 0.55 mmol) were suspended in DMF (1.1 mL). The resulting mixture was heated at 120° C. for 7 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-50% EtOAc/hexanes) to give the title compound in 87 mg. MS: (−) m/z 369.31 (M−1).

b) Ethyl 3-(1-cyano-4-hydroxy-7-(naphthalen-1-yloxy)isoquinoline-3-carboxamido)-2,2-dimethylpropanoate Methyl 1-cyano-4-hydroxy-7-(naphthalen-1-yloxy)isoquinoline-3-carboxylate (15 mg, 0.04 mmol) and ethyl 3-amino-2,2-dimethylpropanoate (24 mg, 0.16 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 16 mg. MS: (−) m/z 482.30 (M−1).

c) 3-(1-Cyano-4-hydroxy-7-(naphthalen-1-yloxy)isoquinoline-3-carboxamido)-2,2-dimethylpropanoic acid Ethyl 3-(1-cyano-4-hydroxy-7-(naphthalen-1-yloxy)isoquinoline-3-carboxamido)-2,2-dimethylpropanoate (16 mg, 0.03 mmol) was dissolved in MeOH (4 mL) and 2 N NaOH (4 mL). After stirring for 5 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 13 mg. MS: (−) m/z 454.03 (M−1).

Example 44

3-[(1-Cyano-4-hydroxy-7-p-tolyloxy-isoquinoline-3-carbonyl)-amino]-2,2-dimethyl-propionic acid

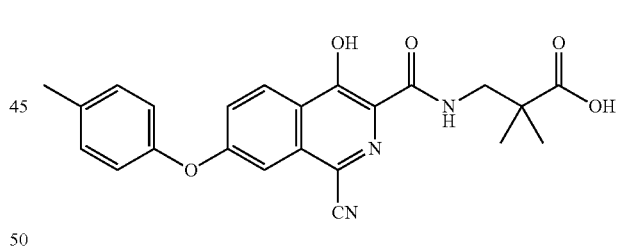

a) 1-Cyano-4-hydroxy-7-p-tolyloxy-isoquinoline-3-carboxylic acid butyl ester 1-Bromo-4-hydroxy-7-p-tolyloxy-isoquinoline-3-carboxylic acid butyl ester (130 mg, 0.30 mmol) and CuCN (54 mg, 0.61 mmol) were suspended in DMF (1.2 mL). The resulting mixture was heated to reflux for 40 minutes and then cooled to room temperature. The reaction crude was poured into CH$_2$Cl$_2$ (30 mL) and stirred vigorously for 10 minutes at room temperature. The resulting suspension was filtered through a pad of celite and the filtrate was washed with H$_2$O and brine sequentially. The organic layer was dried over MgSO$_4$, concentrated, and purified by flash chromatography (0-30% EtOAc/hexanes) to give the title compound in 65 mg. MS: (−) m/z 375.29 (M−1).

b) 3-[(1-Cyano-4-hydroxy-7-p-tolyloxy-isoquinoline-3-carbonyl)-amino]-2,2-dimethyl-propionic acid ethyl ester 1-Cyano-4-hydroxy-7-p-tolyloxy-isoquinoline-3-carboxylic acid butyl ester (19 mg, 0.05 mmol) and ethyl 3-amino-2,2-dimethylpropanoate (29 mg, 0.20 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 18 mg. MS: (−) m/z 446.33 (M−1).

c) 3-[(1-Cyano-4-hydroxy-7-p-tolyloxy-isoquinoline-3-carbonyl)-amino]-2,2-dimethyl-propionic acid 3-[(1-Cyano-4-hydroxy-7-p-tolyloxy-isoquinoline-3-carbonyl)-amino]-2,2-dimethyl-propionic acid ethyl ester (18 mg, 0.04 mmol) was dissolved in MeOH (4 mL) and 2 N NaOH (4 mL). After stirring for 5 hours at room temperature, $H_2O$ (15 mL) and EtOAc (15 mL) were added. To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-30% MeOH/$CH_2Cl_2$) to give the title compound in 9 mg. MS: (−) m/z 417.99 (M−1).

Example 45

(S)-2-Amino-4-(1-cyano-4-hydroxy-7-phenoxyisoquinoline-3-carboxamido)butanoic acid

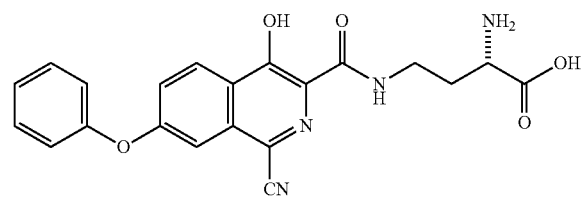 [SMILES: N#Cc1nc(C(=O)NCC[C@H](N)C(=O)O)c(O)c2ccc(Oc3ccccc3)cc12]

a) (S)-4-amino-2-(tert-butoxycarbonylamino)butanoic acid

Boc-L-Dab(Fmoc)-OH (132 mg, 0.3 mmol, PepTech) and piperidine (0.2 mL, 2.02 mmol) were dissolved in DMF (1 mL). The resulting mixture was stirred at room temperature for 30 minutes. The volatiles were removed in vacuo and the residue was used directly in the subsequent step without further purification.

b) (S)-2-(tert-Butoxycarbonylamino)-4-(1-cyano-4-hydroxy-7-phenoxyisoquinoline-3-carboxamido)butanoic acid Methyl 1-cyano-4-hydroxy-7-phenoxyisoquinoline-3-carboxylate (15 mg, 0.05 mmol), (S)-4-amino-2-(tert-butoxycarbonylamino)butanoic acid (crude, 0.28 mmol) and sodium methoxide (15 mg, 0.28 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-20% EtOAc/$CH_2Cl_2$ with 0.5% formic acid) to give the title compound in 20 mg. $^1$H NMR ($CD_3OD$, 200 MHz): δ=8.37 (d, 1H, J=9.0 Hz), 7.64-7.46 (m, 3H), 7.38-7.18 (m, 4H), 4.27-4.14 (m, 1H), 3.56 (t, 2H, J=6.6 Hz), 2.32-1.82 (m, 2H), 1.45 (s, 9H).

c) (S)-2-Amino-4-(1-cyano-4-hydroxy-7-phenoxyisoquinoline-3-carboxamido)butanoic acid (S)-2-(tert-Butoxycarbonylamino)-4-(1-cyano-4-hydroxy-7-phenoxyisoquinoline-3-carboxamido)butanoic acid (20 mg, 0.03 mmol) was dissolved in TFA (2 mL) and $CH_2Cl_2$ (2 mL). The resulting mixture was stirred at room temperature for 3 hours. The volatiles were removed in vacuo and the residue was dissolved again in $CH_2Cl_2$ (2 mL). The volatiles were removed again in vacuo to give the title compound as its TFA salt in 14 mg. MS: (−) m/z 404.91 (M−1).

Example 46

4-(1-Cyano-4-hydroxy-7-phenoxyisoquinoline-3-carboxamido)-4-methylpentanoic acid

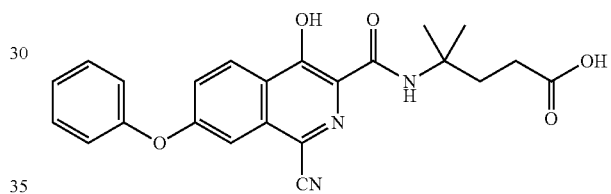

a) Methyl 4-amino-4-methylpentanoate

Methyl 4-methyl-4-nitropentanoate (0.8 g, 4.57 mmol) (Moffett (1963) Org. Syn. Coll. 4:652) and Pd/C (1 g, 10% by weight) were suspended in AcOH (15 mL). The resulting mixture was stirred under a hydrogen atmosphere at room temperature for 16 hours. The reaction mixture was then filtered through a pad of celite. The filtrate was concentrated and the crude was used in the subsequent step without further purification. MS: (+) m/z 146.12.91 (M+1).

b) 1-Cyano-4-hydroxy-7-phenoxyisoquinoline-3-carboxylic acid

Methyl 1-cyano-4-hydroxy-7-phenoxyisoquinoline-3-carboxylate (500 mg, 1.56 mmol) and NaOH (375 mg, 9.38 mmol) were dissolved in $H_2O$ (13 mL), THF (13 mL) and MeOH (13 mL). After stirring for 2 hours at room temperature, $H_2O$ (30 mL) and EtOAc (30 mL) were added. To the stirred mixture was added 1 N hydrochloric acid until pH was 3. The layers were separated and the aqueous layer was extracted twice with EtOAc. The combined organic layers were dried over $MgSO_4$, concentrated to give 300 mg of the title compound. MS: (−) m/z 305.26 (M−1).

c) Methyl 4-(1-cyano-4-hydroxy-7-phenoxyisoquinoline-3-carboxamido)-4-methylpentanoate 1-Cyano-4-hydroxy-7-phenoxyisoquinoline-3-carboxylic acid (47 mg, 0.15 mmol), N-ethylmorpholine (27 μL, 0.21 mmol), methyl 4-amino-4-methylpentanoate (crude as its acetic acid salt, 41 mg, 0.20 mmol), DCC (41 mg, 0.20 mmol) and HOBT (56 mg, 0.41 mmol) were suspended in $CH_2Cl_2$ (1 mL). The resulting mixture was stirred at room temperature for 20 hours. The reaction crude was filtered through a pad of celite and the filtrate was washed with sat'd $NaHCO_3$ solution and $H_2O$. The organic layer was dried over $MgSO_4$, concentrated, and purified by flash chromatography (0-40% EtOAc/hexanes) to give the title compound in 12 mg. MS: (−) m/z 432.22 (M−1).

d) 4-(1-Cyano-4-hydroxy-7-phenoxyisoquinoline-3-carboxamido)-4-methylpentanoic acid Methyl 4-(1-cyano-4-hydroxy-7-phenoxyisoquinoline-3-carboxamido)-4-methylpentanoate (16 mg, 0.04 mmol) was dissolved in MeOH (4 mL) and 2 N NaOH (4 mL). After stirring for 4 hours at room temperature, $H_2O$ (15 mL) and EtOAc (15 mL) were added. To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-30% MeOH/$CH_2Cl_2$ with 0.5% formic acid) to give the title compound in 14 mg. MS: (−) m/z 417.99 (M−1).

Example 47

(S)-3-[(1-Cyano-4-hydroxy-7-phenoxy-isoquinoline-3-carbonyl)-amino]-3-phenyl-propionic acid

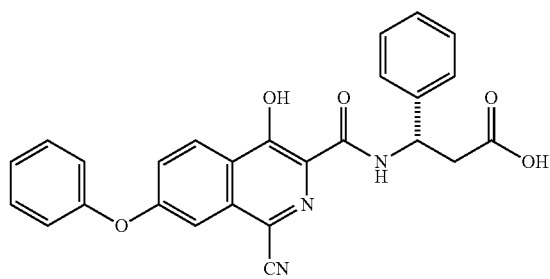 [SMILES: N#Cc1nc(C(=O)N[C@@H](CC(=O)O)c2ccccc2)c(O)c2ccc(Oc3ccccc3)cc12]

Methyl 1-cyano-4-hydroxy-7-phenoxyisoquinoline-3-carboxylate (20 mg, 0.06 mmol), (S)-3-amino-3-phenyl-propionic acid (62 mg, 0.38 mmol) (PepTech Corp., Burlington Mass.) and sodium methoxide (19 mg, 0.35 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/$CH_2Cl_2$ with 0.5% formic acid) to give the title compound in 15 mg. MS: (−) m/z 452.00 (M−1).

Example 48

(R)-3-[(1-Cyano-4-hydroxy-7-phenoxy-isoquinoline-3-carbonyl)-amino]-3-phenyl-propionic acid

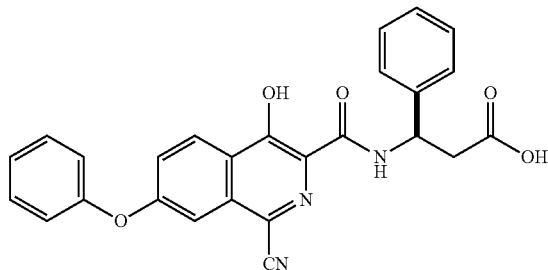 [SMILES: N#Cc1nc(C(=O)N[C@H](CC(=O)O)c2ccccc2)c(O)c2ccc(Oc3ccccc3)cc12]

Methyl 1-cyano-4-hydroxy-7-phenoxyisoquinoline-3-carboxylate (20 mg, 0.06 mmol), (R)-3-amino-3-phenyl-propionic acid (62 mg, 0.38 mmol, PepTech) and sodium methoxide (19 mg, 0.35 mmol) were suspended in 2-methoxyethanol (3 mL). The resulting mixture was heated to reflux for 3 hours and then cooled to room temperature. The solvent was removed in vacuo and the residue was dissolved in $H_2O$ (15 mL) and EtOAc (15 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-50% EtOAc/$CH_2Cl_2$ with 0.5% formic acid) to give the title compound in 17 mg. MS: (−) m/z 451.93 (M−1).

Example 49

(S)-2-Benzyl-3-[(1-cyano-4-hydroxy-7-phenoxy-isoquinoline-3-carbonyl)-amino]-propionic acid

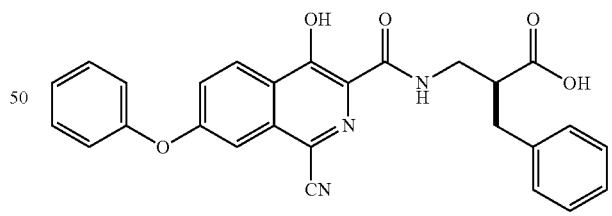

a) (S)-3-Amino-2-benzyl-propionic acid

Boc-(S)-3-amino-2-benzylpropionic acid (105 mg, 0.38 mmol, PepTech) was dissolved in TFA (4 mL) and $CH_2Cl_2$ (4 mL). The resulting mixture was stirred at room temperature for 3 hours. The volatiles were removed in vacuo and the residue was dissolved again in $CH_2Cl_2$ (4 mL). The volatiles were removed again in vacuo to give the title compound as its TFA salt, which was used in the subsequent step without further purification.

b) (S)-2-Benzyl-3-[(1-cyano-4-hydroxy-7-phenoxy-isoquinoline-3-carbonyl)-amino]propionic acid Methyl 1-cyano-4-hydroxy-7-phenoxyisoquinoline-3-carboxylate (20 mg, 0.06 mmol), (S)-3-amino-2-benzyl-propionic acid (crude as TFA salt, 0.38 mmol) and sodium methoxide (40 mg, 0.74 mmol) were suspended in 2-methoxyethanol (3 mL). The resulting mixture was heated to reflux for 3 hours and then cooled to room temperature. The solvent was removed in vacuo and the residue was dissolved in H₂O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-50% EtOAc/CH₂Cl₂ with 0.5% formic acid) to give the title compound in 17 mg. MS: (−) m/z 465.96 (M−1).

Example 50

(R)-2-Amino-4-(1-cyano-4-hydroxy-7-phenoxyisoquinoline-3-carboxamido)butanoic acid

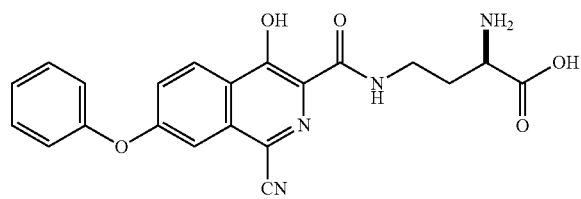

a) (R)-4-Amino-2-(tert-butoxycarbonylamino)butanoic acid

Boc-D-Dab(Fmoc)-OH (206 mg, 0.5 mmol, Oakwood Products) and piperidine (0.3 mL, 3.03 mmol) were dissolved in DMF (1.6 mL). The resulting mixture was stirred at room temperature for 30 minutes. The volatiles were removed in vacuo and the residue was used directly in the subsequent step without further purification.

b) (R)-2-(tert-Butoxycarbonylamino)-4-(1-cyano-4-hydroxy-7-phenoxyisoquinoline-3-carboxamido)butanoic acid Methyl 1-cyano-4-hydroxy-7-phenoxyisoquinoline-3-carboxylate (25 mg, 0.08 mmol), (R)-4-amino-2-(tert-butoxycarbonylamino)butanoic acid (crude, 0.47 mmol) and sodium methoxide (24 mg, 0.44 mmol) were suspended in 2-methoxyethanol (5 mL). The resulting mixture was heated to reflux for 2 hours and then cooled to room temperature. The solvent was removed in vacuo and the residue was dissolved in H₂O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-20% EtOAc/CH₂Cl₂ with 0.5% formic acid) to give the title compound in 20 mg. MS: (−) m/z 505.35 (M−1).

c) (R)-2-Amino-4-(1-cyano-4-hydroxy-7-phenoxy-isoquinoline-3-carboxamido)butanoic acid (R)-2-(tert-Butoxycarbonylamino)-4-(1-cyano-4-hydroxy-7-phenoxyisoquinoline-3-carboxamido)butanoic acid (40 mg, 0.06 mmol) was dissolved in TFA (4 mL) and CH₂Cl₂ (4 mL). The resulting mixture was stirred at room temperature for 3 hours. The volatiles were removed in vacuo and the residue was dissolved again in CH₂Cl₂ (4 mL). The volatiles were removed again in vacuo to give the title compound as its TFA salt in 19 mg. MS: (−) m/z 405.27 (M−1).

Example 51

(R)-2-Acetylamino-4-[(1-cyano-4-hydroxy-7-phenoxy-isoquinoline-3-carbonyl)-amino]-butyric acid

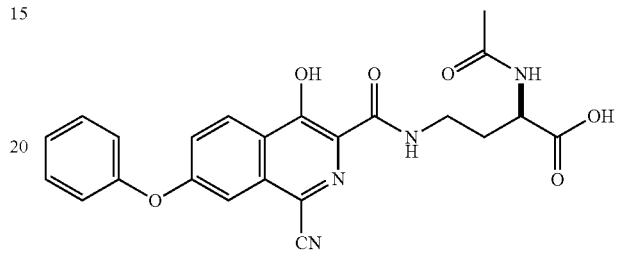

(R)-2-Amino-4-(1-cyano-4-hydroxy-7-phenoxyisoquinoline-3-carboxamido)butanoic acid (15 mg, 0.03 mmol) in CH₂Cl₂ (1 mL) was cooled to 0° C. To the solution were added triethylamine (0.03 mL, 0.21 mmol) and acetic anhydride (4 μL, 0.05 mmol). After stirring for 5 minutes at 0° C., H₂O (10 mL) and EtOAc (10 mL) were added. To the stirred mixture was added 1 N hydrochloric acid (1 mL). The layers were separated and the aqueous layer was extracted twice with EtOAc. The combined organic layers were dried over MgSO₄, concentrated, and purified by flash chromatography (0-20% MeOH/CH₂Cl₂ with 0.5% formic acid) to give the title compound in 10 mg. MS: (−) m/z 447.21 (M−1).

Example 52

(R)-4-(1-Cyano-4-hydroxy-7-phenoxyisoquinoline-3-carboxamido)-2-(3-ethylureido)butanoic acid

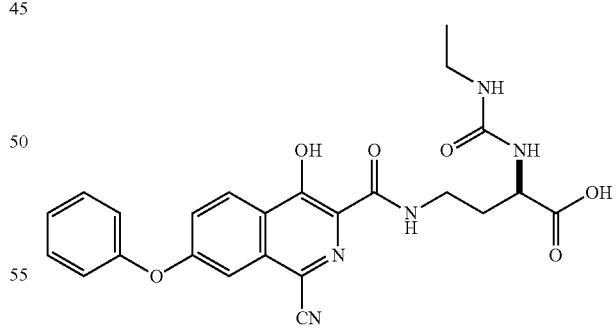

(R)-2-Amino-4-(1-cyano-4-hydroxy-7-phenoxyisoquinoline-3-carboxamido)butanoic acid (15 mg, 0.03 mmol) in CH₂Cl₂ (1 mL) was cooled to 0° C. To the solution were added triethylamine (0.03 mL, 0.21 mmol) and ethyl isocyanate (5 μL, 0.06 mmol). After stirring for 40 minutes at 0° C., H₂O (10 mL) and EtOAc (10 mL) were added. To the stirred mixture was added 1 N hydrochloric acid (1 mL). The layers were separated and the aqueous layer was extracted twice with EtOAc. The combined organic layers were dried over MgSO$_4$, concentrated, and purified by flash chromatography (0-20% MeOH/CH$_2$Cl$_2$ with 0.5% formic acid) to give the title compound in 13 mg. MS: (−) m/z 476.25 (M−1).

Example 53

(R)-4-(1-Cyano-4-hydroxy-7-phenoxyisoquinoline-3-carboxamido)-2-(methoxycarbonylamino)butanoic acid

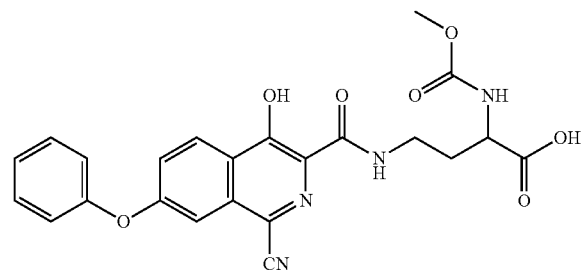 [SMILES: COC(=O)NC(CCNC(=O)c1nc(C#N)c2cc(Oc3ccccc3)ccc2c1O)C(=O)O]

(R)-2-Amino-4-(1-cyano-4-hydroxy-7-phenoxyisoquinoline-3-carboxamido)butanoic acid (15 mg, 0.03 mmol) in CH$_2$Cl$_2$ (1 mL) was cooled to 0° C. To the solution were added triethylamine (0.03 mL, 0.21 mmol) and methyl chloroformate (4 µL, 0.05 mmol). After stirring for 5 minutes at 0° C., H$_2$O (10 mL) and EtOAc (10 mL) were added. To the stirred mixture was added 1 N hydrochloric acid (1 mL). The layers were separated and the aqueous layer was extracted twice with EtOAc. The combined organic layers were dried over MgSO$_4$, concentrated, and purified by flash chromatography (0-20% MeOH/CH$_2$Cl$_2$ with 0.5% formic acid) to give the title compound in 5 mg. MS: (−) m/z 463.21 (M−1).

Example 54

(R)-4-(1-Cyano-4-hydroxy-7-phenoxyisoquinoline-3-carboxamido)-2-(3,3-dimethylureido)butanoic acid

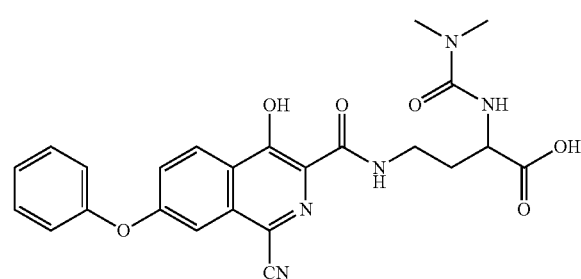 [SMILES: CN(C)C(=O)NC(CCNC(=O)c1nc(C#N)c2cc(Oc3ccccc3)ccc2c1O)C(=O)O]

(R)-2-Amino-4-(1-cyano-4-hydroxy-7-phenoxyisoquinoline-3-carboxamido)butanoic acid (16 mg, 0.03 mmol) in CH$_2$Cl$_2$ (1 mL) was cooled to 0° C. To the solution were added triethylamine (0.05 mL, 0.31 mmol) and dimethylcarbamoyl chloride (4 µL, 0.05 mmol). After stirring for 16 hours at room temperature, H$_2$O (10 mL) and EtOAc (10 mL) were added. To the stirred mixture was added 1 N hydrochloric acid (1 mL). The layers were separated and the aqueous layer was extracted twice with EtOAc. The combined organic layers were dried over MgSO$_4$, concentrated, and purified by flash chromatography (0-20% MeOH/CH$_2$Cl$_2$ with 0.5% formic acid) to give the title compound in 9 mg. MS: (−) m/z 476.25 (M−1).

Example 55

(R)-4-(1-Cyano-4-hydroxy-7-phenoxyisoquinoline-3-carboxamido)-2-ureidobutanoic acid

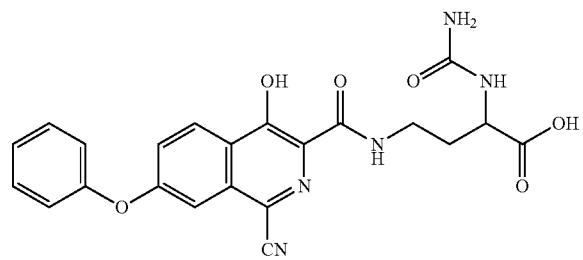 [SMILES: N#Cc1nc(C(=O)NCCC(NC(N)=O)C(=O)O)c(O)c2ccc(Oc3ccccc3)cc12]

(R)-2-Amino-4-(1-cyano-4-hydroxy-7-phenoxyisoquinoline-3-carboxamido)butanoic acid (21 mg, 0.04 mmol) in CH$_2$Cl$_2$ (1.5 mL) was cooled to 0° C. To the solution were added triethylamine (0.05 mL, 0.32 mmol) and (trimethylsilyl)isocyanate (0.02 mL, 0.16 mmol). After stirring for 16 hours at room temperature, H$_2$O (15 mL) and EtOAc (15 mL) were added. To the stirred mixture was added 1 N hydrochloric acid (1 mL). The layers were separated and the aqueous layer was extracted twice with EtOAc. The combined organic layers were dried over MgSO$_4$, concentrated, and purified by flash chromatography (0-20% MeOH/CH$_2$Cl$_2$ with 0.5% formic acid) to give the title compound in 5 mg. MS: (−) m/z 448.29 (M−1).

Example 56

4-(1-Cyano-4-hydroxy-7-phenoxyisoquinoline-3-carboxamido)-2-oxobutanoic acid

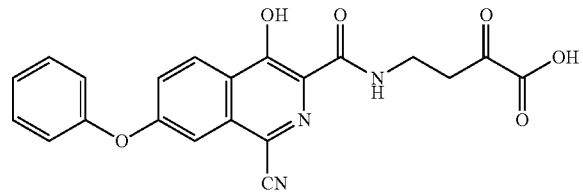 [SMILES: N#Cc1nc(C(=O)NCCC(=O)C(=O)O)c(O)c2ccc(Oc3ccccc3)cc12]

a) (S)-4-(1-Cyano-4-hydroxy-7-phenoxyisoquinoline-3-carboxamido)-2-hydroxybutanoic acid Methyl 1-cyano-4-hydroxy-7-phenoxyisoquinoline-3-carboxylate (200 mg, 0.63 mmol), (S)-4-amino-2-hydroxybutanoic acid (372 mg, 3.13 mmol, Sigma-Aldrich) and sodium methoxide (155 mg, 2.87 mmol) were suspended in 2-methoxyethanol (7 mL). The resulting mixture was heated to reflux for 3 hours and then cooled to room temperature. The solvent was removed in vacuo and the residue was dissolved in H$_2$O (20 mL) and EtOAc (20 mL). To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-20% MeOH/CH₂Cl₂ with 0.5% formic acid) to give the title compound in 180 mg. MS: (−) m/z 406.28 (M−1).

b) (S)-Methyl 4-(1-cyano-4-hydroxy-7-phenoxyisoquinoline-3-carboxamido)-2-hydroxybutanoate To a solution of (S)-4-(1-cyano-4-hydroxy-7-phenoxyisoquinoline-3-carboxamido)-2-hydroxybutanoic acid (73 mg, 0.18 mmol) in anhydrous MeOH (25 mL) was added concentrated H₂SO₄ (3 drops). The resulting mixture was heated to reflux for 20 hours. The volatiles were removed in vacuo and the residue was purified by flash chromatography (0-30% EtOAc/CH₂Cl₂) to give the title compound in 54 mg. MS: (−) m/z 420.26 (M−1).

c) Methyl 4-(1-cyano-4-hydroxy-7-phenoxyisoquinoline-3-carboxamido)-2-oxobutanoate To a solution of (S)-Methyl 4-(1-cyano-4-hydroxy-7-phenoxyisoquinoline-3-carboxamido)-2-hydroxybutanoate (54 mg, 0.13 mmol) in anhydrous CH₂Cl₂ (5 mL) was added Dess-Martin periodinane (65 mg, 0.15 mmol). After stirring for 1 hour at room temperature, 2% Na₂S₂O₃ (6 mL) was added and the resulting mixture was stirred at room temperature for 30 minutes. The layers were separated and the organic layer was washed with H₂O, dried over MgSO₄, concentrated, and purified by flash chromatography (0-20% EtOAc/CH₂Cl₂) to give the title compound in 34 mg. MS: (−) m/z 418.24 (M−1).

d) 4-(1-Cyano-4-hydroxy-7-phenoxyisoquinoline-3-carboxamido)-2-oxobutanoic acid

Methyl 4-(1-cyano-4-hydroxy-7-phenoxyisoquinoline-3-carboxamido)-2-oxobutanoate (34 mg, 0.08 mmol) was dissolved in MeOH (2 mL) and 2 N NaOH (2 mL). After stirring for 2 hours at room temperature, H₂O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-20% MeOH/CH₂Cl₂) to give the title compound in 20 mg. MS: (−) m/z 404.14 (M−1).

Example 57

2-((1-Cyano-4-hydroxy-7-phenoxyisoquinoline-3-carboxamido)methyl)butanoic acid

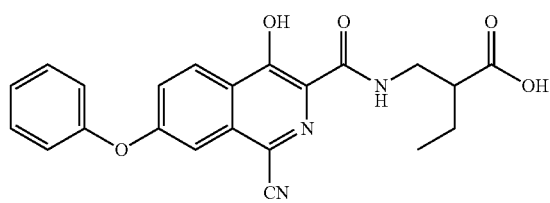 [SMILES: CCC(CNC(=O)c1nc(C#N)c2cc(Oc3ccccc3)ccc2c1O)C(=O)O]

a) Methyl 2-cyanobutanoate

To a solution of methyl 2-cyanoacetate (2.0 mL, 22.61 mmol., Acros) and DBU (3.4 mL, 22.61 mmol) in DMF (22 mL) was added iodoethane (2.0 mL, 24.90 mmol) dropwise at 0° C. The resulting mixture was heated to 70° C. for 20 hours. After cooling to room temperature, H₂O (150 mL) and EtOAc (150 mL) were added. The layers were separated and the aqueous layer was extracted twice with EtOAc. The combined organic layers were dried over MgSO₄, concentrated, and purified by flash chromatography (0-30% EtOAc/hexanes) to give the title compound in 300 mg. ¹H NMR (CDCl₃, 200 MHz): δ=3.82 (s, 3H), 3.48 (dd, 1H, J=5.9 Hz and 6.8 Hz), 2.08-1.92 (m, 2H), 1.12 (t, 3H, J=7.3 Hz).

b) 2-Aminomethyl-butyric acid methyl ester

To a slurry of Raney-Ni (1.9 g, 50% in H₂O, rinsed 3 times with EtOH before use) in EtOH (20 mL) was added methyl 2-cyanobutanoate (200 mg, 1.57 mmol). The resulting mixture was stirred under a hydrogen atmosphere at room temperature for 20 hours. The liquid was then carefully decanted into another flask and the metal was washed twice with EtOH. The combined EtOH solution was concentrated in vacuo to give the title compound in 200 mg, which was used in the subsequent step without further purification.

c) 2-{[(1-Cyano-4-hydroxy-7-phenoxy-isoquinoline-3-carbonyl)-amino]-methyl}-butyric acid methyl ester Methyl 1-cyano-4-hydroxy-7-phenoxyisoquinoline-3-carboxylate (60 mg, 0.19 mmol) and 2-aminomethyl-butyric acid methyl ester (crude, 1.57 mmol) in MeOH (3 mL) were heated at 150° C. in a microwave for 3 hours. The solvent was removed in vacuo and the residue oil was purified by flash chromatography (0-50% EtOAc/hexanes) to give the title compound in 55 mg. MS: (−) m/z 418.14 (M−1).

d) 2-((1-Cyano-4-hydroxy-7-phenoxyisoquinoline-3-carboxamido)methyl)butanoic acid 2-{[(1-Cyano-4-hydroxy-7-phenoxy-isoquinoline-3-carbonyl)-amino]-methyl}-butyric acid methyl ester (55 mg, 0.13 mmol) was dissolved in MeOH (3 mL) and 2 N NaOH (3 mL). After stirring for 16 hours at room temperature, the solvent was partially removed (until 3-4 mL left). H₂O (15 mL) and 1 N hydrochloric acid were added until pH was 1. The resulting suspension was filtered. The solid was washed with H₂O and dried to give the title compound in 35 mg. MS: (−) m/z 404.32 (M−1).

Example 58

2-{[(1-Cyano-4-hydroxy-7-phenoxy-isoquinoline-3-carbonyl)-amino]-methyl}-2-methyl-butyric acid

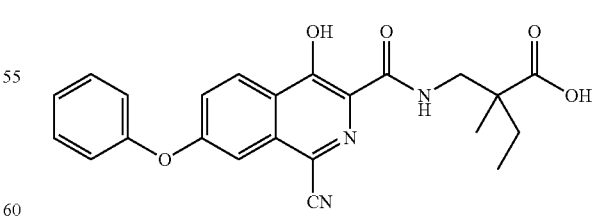

a) 2-Cyano-butyric acid tert-butyl ester

To a solution of cyanoacetic acid tert-butyl ester (10.0 mL, 69.99 mmoL) (TCI America, Portland Oreg.) and DBU (10.5 mL, 69.99 mmol) in DMF (70 mL) was added iodoethane (6.8 mL, 84.00 mmol) dropwise at 0° C. The resulting mixture was heated to 70° C. for 20 hours. After cooling to room temperature, H₂O (350 mL) and EtOAc (350 mL) were added. The layers were separated and the aqueous layer was extracted twice with EtOAc. The combined organic layers were dried over MgSO₄, concentrated, and purified by flash chromatography (0-30% EtOAc/hexanes) to give the title compound in 5 g. ¹H NMR (CDCl₃, 200 MHz): δ=3.36 (dd, 1H, J=6.3 Hz and 6.3 Hz), 2.06-1.88 (m, 2H), 1.49 (s, 9H), 1.11 (t, 3H, J=7.3 Hz).

b) 2-Cyano-2-methyl-butyric acid tert-butyl ester

To a solution of 2-cyano-butyric acid tert-butyl ester (810 mg, 4.79 mmoL) and DBU (1.4 mL, 9.58 mmol) in DMF (5 mL) was added iodomethane (1.2 mL, 19.20 mmol) dropwise at 0° C. The resulting mixture was heated to 40° C. for 24 hours. After cooling to room temperature, H₂O (50 mL) and EtOAc (50 mL) were added. The layers were separated and the aqueous layer was extracted twice with EtOAc. The combined organic layers were dried over MgSO₄, concentrated, and purified by flash chromatography (0-30% EtOAc/hexanes) to give the title compound in 650 mg. ¹H NMR (CDCl₃, 200 MHz): δ=2.05-1.6 (m, 2H), 1.53 (s, 3H), 1.50 (s, 9H), 1.07 (t, 3H, J=7.3 Hz).

c) 2-Aminomethyl-2-methyl-butyric acid tert-butyl ester

To a slurry of Raney-Ni (2.9 g, 50% in H₂O, rinsed 3 times with EtOH before use) in EtOH (40 mL) was added 2-cyano-2-methyl-butyric acid tert-butyl ester (650 mg, 3.55 mmol). The resulting mixture was stirred under a hydrogen atmosphere at room temperature for 16 hours. The liquid was then carefully decanted into another flask and the metal was washed twice with EtOH. The combined EtOH solution was concentrated in vacuo to give the title compound in 600 mg, which was used directly in the subsequent step without further purification.

d) 2-{[(1-Cyano-4-hydroxy-7-phenoxy-isoquinoline-3-carbonyl)-amino]-methyl}-2-methyl-butyric acid tert-butyl ester Methyl 1-cyano-4-hydroxy-7-phenoxyisoquinoline-3-carboxylate (55 mg, 0.17 mmol) and 2-aminomethyl-2-methyl-butyric acid tert-butyl ester (88 mg of the crude, 0.47 mmol) in MeOH (3 mL) were heated at 140° C. in a microwave for 1 hour. The solvent was removed in vacuo and the residue oil was purified by flash chromatography (0-50% EtOAc/hexanes) to give the title compound in 60 mg. MS: (-) m/z 474.24 (M-1).

e) 2-{[(1-Cyano-4-hydroxy-7-phenoxy-isoquinoline-3-carbonyl)-amino]-methyl}-2-methyl-butyric acid 2-{[(1-Cyano-4-hydroxy-7-phenoxy-isoquinoline-3-carbonyl)-amino]-methyl}-2-methyl-butyric acid tert-butyl ester (45 mg, 0.10 mmol) was dissolved in TFA (1.7 mL) and CH₂Cl₂ (1.7 mL). The resulting mixture was stirred at room temperature for 2 hours. The volatiles were removed in vacuo and the residue was dissolved again in CH₂Cl₂ (4 mL). The volatiles were removed again in vacuo to give the title compound in 36 mg. MS: (-) m/z 418.14 (M-1).

Example 59

3{-[1-Cyano-4-hydroxy-7-(naphthalen-2-yloxy)-isoquinoline-3-carbonyl]-amino}-2,2-dimethyl-propionic acid

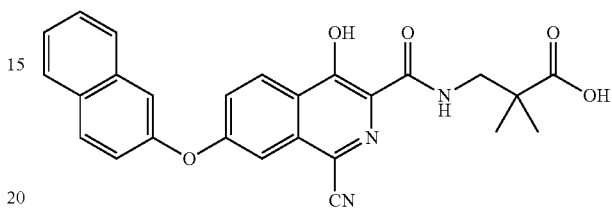

a) 1-Cyano-4-hydroxy-7-(naphthalen-2-yloxy)-isoquinoline-3-carboxylic acid methyl ester 4-Hydroxy-1-iodo-7-(naphthalen-2-yloxy)-isoquinoline-3-carboxylic acid methyl ester (130 mg, 0.28 mmol) and CuCN (49 mg, 0.55 mmol) were suspended in DMF (1.1 mL). The resulting mixture was heated at 120° C. for 7 minutes and then cooled to room temperature. The reaction crude was poured into CH₂Cl₂ (30 mL) and stirred vigorously for 10 minutes at room temperature. The resulting suspension was filtered through a pad of celite and the filtrate was washed with H₂O and brine sequentially. The organic layer was dried over MgSO₄, concentrated, and purified by flash chromatography (0-50% EtOAc/hexanes) to give the title compound in 75 mg. MS: (-) m/z 369.24 (M-1).

b) 3-{[1-Cyano-4-hydroxy-7-(naphthalen-2-yloxy)-isoquinoline-3-carbonyl]-amino}-2,2-dimethyl-propionic acid ethyl ester 1-Cyano-4-hydroxy-7-(naphthalen-2-yloxy)-isoquinoline-3-carboxylic acid methyl ester (15 mg, 0.04 mmol) and ethyl 3-amino-2,2-dimethylpropanoate (24 mg, 0.16 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 18 mg. MS: (-) m/z 482.36 (M-1).

c) 3-{[1-Cyano-4-hydroxy-7-(naphthalen-2-yloxy)-isoquinoline-3-carbonyl]-amino}-2,2-dimethyl-propionic acid 3-{[1-Cyano-4-hydroxy-7-(naphthalen-2-yloxy)-isoquinoline-3-carbonyl]-amino}-2,2-dimethyl-propionic acid ethyl ester (18 mg, 0.04 mmol) was dissolved in MeOH (3 mL) and 2 N NaOH (3 mL). After stirring for 4 hours at room temperature, H₂O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-30% MeOH/CH₂Cl₂) to give the title compound in 10 mg. MS: (−) m/z 453.90 (M−1).

Example 60

3{-[1-Cyano-4-hydroxy-7-(2-methoxy-phenoxy)-isoquinoline-3-carbonyl]-amino}-2,2-dimethyl-propionic acid

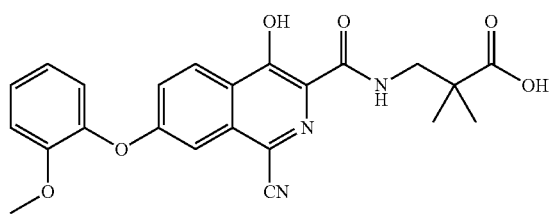 [SMILES: COc1ccccc1Oc1ccc2c(O)c(C(=O)NCC(C)(C)C(=O)O)nc(C#N)c2c1]

a) 1-Cyano-4-hydroxy-7-(2-methoxy-phenoxy)-isoquinoline-3-carboxylic acid methyl ester 4-Hydroxy-1-iodo-7-(2-methoxy-phenoxy)-isoquinoline-3-carboxylic acid methyl ester (150 mg, 0.33 mmol) and CuCN (60 mg, 0.67 mmol) were suspended in DMF (1.3 mL). The resulting mixture was heated at 120° C. for 7 minutes and then cooled to room temperature. The reaction crude was poured into CH₂Cl₂ (30 mL) and stirred vigorously for 10 minutes at room temperature. The resulting suspension was filtered through a pad of celite and the filtrate was washed with H₂O and brine sequentially. The organic layer was dried over MgSO₄, concentrated, and purified by flash chromatography (0-50% EtOAc/hexanes) to give the title compound in 100 mg. MS: (−) m/z 349.28 (M−1).

b) 3-{[1-Cyano-4-hydroxy-7-(2-methoxy-phenoxy)-isoquinoline-3-carbonyl]-amino}-2,2-dimethyl-propionic acid ethyl ester 1-Cyano-4-hydroxy-7-(2-methoxy-phenoxy)-isoquinoline-3-carboxylic acid methyl ester (23 mg, 0.07 mmol) and ethyl 3-amino-2,2-dimethylpropanoate (38 mg, 0.26 mmol) in EtOH (3 mL) were heated at 150° C. in a microwave for 1.5 hours. The solvent was removed in vacuo and the residue oil was purified by flash chromatography (0-50% EtOAc/hexanes) to give the title compound in 20 mg. ¹H NMR (CDCl₃, 200 MHz): δ=8.36 (d, 1H, J=9.0 Hz), 8.29 (t, 1H, J=6.2 Hz), 7.55-7.47 (m, 1H), 7.42-7.39 (m, 1H), 7.33-7.22 (m, 1H), 7.20-6.98 (m, 3H), 4.23 (q, 2H, J=7.0 Hz), 3.80 (s, 3H), 3.60 (d, 2H, J=6.2 Hz), 1.36 (t, 3H, J=7.0 Hz), 1.29 (s, 6H).

c) 3-{[1-Cyano-4-hydroxy-7-(2-methoxy-phenoxy)-isoquinoline-3-carbonyl]amino}-2,2-dimethyl-propionic acid 3-{[1-Cyano-4-hydroxy-7-(2-methoxy-phenoxy)-isoquinoline-3-carbonyl]-amino}-2,2-dimethyl-propionic acid ethyl ester (20 mg, 0.04 mmol) was dissolved in MeOH (3 mL) and 2 N NaOH (3 mL). After stirring for 4 hours at room temperature, H₂O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-30% MeOH/CH₂Cl₂) to give the title compound in 12 mg. MS: (−) m/z 434.01 (M−1).

Example 61

3-[(1-Cyano-4-hydroxy-7-phenoxy-isoquinoline-3-carbonyl)-amino]-4-methyl-pentanoic acid

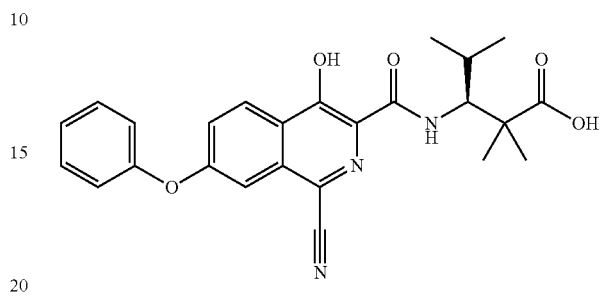

A mixture of 1-Cyano-4-hydroxy-7-phenoxy-isoquinoline-3-carboxylic acid methyl ester (50 mg, 0.16 mmole), (R)-3-amino-4-methylpentanoic acid hydrochloride (52 mg, 0.31 mmole) (Chem-Impex International Inc., Wood Dale Ill.), and sodium methoxide (25 mg, 0.46 mmole) in 2-methoxyethanol was stirred at 130° C. for two hours before it was cooled to room temperature and acidified with 1 N HCl. The mixture was partitioned between dichloromethane and water. The organic layer was dried over anhydrous sodium sulfate and concentrated in vacuo. The residue was purified by flash column chromatography on silica gel with a gradient of 1% acetic acid, ethyl acetate and hexanes to give the title compound as a yellow solid (9 mg): MS: (+) m/z 420.06 (M+1), (−) m/z 418.02 (M−1).

Example 62

3{-[1-Cyano-7-(2-ethyl-phenoxy)-4-hydroxy-isoquinoline-3-carbonyl]-amino}-2,2-dimethyl-propionic acid

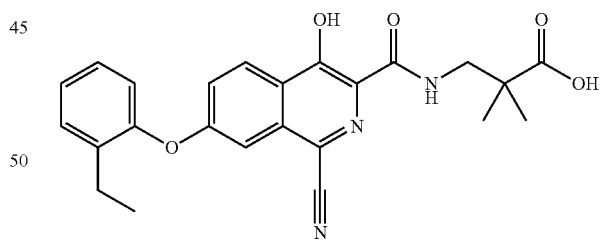

a) 1-Cyano-7-(2-ethyl-phenoxy)-4-hydroxy-isoquinoline-3-carboxylic acid methyl ester A mixture of 7-(2-Ethyl-phenoxy)-4-hydroxy-1-iodo-isoquinoline-3-carboxylic acid methyl ester (1.5 g, 3.34 mmole) and copper cyanide (598 ml, 6.68 mmole) in anhydrous dimethylformamide (13 ml) was refluxed for 5 minutes before it was cooled to room temperature and dichloromethane was added and stirred for 5 minutes. The suspension was filtered. The filtrate was washed with 0.1 N HCl, twice with water, brine, dried over anhydrous sodium sulfate and concentrated in vacuo. The residue was recrystallized with acetonitrile.

The crystal was filtered and dried to give the title compound as a white solid (902 mg): MS: (+) m/z 349.08 (M+1), (−) m/z 347.10 (M−1).

b) 3-{[1-Cyano-7-(2-ethyl-phenoxy)-4-hydroxy-isoquinoline-3-carbonyl]amino}-2,2-dimethyl-propionic acid ethyl ester A mixture of 1-Cyano-7-(2-ethyl-phenoxy)-4-hydroxy-isoquinoline-3-carboxylic acid methyl ester (50 mg, 0.14 mmole) and 3-amino-2,2-dimethyl-propionic acid ethyl ester (41 mg, 0.43 mmole) in anhydrous ethanol (0.7 ml) was stirred at 130° C. for two hours and 150° C. for one hour before it was cooled to room temperature, concentrated and by flash column chromatography on silica gel with a gradient of ethyl acetate and hexanes to give the title compound as a colorless oil (20.3 mg): MS: (+) m/z 462.22 (M+1), (−) m/z 460.10 (M−1).

c) 3-{[1-Cyano-7-(2-ethyl-phenoxy)-4-hydroxy-isoquinoline-3-carbonyl]amino}-2,2-dimethyl-propionic acid A mixture of 3-{[1-Cyano-7-(2-ethyl-phenoxy)-4-hydroxy-isoquinoline-3-carbonyl]-amino}-2,2-dimethyl-propionic acid ethyl ester (20.3 mg, 0.04 mmole) and 1N NaOH (0.4 ml, 0.4 mmole) in a mixture of tetrahydrofuran (0.5 ml) and methanol (1 ml) was stirred room temperature for three days before it was concentrated and acidified with 1N HCl to pH=3. The precipitated was filtered, dried to give the title compound as a white solid (15 mg): MS: (+) m/z 434.21 (M+1), (−) m/z 432.15 (M−1).

Example 63

3-(R)-[(1-Cyano-4-hydroxy-7-phenoxy-isoquinoline-3-carbonyl)-amino]-pentanoic acid

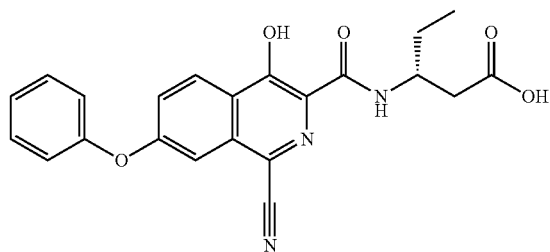 [SMILES: CC[C@H](CC(=O)O)NC(=O)c1nc(C#N)c2cc(Oc3ccccc3)ccc2c1O]

1-Cyano-4-hydroxy-7-phenoxy-isoquinoline-3-carboxylic acid methyl ester (75 mg, 0.234 mmol) and 3-(R)-amino-pentanoic acid (82 mg, 0.7 mmol) were placed in a CEM 10 mL Microwave vessel and sodium methoxide-methanol solution (0.5M; 1.4 mL, 0.7 mmol) was added via syringe. The vessel was sealed and heated to 130° C. in a CEM microwave apparatus for 150 minutes. The reaction mixture was diluted with water and treated with 1N hydrochloric acid. The crude precipitate was purified by MPLC (methylene chloride-ethyl acetate) to provide the title compound as an off-white solid in 73% yield. MS ESI(−) m/e: 403.9928 (M−1).

Example 64

3-(R)-[(1-Cyano-4-hydroxy-7-phenoxy-isoquinoline-3-carbonyl)-amino]-butyric acid

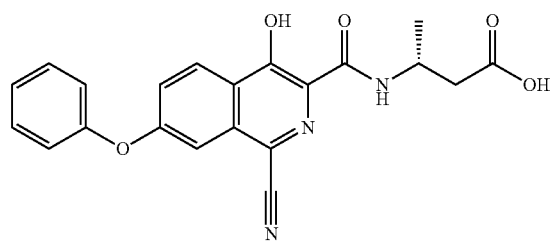 [SMILES: C[C@H](CC(=O)O)NC(=O)c1nc(C#N)c2cc(Oc3ccccc3)ccc2c1O]

1-Cyano-4-hydroxy-7-phenoxy-isoquinoline-3-carboxylic acid methyl ester (75 mg, 0.234 mmol) and 3-(R)-amino-butyric acid (103 mg, 1.0 mmol) were placed in a CEM 10 mL Microwave vessel and dissolved in anhydrous N,N-dimethylformamide (2 mL.) Sodium methoxide (54 mg, 1.0 mmol) was added to solution and the vessel was sealed. The reaction was heated to 140° C. in a CEM microwave apparatus for four hours. Upon completion, the reaction mixture was diluted with water and treated with 1N hydrochloric acid. The precipitate was dissolved in dichloromethane and dried over anhydrous sodium sulfate. The crude product was purified by MPLC (methylene chloride-ethyl acetate) to provide the title compound as a light-yellow solid in 75% yield. MS ESI(−) m/e: 390.091 (M−1).

Example 65

3-[(1-Cyano-4-hydroxy-7-phenoxy-isoquinoline-3-carbonyl)-amino]-2,2-difluoro-propionic acid

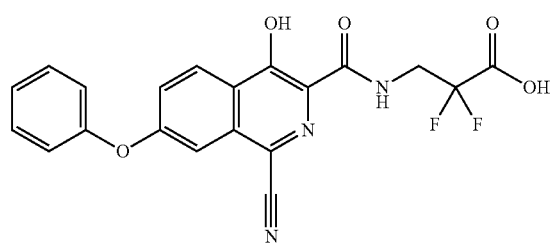 [SMILES: N#Cc1nc(C(=O)NCC(F)(F)C(=O)O)c(O)c2ccc(Oc3ccccc3)cc12]

1-Cyano-4-hydroxy-7-phenoxy-isoquinoline-3-carboxylic acid methyl ester (75 mg, 0.234 mmol) and 3-Amino-2,2-difluoro-propionic acid hydrochloride (122 mg, 0.75 mmol) were placed in a CEM 10 mL Microwave vessel and sodium methoxide-methanol solution (0.5M; 3 mL, 1.5 mmol) was added via syringe. The vessel was sealed and heated to 130° C. in a CEM microwave apparatus for 150 minutes. The reaction mixture was diluted with water and treated with 1N hydrochloric acid and extracted three times with ethyl acetate then dried over sodium sulfate. The solvent was removed in vacuo to provide the title compound as an orange solid in 51% yield. MS ESI(−) m/e: 412.1027 (M−1).

Example 66

3-[(1-Cyano-4-hydroxy-7-phenoxy-isoquinoline-3-carbonyl)-amino]-5-methyl-hexanoic acid

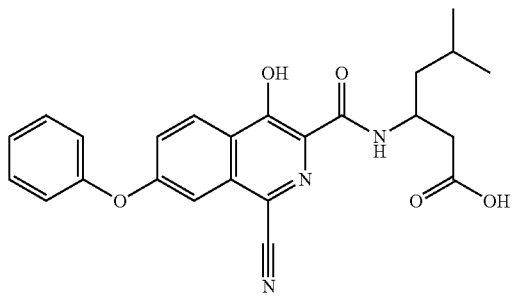 [SMILES: CC(C)CC(CC(=O)O)NC(=O)c1nc(C#N)c2cc(Oc3ccccc3)ccc2c1O]

1-Cyano-4-hydroxy-7-phenoxy-isoquinoline-3-carboxylic acid methyl ester (75 mg, 0.234 mmol) and 3-Amino-5-methyl-hexanoic acid (175 mg, 1.2 mmol) were placed in a CEM 10 mL Microwave vessel and sodium methoxide-methanol solution (0.5M; 2.4 mL, 1.2 mmol) was added via syringe. The vessel was sealed and heated to 130° C. in a CEM microwave apparatus for 4.5 hours. The reaction mixture was diluted with water and treated with 1N hydrochloric acid and extracted three times with ethyl acetate then dried over sodium sulfate. The crude product was purified by MPLC (methylene chloride-methanol) to provide the title compound as an off-white solid in 41% yield. MS ESI(−) m/e: 432.1062 (M−1).

Example 67

(S)-3-[(1-Cyano-4-hydroxy-7-phenoxy-isoquinoline-3-carbonyl)-amino]-4-phenyl-butyric acid

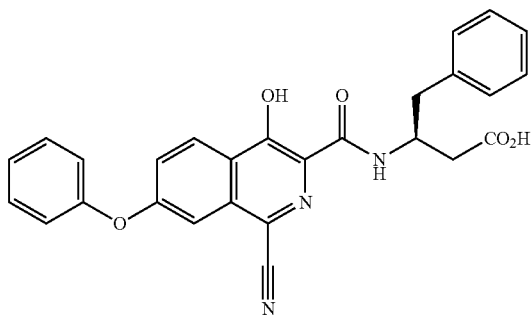 [SMILES: N#Cc1nc(C(=O)N[C@H](CC(=O)O)Cc2ccccc2)c(O)c2ccc(Oc3ccccc3)cc12]

a) (S)-3-[(1-Cyano-4-hydroxy-7-phenoxy-isoquinoline-3-carbonyl)-amino]-4-phenyl-butyric acid tert-butyl ester A mixture of 1-cyano-4-hydroxy-7-phenoxy-isoquinoline-3-carboxylic acid methyl ester (40 mg, 0.125 mmol) and (S)-3-amino-4-phenyl-butyric acid tert-butyl ester (88 mg, 0.375 mmol) (Acros Organics, Thermo Fisher Scientific, Morris Plains N.J.) in 2-methoxyethanol (10 mL) was refluxed for 1.5 h. The resulting mixture was concentrated in vacuo, and the residue was purified by column chromatography (0-40% EtOAc/hexanes) to give 50 mg of the title compound. MS: (−) m/z 522.25 (M−1).

b) (S)-3-[(1-Cyano-4-hydroxy-7-phenoxy-isoquinoline-3-carbonyl)-amino]-4-phenyl-butyric acid (S)-3-[(1-Cyano-4-hydroxy-7-phenoxy-isoquinoline-3-carbonyl)-amino]-4-phenyl-butyric acid tert-butyl ester (50 mg, 0.096 mmol) was dissolved in CH$_2$Cl$_2$ (4 mL) and cooled in an ice bath. Trifluoroacetic acid (4 mL) was added, and the mixture was stirred at r.t. for 2 h. The solvent was evaporated in vacuo, and the residue was partitioned between saturated NaHCO$_3$ and EtOAc. Hydrochloric acid (1 M) was added with vigorous stirring until pH was ~2. The organic layer was dried over MgSO$_4$ and concentrated. The crude product was first purified by column chromatography (0-40% EtOAc/hexanes+2% AcOH), then by preparative TLC (60% EtOAc/hexanes+2% AcOH) to give 20 mg of the title compound as a pale brown solid. MS: (+) m/z 468.14 (M+1).

Example 68

(R)-3-[(1-Cyano-4-hydroxy-7-phenoxy-isoquinoline-3-carbonyl)-amino]-4-phenyl-butyric acid

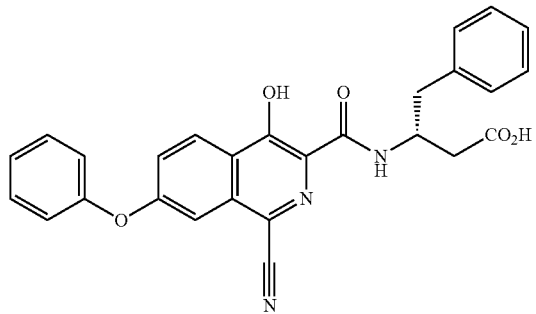 [SMILES: N#Cc1nc(C(=O)N[C@@H](CC(=O)O)Cc2ccccc2)c(O)c2ccc(Oc3ccccc3)cc12]

A mixture of 1-cyano-4-hydroxy-7-phenoxy-isoquinoline-3-carboxylic acid methyl ester (40 mg, 0.125 mmol), (R)-3-amino-4-phenyl-butyric acid HCl salt (270 mg, 1.25 mmol) (PepTech Corporation), and NaOMe (101 mg, 1.88 mmol) in 2-methoxyethanol (10 mL) was refluxed for 1.5 h. The resulting mixture was concentrated in vacuo, and the residue was partitioned between EtOAc and water. Hydrochloric acid (1 M) was added with vigorous stirring until pH ~2. The organic layer was dried over MgSO$_4$ and concentrated. The crude product was purified by column chromatography (5-40% EtOAc/hexanes+2% AcOH). The compound isolated was then dissolved in MeOH (2 mL) and treated with 2 M NaOH (2 mL) for 2 h. Hydrochloric acid (1 M) was added to acidify the mixture, and the mixture was extracted with EtOAc. The organic layer was dried over MgSO$_4$ and concentrated. The residue was purified by column chromatography (5-40% EtOAc/hexanes+2% AcOH) to give 33 mg of the title compound. MS: (+) m/z 468.06 (M+1).

Example 69

(2R,3R)-3-[(1-Cyano-4-hydroxy-7-phenoxy-isoquinoline-3-carbonyl)-amino]-2-methyl-butyric acid

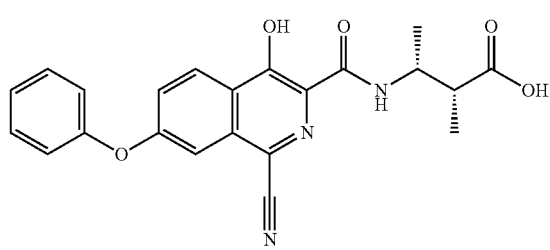 [SMILES: C[C@@H](NC(=O)c1nc(C#N)c2cc(Oc3ccccc3)ccc2c1O)[C@@H](C)C(=O)O]

a) (2R,3R)-3-Amino-2-methyl-butyric acid tert-butyl ester

A mixture of tert-butyl (2R,3R,aR)-3-(N-benzyl-N-α-methylbenzylamino)-2-methyl-butyrate (220 mg, 0.599 mmol) (Davies and Walters (1994) J. Chem. Soc. Perkins Trans. 1:1129-1139) and 20% Pd(OH)$_2$ on carbon (100 mg) in EtOH (10 mL) was stirred under H$_2$ atmosphere (1 atm) for 48 h, then filtered through a pad of Celite. The filtrate was concentrated to give 71 mg of the title compound, which was used in the next step without purification. $^1$H NMR (CDCl$_3$, 200 MHz): δ=3.50-3.70 (m, 1H), 2.65-2.85 (m, 1H), 1.46 (s, 9H), 1.39 (d, 3H, J=7.0 Hz), 1.28 (d, 3H, J=7.0 Hz).

b) (2R,3R)-3-[(1-Cyano-4-hydroxy-7-phenoxy-isoquinoline-3-carbonyl)-amino]-2-methyl-butyric acid A mixture of (2R,3R)-3-amino-2-methyl-butyric acid tert-butyl ester (20 mg, 0.117 mmol), 1-cyano-4-hydroxy-7-phenoxy-isoquinoline-3-carboxylic acid methyl ester (25 mg, 0.078 mmol), and triethylamine (0.050 mL) in EtOH (2 mL) was heated in a microwave reactor at 140° C. for 6 h. The resulting mixture was concentrated to dryness, and the residue was re-dissolved in CH$_2$Cl$_2$ and passed through a plug of silica gel. After evaporating the solvent, the residue was dissolved in CH$_2$Cl$_2$ (3 mL) and treated with trifluoroacetic acid (2 mL) for 2 h. The mixture was concentrated in vacuo, and the resulting residue was dissolved in saturated NaHCO$_3$ and washed several times with ether. The aqueous layer was acidified to pH ~2 and extracted with EtOAc. The organic layer was dried over MgSO$_4$ and concentrated to give 9.4 mg of the title compound as a pale pink solid. MS: (−) m/z 404.32 (M−1).

Example 70

(2S,3R)-3-[(1-Cyano-4-hydroxy-7-phenoxy-isoquinoline-3-carbonyl)-amino]-2-methyl-butyric acid

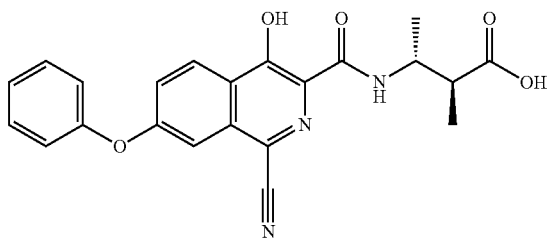 [SMILES: C[C@H](C(=O)O)[C@@H](C)NC(=O)c1nc(C#N)c2cc(Oc3ccccc3)ccc2c1O]

a) 1-Cyano-4-hydroxy-7-phenoxy-isoquinoline-3-carboxylic acid

A mixture of 1-cyano-4-hydroxy-7-phenoxy-isoquinoline-3-carboxylic acid methyl ester (140 mg, 0.44 mmol), 2 M NaOH (3 mL), MeOH (3 mL) and THF (3 mL) was stirred for 5 h at r.t. The resulting mixture was concentrated to approximately one-third of its original volume and then placed in an ice bath. Hydrochloric acid (1 M) was added until pH ~2, and the mixture was extracted with EtOAc. The organic layer was dried over MgSO$_4$ and concentrated to give 132 mg of the title compound as a white solid. MS: (−) m/z 305.26 (M−1).

b) (2S,3R)-3-Amino-2-methyl-butyric acid tert-butyl ester

A mixture of tert-butyl (2S,3R,aR)-3-(N-benzyl-N-α-methylbenzylamino)-2-methyl-butyrate (360 mg, 0.981 mmol) and 20% Pd(OH)$_2$ on carbon (150 mg) in EtOH (10 mL) was stirred under H$_2$ atmosphere (1 atm) for 48 h, then filtered through a pad of Celite. The filtrate was concentrated to give 117 mg of the title compound, which was used in the next step without purification. $^1$H NMR (CDCl$_3$, 200 MHz): δ=3.05-3.25 (m, 1H), 2.18-2.34 (m, 1H), 1.45 (s, 9H), 1.10 (d, 3H, J=7.0 Hz), 1.09 (d, 3H, J=6.6 Hz).

c) (2S,3R)-3-[(1-Cyano-4-hydroxy-7-phenoxy-isoquinoline-3-carbonyl)-amino]-2-methyl-butyric acid tert-butyl ester A flask was charged with 1-cyano-4-hydroxy-7-phenoxy-isoquinoline-3-carboxylic acid (40 mg, 0.13 mmol), HOBt (18 mg, 0.13 mmol) and CH$_2$Cl$_2$ (2 mL). EDC (35 mg, 0.18 mmol) was added, and the mixture was stirred for 10 min. (2S,3R)-3-Amino-2-methyl-butyric acid tert-butyl ester (22 mg, 0.13 mmol) and Hunig's base (0.050 mL, 0.26 mmol) were then added, and the resulting mixture was stirred for 16 h at r.t. Hydrochloric acid (0.1 M) was added to acidify the mixture, and the mixture was extracted with EtOAc. The organic layer was dried over MgSO$_4$ and concentrated. The crude product was purified by column chromatography (0-10% EtOAc/hexanes+2% AcOH) to give 32 mg of the title compound as a white solid. MS: (−) m/z 460.31 (M−1).

d) (2S,3R)-3-[(1-Cyano-4-hydroxy-7-phenoxy-isoquinoline-3-carbonyl)-amino]-2-methyl-butyric acid To a solution of (2S,3R)-3-[(1-cyano-4-phenoxy-isoquinoline-3-carbonyl)-amino]-2-methyl-butyric acid tert-butyl ester (32 mg, 0.069 mmol) in CH$_2$Cl$_2$ (3 mL) was added trifluoroacetic acid (2 mL) at 0° C., and the mixture was stirred at r.t. for 2 h. The mixture was concentrated in vacuo, and the resulting residue was dissolved in saturated NaHCO$_3$ and washed several times with ether. The aqueous layer was acidified to pH ~2 with 4 M HCl, and the resulting precipitate was isolated by filtration to give 24 mg of the title compound as a pale pink solid. MS: (−) m/z 404.32 (M−1).

Example 71

(2S,3S)-3-[(1-Cyano-4-hydroxy-7-phenoxy-isoquinoline-3-carbonyl)-amino]-2-methyl-butyric acid

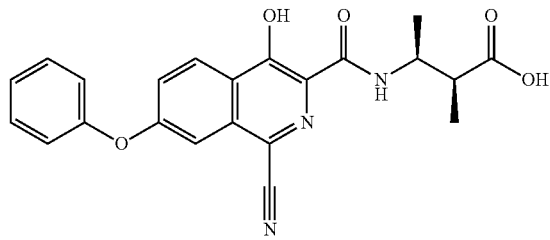 [SMILES: C[C@H](NC(=O)c1nc(C#N)c2cc(Oc3ccccc3)ccc2c1O)[C@H](C)C(=O)O]

a) (2S,3S)-3-Amino-2-methyl-butyric acid tert-butyl ester

A mixture of tert-butyl (2S,3S,αS)-3-(N-benzyl-N-α-methylbenzylamino)-2-methyl-butyrate (245 mg, 0.668 mmol) and 20% Pd(OH)$_2$ on carbon (100 mg) in EtOH (10 mL) was stirred under H$_2$ atmosphere (1 atm) for 48 h, then filtered through a pad of Celite. The filtrate was concentrated to give 86 mg of the title compound, which was used in the next step without purification. $^1$H NMR (CDCl$_3$, 200 MHz): δ=5.5 (broad), 3.45-3.65 (m, 1H), 2.60-2.75 (m, 1H), 1.46 (s, 9H), 1.36 (d, 3H, J=6.6 Hz), 1.26 (d, 3H, J=7.0 Hz).

b) (2S,3S)-3-[(1-Cyano-4-hydroxy-7-phenoxy-isoquinoline-3-carbonyl)-amino]-2-methyl-butyric acid A mixture of (2S,3S)-3-amino-2-methyl-butyric acid tert-butyl ester (20 mg, 0.12 mmol), 1-cyano-4-hydroxy-7-phenoxy-isoquinoline-3-carboxylic acid methyl ester (25 mg, 0.078 mmol), and triethylamine (0.050 mL) in EtOH (2 mL) was heated in a microwave reactor at 140° C. for 6 h. The resulting mixture was concentrated to dryness, and the residue was re-dissolved in CH$_2$Cl$_2$ and passed through a plug of silica gel. After evaporating the solvent, the residue was dissolved in CH$_2$Cl$_2$ (3 mL) and treated with trifluoroacetic acid (2 mL) for 2 h. The mixture was concentrated in vacuo, and the resulting residue was taken up in saturated NaHCO$_3$ and washed several times with ether. The aqueous layer was acidified to pH ~2 and extracted with EtOAc. The organic layer was dried over MgSO$_4$ and concentrated to give 11.1 mg of the title compound as a white solid. MS: (−) m/z 404.32 (M−1).

Example 72

(2R,3S)-3-[(1-Cyano-4-hydroxy-7-phenoxy-isoquinoline-3-carbonyl)-amino]-2-methyl-butyric acid

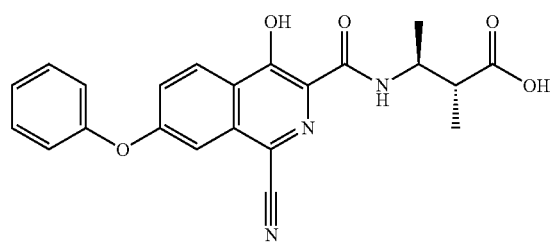 [SMILES: C[C@H](NC(=O)c1nc(C#N)c2cc(Oc3ccccc3)ccc2c1O)[C@@H](C)C(=O)O]

a) (2R,3S)-3-Amino-2-methyl-butyric acid tert-butyl ester

A mixture of tert-butyl (2R,3S,αS)-3-(N-benzyl-N-α-methylbenzylamino)-2-methyl-butyrate (458 mg, 1.25 mmol) and 20% Pd(OH)$_2$ on carbon (200 mg) in EtOH (10 mL) was stirred under H$_2$ atmosphere (1 atm) for 48 h, then filtered through a pad of Celite. The filtrate was concentrated to give 172 mg of the title compound, which was used in the next step without purification. $^1$H NMR (CDCl$_3$, 200 MHz): δ=8.4 (broad), 3.45-3.65 (m, 1H), 2.70-2.80 (m, 1H), 1.46 (s, 9H), 1.42 (d, 3H, J=7.0 Hz), 1.29 (d, 3H, J=7.0 Hz).

b) (2R,3S)-3-[(1-Cyano-4-hydroxy-7-phenoxy-isoquinoline-3-carbonyl)-amino]-2-methyl-butyric acid tert-butyl ester A flask was charged with 1-cyano-4-hydroxy-7-phenoxy-isoquinoline-3-carboxylic acid (40 mg, 0.13 mmol), HOBt (18 mg, 0.13 mmol) and CH$_2$Cl$_2$ (2 mL). EDC (35 mg, 0.18 mmol) was added, and the mixture was stirred for 10 min. (2R,3S)-3-Amino-2-methyl-butyric acid tert-butyl ester (22 mg, 0.13 mmol) and Hunig's base (0.050 mL, 0.26 mmol) were then added, and the resulting mixture was stirred for 3 days at r.t. Hydrochloric acid (0.1 M) was added to acidify the mixture, and the mixture was extracted with EtOAc. The organic layer was dried over MgSO$_4$ and concentrated. The crude product was purified by column chromatography (0-10% EtOAc/hexanes+2% AcOH) to give 30 mg of the title compound as a white solid. MS: (−) m/z 460.31 (M−1).

c) (2R,3S)-3-[(1-Cyano-4-hydroxy-7-phenoxy-isoquinoline-3-carbonyl)-amino]-2-methyl-butyric acid To a solution of (αR,3S)-3-[(1-cyano-4-hydroxy-7-phenoxy-isoquinoline-3-carbonyl)-amino]-2-methyl-butyric acid tert-butyl ester (30 mg, 0.065 mmol) in CH$_2$Cl$_2$ (3 mL) was added trifluoroacetic acid (2 mL) at 0° C., and the mixture was stirred at r.t. for 2 h. The mixture was concentrated in vacuo, and the resulting residue was dissolved in saturated NaHCO$_3$ and washed several times with ether. The aqueous layer was acidified to pH ~2 with 4 M HCl, and the resulting precipitate was isolated by filtration to give 20 mg of the title compound as a pale pink solid. MS: (−) m/z 404.32 (M−1).

Example 73

(S)-3-(1-Cyano-4-hydroxy-7-phenoxyisoquinoline-3-carboxamido)-2-hydroxy-2-methylpropanoic acid

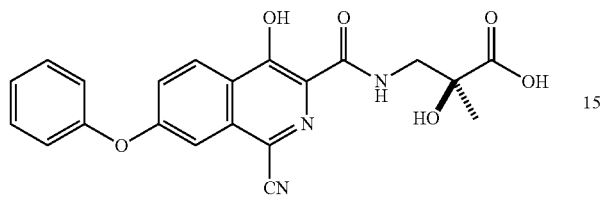

a) (S)-3-Amino-2-hydroxy-2-methylpropanoic acid hydrochloride

Methyl ((2S,4S)-2-tert-butyl-4-methyl-5-oxo-1,3-dioxolan-4-yl)methylcarbamate (310 mg, 1.27 mmol) (Huang et al. (2006) Tetrahedron: Asymmetry 17(22):3152-3157) was suspended in 6 N HCl (12.7 mL) in a sealed tube. The resulting mixture was heated at 110-120° C. for 16 hours and then cooled to room temperature. The reaction crude was diluted with H$_2$O (12 mL) and then extracted twice with EtOAc. The aqueous layer was concentrated to give the title compound in 187 mg, which was used directly in the subsequent step without further purification.

b) (S)-Methyl 3-(1-cyano-4-hydroxy-7-phenoxyisoquinoline-3-carboxamido)-2-hydroxy-2-methylpropanoate A mixture of 1-cyano-4-hydroxy-7-(2-methoxy-phenoxy)-isoquinoline-3-carboxylic acid methyl ester (20 mg, 0.06 mmol), (S)-3-amino-2-hydroxy-2-methylpropanoic acid hydrochloride (20 mg, 0.13 mmol) and NaOMe (14 mg, 0.25 mmol) in MeOH (2 mL) was heated at 140° C. in a microwave for 2 hours. The solvent was removed in vacuo and the residue oil was purified by flash chromatography (0-50% EtOAc/hexanes) to give the title compound in 9 mg. $^1$H NMR (CDCl$_3$, 200 MHz): δ=13.78 (s, 1H), 8.39 (d, 1H, J=9.8 Hz), 8.20 (t, 1H, J=5.9 Hz), 7.60-7.42 (m, 4H), 7.32-7.24 (m, 1H), 7.18-7.12 (m, 2H), 4.11-3.93 (m, 1H), 3.82 (s, 3H), 3.61-3.51 (m, 2H), 1.50 (s, 3H).

c) (S)-3-(1-Cyano-4-hydroxy-7-phenoxyisoquinoline-3-carboxamido)-2-hydroxy-2-methylpropanoic acid (S)-Methyl 3-(1-cyano-4-hydroxy-7-phenoxyisoquinoline-3-carboxamido)-2-hydroxy-2-methylpropanoate (9 mg, 0.02 mmol) was dissolved in MeOH (0.4 mL) and 2 N NaOH (0.4 mL). After stirring for 16 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 6 mg. MS: (−) m/z 406.13 (M−1).

Example 74

(2S,3R)-3-(1-Cyano-4-hydroxy-7-phenoxyisoquinoline-3-carboxamido)-2-hydroxy-4-phenylbutanoic acid a) (2S,3R)-Methyl 3-(1-cyano-4-hydroxy-7-phenoxyisoquinoline-3-carboxamido)-2-hydroxy-4-phenylbutanoate A mixture of 1-cyano-4-hydroxy-7-(2-methoxy-phenoxy)-isoquinoline-3-carboxylic acid methyl ester (15 mg, 0.05 mmol), (2S,3R)-3-amino-2-hydroxy-4-phenylbutanoic acid hydrochloride (40 mg, 0.17 mmol) (Yuan et al. (1993) J Med Chem 36:211-220) and NaOMe (18 mg, 0.33 mmol) in MeOH (2 mL) was heated at 140° C. in a microwave for 2 hours. The solvent was removed in vacuo and the residue oil was purified by flash chromatography (0-10% EtOAc/CH$_2$Cl$_2$) to give the title compound in 4 mg. MS: (−) m/z 496.14 (M−1).

b) (2S,3R)-3-(1-Cyano-4-hydroxy-7-phenoxyisoquinoline-3-carboxamido)-2-hydroxy-4-phenylbutanoic acid (2S,3R)-Methyl 3-(1-cyano-4-hydroxy-7-phenoxyisoquinoline-3-carboxamido)-2-hydroxy-4-phenylbutanoate (4 mg, 0.01 mmol) was dissolved in MeOH (2 mL) and 2 N NaOH (2 mL). After stirring for 6 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 3 mg. MS: (−) m/z 482.30 (M−1).

Example 75

(2R,3R)-3-(1-Cyano-4-hydroxy-7-phenoxyisoquinoline-3-carboxamido)-2-hydroxy-4-phenylbutanoic acid

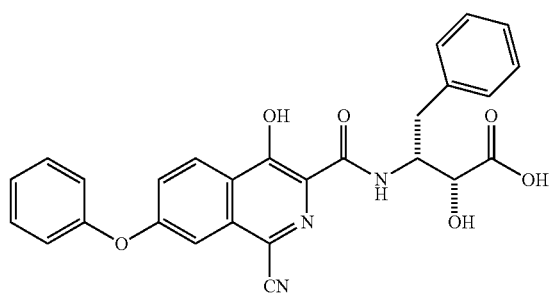 [SMILES: N#Cc1nc(C(=O)N[C@H](Cc2ccccc2)[C@@H](O)C(=O)O)c(O)c2ccc(Oc3ccccc3)cc12]

a) (2R,3R)-Methyl 3-(1-cyano-4-hydroxy-7-phenoxyisoquinoline-3-carboxamido)-2-hydroxy-4-phenylbutanoate A mixture of 1-cyano-4-hydroxy-7-(2-methoxy-phenoxy)-isoquinoline-3-carboxylic acid methyl ester (20 mg, 0.06 mmol), (2R,3R)-methyl 3-amino-2-hydroxy-4-phenylbutanoate (43 mg, 0.13 mmol) and Et$_3$N (0.04 mL, 0.27 mmol) in MeOH (2 mL) was heated at 150° C. in a microwave for 3 hours. The solvent was removed in vacuo and the residue oil was purified by flash chromatography (0-10% EtOAc/CH$_2$Cl$_2$) to give the title compound in 7 mg. MS: (−) m/z 496.34 (M-1).

b) (2R,3R)-3-(1-Cyano-4-hydroxy-7-phenoxyisoquinoline-3-carboxamido)-2-hydroxy-4-phenylbutanoic acid (2R,3R)-Methyl 3-(1-cyano-4-hydroxy-7-phenoxyisoquinoline-3-carboxamido)-2-hydroxy-4-phenylbutanoate (4 mg, 0.01 mmol) was dissolved in MeOH (2 mL) and 2 N NaOH (2 mL). After stirring for 6 hours at room temperature, H$_2$O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO$_4$, concentrated, and purified by flash chromatography (0-30% MeOH/CH$_2$Cl$_2$) to give the title compound in 3 mg. MS: (−) m/z 482.17 (M−1).

Example 76

3-[(1-Cyano-4-hydroxy-7-phenoxy-isoquinoline-3-carbonyl)-amino]-2-hydroxy-propionic acid

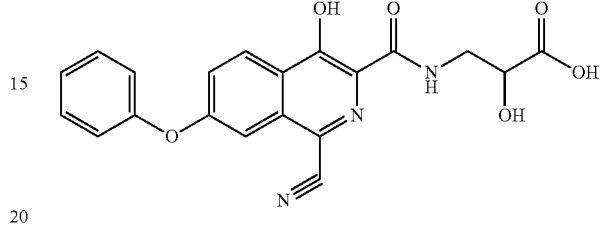

A mixture of 1-cyano-4-hydroxy-7-phenoxy-isoquinoline-3-carboxylic acid methyl ester (100 mg, 0.31 mmol) and 3-mino-2-hydroxy-propionic acid (164 mg, 1.56 mmol) (Aldrich) in 0.5 M NaOMe/MeOH (2.5 mL, 1.25 mmol) was microwaved at 120° C. for 40 min. Reaction mixture was concentrated and the residue was dissolved in water (70 mL). It was acidified by 1 N HCl to pH=3-4 and then extracted with EtOAc. Organic layer was washed with brine, dried over MgSO$_4$, filtered and concentrated to provide the title compound 121 mg (0.3 mmol) in 98% yield. LC-MS ESI−: 392.00 (M−1)$^-$.

Example 77

3-[(1-Cyano-4-hydroxy-7-phenoxy-isoquinoline-3-carbonyl)-amino]-2,2-dimethyl-propionic acid A mixture of 1-cyano-4-hydroxy-7-phenoxy-isoquinoline-3-carboxylic acid methyl ester (82 mg, 0.26 mmol) and 3-amino-2,2-dimethyl-propionic acid (90 mg, 0.77 mmol) (ChemBridge) in 0.5 M NaOMe/MeOH (1.0 mL, 0.5 mmol) was microwaved at 120° C. for 40 min. Reaction mixture was concentrated and the residue was dissolved in water (70 mL). It was acidified by 1 N HCl to pH=3-4. Precipitate was collected, rinsed with water and dried. Crude product was triturated with MeOH (2 mL). solid was collected and dried to provide the title compound 54.4 mg (0.13 mmol) in 51% yield. LC-MS ESI–: 404.03 (M–1)⁻.

Example 78

3-(S)-[(1-Cyano-4-hydroxy-7-phenoxy-isoquinoline-3-carbonyl)-amino]-butyric acid

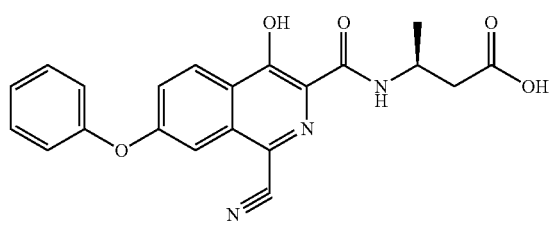 [SMILES: C[C@@H](CC(=O)O)NC(=O)c1nc(C#N)c2cc(Oc3ccccc3)ccc2c1O]

To a mixture of 1-cyano-4-hydroxy-7-phenoxy-isoquinoline-3-carboxylic acid methyl ester (110 mg, 0.34 mmol) and 3-(S)-amino-butyric acid HCl salt (475 mg, 3.4 mmol) (Oakwood Products) in 2-methoxyethanol (10 mL) was added NaOMe solid (330 mg, 6.12 mmol). The resultant mixture was refluxed for 7 h. Reaction mixture was concentrated and the residue was dissolved in water (100 mL). It was acidified by 1 N HCl to pH=3-4 and then extracted with EtOAc. Organic layer was washed with water, brine and dried over MgSO$_4$. It was filtered and concentrated. The crude product was triturated with (1/1) EtOAc/hexanes. Solid was collected and dried in vacuo to provide the title compound 52 mg (0.13 mmol) in 39% yield. LC-MS ESI–: 390.02 (M–1)⁻.

Example 79

3-[(1-Cyano-4-hydroxy-7-phenoxy-isoquinoline-3-carbonyl)-amino]-2-(S)-hydroxy-propionic acid

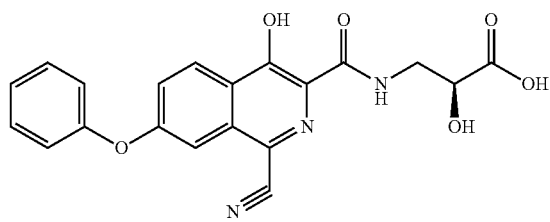 [SMILES: N#Cc1nc(C(=O)NC[C@H](O)C(=O)O)c(O)c2ccc(Oc3ccccc3)cc12]

A mixture of 1-cyano-4-hydroxy-7-phenoxy-isoquinoline-3-carboxylic acid methyl ester (100 mg, 0.31 mmol) and 3-amino-2-(S)-hydroxy-propionic acid (99 mg, 0.94 mmol) (Sigma-Aldrich) in 0.5 M NaOMe/MeOH (1.25 mL, 0.63 mmol) was microwaved at 120° C. for 1 h. Reaction mixture was concentrated and the residue was dissolved in water (70 mL). It was acidified by 1 N HCl to pH=3-4 and then extracted with EtOAc. Organic layer was washed with brine, dried over MgSO$_4$, filtered and concentrated to provide the title compound 113 mg (0.29 mmol) in 93% yield. LC-MS ESI–: 391.98 (M–1)⁻.

Example 80

4-[(1-Cyano-4-hydroxy-7-phenoxy-isoquinoline-3-carbonyl)-amino]-butyric acid

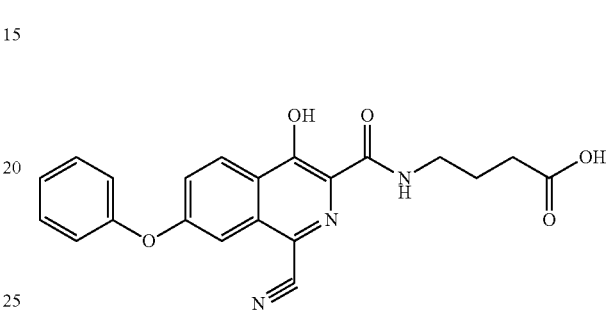

A mixture of 1-cyano-4-hydroxy-7-phenoxy-isoquinoline-3-carboxylic acid methyl ester (100 mg, 0.31 mmol) and 4-aminobutyric acid (97 mg, 0.94 mmol) (Aldrich) in 0.5 M NaOMe/MeOH (1.25 mL, 0.63 mmol) was microwaved at 120° C. for 1 h. Reaction mixture was diluted with water (60 mL), acidified by 1 N HCl to pH=3-4. Precipitate was collected, rinsed with water and dried in vacuo to provide the title compound 109 mg (0.28 mmol) in 89% yield. LC-MS ESI–: 390.04 (M–1)⁻.

Example 81

5-[(1-Cyano-4-hydroxy-7-phenoxy-isoquinoline-3-carbonyl)-amino]-pentanoic acid

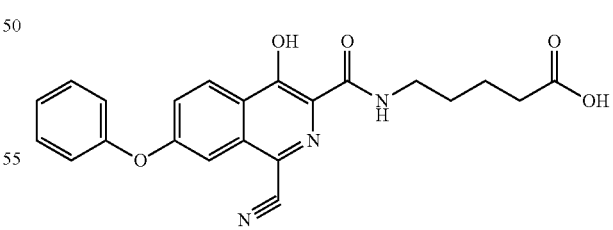

A mixture of 1-cyano-4-hydroxy-7-phenoxy-isoquinoline-3-carboxylic acid methyl ester (100 mg, 0.31 mmol) and 5-amino-pentanoic acid (110 mg, 0.94 mmol) (Aldrich) in 0.5 M NaOMe/MeOH (1.25 mL, 0.63 mmol) was microwaved at 120° C. for 1 h. Reaction mixture was diluted with water (60 mL), acidified by 1 N HCl to pH=3-4. Precipitate was collected and dried. The crude product was triturated with MeOH (2 mL). Solid was collected and dried in vacuo to provide the title compound 65 mg (0.16 mmol) in 52% yield. LC-MS ESI−: 404.03 (M−1)⁻.

Example 82

3-[(1-Cyano-4-hydroxy-7-phenoxy-isoquinoline-3-carbonyl)-amino]-3-methyl-butyric acid

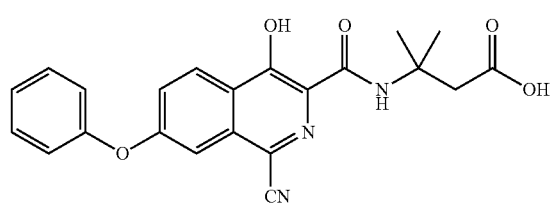 [SMILES: CC(C)(CC(=O)O)NC(=O)c1nc(C#N)c2cc(Oc3ccccc3)ccc2c1O]

To mixture of 1-cyano-4-hydroxy-7-phenoxy-isoquinoline-3-carboxylic acid methyl ester (100 mg, 0.31 mmol) and 3-amino-3-methyl-butyric acid ((97 mg, 0.94 mmol) (Oakwood) in DMF (3 mL) was added NaOMe solid (68 mg, 1.25 mmol). The resultant mixture was heated in a 150-160° C. oil bath for 3 h. Reaction mixture was diluted with water (100 mL) and acidified by 1 N HCl to pH=3-4. Precipitate was collected and dried. Crude residue was purified by silica gel chromatography, eluting with 10-50% EtOAc/CH$_2$Cl$_2$. Fractions containing the produce were collected and concentrated. It was triturated with MeOH (2 mL). Solid was collected and dried in vacuo to provide the title compound 51 mg (0.13 mmol) in 41% yield. LC-MS ESI−: 404.06 (M−1)⁻.

Example 83

4-[(1-Cyano-4-hydroxy-7-phenoxy-isoquinoline-3-carbonyl)-amino]-2-(S)-hydroxy-butyric acid

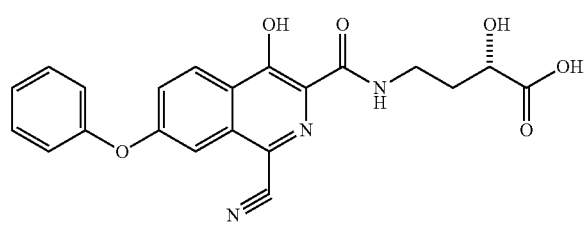 [SMILES: N#Cc1nc(C(=O)NCC[C@H](O)C(=O)O)c(O)c2ccc(Oc3ccccc3)cc12]

A mixture of 1-cyano-4-hydroxy-7-phenoxy-isoquinoline-3-carboxylic acid methyl ester (100 mg, 0.31 mmol) and 4-amino-2-(S)-hydroxy-butyric acid (112 mg, 0.94 mmol) (Aldrich) in 0.5 M NaOMe/MeOH (1.25 mL, 0.63 mmol) was microwaved at 120° C. for 1 h. Reaction mixture was diluted with water (60 mL), acidified by 1 N HCl to pH=3-4 and extracted with EtOAc. The organic layer was washed with brine, dried over MgSO$_4$, filtered and concentrated to provide the title compound 119 mg (0.29 mmol) in 93% yield. LC-MS ESI−: 406.00 (M−1)⁻.

Example 84

4-[(1-Cyano-4-hydroxy-7-phenoxy-isoquinoline-3-carbonyl)-amino]-2,2-dimethyl-butyric acid

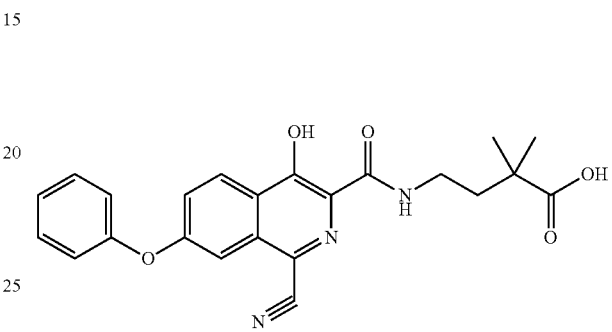

a) 4-[(1-Cyano-4-hydroxy-7-phenoxy-isoquinoline-3-carbonyl)-amino]-2,2-dimethyl-butyric acid methyl ester To a mixture of 1-cyano-4-hydroxy-7-phenoxy-isoquinoline-3-carboxylic acid methyl ester (90 mg, 0.28 mmol) and 4-amino-2,2-dimethyl-butyric acid methyl ester, trifluoroacetic acid salt (290 mg, 1.12 mmol) in MeOH (0.5 mL) was added 0.5 M NaOMe/MeOH solution until the pH of the mixture reaches 8 (1.24 mL, 0.61 mmol was added). The resultant mixture was refluxed overnight. Reaction mixture was diluted with water (50 mL), acidified by 1 N HCl to pH=4 and then extracted with EtOAc. Organic layer was washed with brine, dried over MgSO$_4$, filtered and concentrated. Residue was purified by silica gel chromatography, eluting with 5-50% EtOAc/hexnaes. Fractions containing the desired product were collected and concentrated. The resultant solid was triturated with MeOH (2 mL). Solid was collected and dried in vacuo to provide the title compound 23 mg (0.053 mmol) in 19% yield. LC-MS ESI−: 432.13 (M−1)⁻.

b) 4-[(1-Cyano-4-hydroxy-7-phenoxy-isoquinoline-3-carbonyl)-amino]-2,2-dimethyl-butyric acid A mixture of 4-[(1-cyano-4-hydroxy-7-phenoxy-isoquinoline-3-carbonyl)-amino]-2,2-dimethyl-butyric acid methyl eater (23 mg, 0.05 mmol) in 3 mL of (1/1/1) 1N NaOH/THF/MeOH solution was stirred at room temperature overnight. Reaction mixture was diluted with water (50 mL) and acidified by 1 N HCl to pH=3-4. Precipitated was col-

Example 85

2-(S)-tert-Butoxycarbonylamino-3-[(1-cyano-4-hydroxy-7-phenoxy-isoquinoline-3-carbonyl)-amino]-propionic acid

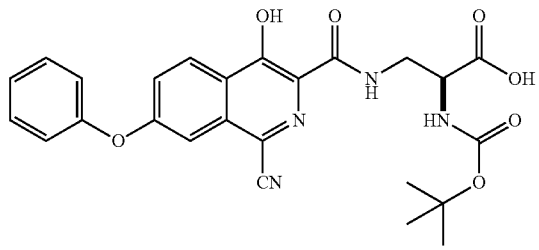 [SMILES: CC(C)(C)OC(=O)N[C@@H](CNC(=O)c1nc(C#N)c2cc(Oc3ccccc3)ccc2c1O)C(=O)O]

A 20-mL scintillation vial was charged with 1-cyano-4-hydroxy-7-phenoxy-isoquinoline-3-carboxylic acid methyl ester (100 mg, 0.31 mmol), 3-amino-2-tert-butoxycarbonylamino-propionic acid (319 mg, 1.56 mmol) (Bachem) and 0.5 M NaOMe/MeOH solution (2.5 mL, 1.25 mmol). The vial was close capped and heated in a 90-100° C. oil bath for 2 days. Reaction mixture was diluted with water (70 mL), acidified by 1 N HCl to pH=3-4. Precipitate was collected, rinsed with water and dried in vacuo to provide the title compound 108 mg (0.22 mmol) in 71% yield. LC-MS ESI–: 491.16 (M–1)⁻.

Example 86

2-(S)-Amino-3-[(1-cyano-4-hydroxy-7-phenoxy-isoquinoline-3-carbonyl)-amino]-propionic acid

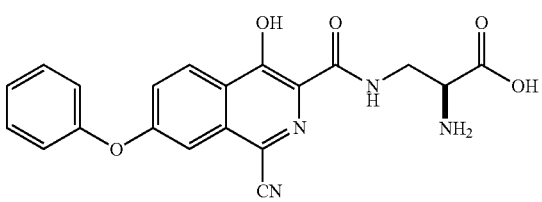 [SMILES: N#Cc1nc(C(=O)NC[C@H](N)C(=O)O)c(O)c2ccc(Oc3ccccc3)cc12]

To a mixture of 2-(S)-tert-butoxycarbonylamino-3-[(1-cyano-4-hydroxy-7-phenoxy-isoquinoline-3-carbonyl)-amino]-propionic acid (90 mg, 0.18 mmol) in CH$_2$Cl$_2$ (2 mL) was added TFA (0.5 mL). The resultant mixture was stirred at room temperature for 4 h. Reaction mixture was concentrated and residue was treated with water (80 mL). The pH value was adjusted to 9-10 by 1 N NaOH aq. Solution. Then it was acidified by 1 N HCl to pH=4-5. Precipitate was collected, rinsed with water and dried in vacuo to provide the title compound 11.5 mg (0.027 mmol) in 55% yield. LC-MS ESI–: 418.08 (M–1)⁻.

Example 87

2-(S)-Benzyloxycarbonylamino-3-[(1-cyano-4-hydroxy-7-phenoxy-isoquinoline-3-carbonyl)-amino]-propionic acid

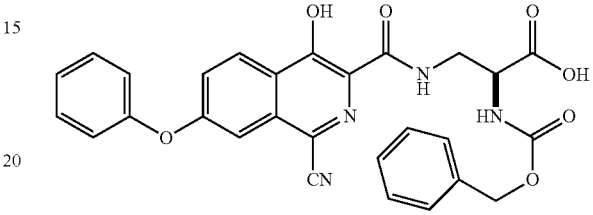

To mixture of 1-cyano-4-hydroxy-7-phenoxy-isoquinoline-3-carboxylic acid methyl ester (200 mg, 0.63 mmol) and 3-amino-2-(S)-benzyloxycarbonylamino-propionic acid (745 mg, 3.12 mmol) (Bachem) in 2-methoxyethanol (10 mL) was added NaOMe solid (135 mg, 2.5 mmol). The resultant mixture was refluxed overnight. Reaction mixture was concentrated. Residue was dissolved in water (100 mL) and acidified by 1 N HCl to pH=3-4. Precipitate was collected, rinsed with water and dried. It was purified by silica gel chromatography, eluting with 10-100% EtOAc (with 0.075% acetic acid)/CH$_2$Cl$_2$ (with 0.01% acetic acid) to provide the title compound 91 mg (0.17 mmol) in 28% yield. LC-MS ESI–: 525.05 (M–1)⁻.

Example 88 trans-4-[(1-Cyano-4-hydroxy-7-phenoxy-isoquinoline-3-carbonyl)-amino]-cyclohexanecarboxylic acid

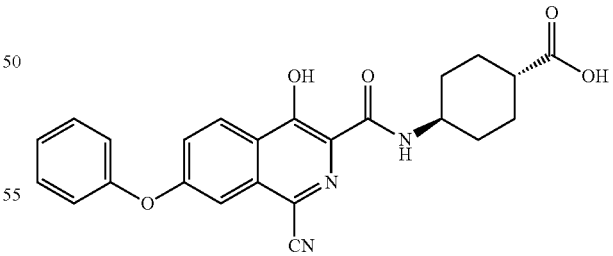

To a mixture of 1-cyano-4-hydroxy-7-phenoxy-isoquinoline-3-carboxylic acid methyl ester (60 mg, 0.19 mmol) and trans-4-amino-cyclohexanecarboxylic acid (107 mg, 0.75 mmol) in 3 mL of 2-methoxyethanol was added NaOMe solid (30 mg, 0.56 mmol). The resultant mixture was microwaved at 140° C. for 1 h. Reaction mixture was concentrated and residue was dissolved in water (60 mL). It was acidified by 1 N HCl to pH=3-4. Precipitate was collected, and rinsed with water and MeOH. Solid was dried to provide the title compound 40 mg (0.093 mmol) in 49% yield. LC-MS ESI−: 430.00 (M−1)−.

Example 89

4-[(1-Cyano-4-hydroxy-7-phenoxy-isoquinoline-3-carbonyl)-amino]-3,3-dimethyl-butyric acid

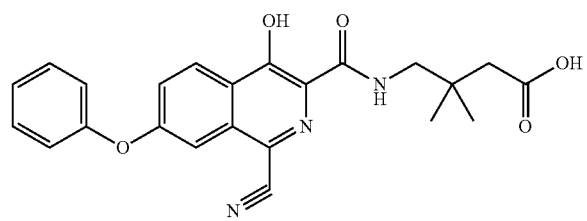 [SMILES: CC(C)(CNC(=O)c1nc(C#N)c2cc(Oc3ccccc3)ccc2c1O)CC(=O)O]

A mixture of 1-cyano-4-hydroxy-7-phenoxy-isoquinoline-3-carboxylic acid methyl ester (70 mg, 0.22 mmol) and 4-amino-3,3-dimethyl-butyric acid HCl salt (110 mg, 0.66 mmol) (Oakwood Products) in 0.5 M NaOMe/MeOH (2.62 mL, 1.3 μmol) was microwaved at 120° C. for 1 h. Reaction mixture was concentrated and residue was dissolved in water (50 mL), It was acidified by 1 N HCl to pH=3-4 and extracted with EtOAc. Organic layer was washed with brine, dried over MgSO$_4$, filtered and concentrated. Crude product was purified by chromatography, eluting with 50-100% EtOAc/hexanes to provide the title compound 7.2 mg (0.017 mmol) in 7.8% yield. LC-MS ESI−: 417.95 (M−1)−.

Example 90

{1-[(1-Cyano-4-hydroxy-7-phenoxy-isoquinoline-3-carbonyl)-amino]-cyclohexyl}-acetic acid

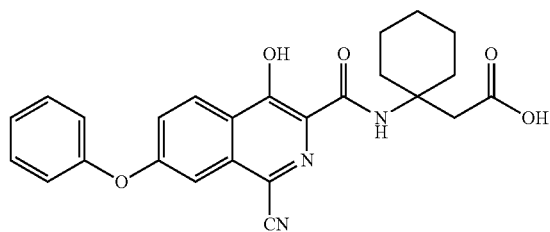 [SMILES: N#Cc1nc(C(=O)NC2(CC(=O)O)CCCCC2)c(O)c2ccc(Oc3ccccc3)cc12]

To a mixture of 1-cyano-4-hydroxy-7-phenoxy-isoquinoline-3-carboxylic acid methyl ester (100 mg, 0.3 μmol) and (1-amino-cyclohexyl)-acetic acid (245 mg, 1.56 mmol) (Matrix Scientific, Columbia S.C.) in 3 mL of DMF was added NaOMe solid (67 mg, 1.25 mmol). The resultant mixture was heated in a 150° C. oil bath for 7 h. Reaction mixture was diluted with water (100 mL) and acidified by 1 N HCl to pH=3-4. Precipitate was collected, dried and the purified by silica gel chromatography, eluting with 10-70% EtOAc/hexanes to provide the title compound 27 mg (0.06 mmol) in 19% yield. LC-MS ESI−: 443.95 (M−1)−.

Example 91

3-[(1-Cyano-4-hydroxy-7-phenoxy-isoquinoline-3-carbonyl)-amino]-3-phenyl-propionic acid

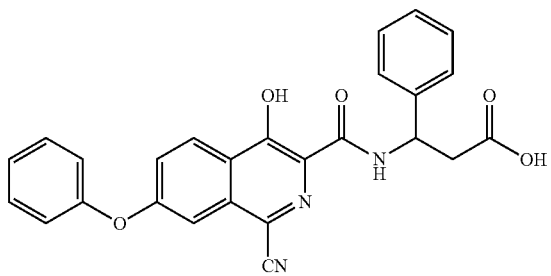 [SMILES: N#Cc1nc(C(=O)NC(CC(=O)O)c2ccccc2)c(O)c2ccc(Oc3ccccc3)cc12]

To a mixture of 1-cyano-4-hydroxy-7-phenoxy-isoquinoline-3-carboxylic acid methyl ester (100 mg, 0.31 mmol) and 3-amino-3-phenyl-propionic acid (257 mg, 1.56 mmol) (Sigma-Aldrich) in 3 mL of DMF was added NaOMe solid (67 mg, 1.25 mmol). The resultant mixture was heated in a 150° C. oil bath for 3 h. After cooled, insoluble was filtered off. Filtrate was diluted with water (100 mL). This suspension mixture was brought to clear by adding 1 N NaOH (pH=ca. 10). It was then acidified by 1 N HCl to pH=3-4 and extracted with EtOAc. Organic layer was washed with brine, dried over MgSO$_4$, filtered and concentrated to provide the title compound 103 mg (0.227 mmol) in 73% yield. LC-MS ESI−: 451.95 (M−1)−.

Example 92

3-[(1-Cyano-4-hydroxy-7-phenoxy-isoquinoline-3-carbonyl)-amino]-2-(R)-methyl-propionic acid

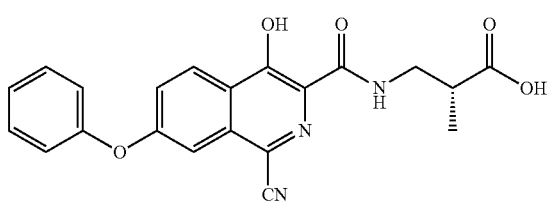

a). 3-Amino-2-(R)-methyl-propionic acid, trifluoroacetic acid salt

A mixture of 3-tert-butoxycarbonylamino-2-(R)-methyl-propionic acid (250 mg, 1.23 mmol) (Sigma-Aldrich) in (½) TFA/CH$_2$Cl$_2$ (3 mL) was stirred at room temperature for 4 h and conc. residue was lyophilized from water to provide the title compound 313 mg. This compound was used directly to next reaction without further purification.

b). 3-[(1-Cyano-4-hydroxy-7-phenoxy-isoquinoline-3-carbonyl)-amino]-2-(R)-methyl-propionic acid To a mixture of 1-cyano-4-hydroxy-7-phenoxy-isoquinoline-3-carboxylic acid methyl ester (50 mg, 0.16 mmol) and 3-amino-2-(R)-methyl-propionic acid, trifluoroacetic acid salt (32 mg, 0.32 mmol) was added 0.5 M NaOMe/MeOH solution (1.52 mL) (to bring the pH of the mixture to 8). The resultant mixture was microwaved at 130° C. for 1 h. Reaction mixture was diluted with water (80 mL) and acidified by 1 N HCl to pH=3-4. It was extracted with EtOAc. Organic layer was washed with brine, dried over MgSO$_4$, filtered and concentrated. Crude product was purified by silica gel chromatography, eluting with 5-100% EtOAc/CH$_2$Cl$_2$, to provide the title compound 8.6 mg (0.022 mmol) in 14% yield. LC-MS ESI–: 390.12 (M–1)⁻.

Example 93

3-[(1-Cyano-4-hydroxy-7-phenoxy-isoquinoline-3-carbonyl)-amino]-2-(S)-methyl-propionic acid

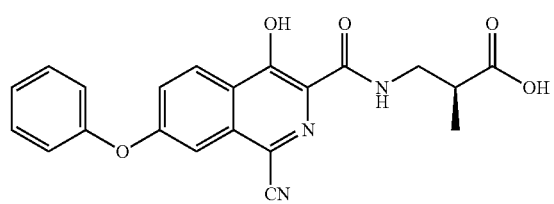 [SMILES: C[C@@H](CNC(=O)c1nc(C#N)c2cc(Oc3ccccc3)ccc2c1O)C(=O)O]

a) 3-Amino-2-(S)-methyl-propionic acid, trifluoroacetic acid salt

A mixture of 3-tert-butoxycarbonylamino-2-(R)-methyl-propionic acid (250 mg, 1.23 mmol) (Sigma-Aldrich) in (½) TFA/CH$_2$Cl$_2$ (3 mL) was stirred at room temperature for 4 h and conc. Residue was taken up with toluene and concentrated again to provide the title compound 330 mg. This compound was used directly to next reaction without further purification.

b). 3-[(1-Cyano-4-hydroxy-7-phenoxy-isoquinoline-3-carbonyl)-amino]-2-(S)-methyl-propionic acid To a mixture of 1-cyano-4-hydroxy-7-phenoxy-isoquinoline-3-carboxylic acid methyl ester (50 mg, 0.16 mmol) and 3-amino-2-(S)-methyl-propionic acid, trifluoroacetic acid salt (48 mg, 0.47 mmol) in EtOH (2 mL) was added NaOMe solid (60 mg) (amount needed to adjust the pH of the mixture to 8-9). The resultant mixture was microwaved at 140° C. for 1 h. Reaction mixture was diluted with water (60 mL) and acidified by 1 N HCl to pH=3-4. It was extracted with EtOAc. Organic layer was dried over MgSO$_4$, filtered and concentrated. Crude product was purified by silica gel chromatography, eluting with 5-100% EtOAc/CH$_2$Cl$_2$, to provide the title compound 16.8 mg (0.043 mmol) in 28% yield. $^1$H NMR (200 MHz) in DMSO-d6, δ ppm: 14.78 (s, 1H), 12.37 (s, 1H), 9.29 (br s, 1H), 8.41 (d, J=9.2 Hz, 1H), 7.73 (br d, J=10.6 Hz, 1H), 7.54 (m, 2H), 7.30 (m, 4H), 3.58 (m, 1H), 3.43 (m, 1H), 2.81 (m, 1H), 1.10 (d, J=7.0 Hz, 3H).

Example 94

4-[(1-Cyano-4-hydroxy-7-phenoxy-isoquinoline-3-carbonyl)-amino]-2-(S)-methoxy-butyric acid

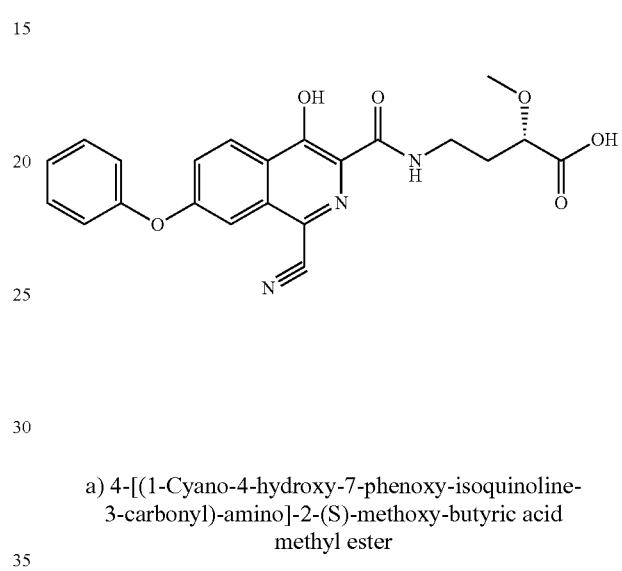

a) 4-[(1-Cyano-4-hydroxy-7-phenoxy-isoquinoline-3-carbonyl)-amino]-2-(S)-methoxy-butyric acid methyl ester To a mixture of 4-[(1-Cyano-4-hydroxy-7-phenoxy-isoquinoline-3-carbonyl)-amino]-2-(S)-hydroxy-butyric acid (250 mg, 0.61 mmol) in 3 mL of MeOH was added slowly thionyl chloride (219 mg, 1.83 mmol). The resultant mixture was stirred at room temperature overnight. Reaction mixture was partitioned between water and EtOAc. Organic layer was washed with brine, dried over MgSO$_4$, filtered and concentrated. Crude product was purified by silica gel chromatography, eluting with 5-90% EtOAc/hexanes, to provide the title compound 180 mg (0.43 mmol) in 70% yield. $^1$H NMR (200 MHz) in DMSO-d6, δ ppm: 14.91 (s, 1H), 9.33 (br t, 1H), 8.41 (d, J=9.2 Hz, 1H), 7.75 (d, J=9.2 Hz, 1H), 7.54 (m, 3H), 7.30 (m, 4H), 5.60 (br s, 1H), 4.12 (m, 1H), 3.60 (s, 3H), 3.43 (m, 2H), 2.07-1.63 (m, 2H).

b) 4-[(1-Cyano-4-hydroxy-7-phenoxy-isoquinoline-3-carbonyl)-amino]-2-(S)-methoxy-butyric acid( To a mixture of 4-[(1-ayano-4-hydroxy-7-phenoxy-isoquinoline-3-carbonyl)-amino]-2-(S)-methoxy-butyric acid methyl ester (180 mg, 0.43 mmol) in DMF (2 mL) at 0° C. was added NaH (60%) (60 mg, 1.5 mmol). It was stirred at 0° C. for 3 min, then added iodomethane (152 mg, 1.07 mmol). The resultant mixture was stirred at 0° C. to room temperature overnight. To the reaction mixture was added 3 mL of 1 N NaOH aq. solution and it was allowed to be stirred at room temperature for 4 h. The reaction mixture was diluted with water and acidified by 1 N HCl to pH=3-4. It was extracted with EtOAc. The organic layer was washed with brine, dried over MgSO$_4$, filtered and concentrated. Residue was recrystallized from ether/hexanes to provide the title compound 73 mg (0.17 mmol) in 43% yield. LC-MS ESI−: 420.13 (M−1)⁻.

Example 95

5-[(1-Cyano-4-hydroxy-7-phenoxy-isoquinoline-3-carbonyl)-amino]-2,2-dimethyl-pentanoic acid

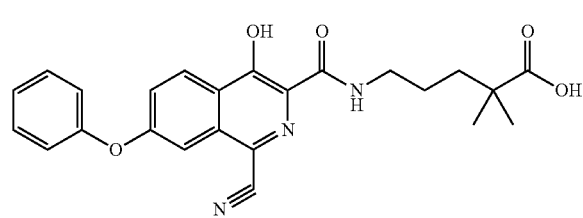 [SMILES: CC(C)(CCCNC(=O)c1nc(C#N)c2cc(Oc3ccccc3)ccc2c1O)C(=O)O]

a). 5-Amino-2,2-dimethyl-pentanoic acid methyl ester, trifluoro-acetic acid salt A mixture of 2,2-dimethyl-5-(trityl-amino)-pentanoic acid methyl ester (1.13 g, 2.8 mmol) (prepared according to Mizota et al. (2011) Tetrahedron Lett. 52(41), 5388-5391) in (½) TFA/$CH_2Cl_2$ (10.5 mL) was stirred at room temperature for 3 h. It was concentrated and residue was taken up with 100 mL of water. Insoluble was filtered off. Filtrate was concentrated to provide the title compound 1.02 g, which was used directly to next reaction without further purification.

b). 5-Amino-2,2-dimethyl-pentanoic acid, HCl salt

A mixture of 5-amino-2,2-dimethyl-pentanoic acid methyl ester, trifluoro-acetic acid salt (1.0 g) in 14 mL of 6 N HCl solution was refluxed for 7 h. Reaction mixture was concentrated and residue was triturated in EtOAc (100 mL). Solid was collected and dried to provide the title compound 0.39 g (2.1 mmol) (76% yield in two steps). $^1$H NMR (200 MHz) in DMSO-d6, δ ppm: 12.19 (s, 1H), 7.82 (br s, 2H), 2.72 (br m, 2H), 1.48 (br s, 4H), 1.09 (s, 6H).

c) 5-[(1-Cyano-4-hydroxy-7-phenoxy-isoquinoline-3-carbonyl)-amino]-2,2-dimethyl-pentanoic acid A mixture of 1-cyano-4-hydroxy-7-phenoxy-isoquinoline-3-carboxylic acid methyl ester (80 mg, 0.25 mmol) and 5-Amino-2,2-dimethyl-pentanoic acid HCl salt (136 mg, 0.75 mmol) in 0.5 M NaOMe/MeOH (2.5 mL, 5 mmol) was microwaved at 120° C. for 2.5 h. Reaction mixture was diluted with water (100 mL) and acidified by 1 N HCl to pH=3-4. It was extracted with EtOAc. Organic layer was washed with brine, dried over $MgSO_4$, filtered and concentrated. Crude product was purified by silica gel chromatography, eluting with 10-100% EtOAc/hexanes to provide the title compound 17 mg (0.04 mmol) in 16% yield. LC-MS ESI−: 431.94 (M−1)⁻.

Example 96

4-Carboxymethyl-4-[(1-cyano-4-hydroxy-7-phenoxy-isoquinoline-3-carbonyl)-amino]-piperidine-1-carboxylic acid tert-butyl ester

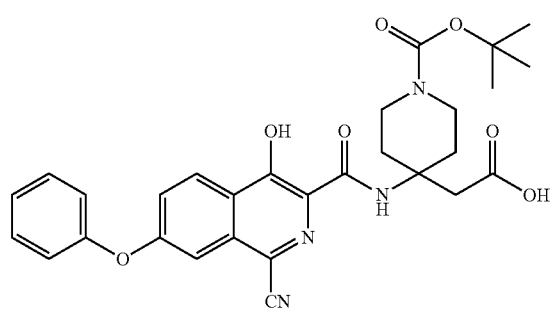 [SMILES: CC(C)(C)OC(=O)N1CCC(CC(=O)O)(NC(=O)c2nc(C#N)c3cc(Oc4ccccc4)ccc3c2O)CC1]

a) 4-Amino-4-carboxymethyl-piperidine-1-carboxylic acid tert-butyl ester

A mixture of 4-oxo-piperidine-1-carboxylic acid tert-butyl ester (3.5 g, 17.55 mmol) (Sigma-Aldrich), malonic acid (2.0 g, 19.30 mmol) and ammonium acetate (3.1 g, 40.36 mmol) in n-BuOH was refluxed for 3 h. After cooled, white solid was collected, rinsed with EtOAc and dried in vacuo to provide the title compound 1.61 g (6.2 mmol) in 36% yield. $^1$H NMR (200 MHz) in $D_2O$, δ ppm: 3.66 (br m, 2H), 3.10 (br m, 2H), 2.45 (s, 2H), 1.69 (br m, 4H), 1.28 (s, 9H).

b) 4-Carboxymethyl-4-[(1-cyano-4-hydroxy-7-phenoxy-isoquinoline-3-carbonyl)-amino]-piperidine-1-carboxylic acid tert-butyl ester A 20-mL scintillation vial was charged with 1-cyano-4-hydroxy-7-phenoxy-isoquinoline-3-carboxylic acid methyl ester (100 mg, 0.31 mmol), 4-amino-4-carboxymethyl-piperidine-1-carboxylic acid tert-butyl ester (322 mg, 1.25 mmol), NaOMe (59 mg, 1.09 mmol) and dimethylacetamide (3 mL). It was close-capped and heated in a 150° C. oil bath for 4 h. Reaction mixture was diluted with water (70 mL) and acidified by 1 N HCl to pH=4-5. Precipitate was collected, rinsed with water and dried. Crude product was purified by silica gel chromatography, eluting with 10-100% EtOAc/ hexanes, to provide the title compound 92 mg (0.16 mmol) in 54% yield. LC-MS ESI–: 545.08 (M–1)⁻.

Example 97

3-{[7-(2-Chloro-4-fluoro-phenoxy)-1-cyano-4-hydroxy-isoquinoline-3-carbonyl]-amino}-propionic acid

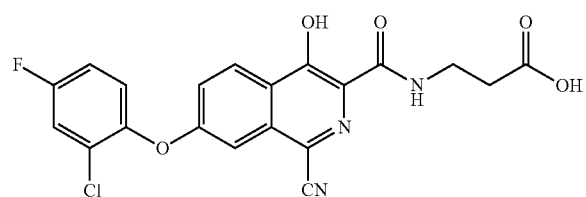 [SMILES: N#Cc1nc(C(=O)NCCC(=O)O)c(O)c2ccc(Oc3ccc(F)cc3Cl)cc12]

a) 4-(2-Chloro-4-fluoro-phenoxy)-2-{[(2,5-dimethoxy-benzyl)-ethoxycarbonylmethyl-amino]-methyl}-benzoic acid ethyl ester To a mixture of 4-bromo-2-{[(2,5-dimethoxy-benzyl)-ethoxycarbonylmethyl-amino]-methyl}-benzoic acid ethyl ester (3.44 g, 6.96 mmol) and 2-chloro-4-fluorophenol (2.04 g, 13.9 mmol) in NMP (6.8 mL) was added Cs₂CO₃ (4.53 g, 13.9 mmol). The resultant mixture was degassed and re-filled with N2 gas prior to the addition of 2,2,6,6-tetramethyl-heptane-3,5-dione (128 mg, 0.70 mmol) and Cu(I)Cl (344 mg, 3.48 mmol). It was de-gassed and filled with N₂ gas again. The resultant mixture was heated in a 130° C. oil bath for 24 h. Reaction mixture was filteredthrough a pad of celite and washed with EtOAc until no UV active spot was detected from the filtrate. Filtrate was washed with 1 N HCl (100 mL and 50 mL), water and brine. It was dried over MgSO₄, filtered and concentrated. Crude product was purified by silica gel chromatography, eluting with CH₂Cl₂, to provide the title compound 2.07 g (3.70 mmol) in 44% yield. ¹H NMR (200 MHz) in CDCl₃, δ ppm: 7.80 (d, J=8.4 Hz, 1H), 7.38 (d, J=2.6 Hz, 1H), 7.20 (m, 1H), 7.03 (m, 3H), 6.73 (dd, J=8.4, 2.6 Hz, 1H), 6.38 (m, 2H), 4.29 (q, J=7.2 Hz, 2H), 4.18 (s, 2H), 4.11 (q, J=7.0 Hz, 2H), 3.79 (s, 3H), 3.72 (s, 3H), 3.70 (s, 2H), 3.28 (s, 2H), 1.4-1.2 (m, 6H).

b) 7-(2-Chloro-4-fluoro-phenoxy)-1-cyano-4-hydroxy-isoquinoline-3-carboxylic acid ethyl ester 4-(2-Chloro-4-fluoro-phenoxy)-2-{[(2,5-dimethoxy-benzyl)-ethoxycarbonylmethyl-amino]-methyl}-benzoic acid ethyl ester (2.07 g, 3.70 mmol) was dissolved in THF (30 mL) and was cooled to –78° C. Then to the cold mixture was added slowly a solution of potassium tert-pentoxide (1.7 M in toluene). The resultant mixture was stirred at –78° C. for 20 min, then at room temperature for 2 h. It was quenched with 150 mL of (2/1) saturated NH₄Cl aq. Solution/ice and extracted with EtOAc. Organic layer was washed with water, brine, dried over MgSO₄, filtered and concentrated. The residue was dissolved in CH₂Cl₂ (31 mL) and then slowly added thionyl chloride (875 mg, 7.4 mmol). The resultant mixture was stirred at room temperature overnight. Reaction mixture was quenched with by 100 g of ice and stirred for 10 min. It was neutralized with saturate NaHCO₃ to pH=7-8 and extracted with EtOAc with CH₂Cl₂. Organic layer was washed with brine, dried over MgSO₄, filtered and concentrated. Crude product was purified by chromatography, eluting with 5-70% EtOAc/hexanes, to provide the title compound 0.71 g (1.97 mmol) in 53% yield. LC-MS ESI+: 361.99 (M+1)⁺.

c) 3-{[7-(2-Chloro-4-fluoro-phenoxy)-1-cyano-4-hydroxy-isoquinoline-3-carbonyl]amino}-propionic acid A mixture of 4-hydroxy-7-(4-fluoro-2-chloro-phenoxy)-isoquinoline-3-carboxylic acid ethyl ester (40 mg, 0.11 mmol) and beta-alanine (30 mg, 0.33 mmol) in 0.5 M NaOMe/MeOH (0.44 mL, 0.22 mmol) was microwaved at 120° C. for 1 h. Reaction mixture was diluted with water (50 mL), acidified by 1 N HCl to pH=3-4. Precipitate was collected, rinsed with water and dried in vacuo to provide the title compound 31 mg (0.077 mmol) in 70% yield. LC-MS ESI–: 402.85 (M–1)⁻.

Example 98

5-{[7-(2-Chloro-4-fluoro-phenoxy)-1-cyano-4-hydroxy-isoquinoline-3-carbonyl]-amino}-pentanoic acid

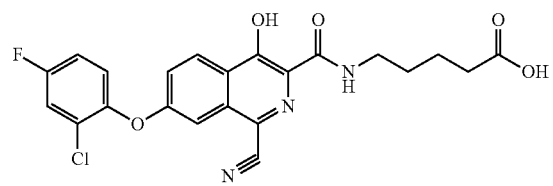 [SMILES: N#Cc1nc(C(=O)NCCCCC(=O)O)c(O)c2ccc(Oc3ccc(F)cc3Cl)cc12]

a). 1-Bromo-4-hydroxy-7-(4-fluoro-2-chloro-phenoxy)-isoquinoline-3-carboxylic acid ethyl ester A mixture of 4-hydroxy-7-(4-fluoro-2-chloro-phenoxy)-isoquinoline-3-carboxylic acid ethyl ester (610 mg, 1.69 mmol) and NBS (331 mg, 1.86 mmol) in CH₂Cl₂ (17 mL) was refluxed for 3 h and then concentrated. Residue was triturate with acetone (15 mL). Solid was collected and dried to provide the title compound 540 mg (1.22 mmol) in 73% yield. ¹H NMR (200 MHz) in CDCl₃, δ ppm: 11.90 (s, 1H), 8.37 (d, J=8.8 Hz, 1H), 7.47 (m, 2H), 7.15 (m, 3H), 4.54 (br q, J=7.3 Hz, 2H), 1.49 (br t, J=7.3 Hz, 3H).

b). 1-Cyano-4-hydroxy-7-(4-fluoro-2-chloro-phenoxy)-isoquinoline-3-carboxylic acid ethyl ester A 20-mL scintillation vial was charged with 1-bromo-4-hydroxy-7-(4-fluoro-2-chloro-phenoxy)-isoquinoline-3-carboxylic acid ethyl ester (340 mg, 0.77 mmol), CuCN (138 mg, 1.54 mmol) and NMP (1.8 mL). It was filled with N₂ gas and close-capped. The mixture was stirred in a 130° C. oil bath for 3 h. Reaction mixture was diluted with CH₂Cl₂ (100 mL) and stirred at room temperature for 3 days. To the mixture was added 100 mL of 0.5 N HCl aq. solution. It was stirred vigorously for 3 min. Two phases were separated. Organic layer was washed with brine, dried over MgSO₄, filtered and concentrated. Crude product was purified by silica gel chromatography, eluting with 5-50% EtOAc/hexanes to provide the title compound 231 mg (0.60 mmol) in 78% yield. ¹H NMR (200 MHz) in CDCl₃, δ ppm: 12.42 (s, 1H), 8.45 (d, J=8.8 Hz, 1H), 7.54 (dd, J=9.2, 2.6 Hz, 1H), 7.40-7.10 (m, 4H), 4.58 (q, J=7.0 Hz, 2H), 1.51 (t, J=7.0 Hz, 3H).

c). 5-{[7-(2-Chloro-4-fluoro-phenoxy)-1-cyano-4-hydroxy-isoquinoline-3-carbonyl]amino}-pentanoic acid A mixture of 1-cyano-4-hydroxy-7-(4-fluoro-2-chlorophenoxy)-isoquinoline-3-carboxylic acid ethyl ester (50 mg, 0.13 mmol) and 5-amino-petanoic acid (45 mg, 0.39 mmol) in 0.5 M NaOMe/MeOH solution was microwaved at 130° C. for 1 h. Reaction mixture was diluted with water (60 mL) and acidified by 1 N HCl to pH=3-4. Precipitate was collected and dried. Crude product was then purified by silica gel chromatography, eluting with 5-70% EtOAc/hexanes to provide the title compound 27 mg (0.06 mmol) in 45% yield. LC-MS ESI–: 455.89 (M–1)⁻.

Example 99

3-{[7-(2-Chloro-4-fluoro-phenoxy)-1-cyano-4-hydroxy-isoquinoline-3-carbonyl]-amino}-2,2-dimethyl-propionic acid

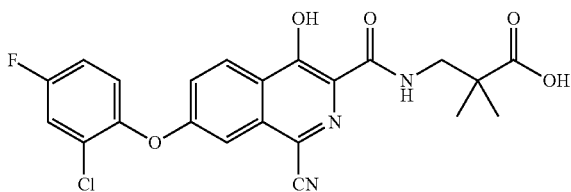 [SMILES: CC(C)(CNC(=O)c1nc(C#N)c2cc(Oc3ccc(F)cc3Cl)ccc2c1O)C(=O)O]

a). 3-{[7-(2-Chloro-4-fluoro-phenoxy)-1-cyano-4-hydroxy-isoquinoline-3-carbonyl]amino}-2,2-dimethyl-propionic acid tert-butyl ester A mixture of A mixture of 1-cyano-4-hydroxy-7-(4-fluoro-2-chloro-phenoxy)-isoquinoline-3-carboxylic acid ethyl ester (40 mg, 0.10 mmol) and 3-amino-2,2-dimethyl-propionic acid tert-butyl ester (43 mg, 0.25 mmol) in 1 mL of MeOH was microwaved at 130° C. for 1 h. Reaction mixture was quenched with acetic acid (0.3 mmol) and then concentrated. Residue was purified by silica gel chromatography, eluting with 5-60% EtOAc/hexanes, to provide the title compound 41 mg (0.08 mmol) in 80% yield. ¹H NMR (200 MHz) in CDCl₃, δ ppm: 14.07 (s, 1H), 8.41 (d, J=9.2 Hz, 1H), 8.32 (br t, 1H), 7.50 (dd J=9.1, 2.6 Hz, 1H), 7.38-7.10 (m, 4H), 3.55 (d, J=6.8, 2 H), 1.23 (s, 6H).

b). 3-{[7-(2-Chloro-4-fluoro-phenoxy)-1-cyano-4-hydroxy-isoquinoline-3-carbonyl]amino}-2,2-dimethyl-propionic acid A mixture of 3-{[7-(2-chloro-4-fluoro-phenoxy)-1-cyano-4-hydroxy-isoquinoline-3-carbonyl]-amino}-2,2-dimethyl-propionic acid tert-butyl ester (40 mg, 0.08) in (½) TFA/CH₂Cl₂ (3 mL) was stirred at room temperature for 4 h. Reaction mixture was concentrated. The residue was dissolved in water (30 mL) and the pH was adjusted to 10 by 1 N NaOH. It was then acidified by 1 N HCl to pH=3-4. Precipitate was collected, rinsed with water and dried in vacuo to provide the title compound 24 mg (0.053 mmol) in 66% yield. LC-MS ESI–: 456.05 (M–1)⁻.

Example 100

5-{[7-(2,6-Difluoro-phenoxy)-4-hydroxy-isoquinoline-3-carbonyl]-amino}-pentanoic acid

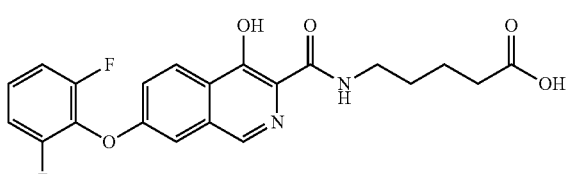

A mixture of 7-(2,6-difluoro-phenoxy)-4-hydroxy-isoquinoline-3-carboxylic acid ethyl ester (40 mg, 0.12 mmol) and valeric acid (203 mg, 1.74 mmol) in 0.5 M NaOMe/MeOH (2.4 mL, 1.2 mmol) was microwaved at 120° C. for 1 h. Reaction mixture was diluted with water (80 mL), acidified by 1 N HCl and then extracted with EtOAc. Organic layer was washed with brine, dried over MgSO₄, filtered and concentrated. Crude product was purified by silica gel chromatography, eluting with 10-100% EtOAc/hexanes then EtOAc (with 0.1% acetic acid), to provide the title compound 26 mg (0.063 mmol) in 52% yield as a white solid. LC-MS ESI–: 415.09 (M–1)⁻.

Example 101

3{-[1-Cyano-7-(4-fluoro-phenoxy)-4-hydroxy-isoquinoline-3-carbonyl]-amino}-2,2-dimethyl-propionic acid

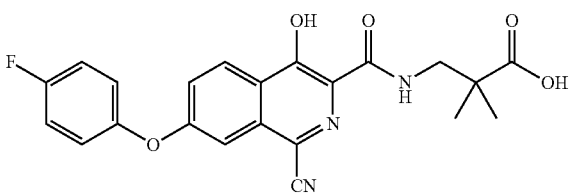 [SMILES: CC(C)(CNC(=O)c1nc(C#N)c2cc(Oc3ccc(F)cc3)ccc2c1O)C(=O)O]

A mixture of 1-cyano-7-(4-fluoro-phenoxy)-4-hydroxy-isoquinoline-3-carboxylic acid butyl ester (80 mg, 0.21 mmol) (prepared according to U.S. Pat. No. 7,928,120) and 3-Amino-2,2-dimethyl-propionic acid tert-butyl ester (71 mg, 0.41 mmol) in MeOH (1.5 mL) was microwaved at 120° C. For 1 h. Reaction mixture was diluted with water (80 mL), acidified by 1 N HCl and then extracted with EtOAc. Organic layer was washed with brine, dried over MgSO₄, filtered and concentrated. Residue was then treated with 3 mL of (½) TFA/CH₂Cl₂. Resultant mixture was stirred at room tempera-

Example 102

3-{-[1-Cyano-7-(4-fluoro-phenoxy)-4-hydroxy-isoquinoline-3-carbonyl]-amino}-3-methyl-butyric acid

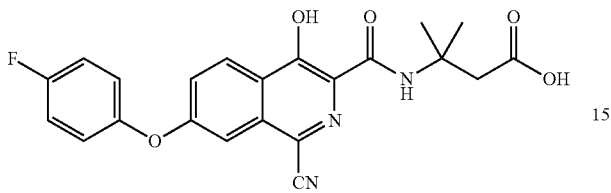

To a mixture of 1-cyano-7-(4-fluoro-phenoxy)-4-hydroxy-isoquinoline-3-carboxylic acid butyl ester (60 mg, 0.16 mmol) and 3-amino-3-methyl-butyric acid (92 mg, 0.79 mmol) in DMF (1.5 mL) was added NaOMe solid (34 mg, 0.63 mmol). The resultant mixture was stirred in a 150-160° C. oil bath for 4 h. Reaction mixture was diluted with water (60 mL) and basified by 1 N NaOH to pH=10. It was extracted with EtOAc (30 mL), which was discarded. Aqueous layer was acidified by 1 N HCl to pH=3-4. Precipitate was collected and dried. Crude product was then triturated with MeOH (4 mL). Solid was collected and dried in vacuo to provide the title compound 24 mg (0.057 mmol) in 35% yield. LC-MS ESI–: 422.07 (M–1)⁻.

Example 103

2-(S)-Hydroxy-3-{[4-hydroxy-7-(4-methoxy-phenoxy)-isoquinoline-3-carbonyl]-amino}-propionic acid

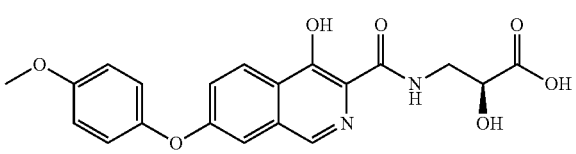 [SMILES: COc1ccc(Oc2ccc3c(O)c(C(=O)NC[C@H](O)C(=O)O)ncc3c2)cc1]

a). 4-Hydroxy-7-(4-methoxy-phenoxy)-isoquinoline-3-carboxylic acid methyl ester To a mixture of 4-hydroxy-7-(4-methoxy-phenoxy)-isoquinoline-3-carboxylic acid butyl ester (prepared according to U.S. Pat. No. 7,928,120) (20 mg, 0.054 mmol) in DMF (0.5 mL) was added 0.5 M NaOMe/MeOH (0.32 mL, 0.16 mmol). The resultant mixture was microwaved at 80° C. for 1.5 h. Reaction mixture was diluted with water (70 mL) and acidified by 1 N HCl to pH=4. Precipitate was collected and dried in vacuo to provide the title compound 15 mg (0.046 mmol) in 85% yield. LC-MS ESI+: 326.10 (M+1)⁺.

b). 2-(S)-Hydroxy-3-{[4-hydroxy-7-(4-methoxy-phenoxy)-isoquinoline-3-carbonyl]-amino}-propionic acid A mixture of 4-hydroxy-7-(4-methoxy-phenoxy)-isoquinoline-3-carboxylic acid methyl ester (100 mg, 0.31 mmol) and 3-amino-2-(S)-hydroxy-propionic acid (97 mg, 0.92 mmol) in 0.5 M NaOMe/MeOH solution (1.23 mL, 0.62 mmol) was microwaved at 120° C. for 2 h. After cooled, solid precipitate was collected and rinsed with cold MeOH (1 mL). Solid was dissolved in water (40 mL), acidified by 1 N HCl to pH=3-4 and extracted with EtOAc. Organic layer was dried over MgSO₄, filtered and concentrated to provide the title compound 54 mg (0.14 mmol) in 15% yield. LC-MS ESI–: 397.02 (M–1)⁻.

Example 104

3-{[4-Hydroxy-7-(4-methoxy-phenoxy)-isoquinoline-3-carbonyl]-amino}-2,2-dimethyl-propionic acid

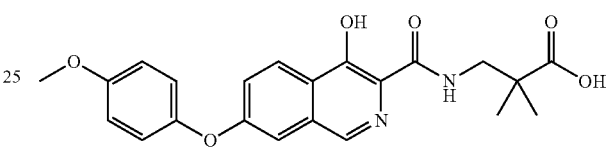

a). 3-{[4-Hydroxy-7-(4-methoxy-phenoxy)-isoquinoline-3-carbonyl]-amino}-2,2-dimethyl-propionic acid methyl eater A mixture of 4-hydroxy-7-(4-methoxy-phenoxy)-isoquinoline-3-carboxylic acid methyl ester (100 mg, 0.31 mmol) and 3-amino-2,2-dimethyl-propionic acid methyl ester HCl salt (103 mg, 0.62 mmol) (Key Organics Ltd, Cornwall UK) in 0.5 M NaOMe/MeOH (1.23 mL, 0.62 mmol) was microwaved at 120° C. for 3 h. Additional 1 equivalent of 3-amino-2,2-dimethyl-propionic acid methyl ester HCl salt was added to the reaction mixture and it was microwaved again for another 3 h. Reaction mixture was diluted with water (70 mL), acidified by 1 N HCl to pH=3-4 and extracted with EtOAc. Organic layer was washed with brine, dried over MgSO4, filtered and concentrated. Crude product was purified by silica gel chromatography, eluting with 10-70% EtOAc/hexanes to provide the title compound 63 mg (0.15 mmol) in 49% yield as an gummy oil product. LC-MS ESI+: 425.15 (M+1)⁺.

b). 3-{[4-Hydroxy-7-(4-methoxy-phenoxy)-isoquinoline-3-carbonyl]-amino}-2,2-dimethyl-propionic acid A mixture of 3-{[4-hydroxy-7-(4-methoxy-phenoxy)-isoquinoline-3-carbonyl]-amino}-2,2-dimethyl-propionic acid methyl eater (61 mg, 0.14 mmol) and LiOH.H₂O (91 mg, 2.16 mmol) in (1.5/1) MeOH/H2O (7 mL) was stirred at room temperature overnight. Reaction mixture was diluted with water (75 mL), acidified by 1 N HCl to pH=3-4. Precipitate was collected, rinsed with water and dried in vacuo to provide the title compound 39 mg (0.095 mmol) in 68% yield. LC-MS ESI−: 409.06 (M−1)⁻.

Example 105

5-{[4-Hydroxy-7-(4-methoxy-phenoxy)-isoquinoline-3-carbonyl]-amino}-pentanoic acid

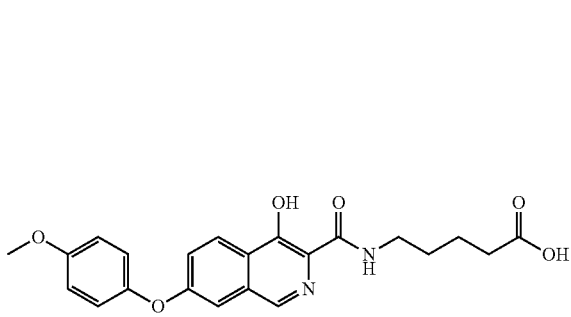 [SMILES: COc1ccc(Oc2ccc3c(O)c(C(=O)NCCCCC(=O)O)ncc3c2)cc1]

A mixture of 4-hydroxy-7-(4-methoxy-phenoxy)-isoquinoline-3-carboxylic acid methyl ester (100 mg, 0.31 mmol) and valeric acid (180 mg, 1.54 mmol) in 0.5 M NaOMe/MeOH (2.5 mL, 1.23 mmol) was microwaved at 120° C. for 1 h. Reaction mixture was diluted with water (100 mL) and filtered through a pad of celite. Filtrate was acidified by 1 N HCl and extracted with EtOAc. Organic layer was washed with brine, dried over MgSO₄, filtered and concentrated. Crude product was purified by silica gel chromatography, eluting with 10-90% EtOAc/hexanes to provide the title compound 49 mg (0.12 mmol) in 39% yield. LC-MS ESI−: 409.11 (M−1)⁻.

Example 106

{1-[(1-Cyano-4-hydroxy-7-phenoxy-isoquinoline-3-carbonyl)-amino]-cyclobutyl}-acetic acid

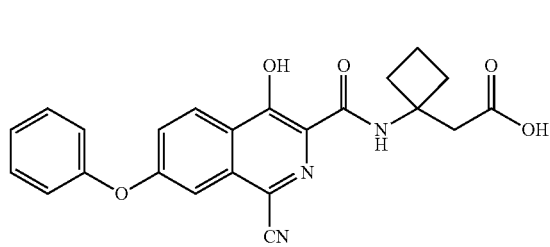 [SMILES: N#Cc1nc(C(=O)NC2(CC(=O)O)CCC2)c(O)c2ccc(Oc3ccccc3)cc12]

To a mixture of 1-cyano-4-hydroxy-7-phenoxy-isoquinoline-3-carboxylic acid methyl ester (45 mg, 0.14 mmol) and (1-amino-cyclobutyl)-acetic acid (91 mg, 0.70 mmol) (APAC Pharmaceuticals LLC, Columbia Md.) in DMA (2 mL) was added NaOMe solid (38 mg, 0.70 mmol). The resultant mixture was heated in a 150° C. oil bath for 3 h. Reaction mixture was diluted with water and acidified by 1 N HCl to pH=3-4. Precipitate was collected, rinsed with water and dried in vacuo to provide the title compound 54 mg (0.13 mmol) in 92% yield. LC-MS ESI−: 416.17 (M−1)⁻.

Example 107

3-(R)-[(1-Cyano-4-hydroxy-7-phenoxy-isoquinoline-3-carbonyl)-amino]-5-phenyl-pentanoic acid

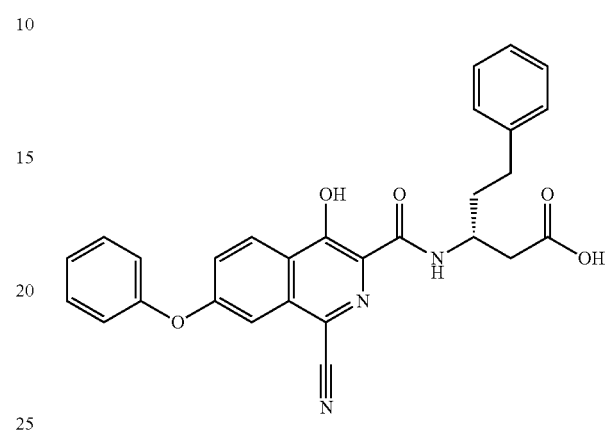

1-Cyano-4-hydroxy-7-phenoxy-isoquinoline-3-carboxylic acid methyl ester (75 mg, 0.234 mmol) and 3-(R)-Amino-5-phenyl-pentanoic acid (193 mg, 1.0 mmol) were placed in a CEM 10 mL Microwave vessel and sodium methoxide-methanol solution (0.5 M; 2.0 mL, 1.0 mmol) was added via syringe. The vessel was sealed and heated to 130° C. in a CEM microwave apparatus for 4.5 hours. The reaction mixture was diluted with water and treated with 1N hydrochloric acid and extracted three times with ethyl acetate then dried over sodium sulfate. The crude product was purified by MPLC (methylene chloride-methanol) to provide the title compound as an off-white solid in 43% yield. MS ESI(−) m/e: 480.1305 (M−1).

Example 108

3-[(4-Hydroxy-1-methyl-7-phenoxy-isoquinoline-3-carbonyl)-amino]-propionic acid

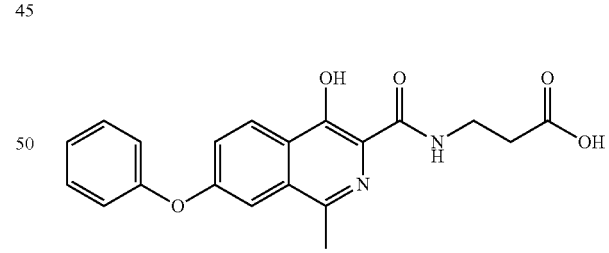

a) 4-Hydroxy-1-methyl-7-phenoxy-isoquinoline-3-carboxylic acid methyl ester

To a mixture of 1-bromo-4-hydroxy-7-phenoxy-isoquinoline-3-carboxylic acid methyl ester (500 mg, 1.34 mmol) in N-methylpyrrolidone (NMP) (7 mL) was added SnMe₄ (358 mg, 2.0 mmol) and resin-bound-Pd(PPh₃)₂Cl₂ (Sigma-Aldrich) (1-2 mmol/g) (40 mg, ca. 0.03 mmol). The resultant mixture was stirred in a 130° C. oil bath for 3 h. Reaction mixture was filtered and rinsed with NMP (1 mL). Filtrate was poured into water (120 mL) and stirred at room temperature until good precipitate formed. Solid was collected and rinsed with water (100 mL) and then hexanes (50 mL). Solid was dried and purified by silica gel chromatography, eluting with 2-50% EtOAc/hexanes, to provide the title compound 240 mg (0.78 mmol) in 58% yield. $^1$H NMR (200 MHz) CDCl$_3$, δ in ppm: 11.68 (s, 1H), 8.37 (d, J=9.3 Hz, 1H), 7.48-7.08 (m, 7H), 4.07 (s, 3H), 2.75 (s, 3H).

b) 3-[(4-Hydroxy-1-methyl-7 phenoxy-isoquinoline-3-carbonyl)-amino]-propionic acid A mixture of 4-hydroxy-1-methyl-7-phenoxy-isoquinoline-3-carboxylic acid methyl ester (120 mg, 0.39 mmol) and beta-alanine (242 mg, 2.72 mmol) in 0.5 M NaOMe/MeOH solution (4.5 mL, 2.25 mmol) was microwaved at 120° C. for 30 min. Reaction mixture was concentrated and dissolved in water (100 mL). It was acidified by 1 N HCl to pH=3-4. Gummy precipitate was collected by filtration and dissolved in EtOAc. It was dried over MgSO4, filtered and concentrated to provide the title compound 116 mg (0.32 mmol) in 81% yield. LC-MS ESI−: 365.16 (M−1)⁻.

Example 109

3{-[1-Cyano-6-(2,6-dimethyl-phenoxy)-4-hydroxy-isoquinoline-3-carbonyl]-amino}-propionic acid

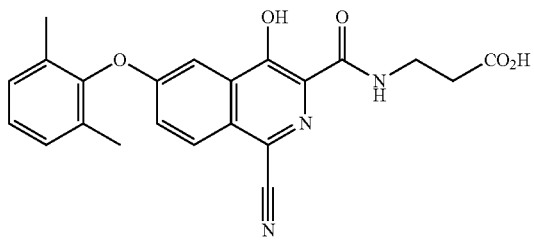 [SMILES: Cc1cccc(C)c1Oc1ccc2c(C#N)nc(C(=O)NCCC(=O)O)c(O)c2c1]

a) 1-Cyano-6-(2,6-dimethyl-phenoxy)-4-hydroxy-isoquinoline-3-carboxylic acid butyl ester A mixture of 1-bromo-6-(2,6-dimethyl-phenoxy)-4-hydroxy-isoquinoline-3-carboxylic acid butyl ester (2 g, 4.5 mmol) (prepared according to U.S. Pat. No. 7,928,120) and CuCN (0.81 g, 9.0 mmol) in DMF (30 mL) was refluxed for 1.5 h. The resulting mixture was poured into a mixture of water (200 mL) and CH$_2$Cl$_2$ (200 mL). 4 M HCl was added with vigorous stirring until no solid was observed. The aqueous layer was extracted with additional CH$_2$Cl$_2$, and the organic layers were combined, dried over MgSO$_4$ and concentrated. The crude product was purified by column chromatography (10-80% CH$_2$Cl$_2$/hexanes) to give 1.44 g of the title compound as a pale pink solid. MS: (+) m/z 391.34 (M+1).

b) 3-{[1-Cyano-6-(2,6-dimethyl-phenoxy)-4-hydroxy-isoquinoline-3-carbonyl]amino}-propionic acid A mixture of 1-cyano-6-(2,6-dimethyl-phenoxy)-4-hydroxy-isoquinoline-3-carboxylic acid butyl ester (80 mg, 0.20 mmol), β-alanine (365 mg, 4.10 mmol) and NaOMe (166 mg, 3.07 mmol) in 2-methoxyethanol (10 mL) was refluxed for 2 h. After the mixture was cooled to r.t., solvent was evaporated. The residue was partitioned between EtOAc (50 mL) and water (50 mL). 1 M HCl was added with vigorous stirring until pH was ~2. The organic layer was dried over MgSO$_4$ and concentrated. The crude product was purified by column chromatography (0-60% EtOAc/hexanes+2% AcOH) to give 47 mg of the title compound. MS: (+) m/z 406.21 (M+1).

Example 110

4-{[1-Cyano-6-(2,6-dimethyl-phenoxy)-4-hydroxy-isoquinoline-3-carbonyl]-amino}-butyric acid

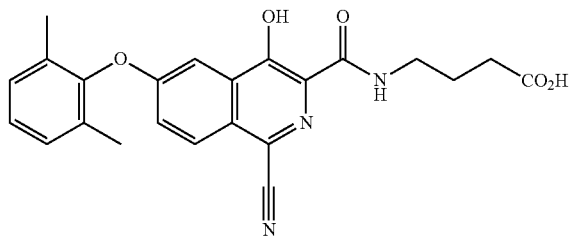 [SMILES: Cc1cccc(C)c1Oc1ccc2c(C#N)nc(C(=O)NCCCC(=O)O)c(O)c2c1]

A mixture of 1-cyano-6-(2,6-dimethyl-phenoxy)-4-hydroxy-isoquinoline-3-carboxylic acid butyl ester (80 mg, 0.20 mmol), 4-aminobutyric acid (423 mg, 4.10 mmol) and NaOMe (166 mg, 3.07 mmol) in 2-methoxyethanol (10 mL) was refluxed for 2 h. After the mixture was cooled to r.t., solvent was evaporated. The residue was partitioned between EtOAc (50 mL) and water (50 mL). 1 M HCl was added with vigorous stirring until pH was ~2. The organic layer was dried over MgSO$_4$ and concentrated. The crude product was purified by column chromatography (0-60% EtOAc/hexanes+2% AcOH) to give 75 mg of the title compound as a pink solid. MS: (+) m/z 420.23 (M+1).

Example 111

5-{[1-Cyano-6-(2,6-dimethyl-phenoxy)-4-hydroxy-isoquinoline-3-carbonyl]-amino}-pentanoic acid

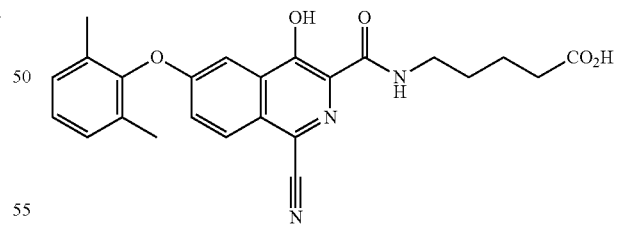

A mixture of 1-cyano-6-(2,6-dimethyl-phenoxy)-4-hydroxy-isoquinoline-3-carboxylic acid butyl ester (80 mg, 0.20 mmol), 5-aminovaleric acid (480 mg, 4.10 mmol) and NaOMe (166 mg, 3.07 mmol) in 2-methoxyethanol (10 mL) was refluxed for 2 h. After the mixture was cooled to r.t., solvent was evaporated. The residue was partitioned between EtOAc (50 mL) and water (50 mL). 1 M HCl was added with vigorous stirring until pH was ~2. The organic layer was dried over MgSO$_4$ and concentrated. The crude product was puri-fied by column chromatography (0-60% EtOAc/hexanes+2% AcOH) to give 67 mg of the title compound as a pale pink solid. MS: (+) m/z 434.18 (M+1).

Example 112

3-[(4-Hydroxy-6-phenoxy-isoquinoline-3-carbonyl)-amino]-propionic acid

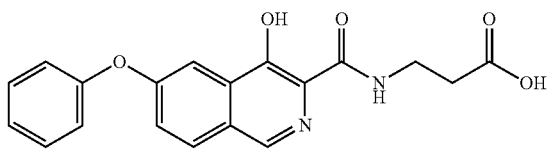 [SMILES: O=C(O)CCNC(=O)c1ncc2ccc(Oc3ccccc3)cc2c1O]

A mixture of 4-hydroxy-6-phenoxy-isoquinoline-3-carboxylic acid butyl ester (200 mg, 0.59 mmol) (prepared according to U.S. Pat. No. 7,629,357) and beta-alanine (792 mg, 8.9 mmol) in 0.5 M NaOMe/MeOH solution was refluxed overnight. Reaction mixture was concentrated and residue was dissolved in water (150 mL). It was cidified by 1 N HCl to pH=3-4. Precipitate was collected, rinsed with water and dried in vacuo to provide the title compound 196 mg (0.56 mmol) in 94% yield. LC-MS ESI-: 351.05 (M-1)-.

Example 113

4-[(4-Hydroxy-6-phenoxy-isoquinoline-3-carbonyl)-amino]-butyric acid

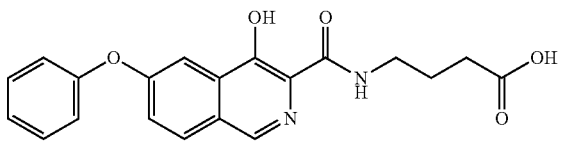 [SMILES: O=C(O)CCCNC(=O)c1ncc2ccc(Oc3ccccc3)cc2c1O]

A mixture of 4-hydroxy-6-phenoxy-isoquinoline-3-carboxylic acid butyl ester (150 mg, 0.45 mmol) and 4-aminobutyric acid (688 mg, 6.68 mmol) in 0.5 M NaOMe/MeOH (8.9 mL, 4.45 mmol) was refluxed overnight. Reaction mixture was concentrated and residue was dissolved in water (150 mL). It was acidified by 1 N HCl to pH=3-4. Precipitate was collected, rinsed with water and dried in vacuo to provide the title compound 151 mg (0.41 mmol) in 92% yield. LC-MS ESI-: 365.08 (M-1)-.

Example 114

5-[(4-Hydroxy-7-phenylsulfanyl-isoquinoline-3-carbonyl)-amino]-pentanoic acid

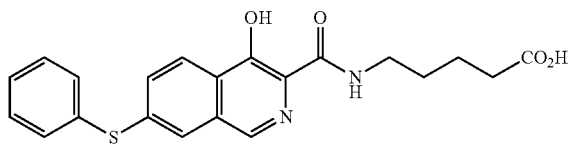 [SMILES: O=C(O)CCCCNC(=O)c1ncc2cc(Sc3ccccc3)ccc2c1O]

A mixture of 4-hydroxy-7-phenylsulfanyl-isoquinoline-3-carboxylic acid butyl ester (50 mg, 0.14 mmol) (prepared according to WO 2004108681), 5-aminovaleric acid (830 mg, 7.08 mmol) and NaOMe (11 mL, 5.31 mmol, 0.5 M in MeOH) was refluxed for 3 days. Solvent was evaporated, and the residue was partitioned between EtOAc and water. 1 M HCl was added with stirring until pH was ~1. The organic layer was dried over MgSO₄ and concentrated. The crude product was purified by column chromatography (0-60% EtOAc/hexanes+2% AcOH) to give 40 mg of the title compound. MS: (+) m/z 397.11 (M+1).

Example 115

4-[(4-Hydroxy-7-phenylsulfanyl-isoquinoline-3-carbonyl)-amino]-butyric acid

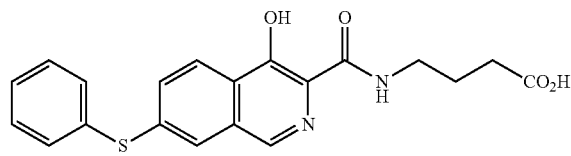 [SMILES: O=C(O)CCCNC(=O)c1ncc2cc(Sc3ccccc3)ccc2c1O]

A mixture of 4-hydroxy-7-phenylsulfanyl-isoquinoline-3-carboxylic acid butyl ester (50 mg, 0.14 mmol) (prepared according to WO 2004108681), 4-aminobutyric acid (730 mg, 7.08 mmol) and NaOMe (11 mL, 5.31 mmol, 0.5 M in MeOH) was refluxed for 3 days, then partitioned between EtOAc and water. 1 M HCl was added with stirring until pH was ~1. The organic layer was dried over MgSO₄ and concentrated. The crude product was purified by column chromatography (0-60% EtOAc/hexanes+2% AcOH) to give 49 mg of the title compound. MS: (+) m/z 383.09 (M+1).

Example 116

3-{[4-Hydroxy-7-(3-phenyl-ureido)-isoquinoline-3-carbonyl]-amino}-propionic acid

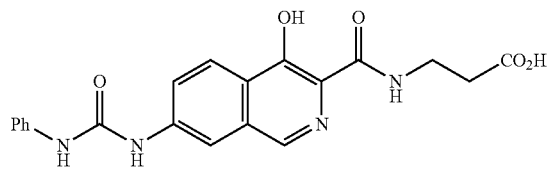 [SMILES: O=C(O)CCNC(=O)c1ncc2cc(NC(=O)Nc3ccccc3)ccc2c1O]

a) 4-Hydroxy-7-(3-phenyl-ureido)-isoquinoline-3-carboxylic acid ethyl ester

7-Bromo-4-hydroxy-isoquinoline-3-carboxylic acid ethyl ester (250 mg, 0.8443 mmol) was combined in an oven-dried flask with phenyl urea (138 mg, 1.013 mmol), cesium carbonate (550 mg, 1.69 mmol), XantPhos (49 mg, 0.0844 mmol) and tris(dibenzylideneacetone)dipalladium(0) (25 mg, 0.0422 mmol). The flask was flushed with dry nitrogen and charged with dioxane (5 mL) and the solution brought to reflux. After 44 h, the reaction was cooled and the solution partitioned between equal volumes of ethyl acetate and brine resulting in precipitation. Filtration of the solid followed by vacuum drying provided the desired urea product in 84% yield. MS ESI(+) m/e: 352.0330 (M+1).

b) 3-{[4-Hydroxy-7-(3-phenyl-ureido)-isoquinoline-3-carbonyl]amino}-propionic acid 4-Hydroxy-7-(3-phenyl-ureido)-isoquinoline-3-carboxylic acid ethyl ester (75 mg, 0.2135 mmol) and B-alanine (191 mg, 2.135 mmol) were combined in a dry flask. 0.5M sodium methoxide in methanol (4.2 mL, 2.135 mmol) was added with stirring and the solution brought to reflux and held for 24 h. The mixture was cooled, concentrated in vacuo and the residue dissolved in water. The solution was acidified to pH 3 with 1M hydrochloric acid and the precipitate isolated by filtration. The crude product was purified by trituration with a minimal volume of methanol to provide the title compound in 57% yield. MS ESI(+) m/e: 395.1345 (M+1).

Example 117

(S)-2-Hydroxy-3-{[4-hydroxy-7-(3-phenyl-ureido)-isoquinoline-3-carbonyl]-amino}-propionic acid

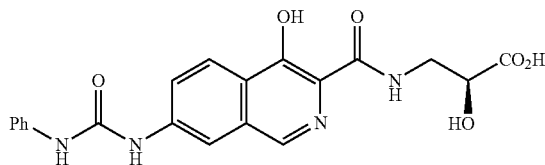 [SMILES: O=C(Nc1ccccc1)Nc1ccc2c(O)c(C(=O)NC[C@H](O)C(=O)O)ncc2c1]

(S)-2-Hydroxy-3-{[4-hydroxy-7-(3-phenyl-ureido)-isoquinoline-3-carbonyl]-amino}-propionic acid was prepared from 4-Hydroxy-7-(3-phenyl-ureido)-isoquinoline-3-carboxylic acid ethyl ester from under conditions analogous to Example 116(b) using (S)-isoserine. MS ESI(+) m/e: 411.0449 (M+1).

Example 118

3-{[7-(4-Fluoro-benzoylamino)-4-hydroxy-isoquinoline-3-carbonyl]-amino}-propionic acid

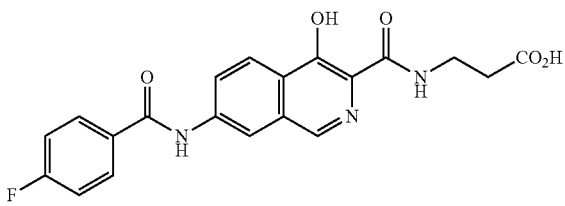 [SMILES: O=C(O)CCNC(=O)c1ncc2cc(NC(=O)c3ccc(F)cc3)ccc2c1O]

a) 7-(4-Fluoro-benzoylamino)-4-hydroxy-isoquinoline-3-carboxylic acid ethyl ester 7-(4-Fluoro-benzoylamino)-4-hydroxy-isoquinoline-3-carboxylic acid ethyl ester was prepared from 7-Bromo-4-hydroxy-isoquinoline-3-carboxylic acid ethyl ester under conditions analogous to Example 116(a) using 4-Fluorobenzamide. $^1$H NMR (200 MHz, CDCl$_3$): δ ppm=11.87 (s, 1H), 8.79 (s, 1H), 8.58 (s, 1H), 8.36 (d, 1H), 8.12 (br s, 1H), 7.95 (m, 2H), 7.74 (d, 1H), 7.15-7.24 (m, 3H), 4.56 (q, 2H), 1.51 (t, 3H.)

b) 3-{[7-(4-Fluoro-benzoylamino)-4-hydroxy-isoquinoline-3-carbonyl]amino}-propionic acid 3-{[7-(4-Fluoro-benzoylamino)-4-hydroxy-isoquinoline-3-carbonyl]-amino}-propionic acid was prepared from 7-(4-Fluoro-benzoylamino)-4-hydroxy-isoquinoline-3-carboxylic acid ethyl ester under conditions analogous to Example 116(b) using beta-alanine. MS ESI(−) m/e: 395.9953 (M−1).

Example 119

4-{[4-Hydroxy-7-(3-phenyl-ureido)-isoquinoline-3-carbonyl]-amino}-butyric acid

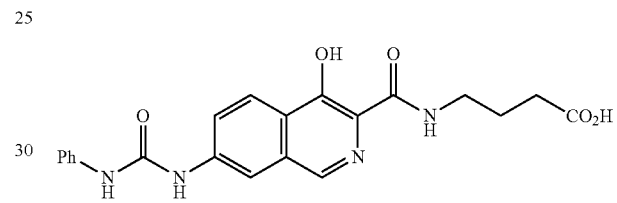

4-{[4-Hydroxy-7-(3-phenyl-ureido)-isoquinoline-3-carbonyl]-amino}-butyric acid was prepared from 4-Hydroxy-7-(3-phenyl-ureido)-isoquinoline-3-carboxylic acid ethyl ester under conditions analogous to Example 116(b) using 3-aminobutyric acid. MS ESI(−) m/e: 406.9654 (M−1).

Example 120

4-{[7-(4-Fluoro-benzoylamino)-4-hydroxy-isoquinoline-3-carbonyl]-amino}-butyric acid

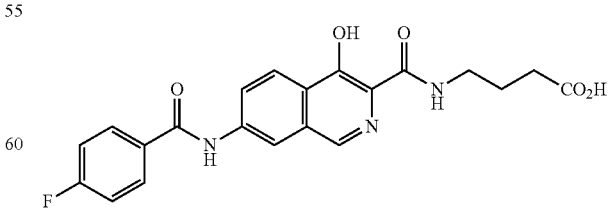

4-{[7-(4-Fluoro-benzoylamino)-4-hydroxy-isoquinoline-3-carbonyl]-amino}-butyric acid was prepared from 7-(4-Fluoro-benzoylamino)-4-hydroxy-isoquinoline-3-carboxylic acid ethyl ester under conditions analogous to Example 116 (b) using 3-aminobutyric acid. MS ESI(−) m/e: 409.9897 (M−1).

Example 121

3-[(1-Cyano-4-hydroxy-7-phenylsulfanyl-isoquinoline-3-carbonyl)-amino]-2,2-dimethyl-propionic acid

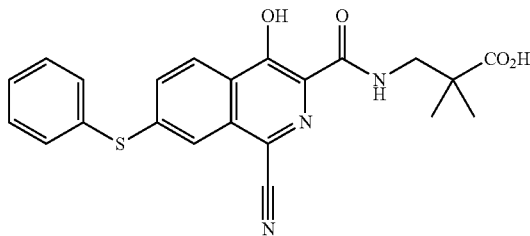 [SMILES: CC(C)(CNC(=O)c1nc(C#N)c2cc(Sc3ccccc3)ccc2c1O)C(=O)O]

a) 1-Cyano-4-hydroxy-7-phenylsulfanyl-isoquinoline-3-carboxylic acid butyl ester A mixture of 4-hydroxy-7-phenylsulfanyl-isoquinoline-3-carboxylic acid butyl ester (300 mg, 0.85 mmol) (prepared according to WO 2004108681) and bis(2,4,6-trimethylpyridine)iodine(I) hexafluorophosphate (1.09 g, 2.12 mmol) in $CH_2Cl_2$ (10 mL) was stirred at r.t. for 16 h, then diluted with $CH_2Cl_2$ (50 mL). The resulting mixture was washed with 5% sodium thiosulfate and 1 M HCl. The organic layer was dried over $MgSO_4$ and concentrated. To the residue were added CuCN (152 mg, 1.70 mmol) and anhydrous DMF (10 mL), and the resulting mixture was refluxed for 20 min. The reaction mixture was poured into a mixture of $CH_2Cl_2$ and water. 4 M HCl was added with vigorous stirring until no solid was observed. The aqueous layer was extracted with additional $CH_2Cl_2$, and the organic layers were combined, dried over $MgSO_4$ and concentrated. The crude product was purified by column chromatography (0-30% EtOAc/hexanes) to give 274 mg of the title compound as a white solid. MS: (+) m/z 379.09 (M+1).

b) 3-[(1-Cyano-4-hydroxy-7-phenylsulfanyl-isoquinoline-3-carbonyl)-amino]-2,2-dimethyl-propionic acid methyl ester A mixture of 1-cyano-4-hydroxy-7-phenylsulfanyl-isoquinoline-3-carboxylic acid butyl ester (50 mg, 0.13 mmol) and 3-amino-2,2-dimethyl-propionic acid methyl ester (52 mg, 0.40 mmol) in MeOH (2 mL) was heated at 150° C. in a microwave reactor for 3 h. The solvent was evaporated, and the residue was purified by column chromatography (0-40% EtOAc/hexanes+2% AcOH) to give 46 mg of the title compound. $^1$H NMR (CDCl$_3$, 200 MHz): δ ppm=14.0 (s, 1H), 8.20-8.35 (m, 2H), 7.87 (d, 1H, J=1.2 Hz), 6.40-6.70 (m, 6H), 3.79 (s, 3H), 3.61 (d, 2H, J=7.0 Hz), 1.30 (s, 6H).

c) 3-[(1-Cyano-4-hydroxy-7-phenylsulfanyl-isoquinoline-3-carbonyl)-amino]-2,2-dimethyl-propionic acid A mixture of 3-[(1-cyano-4-hydroxy-7-phenylsulfanyl-isoquinoline-3-carbonyl)-amino]-2,2-dimethyl-propionic acid methyl ester (46 mg, 0.11 mmol), 2 M NaOH (2 mL) and MeOH (2 mL) was stirred at r.t. for 3 h. 1 M HCl was added until pH was ~2, and the resulting suspension was extracted with EtOAc. The organic layer was dried over $MgSO_4$ and concentrated. The crude product was purified by column chromatography (0-25% EtOAc/hexanes+2% AcOH) to give 29 mg of the title compound. MS: (−) m/z 420.09 (M−1).

Example 122

3-[(1-Cyano-4-hydroxy-7-phenethyl-isoquinoline-3-carbonyl)-amino]-2,2-dimethyl-propionic acid

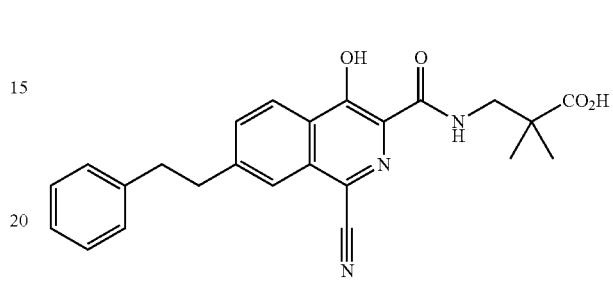

a) 4-Hydroxy-7-phenylethynyl-isoquinoline-3-carboxylic acid methyl ester

A mixture of 7-bromo-4-hydroxy-isoquinoline-3-carboxylic acid methyl ester (500 mg, 1.77 mmol), tributyl(phenylethynyl)tin (0.8 mL, 2.13 mmol), and $PdCl_2(PPh_3)_2$ (249 mg, 0.35 mmol) in DMF (18 mL) was heated at 120° C. for 2 h under $N_2$ atmosphere. After cooling the mixture to r.t., water and EtOAc were added. 1 M HCl was added with stirring until pH was ~2. The aqueous layer was extracted with additional EtOAc, and the organic layers were combined, washed with water, and dried over $MgSO_4$. After evaporating the solvent, the crude product was purified by column chromatography (0-40% EtOAc/hexanes) to give 560 mg of the title compound as a yellow solid. MS: (+) m/z 304.10 (M+1).

b) 4-Hydroxy-7-phenethyl-isoquinoline-3-carboxylic acid methyl ester

A mixture of 4-hydroxy-7-phenylethynyl-isoquinoline-3-carboxylic acid methyl ester (60 mg, 0.20 mmol), 10% Pd/C (200 mg), EtOH (10 mL) and EtOAc (20 mL) was stirred under $H_2$ atmosphere for 48 h. The resulting mixture was filtered, and the filtrate was concentrated. The residue was purified by column chromatography (0-40% EtOAc/hexanes) to give 350 mg of the title compound. MS: (+) m/z 308.26 (M+1).

c) 1-Cyano-4-hydroxy-7-phenethyl-isoquinoline-3-carboxylic acid methyl ester

A mixture of 4-hydroxy-7-phenethyl-isoquinoline-3-carboxylic acid methyl ester (250 mg, 0.81 mmol) and bis(2,4,6-trimethylpyridine)iodine(I) hexafluorophosphate (1.05 g, 2.04 mmol) in $CH_2Cl_2$ (10 mL) was stirred at r.t. for 16 h, then diluted with $CH_2Cl_2$. The resulting mixture was washed with 5% sodium thiosulfate and 1 M HCl. The organic layer was dried over $MgSO_4$ and concentrated. To the residue were added CuCN (150 mg, 1.62 mmol) and anhydrous DMF (8 mL), and the resulting mixture was refluxed for 20 min. After cooling to r.t., the reaction mixture was poured into a mixture of $CH_2Cl_2$ (50 mL) and water (50 mL). 4 M HCl was added with vigorous stirring until no solid was observed. The aqueous layer was extracted with additional $CH_2Cl_2$, and the organic layers were combined, dried over $MgSO_4$ and concentrated. The crude product was purified by column chromatography (20-100% $CH_2Cl_2$/hexanes) to give 200 mg of the title compound as a light yellow solid. MS: (+) m/z 333.28 (M+1).

d) 3[(1-Cyano-4-hydroxy-7-phenethyl-isoquinoline-3-carbonyl)-amino]-2,2-dimethyl-propionic acid methyl ester A mixture of 1-cyano-4-hydroxy-7-phenethyl-isoquinoline-3-carboxylic acid methyl ester (50 mg, 0.15 mmol) and 3-amino-2,2-dimethyl-propionic acid methyl ester (99 mg, 0.75 mmol) in EtOH (2 mL) was heated at 150° C. in a microwave reactor for 3 h. The solvent was evaporated, and the residue was purified by column chromatography (0-25% EtOAc/hexanes) to give 55 mg of the title compound. $^1H$ NMR ($CDCl_3$, 200 MHz): δ=14.0 (s, 1H), 8.20-8.40 (m, 2H), 7.98 (d, 1H, J=0.8 Hz), 7.64 (dd, 1H, J=8.6 Hz, 1.6 Hz), 7.10-7.40 (m, 5H), 3.79 (s, 3H), 3.63 (d, 2H, J=6.6 Hz), 3.00-3.30 (m, 4H), 1.31 (s, 6H).

e) 3-[(1-Cyano-4-hydroxy-7-phenethyl-isoquinoline-3-carbonyl)-amino]-2,2-dimethyl-propionic acid A mixture of 3-[(1-cyano-4-hydroxy-7-phenethyl-isoquinoline-3-carbonyl)-amino]-2,2-dimethyl-propionic acid methyl ester (55 mg, 0.13 mmol), 2 M NaOH (2 mL) and MeOH (2 mL) was stirred at r.t. for 3 h. 1 M HCl was added until pH was ~2, and the resulting suspension was extracted with EtOAc. The organic layer was dried over $MgSO_4$ and concentrated. The crude product was purified by column chromatography (0-30% EtOAc/hexanes+2% AcOH) to give 38 mg of the title compound. MS: (−) m/z 416.14 (M−1).

Example 123

3-[(1-Cyano-4-hydroxy-6-phenoxy-isoquinoline-3-carbonyl)-amino]-2,2-dimethyl-propionic acid

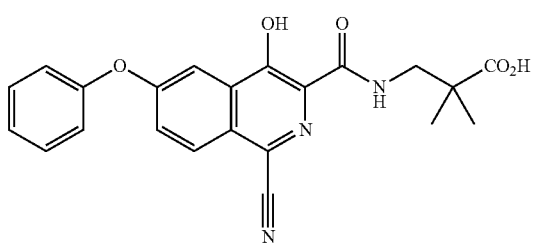 [SMILES: CC(C)(CNC(=O)c1nc(C#N)c2ccc(Oc3ccccc3)cc2c1O)C(=O)O]

a) 3[(1-Cyano-4-hydroxy-6-phenoxy-isoquinoline-3-carbonyl)-amino]-2,2-dimethyl-propionic acid methyl ester A mixture of 1-cyano-4-hydroxy-6-phenoxy-isoquinoline-3-carboxylic acid butyl ester (50 mg, 0.14 mmol) (prepared according to U.S. Pat. No. 7,928,120) and 3-amino-2,2-dimethyl-propionic acid methyl ester (90 mg, 0.70 mmol) in EtOH (2 mL) was heated at 150° C. in a microwave reactor for 3 h. The solvent was evaporated, and the residue was purified by column chromatography (0-30% EtOAc/hexanes) to give 38 mg of the title compound. $^1H$ NMR ($CDCl_3$, 200 MHz): δ ppm=13.9 (s, 1H), 8.20-8.40 (m, 2H), 7.10-7.70 (m, 7H), 3.79 (s, 3H), 3.62 (d, 2H, J=7.0 Hz), 1.30 (s, 6H).

b) 3[(1-Cyano-4-hydroxy-6-phenoxy-isoquinoline-3-carbonyl)-amino]-2,2-dimethyl-propionic acid A mixture of 3-[(1-cyano-4-hydroxy-6-phenoxy-isoquinoline-3-carbonyl)-amino]-2,2-dimethyl-propionic acid methyl ester (38 mg, 0.091 mmol), 2 M NaOH (2 mL) and MeOH (2 mL) was stirred at r.t. for 3 h. 1 M HCl was added until pH was ~2, and the resulting suspension was extracted with EtOAc. The organic layer was dried over $MgSO_4$ and concentrated. The crude product was purified by column chromatography (0-25% EtOAc/hexanes+2% AcOH) to give 20 mg of the title compound. MS: (−) m/z 404.11 (M−1).

Example 124

5-[(4-Hydroxy-7-phenylamino-isoquinoline-3-carbonyl)-amino]-pentanoic acid

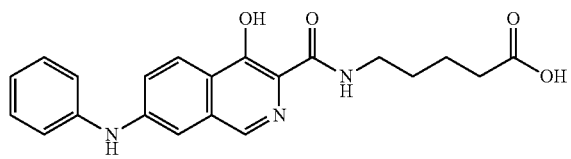 [SMILES: O=C(O)CCCCNC(=O)c1ncc2cc(Nc3ccccc3)ccc2c1O]

a) Methyl 4-hydroxy-7-(phenylamino)isoquinoline-3-carboxylate

A mixture of 7-bromo-4-hydroxy-isoquinoline-3-carboxylic acid methyl ester (141.0 mg, 0.50 mmol), xantphos (28.9 mg, 0.05 mmol, Strem), $Pd_2(dba)_3$ (22.9 mg, 0.03 mmol, Sigma-Aldrich), $Cs_2CO_3$ (488.7 mg, 1.5 mmol) and aniline (0.1 mL, 1 mmol) in DMF (5 mL) was stirred at 135° C. for 16 hours under a nitrogen atmosphere. After cooling to room temperature, the mixture was diluted with $CH_2Cl_2$ (50 mL) and $H_2O$ (50 mL). The layers were separated and the aqueous layer was extracted twice with $CH_2Cl_2$. The combined organic layers were dried over $MgSO_4$, concentrated, and purified by flash chromatography (0-30% MeOH/$CH_2Cl_2$) to give the title compound in 62.4 mg. MS: (−) m/z 293.04 (M−1).

b) 5-[(4-Hydroxy-7-phenylamino-isoquinoline-3-carbonyl)-amino]-pentanoic acid

A mixture of methyl 4-hydroxy-7-(phenylamino)isoquinoline-3-carboxylate (30.0 mg, 0.09 mmol), 5-aminovaleric acid (216.3 mg, 1.9 mmol, Sigma-Aldrich) and NaOMe in MeOH (2.8 mL, 1.4 mmol, 0.5 M solution, Sigma-Aldrich) was heated to reflux for 20 hours before cooling to room temperature. The solvent was removed in vacuo and the residue was dissolved in $H_2O$ (10 mL) and EtOAc (10 mL). To the stirred mixture was added 1 N hydrochloric acid until pH was 1. The layers were separated and the aqueous layer was extracted twice with EtOAc. The combined organic layers were dried over $MgSO_4$, concentrated, and purified by flash chromatography (0-30% MeOH/CH₂Cl₂) to give the title compound in 27 mg. MS: (+) m/z 380.11 (M+1).

Example 125

5-{[4-Hydroxy-7-(4-methoxy-benzylamino)-isoquinoline-3-carbonyl]-amino}-pentanoic acid

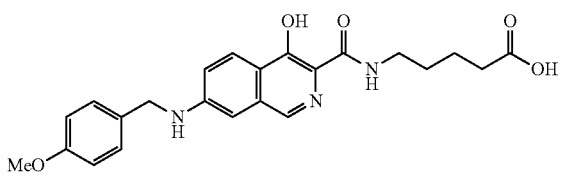 [SMILES: COc1ccc(CNc2ccc3c(O)c(C(=O)NCCCCC(=O)O)ncc3c2)cc1]

a) Methyl 4-(benzyloxy)-7-bromoisoquinoline-3-carboxylate

A mixture of 7-bromo-4-hydroxy-isoquinoline-3-carboxylic acid methyl ester (955.0 mg, 3.4 mmol), K₂CO₃ (1.2 g, 8.5 mmol), KI (56.2 mg, 0.3 mmol) and BnBr (0.6 mL, 4.7 mmol) in DMF (17 mL) was stirred at 60° C. for 16 hours. After cooling to room temperature, the mixture was diluted with EtOAc (100 mL) and H₂O (100 mL). The layers were separated and the aqueous layer was extracted twice with EtOAc. The combined organic layers were dried over MgSO₄, concentrated, and purified by flash chromatography (0-20% EtOAc/CH₂Cl₂) to give the title compound in 1.1 g. MS: (+) m/z 372.20 (M+1).

b) Methyl 4-(benzyloxy)-7-(4-methoxybenzylamino)isoquinoline-3-carboxylate

A mixture of methyl 4-(benzyloxy)-7-bromoisoquinoline-3-carboxylate (372.0 mg, 1.0 mmol), 4-methoxybenzylamine (0.2 mL, 1.5 mmol, TCI), CuI (19.0 mg, 0.1 mmol), proline (23.0 mg, 0.2 mmol) and K₂CO₃ (276.4 mg, 2.0 mmol) in DMSO (0.6 mL) was stirred at 80° C. for 24 hours under a nitrogen atmosphere. After cooling to room temperature, the mixture was diluted with CH₂Cl₂ (50 mL) and H₂O (50 mL). The layers were separated and the aqueous layer was extracted twice with CH₂Cl₂. The combined organic layers were dried over MgSO₄, concentrated, and purified by flash chromatography (0-30% EtOAc/CH₂Cl₂) to give the title compound in 137.0 mg. $^1$H NMR (CDCl₃, 200 MHz): δ=8.82 (s, 1H), 7.96 (d, 1H, J=9.0 Hz), 7.54 (d, 2H, J=6.6 Hz), 7.42-7.27 (m, 5H), 7.05 (d, 1H, J=9.0 Hz), 6.93-6.87 (m, 3H), 5.18 (s, 2H), 4.38 (d, 2H, J=5.0 Hz), 4.00 (s, 3H), 3.82 (s, 3H).

c) Methyl 4-hydroxy-7-(4-methoxybenzylamino)isoquinoline-3-carboxylate

To a solution of methyl 4-(benzyloxy)-7-(4-methoxybenzylamino)isoquinoline-3-carboxylate (200.0 mg, 0.47 mmol) in EtOAc (21 mL) was added a suspension of Pd/C (171.3 mg, 0.16 mmol, 10% by weight) in EtOH (21 mL). The resulting mixture was stirred at room temperature under a hydrogen atmosphere for 16 hours. The resulting suspension was filtered through a pad of celite. The filtrate was concentrated in vacuo and then purified by flash chromatography (0-30% EtOAc/CH₂Cl₂) to give the title compound in 120.0 mg. $^1$H NMR (CDCl₃, 200 MHz): δ=11.63 (s, 1H), 8.51 (s, 1H), 8.13 (d, 1H, J=9.0 Hz), 7.30 (d, 2H, J=6.6 Hz), 7.06 (d, 1H, J=9.0 Hz), 6.94-6.82 (m, 3H), 4.39 (s, 2H), 4.04 (s, 3H), 3.80 (s, 3H).

d) 5-{[4-Hydroxy-7-(4-methoxy-benzylamino)-isoquinoline-3-carbonyl]amino}-pentanoic acid A mixture of methyl 4-hydroxy-7-(4-methoxybenzylamino)isoquinoline-3-carboxylate (21.0 mg, 0.06 mmol), 5-aminovaleric acid (269.3 mg, 2.3 mmol, Sigma-Aldrich) and NaOMe in MeOH (3.0 mL, 1.5 mmol, 0.5 M solution, Sigma-Aldrich) was heated to reflux for 20 hours before cooling to room temperature. The solvent was removed in vacuo and the residue was dissolved in H₂O (10 mL) and EtOAc (10 mL). To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-30% MeOH/CH₂Cl₂) to give the title compound in 14 mg. MS: (−) m/z 422.13 (M−1).

Example 126

3-{[4-Hydroxy-7-(4-methoxy-benzylamino)-isoquinoline-3-carbonyl]-amino}-2,2-dimethyl-propionic acid

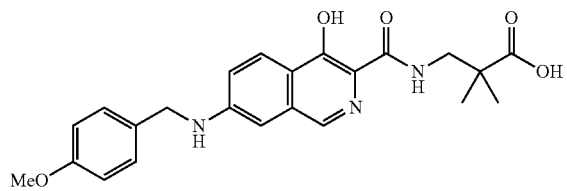 [SMILES: COc1ccc(CNc2ccc3c(O)c(C(=O)NCC(C)(C)C(=O)O)ncc3c2)cc1]

a) Methyl 3-(4-hydroxy-7-(4-methoxybenzylamino)isoquinoline-3-carboxamido)-2,2-dimethylpropanoate Methyl 4-hydroxy-7-(4-methoxybenzylamino)isoquinoline-3-carboxylate (49.0 mg, 0.14 mmol) and methyl 3-amino-2,2-dimethylpropanoate (114.0 mg, 0.87 mmol) in MeOH (3 mL) were heated at 150° C. in a microwave for 4 hours. The solvent was removed in vacuo and the residue oil was purified by flash chromatography (0-10% EtOAc/CH₂Cl₂) to give the title compound in 15 mg. $^1$H NMR (CDCl₃, 200 MHz): δ=13.10 (s, 1H), 8.40-8.28 (m, 2H), 8.10 (d, 1H, J=9.0 Hz), 7.30 (d, 2H, J=6.6 Hz), 7.05 (d, 1H, J=9.0 Hz), 6.92-6.80 (m, 3H), 5.14 (s, 1H), 4.38 (s, 2H), 3.81 (s, 3H), 3.68 (s, 3H), 3.59 (d, 2H, J=6.6 Hz), 1.28 (s, 6H).

b) 3-{[4-Hydroxy-7-(4-methoxy-benzylamino)-isoquinoline-3-carbonyl]amino}-2,2-dimethyl-propionic acid Methyl 3-(4-hydroxy-7-(4-methoxybenzylamino)isoquinoline-3-carboxamido)-2,2-dimethylpropanoate (15 mg, 0.03 mmol) was dissolved in MeOH (2 mL) and 2 N NaOH (2 mL). After stirring for 5 hours at room temperature, H₂O (15 mL) and EtOAc (15 mL) were added. To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-20% MeOH/CH₂Cl₂) to give the title compound in 13 mg. MS: (−) m/z 422.13 (M−1).

Example 127

3-[(4-Hydroxy-7-phenylsulfanyl-isoquinoline-3-carbonyl)-amino]-2,2-dimethyl-propionic acid

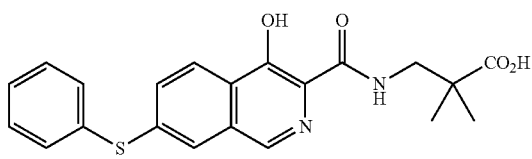 [SMILES: CC(C)(CNC(=O)c1ncc2cc(Sc3ccccc3)ccc2c1O)C(=O)O]

a) Cyano-dimethyl-acetic acid methyl ester

A mixture of cyano-acetic acid methyl ester (11 g, 111 mmol), Cs₂CO₃ (108 g, 333 mmol) and methyl iodide (35 mL, 556 mmol) in anhydrous DMF (300 mL) was stirred at r.t. for 3 days. Brine (100 mL) and ether (250 mL) were added, and the aqueous layer was extracted with additional ether (250 mL). The organic layers were combined, washed with water (4×200 mL), and dried over MgSO₄. The solvent was evaporated to give 11 g of the title compound as a yellow oil. $^1$H NMR (CDCl₃, 200 MHz): δ ppm=3.83 (s, 3H), 1.63 (s, 6H).

b) 3-tert-Butoxycarbonylamino-2,2-dimethyl-propionic acid methyl ester

A mixture of cyano-dimethyl-acetic acid methyl ester (5 g, 39.4 mmol), Boc anhydride (17.2 g, 78.7 mmol), and NiCl₂ (0.51 g, 3.94 mmol) in MeOH (200 mL) was cooled in an ice bath. NaBH₄ (10.4 g, 276 mmol) was slowly added over 1 h at 0° C., and the resulting mixture was stirred at r.t. for 16 h. Diethylenetriamine (4.3 mL, 39.4 mmol) was then added, and the mixture was stirred for 30 min. The solvent was evaporated, and the residue was partitioned between EtOAc (200 mL) and saturated NaHCO₃ (400 mL). The aqueous layer was extracted with additional EtOAc, and the organic layers were combined, dried over MgSO₄, and concentrated. The crude product was purified by column chromatography (0-40% EtOAc/hexanes) to give 2.5 g of the title compound as a clear oil. $^1$H NMR (CDCl₃, 200 MHz): δ ppm=4.95 (br s, 1H), 3.69 (s, 3H), 3.24 (d, 2H, J=6.6 Hz), 1.44 (s, 9H), 1.20 (s, 6H).

c) 3-Amino-2,2-dimethyl-propionic acid TFA salt

To a solution of 3-tert-butoxycarbonylamino-2,2-dimethyl-propionic acid methyl ester (2.5 g, 10.8 mmol) in MeOH (30 mL) was added 1 M NaOH (27 mL, 27 mmol), and the resulting mixture was stirred at r.t. for 16 h. 1 M HCl was added until pH was ~3, and the mixture was extracted with EtOAc. The organic layer was dried over MgSO₄ and concentrated. The residue obtained was dissolved CH₂Cl₂ (10 mL), and TFA (7 mL) was added. The resulting mixture was stirred at r.t. for 3 days, then concentrated to dryness to give 2.1 g of the title compound as a gray solid. $^1$H NMR (DMSO-d₆, 200 MHz): δ ppm=7.8 (br s, 3H), 2.80-3.00 (m, 2H), 1.18 (s, 6H).

d) 3-[(4-Hydroxy-7-phenylsulfanyl-isoquinoline-3-carbonyl)-amino]-2,2-dimethyl-propionic acid A mixture of 4-hydroxy-7-phenylsulfanyl-isoquinoline-3-carboxylic acid butyl ester (60 mg, 0.17 mmol) (prepared according to WO 2004108681), 3-amino-2,2-dimethyl-propionic acid TFA salt (157 mg, 0.68 mmol) and NaOMe (73 mg, 1.36 mmol) in EtOH (2 mL) was heated at 150° C. in a microwave reactor for 6 h. The solvent was evaporated, and the residue was partitioned between water and EtOAc. 1 M HCl was added with vigorous stirring until pH was ~2. The organic layer was dried over MgSO₄ and concentrated. The crude product was purified by column chromatography (0-30% EtOAc/hexanes+2% AcOH) to give 18 mg of the title compound as a yellow solid. MS: (+) m/z 397.11 (M+1).

Example 128

5-[(1-Cyano-4-hydroxy-6-phenoxy-isoquinoline-3-carbonyl)-amino]-pentanoic acid

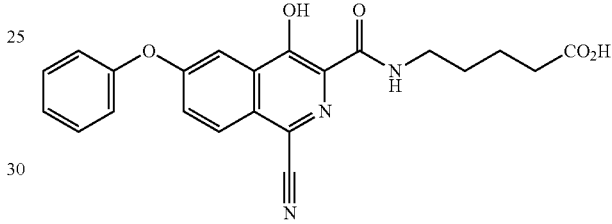

A mixture of 1-cyano-4-hydroxy-6-phenoxy-isoquinoline-3-carboxylic acid butyl ester (60 mg, 0.17 mmol) (prepared according to U.S. Pat. No. 7,928,120), 5-aminovaleric acid (970 mg, 8.28 mmol) and NaOMe (360 mg, 6.62 mmol) in 2-methoxyethanol (15 mL) was refluxed for 1.5 h. Solvent was evaporated, and the residue was partitioned between EtOAc and water. 1 M HCl was added with stirring until pH was ~2. The organic layer was dried over MgSO₄ and concentrated. The crude product was purified by preparative TLC (40% EtOAc/hexanes+2% AcOH) to give 33 mg of the title compound. MS: (+) m/z 406.13 (M+1).

Example 129

3-[(4-Hydroxy-7-phenyl-isoquinoline-3-carbonyl)-amino]-2,2-dimethyl-propionic acid

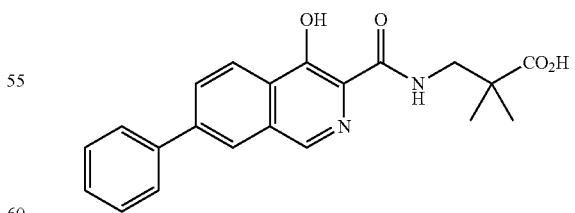

a) 4-Hydroxy-7-phenyl-isoquinoline-3-carboxylic acid methyl ester

A mixture of 7-bromo-4-hydroxy-isoquinoline-3-carboxylic acid methyl ester (400 mg, 1.42 mmol), tributylphenyltin (0.6 mL, 1.70 mmol), and PdCl₂(PPh₃)₂ (200 mg, 0.28 mmol) in DMF (14 mL) was heated at 120° C. for 2 h under N₂ atmosphere. After cooling the mixture to r.t., brine (10 mL) and EtOAc (30 mL) were added. 1 M HCl was added with stirring until pH was ~3. The aqueous layer was extracted with additional EtOAc, and the organic layers were combined, washed with water, and dried over MgSO₄. After evaporating the solvent, the crude product was purified by column chromatography (0-40% EtOAc/hexanes) to give 300 mg of the title compound. ¹H NMR (CDCl₃, 200 MHz): δ ppm=11.7 (s, 1H), 8.87 (s, 1H), 8.46 (d, 1H, J=8.6 Hz), 8.15 (d, 1H, J=1.4 Hz), 8.04 (dd, 1H, J=8.6 Hz, 2.0 Hz), 7.65-7.80 (m, 2H), 7.40-7.60 (m, 3H), 4.12 (s, 3H).

b) 3-[(4-Hydroxy-7-phenyl-isoquinoline-3-carbonyl)-amino]-2,2-dimethyl-propionic acid A mixture of 4-hydroxy-7-phenyl-isoquinoline-3-carboxylic acid methyl ester (60 mg, 0.22 mmol), 3-amino-2,2-dimethyl-propionic acid TFA salt (200 mg, 0.86 mmol) and NaOMe (93 mg, 1.72 mmol) in EtOH (2.2 mL) was heated at 150° C. in a microwave reactor for 6 h. The solvent was evaporated, and the residue was partitioned between water and EtOAc. 1 M HCl was added with vigorous stirring until pH was ~2. The organic layer was dried over MgSO₄ and concentrated. The crude product was purified by column chromatography (0-30% EtOAc/hexanes+2% AcOH) to give 38 mg of the title compound. MS: (+) m/z 365.11 (M+1).

Example 130

3-{[7-(3-Cyclohexyl-ureido)-4-hydroxy-isoquinoline-3-carbonyl]-amino}-propionic acid

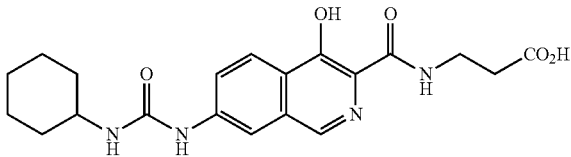 [SMILES: O=C(O)CCNC(=O)c1ncc2cc(NC(=O)NC3CCCCC3)ccc2c1O]

a) 7-(3-Cyclohexyl-ureido)-4-hydroxy-isoquinoline-3-carboxylic acid ethyl ester 7-(3-Cyclohexyl-ureido)-4-hydroxy-isoquinoline-3-carboxylic acid ethyl ester was prepared from 7-Bromo-4-hydroxy-isoquinoline-3-carboxylic acid ethyl ester under conditions analogous to Example 116(a) using cyclohexyl urea. ¹H NMR (200 MHz, CDCl₃): δ ppm=11.79 (br s, 1H), 8.66 (s, 1H), 8.20 (m, 2H), 7.67 (br s, 1H), 7.50 (d, 1H), 5.30 (d, 1H), 4.53 (q, 2H), 3.71-3.63 (m, 1H), 1.98 (br d, 2H), 1.68-1.07 (m, 19H.)

b) 3-{[7-(3-Cyclohexyl-ureido)-4-hydroxy-isoquinoline-3-carbonyl]amino}-propionic acid 3-{[7-(3-Cyclohexyl-ureido)-4-hydroxy-isoquinoline-3-carbonyl]-amino}-propionic acid was prepared from 7-(3-Cyclohexyl-ureido)-4-hydroxy-isoquinoline-3-carboxylic acid ethyl ester under conditions analogous to Example 116 (b) using beta-alanine. MS ESI(−) m/e: 399.1460 (M−1).

Example 131

4-{[7-(3-Cyclohexyl-ureido)-4-hydroxy-isoquinoline-3-carbonyl]-amino}-butyric acid

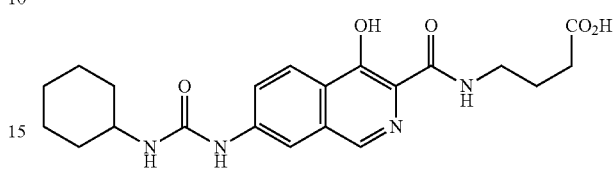

4-{[7-(3-Cyclohexyl-ureido)-4-hydroxy-isoquinoline-3-carbonyl]-amino}-butyric acid was prepared from 7-(3-Cyclohexyl-ureido)-4-hydroxy-isoquinoline-3-carboxylic acid ethyl ester under conditions analogous to Example 116(b) using 3-aminobutyric acid. MS ESI(−) m/e: 413.1448 (M−1).

Example 132

3-{[7-(4-Fluoro-phenyl)-4-hydroxy-isoquinoline-3-carbonyl]-amino}-propionic acid

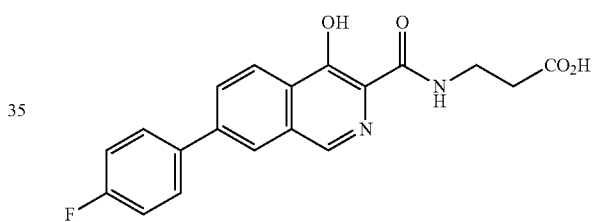

a) 7-(4-Fluoro-phenyl)-4-hydroxy-isoquinoline-3-carboxylic acid ethyl ester

7-Bromo-4-hydroxy-isoquinoline-3-carboxylic acid ethyl ester (250 mg, 0.8443 mmol) was dissolved in dry DMF and 4 Å molecular sieves were added to maintain dryness. 4-fluorophenyl-tri-n-butylstannane (392 mg, 1.013 mmol) and bis (triphenylphosphine)palladium(II) dichloride (71 mg, 0.1013 mmol) were added sequentially and the reaction heated to 120° C. in an oil bath. Upon completion, the reaction was cooled and diluted with ethyl acetate. The solution was washed with water then brine and the organic phase dried over sodium sulfate. The crude material was purified by medium pressure liquid chromatography (15 to 45% ethyl acetate in hexanes) to give the desired material in 55% yield as a thick yellow oil. ¹H NMR (200 MHz, CDCl₃): δ ppm=11.88 (s, 1H), 8.83 (s, 1H), 8.41 (d, 1H), 8.05 (s, 1H), 7.93 (d, 1H), 7.66 (m, 2H), 7.18 (t, 2H), 4.57 (q, 2H), 1.52 (t, 3H.)

b) 3-{[7-(4-Fluoro-phenyl)-4-hydroxy-isoquinoline-3-carbonyl]amino}-propionic acid 3-{[7-(4-Fluoro-phenyl)-4-hydroxy-isoquinoline-3-carbonyl]-amino}-propionic acid was prepared from 7-(4-Fluoro-phenyl)-4-hydroxy-isoquinoline-3-carboxylic acid ethyl ester under conditions analogous to Example 116(b) using beta-alanine. MS ESI(−) m/e: 353.1196 (M−1).

Example 133

3-{[7-(3-Benzyl-ureido)-4-hydroxy-isoquinoline-3-carbonyl]-amino}-propionic acid

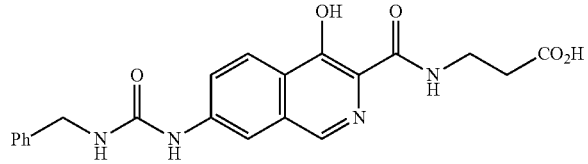 [SMILES: O=C(O)CCNC(=O)c1ncc2cc(NC(=O)NCc3ccccc3)ccc2c1O]

a) 7-(3-Benzyl-ureido)-4-hydroxy-isoquinoline-3-carboxylic acid ethyl ester 7-(3-Benzyl-ureido)-4-hydroxy-isoquinoline-3-carboxylic acid ethyl ester was prepared from 7-bromo-4-hydroxy-isoquinoline-3-carboxylic acid ethyl ester under conditions analogous to Example 116(a) using benzyl urea. The crude product was used in the following steps without purification.

b) 3-{[7-(3-Benzyl-ureido)-4-hydroxy-isoquinoline-3-carbonyl]amino}-propionic acid 3-{[7-(3-Benzyl-ureido)-4-hydroxy-isoquinoline-3-carbonyl]-amino}-propionic acid was prepared from 7-(3-Benzyl-ureido)-4-hydroxy-isoquinoline-3-carboxylic acid ethyl ester under conditions analogous to Example 116(b) using beta-alanine. MS ESI(−) m/e: 407.0882 (M−1).

Example 134

4-{[7-(3-Benzyl-ureido)-4-hydroxy-isoquinoline-3-carbonyl]-amino}-butyric acid

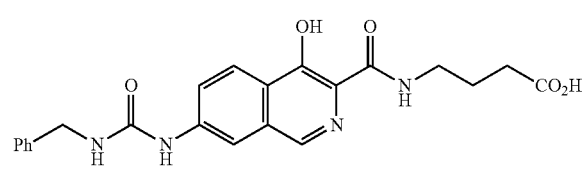 [SMILES: O=C(O)CCCNC(=O)c1ncc2cc(NC(=O)NCc3ccccc3)ccc2c1O]

4-{[7-(3-Benzyl-ureido)-4-hydroxy-isoquinoline-3-carbonyl]-amino}-butyric acid was prepared from 7-(3-Benzyl-ureido)-4-hydroxy-isoquinoline-3-carboxylic acid ethyl ester under conditions analogous to Example 116(b) using 3-aminobutyric acid. MS ESI(−) m/e: 421.1142 (M−1).

Example 135

3-[(7-Cyclohexanesulfonyl-4-hydroxy-isoquinoline-3-carbonyl)-amino]-propionic acid

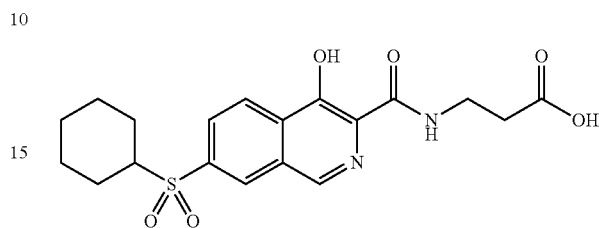

A mixture of 7-cyclohexanesulfonyl-4-hydroxy-isoquinoline-3-carboxylic acid butyl ester (20 mg, 0.05 mmol) (prepared according to U.S. Pat. No. 7,629,357) and beta-alanine (45 mg, 0.5 mmol) in 0.5 M NaOMe/MeOH (0.8 mL, 0.4 mmol) was microwaved at 120° C. for 30 min. Reaction mixture was diluted with water (50 mL) and acidified by 1 N HCl to pH=3-4. Precipitate was collected, rinsed with water and dried in vacuo to provide the title compound 9.4 mg (0.023 mmol) in 46% yield. LC-MS ESI−: 405.05 (M−1)−.

Example 136

3-{[1-(5-Fluoro-pyridin-3-yl)-4-hydroxy-7-phenoxy-isoquinoline-3-carbonyl]-amino}-2,2-dimethyl-propionic acid

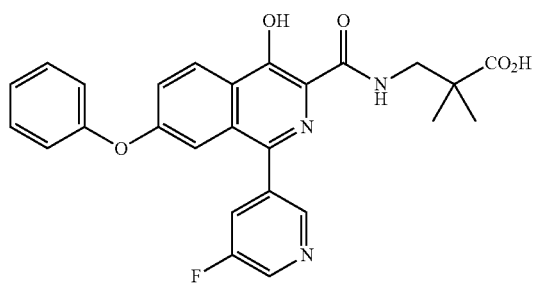 [SMILES: CC(C)(CNC(=O)c1nc(-c2cncc(F)c2)c2cc(Oc3ccccc3)ccc2c1O)C(=O)O]

a) 1-(5-Fluoro-pyridin-3-yl)-4-hydroxy-7-phenoxy-isoquinoline-3-carboxylic acid methyl ester A mixture of 1-bromo-4-hydroxy-7-phenoxy-isoquinoline-3-carboxylic acid methyl ester (150 mg, 0.40 mmol), 5-fluoropyridine-3-boronic acid (70 mg, 0.48 mmol), Pd(PPh$_3$)$_4$ (46 mg, 0.040 mmol) and Cs$_2$CO$_3$ (261 mg, 0.80 mmol) in DMF (4 mL) was heated at 100° C. for 16 h under N$_2$ atmosphere. After cooling the mixture to r.t., brine (10 mL) and EtOAc (40 mL) were added. 1 M HCl was added with stirring until pH was ~4. The aqueous layer was extracted with additional EtOAc, and the organic layers were combined, washed with water, and dried over MgSO$_4$. After evaporating the solvent, the crude product was purified by column chromatography (0-35% EtOAc/hexanes) to give 51 mg of the title compound. MS: (+) m/z 391.09 (M+1).

b) 3-{[1-(5-Fluoro-pyridin-3-yl)-4-hydroxy-7-phenoxy-isoquinoline-3-carbonyl]amino}-2,2-dimethyl-propionic acid A mixture of 1-(5-fluoro-pyridin-3-yl)-4-hydroxy-7-phenoxy-isoquinoline-3-carboxylic acid methyl ester (51 mg, 0.13 mmol), 3-amino-2,2-dimethyl-propionic acid TFA salt (121 mg, 0.52 mmol) and NaOMe (56 mg, 1.05 mmol) in EtOH (3 mL) was heated at 150° C. in a microwave reactor for 6 h. The solvent was evaporated, and the residue was partitioned between water (20 mL) and EtOAc (20 mL). 1 M HCl was added with vigorous stirring until pH was ~3. The organic layer was dried over MgSO₄ and concentrated. The crude product was purified by column chromatography (0-35% EtOAc/hexanes+2% AcOH) to give 30 mg of the title compound as a yellow solid. MS: (+) m/z 476.14 (M+1).

Example 137

3-[(1-Cyano-4-hydroxy-7-phenyl-isoquinoline-3-carbonyl)-amino]-propionic acid

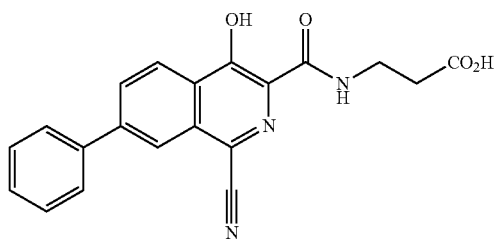 [SMILES: N#Cc1nc(C(=O)NCCC(=O)O)c(O)c2ccc(-c3ccccc3)cc12]

a) 1-Cyano-4-hydroxy-7-phenyl-isoquinoline-3-carboxylic acid methyl ester

A mixture of 4-hydroxy-7-phenyl-isoquinoline-3-carboxylic acid methyl ester (170 mg, 0.61 mmol) and bis(2,4,6-trimethylpyridine)iodine(I) hexafluorophosphate (783 mg, 1.52 mmol) in CH₂Cl₂ (10 mL) was stirred at r.t. for 16 h, then diluted with CH₂Cl₂ (50 mL). The resulting mixture was washed with 5% sodium thiosulfate and 1 M HCl. The organic layer was dried over MgSO₄ and concentrated. To the residue were added CuCN (102 mg, 1.14 mmol) and anhydrous DMF (6 mL), and the resulting mixture was refluxed for 20 min. After cooling to r.t., the reaction mixture was poured into a mixture of CH₂Cl₂ (100 mL) and water (100 mL). 4 M HCl was added with vigorous stirring until no solid was observed. The aqueous layer was extracted with additional CH₂Cl₂, and the organic layers were combined, dried over MgSO₄ and concentrated. The crude product was purified by column chromatography (20-100% CH₂Cl₂/hexanes) to give 93 mg of the title compound as a light brown solid. MS: (+) m/z 305.06 (M+1).

b) 3-[(1-Cyano-4-hydroxy-7-phenyl-isoquinoline-3-carbonyl)-amino]-propionic acid A mixture of 1-cyano-4-hydroxy-7-phenyl-isoquinoline-3-carboxylic acid methyl ester (46 mg, 0.15 mmol), β-alanine (674 mg, 7.57 mmol) and NaOMe (327 mg, 6.05 mmol) in 2-methoxyethanol (12 mL) was refluxed for 1.5 h. After the mixture was cooled to r.t., solvent was evaporated. The residue was partitioned between EtOAc (50 mL) and water (50 mL). 1 M HCl was added with vigorous stirring until pH was ~2. The organic layer was dried over MgSO₄ and concentrated. The crude product was purified by column chromatography (0-60% EtOAc/hexanes+2% AcOH) to give 30 mg of the title compound as a pale pink solid. MS: (−) m/z 360.07 (M−1).

Example 138

3-[(1-Cyano-4-hydroxy-7-phenyl-isoquinoline-3-carbonyl)-amino]-2,2-dimethyl-propionic acid

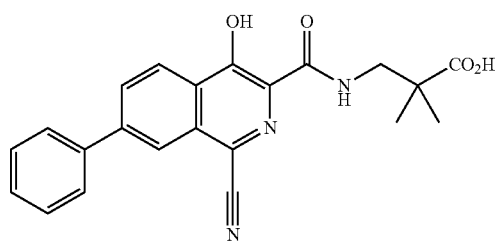 [SMILES: CC(C)(CNC(=O)c1nc(C#N)c2cc(-c3ccccc3)ccc2c1O)C(=O)O]

A mixture of 1-cyano-4-hydroxy-7-phenyl-isoquinoline-3-carboxylic acid methyl ester (47 mg, 0.15 mmol), 3-amino-2,2-dimethyl-propionic acid TFA salt (143 mg, 0.62 mmol) and NaOMe (67 mg, 1.24 mmol) in EtOH (3 mL) was heated at 150° C. in a microwave reactor for 2 h. The solvent was evaporated, and the residue was partitioned between water (30 mL) and EtOAc (30 mL). 1 M HCl was added with vigorous stirring until pH was ~2. The organic layer was dried over MgSO₄ and concentrated. The crude product was purified by column chromatography (0-25% EtOAc/hexanes+2% AcOH) to give 36 mg of the title compound as a light brown solid. MS: (−) m/z 388.13 (M−1).

Example 139

3-{[1-cyano-7-(4-Fluoro-benzoylamino)-4-hydroxy-isoquinoline-3-carbonyl]-amino}-2,2-dimethyl-propionic acid

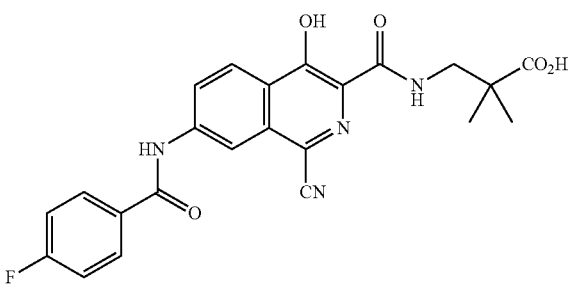 [SMILES: CC(C)(CNC(=O)c1nc(C#N)c2cc(NC(=O)c3ccc(F)cc3)ccc2c1O)C(=O)O]

a) 7-Bromo-4-hydroxy-1-iodo-isoquinoline-3-carboxylic acid ethyl ester

7-Bromo-4-hydroxy-isoquinoline-3-carboxylic acid ethyl ester (1.0 g, 3.37 mmol) was dissolved in dry dichloromethane (30 mL) and bis(2,4,6-trimethylpyridine)iodine(I) hexafluorophosphate (3.5 g, 6.754 mmol) was added in one portion as a solid. The solution was protected from light and permitted to stir overnight at room temperature. Upon completion, the reaction was quenched by addition of aqueous sodium thiosulfate (2.0 g in 50 mL of water. The layers were separated and the organic phase washed with 1M hydrochloric acid, brine and dried over anhydrous sodium sulfate. The crude material was purified by silica gel chromatography (3-15% ethyl acetate in hexanes) to provide the iodo-isoquinoline in 77% yield which was used immediately in the next step.

b) 7-Bromo-1-cyano-4-hydroxy-isoquinoline-3-carboxylic acid ethyl ester

7-Bromo-4-hydroxy-1-iodo-isoquinoline-3-carboxylic acid ethyl ester (1.0 g, 2.37 mmol) was dissolved in anhydrous NMP and cuprous cyanide was added (255 mg, 2.844 mmol) was added as a solid in one portion. The solution was heated to 120° C. in an oil bath. Upon completion, the reaction was cooled, diluted with 15 volumes of dichloromethane and stirred overnight. The following day the solution was washed with 1M hydrochloric acid, water, then brine and dried over sodium sulfate. The crude material was purified by medium pressure liquid chromatography (20 to 75% ethyl acetate in hexanes) to give the desired material in 85% yield as tan solid. $^1$H NMR (200 MHz, CDCl$_3$): δ ppm=12.48 (s, 1H), 8.46 (s, 1H), 8.32 (d, 1H), 7.94 (d, 1H), 4.59 (q, 2H), 1.53 (t, 3H.)

c) 1-Cyano-7-(4-fluoro-benzoylamino)-4-hydroxy-isoquinoline-3-carboxylic acid ethyl ester 1-Cyano-7-(4-fluoro-benzoylamino)-4-hydroxy-isoquinoline-3-carboxylic acid ethyl ester was prepared from 7-Bromo-1-cyano-4-hydroxy-isoquinoline-3-carboxylic acid ethyl ester under conditions analogous to Example 116 (a) using 4-fluorobenzamide. $^1$H NMR (200 MHz, DMSO): δ ppm=10.85 (s, 1H), 8.83 (s, 1H), 8.39 (m, 2H), 8.11 (m, 2H), 7.37 (m, 3H) 4.49 (q, 2H), 1.41 (t, 3H.)

d) 3-{[1-Cyano-7-(4-fluoro-benzoylamino)-4-hydroxy-isoquinoline-3-carbonyl]-amino}-2,2-dimethyl-propionic acid ethyl ester 1-Cyano-7-(4-fluoro-benzoylamino)-4-hydroxy-isoquinoline-3-carboxylic acid ethyl ester (70 mg, 0.2636 mmol) was dissolved/suspended in ethanol (4 mL) and 3-Amino-2,2-dimethyl-propionic acid ethyl ester (115 mg, 0.791 mmol) was added via syringe. The reaction was brought to reflux and maintained for 70 h. The reaction was cooled, concentrated and purified by medium pressure liquid chromatography (15 to 50% ethyl acetate in hexanes) to give the product as a white solid which was used immediately in the following reaction.

e) 3-{[1-Cyano-7-(4-fluoro-benzoylamino)-4-hydroxy-isoquinoline-3-carbonyl]-amino}-2,2-dimethyl-propionic acid 3-{[1-Cyano-7-(4-fluoro-benzoylamino)-4-hydroxy-isoquinoline-3-carbonyl]-amino}-2,2-dimethyl-propionic acid ethyl ester (60 mg, 0.125 mmol) was methanol (7 mL) and aqueous sodium hydroxide (7 mL, 2M) was added via syringe. The reaction was permitted to stir overnight at room temperature. Upon completion, the reaction was concentrated, diluted with water and acidified to pH 3 with 1M hydrochloric acid. The resulting precipitate was isolated by filtration and dried to provide the title compound as a white solid in 50% yield. MS ESI(-) m/e: 449.1046 (M-1), MS ESI(+) m/e: 451.0812 (M+1).

Example 140

3{-[1-Cyano-4-hydroxy-7-(3-phenyl-ureido)-isoquinoline-3-carbonyl]-amino}-2,2-dimethyl-propionic acid

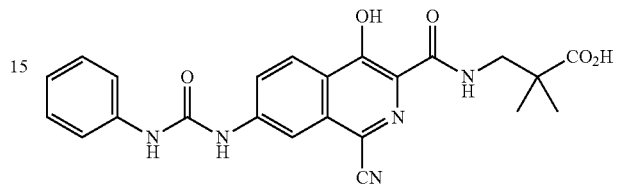

a)
7-Bromo-4-hydroxy-1-iodo-isoquinoline-3-carboxylic acid ethyl ester

7-Bromo-4-hydroxy-isoquinoline-3-carboxylic acid ethyl ester (1.0 g, 3.37 mmol) was dissolved in dry dichloromethane (30 mL) and bis(2,4,6-trimethylpyridine)iodine(I) hexafluorophosphate (3.5 g, 6.754 mmol) was added in one portion as a solid. The solution was protected from light and permitted to stir overnight at room temperature. Upon completion, the reaction was quenched by addition of aqueous sodium thiosulfate (2.0 g in 50 mL of water. The layers were separated and the organic phase washed with 1M hydrochloric acid, brine and dried over anhydrous sodium sulfate. The crude material was purified by silica gel chromatography (3-15% ethyl acetate in hexanes) to provide the iodo-isoquinoline in 77% yield which was used immediately in the next step.

b) 7-Bromo-1-cyano-4-hydroxy-isoquinoline-3-carboxylic acid ethyl ester

7-Bromo-4-hydroxy-1-iodo-isoquinoline-3-carboxylic acid ethyl ester (1.0 g, 2.37 mmol) was dissolved in anhydrous NMP and cuprous cyanide was added (255 mg, 2.844 mmol) was added as a solid in one portion. The solution was heated to 120° C. in an oil bath. Upon completion, the reaction was cooled, diluted with 15 volumes of dichloromethane and stirred overnight. The following day the solution was washed with 1M hydrochloric acid, water, then brine and dried over sodium sulfate. The crude material was purified by medium pressure liquid chromatography (20 to 75% ethyl acetate in hexanes) to give the desired material in 85% yield as tan solid. $^1$H NMR (200 MHz, CDCl$_3$): δ ppm=12.48 (s, 1H), 8.46 (s, 1H), 8.32 (d, 1H), 7.94 (d, 1H), 4.59 (q, 2H), 1.53 (t, 3H.)

c) 1-Cyano-4-hydroxy-7-(3-phenyl-ureido)-isoquinoline-3-carboxylic acid ethyl ester 1-Cyano-4-hydroxy-7-(3-phenyl-ureido)-isoquinoline-3-carboxylic acid ethyl ester was prepared from Example 140 (b) under conditions analogous to Example 116(a) using phenyl urea. MS ESI(-) m/e: 375.0860 (M-1), MS ESI(+) m/e: 377.1258 (M+1).

d) 3-{[1-Cyano-4-hydroxy-7-(3-phenyl-ureido)-isoquinoline-3-carbonyl]amino}-2,2-dimethyl-propionic acid ethyl ester 1-Cyano-4-hydroxy-7-(3-phenyl-ureido)-isoquinoline-3-carboxylic acid ethyl ester (40 mg, 0.106 mmol) was dissolved/suspended in ethanol (3 mL) and 3-Amino-2,2-dimethyl-propionic acid ethyl ester (46 mg, 0.318 mmol) was added via syringe. The reaction was brought to reflux and maintained for 50 h. The reaction was cooled, concentrated and purified by medium pressure liquid chromatography (15 to 60% ethyl acetate in hexanes) to give the product as a white solid which was used immediately in the following reaction.

e) 3-{[1-Cyano-4-hydroxy-7-(3-phenyl-ureido)-isoquinoline-3-carbonyl]amino}-2,2-dimethyl-propionic acid 3-{[1-Cyano-4-hydroxy-7-(3-phenyl-ureido)-isoquinoline-3-carbonyl]-amino}-2,2-dimethyl-propionic acid ethyl ester (35 mg, 0.0736 mmol) was methanol (5 mL) and aqueous sodium hydroxide (5 mL, 2M) was added via syringe. The reaction was permitted to stir overnight at room temperature. Upon completion, the reaction was concentrated, diluted with water and acidified to pH 3 with 1M hydrochloric acid. The resulting precipitate was isolated by filtration and dried to provide the title compound as a white solid in 73% yield. MS ESI(−) m/e: 446.0440 (M−1), MS ESI(+) m/e: 448.1482 (M+1).

Example 141

3-({7-[3-(4-Fluoro-phenyl)-ureido]-4-hydroxy-isoquinoline-3-carbonyl}-amino)-propionic acid

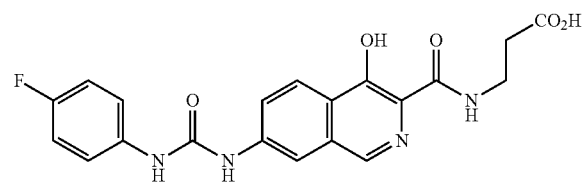 [SMILES: O=C(O)CCNC(=O)c1ncc2cc(NC(=O)Nc3ccc(F)cc3)ccc2c1O]

a) 7-[3-(4-Fluoro-phenyl)-ureido]-4-hydroxy-isoquinoline-3-carboxylic acid ethyl ester 7-[3-(4-Fluoro-phenyl)-ureido]-4-hydroxy-isoquinoline-3-carboxylic acid ethyl ester was prepared from 7-Bromo-4-hydroxy-isoquinoline-3-carboxylic acid ethyl ester under conditions analogous to Example 116(a) using 4-Fluorophenylurea. MS ESI(+) m/e: 370.0130 (M+1).

b) 3-({7-[3-(4-Fluoro-phenyl)-ureido]-4-hydroxy-isoquinoline-3-carbonyl}-amino)-propionic acid 3-({7-[3-(4-Fluoro-phenyl)-ureido]-4-hydroxy-isoquinoline-3-carbonyl}-amino)-propionic acid was prepared from 7-[3-(4-Fluoro-phenyl)-ureido]-4-hydroxy-isoquinoline-3-carboxylic acid ethyl ester under conditions analogous to Example 116(b) using β-alanine. MS ESI(−) m/e: 411.1046 (M−1), MS ESI(+) m/e: 413.0810 (M+1).

Example 142

4-([7-[3-(4-Fluoro-phenyl)-ureido]-4-hydroxy-isoquinoline-3-carbonyl]-amino)-butyric acid

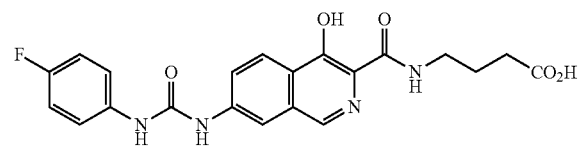 [SMILES: O=C(O)CCCNC(=O)c1ncc2cc(NC(=O)Nc3ccc(F)cc3)ccc2c1O]

4-({7-[3-(4-Fluoro-phenyl)-ureido]-4-hydroxy-isoquinoline-3-carbonyl}-amino)-butyric acid was prepared from 7-[3-(4-Fluoro-phenyl)-ureido]-4-hydroxy-isoquinoline-3-carboxylic acid ethyl ester under conditions analogous to Example 116(b) using 3-aminobutyric acid. MS ESI(+) m/e: 427.1712 (M+1).

Example 143

3-[(4-Hydroxy-7-phenoxy-1-phenyl-isoquinoline-3-carbonyl)-amino]-2,2-dimethyl-propionic acid

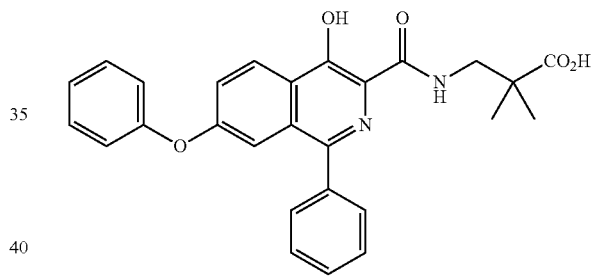

a) 4-Hydroxy-7-phenoxy-1-phenyl-isoquinoline-3-carboxylic acid methyl ester A mixture of 1-bromo-4-hydroxy-7-phenoxy-isoquinoline-3-carboxylic acid methyl ester (150 mg, 0.40 mmol), phenylboronic acid (60 mg, 0.48 mmol), Pd(PPh$_3$)$_4$ (46 mg, 0.040 mmol) and Cs$_2$CO$_3$ (261 mg, 0.80 mmol) in DMF (4 mL) was heated at 100° C. for 16 h under N$_2$ atmosphere. After cooling the mixture to r.t., brine (20 mL) and EtOAc (50 mL) were added. 1 M HCl was added with stirring until pH was ~2. The aqueous layer was extracted with additional EtOAc, and the organic layers were combined, washed with water, and dried over MgSO$_4$. After evaporating the solvent, the crude product was purified by column chromatography (0-25% EtOAc/hexanes+2% AcOH) to give 98 mg of the title compound as a white solid. MS: (+) m/z 372.09 (M+1).

b) 3-[(4-Hydroxy-7-phenoxy-1-phenyl-isoquinoline-3-carbonyl)-amino]-2,2-dimethyl-propionic acid A mixture of 4-hydroxy-7-phenoxy-1-phenyl-isoquinoline-3-carboxylic acid methyl ester (50 mg, 0.13 mmol), 3-amino-2,2-dimethyl-propionic acid TFA salt (125 mg, 0.54 mmol) and NaOMe (58 mg, 1.08 mmol) in EtOH (2 mL) was heated at 150° C. in a microwave reactor for 6 h. The solvent was evaporated, and the residue was partitioned between water (30 mL) and EtOAc (30 mL). 1 M HCl was added with vigorous stirring until pH was ~2. The organic layer was dried over MgSO₄ and concentrated. The crude product was purified by column chromatography (0-30% EtOAc/hexanes+2% AcOH) to give 44 mg of the title compound as a yellow solid. MS: (+) m/z 457.26 (M+1).

Example 144

3-[(4-Hydroxy-7-phenoxy-1-phenyl-isoquinoline-3-carbonyl)-amino]-propionic acid

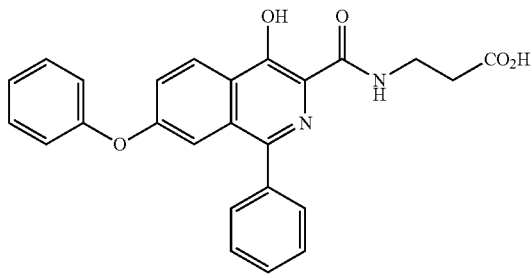 [SMILES: O=C(O)CCNC(=O)c1nc(-c2ccccc2)c2cc(Oc3ccccc3)ccc2c1O]

A mixture of 4-hydroxy-7-phenoxy-1-phenyl-isoquinoline-3-carboxylic acid methyl ester (46 mg, 0.12 mmol), β-alanine (552 mg, 6.2 mmol) and NaOMe (9.3 mL, 4.65 mmol, 0.5 M in MeOH) was refluxed for 16 h. After cooling to r.t., the solvent was evaporated. The residue was partitioned between EtOAc (50 mL) and water (50 mL). 1 M HCl was added with stirring until pH was ~2. The organic layer was dried over MgSO₄ and concentrated. The crude product was purified by column chromatography (0-35% EtOAc/hexanes+2% AcOH) to give 47 mg of the title compound as a light yellow solid. MS: (+) m/z 429.13 (M+1).

Example 145

3-[(4-Hydroxy-7-phenoxy-1-trifluoromethyl-isoquinoline-3-carbonyl)-amino]-propionic acid

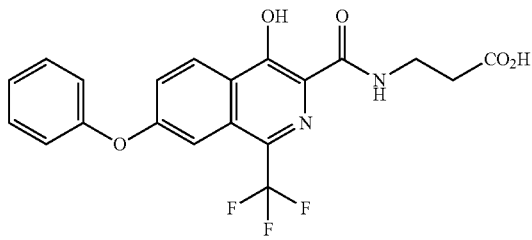 [SMILES: O=C(O)CCNC(=O)c1nc(C(F)(F)F)c2cc(Oc3ccccc3)ccc2c1O]

a) 4-Hydroxy-7-phenoxy-1-trifluoromethyl-isoquinoline-3-carboxylic acid methyl ester A mixture of 1-bromo-4-hydroxy-7-phenoxy-isoquinoline-3-carboxylic acid methyl ester (200 mg, 0.53 mmol), difluoro-fluorosulfonyl-acetic acid methyl ester (0.2 mL, 1.60 mmol), and CuI (306 mg, 1.60 mmol) in DMF (5.3 mL) was heated at 80° C. for 16 h under N₂ atmosphere. After cooling the mixture to r.t., brine (20 mL) and EtOAc (50 mL) were added. The aqueous layer was extracted with additional EtOAc, and the organic layers were combined, washed with water, and dried over MgSO₄. After evaporating the solvent, the crude product was purified by column chromatography (0-20% EtOAc/hexanes+2% AcOH) to give 137 mg of the title compound as a white solid. MS: (+) m/z 364.01 (M+1).

b) 3-[(4-Hydroxy-7 phenoxy-1-trifluoromethyl-isoquinoline-3-carbonyl)-amino]-propionic acid A mixture of 4-hydroxy-7-phenoxy-1-trifluoromethyl-isoquinoline-3-carboxylic acid methyl ester (41 mg, 0.11 mmol), β-alanine (503 mg, 5.65 mmol) and NaOMe (8.5 mL, 4.24 mmol, 0.5 M in MeOH) was refluxed for 16 h. After cooling to r.t., the solvent was evaporated. The residue was partitioned between EtOAc (50 mL) and water (50 mL). 1 M HCl was added with stirring until pH was ~2. The organic layer was dried over MgSO₄ and concentrated. The crude product was purified by column chromatography (0-35% EtOAc/hexanes+2% AcOH) to give 40 mg of the title compound as a white solid. MS: (+) m/z 421.06 (M+1).

Example 146

3-[(7-Benzyl-4-hydroxy-isoquinoline-3-carbonyl)-amino]-2,2-dimethyl-propionic acid

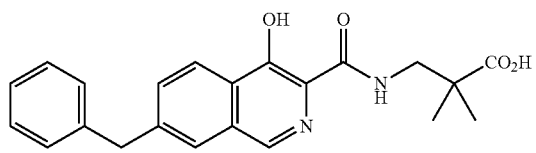 [SMILES: CC(C)(CNC(=O)c1ncc2cc(Cc3ccccc3)ccc2c1O)C(=O)O]

a) 7-Benzyl-4-hydroxy-isoquinoline-3-carboxylic acid methyl ester

To a mixture of 4-benzyloxy-7-bromo-isoquinoline-3-carboxylic acid methyl ester (150 mg, 0.40 mmol), Pd(PPh₃)₄ (47 mg, 0.040 mmol) and THF (4 mL) was added benzylzinc bromide (2 mL, 1.0 mmol, 0.5 M in THF), and the resulting mixture was refluxed for 16 h under nitrogen atmosphere. After cooling the mixture to r.t., saturated NH₄Cl (50 mL) and CH₂Cl₂ (50 mL) were added. The aqueous layer was extracted with additional CH₂Cl₂, and the organic layers were combined and dried over MgSO₄. After evaporating the solvent, the crude product was purified by column chromatography (0-35% EtOAc/hexanes) to give 19 mg of the title compound as a yellow solid. MS: (+) m/z 294.05 (M+1).

b) 3-[(7-Benzyl-4-hydroxy-isoquinoline-3-carbonyl)-amino]-2,2-dimethyl-propionic acid A mixture of 7-benzyl-4-hydroxy-isoquinoline-3-carboxylic acid methyl ester (19 mg, 0.065 mmol), 3-amino-2,2-dimethyl-propionic acid TFA salt (60 mg, 0.26 mmol) and NaOMe (28 mg, 0.52 mmol) in EtOH (2 mL) was heated at 150° C. in a microwave reactor for 6 h. The solvent was evaporated, and the residue was partitioned between water (30 mL) and EtOAc (30 mL). 1 M HCl was added with vigorous stirring until pH was ~2. The organic layer was dried over MgSO₄ and concentrated. The crude product was purified by column chromatography (0-30% EtOAc/hexanes+2% AcOH) to give 9.5 mg of the title compound. MS: (+) m/z 379.17 (M+1).

Example 147

5-{[1-(5-Fluoro-pyridin-3-yl)-4-hydroxy-7-phenoxy-isoquinoline-3-carbonyl]-amino}-pentanoic acid

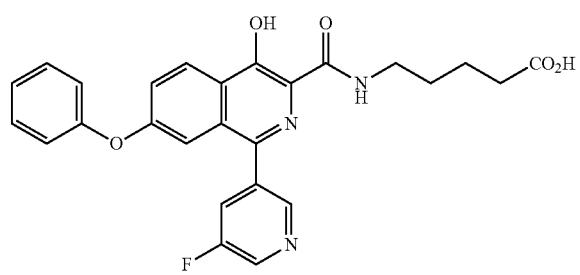 [SMILES: O=C(O)CCCCNC(=O)c1nc(-c2cncc(F)c2)c2cc(Oc3ccccc3)ccc2c1O]

A mixture of 1-(5-fluoro-pyridin-3-yl)-4-hydroxy-7-phenoxy-isoquinoline-3-carboxylic acid methyl ester (50 mg, 0.13 mmol), 5-aminovaleric acid (751 mg, 6.41 mmol) and NaOMe (10 mL, 5.13 mmol, 0.5 M in MeOH) was refluxed for 16 h. After cooling the mixture to r.t., the solvent was evaporated. The residue was partitioned between water and EtOAc. 1 M HCl was added with vigorous stirring until pH was ~2. The organic layer was dried over MgSO$_4$ and concentrated. The crude product was purified by column chromatography (5-50% EtOAc/hexanes+2% AcOH) to give 33 mg of the title compound as an off-white solid. MS: (+) m/z 476.12 (M+1).

Example 148

4-{[7-(4-Fluoro-phenyl)-4-hydroxy-isoquinoline-3-carbonyl]-amino}-butyric acid

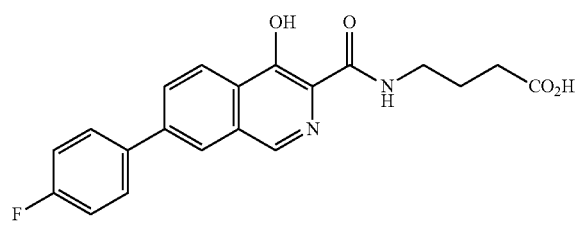 [SMILES: O=C(O)CCCNC(=O)c1ncc2cc(-c3ccc(F)cc3)ccc2c1O]

4-{[7-(4-Fluoro-phenyl)-4-hydroxy-isoquinoline-3-carbonyl]-amino}-butyric acid was prepared from 7-(4-Fluoro-phenyl)-4-hydroxy-isoquinoline-3-carboxylic acid ethyl ester under conditions analogous to Example 116(b) using 3-aminobutyric acid. MS ESI(-) m/e: 367.0542 (M-1), MS ESI(+) m/e: 369.0940 (M+1).

Example 149

5-{[7-(4-Fluoro-phenyl)-4-hydroxy-isoquinoline-3-carbonyl]-amino}-pentanoic acid

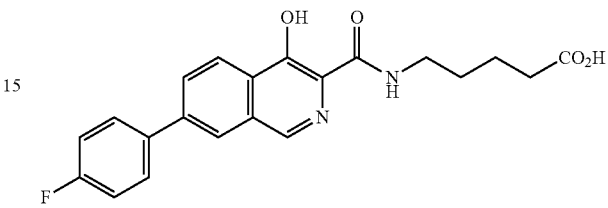

5-{[7-(4-Fluoro-phenyl)-4-hydroxy-isoquinoline-3-carbonyl]-amino}-pentanoic acid was prepared from 7-(4-Fluoro-phenyl)-4-hydroxy-isoquinoline-3-carboxylic acid ethyl ester under conditions analogous to Example 116(b) using 4-aminopentanoic acid. MS ESI(-) m/e: 381.0781 (M-1), MS ESI(+) m/e: 383.1180 (M+1).

Example 150

3-{[7-(4-Fluoro-phenyl)-4-hydroxy-isoquinoline-3-carbonyl]-amino}-2,2-dimethyl-propionic acid

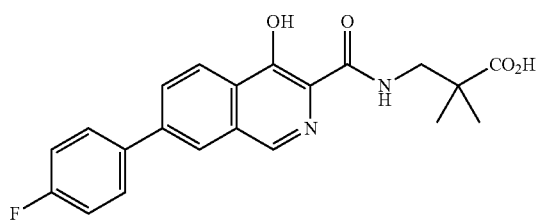 [SMILES: CC(C)(CNC(=O)c1ncc2cc(-c3ccc(F)cc3)ccc2c1O)C(=O)O]

a) 3-{[7-(4-Fluoro-phenyl)-4-hydroxy-isoquinoline-3-carbonyl]amino}-2,2-dimethyl-propionic acid ethyl ester 3-{[7-(4-Fluoro-phenyl)-4-hydroxy-isoquinoline-3-carbonyl]-amino}-2,2-dimethyl-propionic acid ethyl ester was prepared from 7-(4-Fluoro-phenyl)-4-hydroxy-isoquinoline-3-carboxylic acid ethyl ester under conditions analogous to Example 139(d). $^1$H NMR (200 MHz, CDCl$_3$): δ ppm=13.26 (s, 1H), 8.63 (s, 1H), 8.52 (br t, 1H), 8.35 (d, 1H), 7.99 (s, 1H), 7.88 (d, 1H), 7.65 (m, 2H), 7.16 (t, 2H), 4.21 (q, 2H), 3.61 (d, 2H), 1.3 (m, 9H.)

b) 3-{[7-(4-Fluoro-phenyl)-4-hydroxy-isoquinoline-3-carbonyl]amino}-2,2-dimethyl-propionic acid 3-{[7-(4-Fluoro-phenyl)-4-hydroxy-isoquinoline-3-carbonyl]-amino}-2,2-dimethyl-propionic acid was prepared from 3-{[7-(4-Fluoro-phenyl)-4-hydroxy-isoquinoline-3-carbonyl]-amino}-2,2-dimethyl-propionic acid ethyl ester under conditions analogous to Example 139(e). MS ESI(−) m/e: 381.0781 (M−1), MS ESI(+) m/e: 383.1180 (M+1).

Example 151

3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid

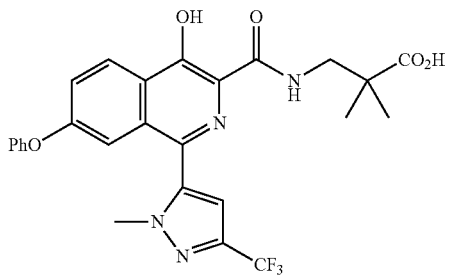 [SMILES: Cn1nc(C(F)(F)F)cc1-c1nc(C(=O)NCC(C)(C)C(=O)O)c(O)c2ccc(Oc3ccccc3)cc12]

a) 4-Hydroxy-1-(2-methyl-5-trifluoromethyl-2H-pyrazol-3-yl)-7-phenoxy-isoquinoline-3-carboxylic acid methyl ester 4-Hydroxy-1-(2-methyl-5-trifluoromethyl-2H-pyrazol-3-yl)-7-phenoxy-isoquinoline-3-carboxylic acid methyl ester was prepared from 1-bromo-4-hydroxy-7-phenoxy-isoquinoline-3-carboxylic acid methyl ester using 1-methyl-5-tributylstannanyl-3-trifluoromethyl-1H-pyrazole under conditions analogous to Example 132(a). MS ESI(−) m/e: 442.0128 (M−1.)

b) 3-{[4-Hydroxy-1-(2-methyl-5-trifluoromethyl-2H-pyrazol-3-yl)-7-phenoxy-isoquinoline-3-carbonyl]amino}-2,2-dimethyl-propionic acid ethyl ester 3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid ethyl ester was prepared from 4-Hydroxy-1-(2-methyl-5-trifluoromethyl-2H-pyrazol-3-yl)-7-phenoxy-isoquinoline-3-carboxylic acid methyl ester under conditions analogous to Example 139(d). The isolated product was used immediately in the following reaction.

c) 3-{[4-Hydroxy-1-(2-methyl-5-trisuoromethyl-2H-pyrazol-3-yl)-7-phenoxy-isoquinoline-3-carbonyl] amino}-2,2-dimethyl-propionic acid 3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid was prepared from 3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid ethyl ester under conditions analogous to Example 139(e). MS ESI(−) m/e: 527.0135 (M−1.)

Example 152

3-[(7-Benzyloxy-1-cyano-4-hydroxy-isoquinoline-3-carbonyl)-amino]-3-methyl-butyric acid

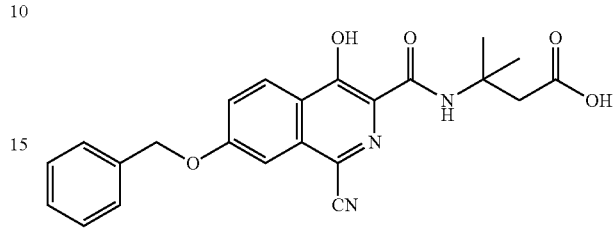

7-Benzyloxy-1-cyano-4-hydroxy-isoquinoline-3-carboxylic acid ethyl ester (US Patent Publication No. 2007/627906) (40 mg, 0.115 mmol) was dissolved in anhydrous DMF (2 mL). 3-Amino-3-methyl-butyric acid (68 mg, 0.5742 mmol) and solid sodium methoxide (25 mg, 0.459 mmol) were added sequentially and the mixture heated to 140° C. in an oil bath for 3.5 h. Upon completion, the reaction mixture was cooled and diluted with water. The solution was acidified to pH 3 with 1M hydrochloric acid inducing precipitation of the product. The free acid was isolated by filtration and dried to provide the title compound as a tan solid in 92% yield. MS ESI(−) m/e: 417.9596 (M−1), MS ESI(+) m/e: 419.9934 (M+1).

Example 153

3-[(7-Benzyloxy-1-cyano-4-hydroxy-isoquinoline-3-carbonyl)-amino]-2,2-dimethyl-propionic acid

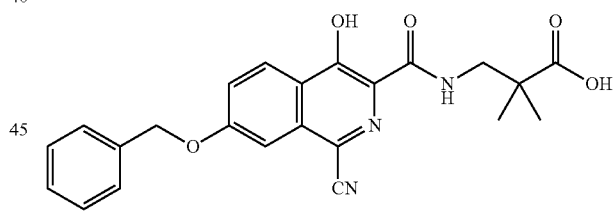

a) 3-[(7-Benzyloxy-1-cyano-4-hydroxy-isoquinoline-3-carbonyl)-amino]-2,2-dimethyl-propionic acid ethyl ester 3-[(7-Benzyloxy-1-cyano-4-hydroxy-isoquinoline-3-carbonyl)-amino]-2,2-dimethyl-propionic acid ethyl ester was prepared from 7-Benzyloxy-1-cyano-4-hydroxy-isoquinoline-3-carboxylic acid ethyl ester under conditions analogous to Example 139(d). $^1$H NMR (200 MHz, CDCl$_3$): δ ppm=8.29 (m, 2H), 7.42 (m, 7H), 5.25 (d, 2H), 4.24 (q, 2H), 3.60 (d, 2H), 1.41-1.28 (m, 9H.)

b) 3-[(7-Benzyloxy-1-cyano-4-hydroxy-isoquinoline-3-carbonyl)-amino]-2,2-dimethyl-propionic acid 3-[(7-Benzyloxy-1-cyano-4-hydroxy-isoquinoline-3-carbonyl)-amino]-2,2-dimethyl-propionic acid was prepared from 3-[(7-Benzyloxy-1-cyano-4-hydroxy-isoquinoline-3-carbonyl)-amino]-2,2-dimethyl-propionic acid ethyl ester under conditions analogous to Example 139(e). MS ESI(−) m/e: 417.9833 (M−1), MS ESI(+) m/e: 419.9543 (M+1).

Example 154

1-{[(1-Cyano-4-hydroxy-7-phenylsulfanyl-isoquinoline-3-carbonyl)-amino]-methyl}-cyclobutanecarboxylic acid

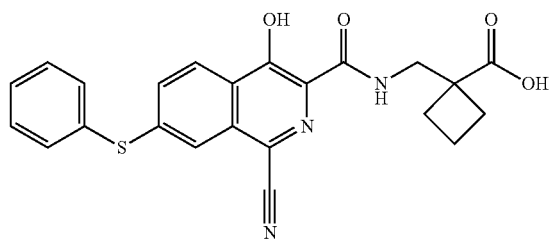

a) 1-Cyano-4-hydroxy-7-phenylsulfanyl-isoquinoline-3-carboxylic acid methyl ester A mixture of 1-bromo-4-hydroxy-7-phenylsulfanyl-isoquinoline-3-carboxylic acid methyl ester (0.91 g, prepared according to Arend et al. WO 2004108681) and CuCN (436 mg) in DMF (5 mL) was refluxed for 1 h; then cooled, diluted with DCM, filtered, then washed with water, dil. NaCl solution, dried over sodium sulphate, filtered, concentrated, the residue was column purified to give the desired product (195 mg). LC MS ESI: 337 (M+1)⁺.

b) 1-{[(1-Cyano-4-hydroxy-7-phenylsulfanyl-isoquinoline-3-carbonyl)-amino]-methyl}-cyclobutanecarboxylic acid tert-butyl ester A mixture of 1-cyano-4-hydroxy-7-phenylsulfanyl-isoquinoline-3-carboxylic acid methyl ester (43 mg) and 1-aminomethyl-cyclobutanecarboxylic acid tert-butyl ester (48 mg) in EtOH (0.5 mL) was microwaved at 140° C. for 1 h. The mixture was cooled, concentrated and the residue was column purified to give the desired product (58 mg). LC MS ESI+: 490 (M+1)⁺.

c) 1-{[(1-Cyano-4-hydroxy-7-phenylsulfanyl-isoquinoline-3-carbonyl)-amino]-methyl}-cyclobutanecarboxylic acid A mixture of 1-{[(1-cyano-4-hydroxy-7-phenylsulfanyl-isoquinoline-3-carbonyl)-amino]-methyl}-cyclobutanecarboxylic acid tert-butyl ester (58 mg), TFA (2 mL) and DCM (6 mL) was stirred at rt for 1 h; then concentrated, the residue was dissolved in water and added 2 M HCl solution, solids were collected via filtration, washed with water and air dried to give the desired product (50 mg). LC MS ESI+: 434 (M+1)⁺.

Example 155

3-[(1-Cyano-4-hydroxy-6-o-tolyloxy-isoquinoline-3-carbonyl)-amino]-2,2-dimethyl-propionic acid

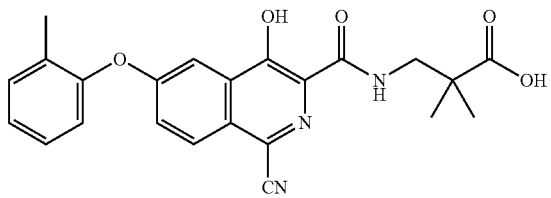 [SMILES: Cc1ccccc1Oc1ccc2c(C#N)nc(C(=O)NCC(C)(C)C(=O)O)c(O)c2c1]

a) 4-(o-Tolyloxy)phthalonitrile

A mixture of 4-nitrophthalonitrile (10.6 g, 60.0 mmol), o-cresol (7.9 g, 72.0 mmol) and K₂CO₃ (16.6 g, 120.0 mmol) in DMF (70 mL) was heated to 60° C. under a nitrogen atmosphere for 3 hours. The crude reaction was then poured into H₂O (300 mL). The resulting mixture was extracted twice with EtOAc. The combined organic layers were washed with sat'd NaHCO₃ solution, dried over MgSO₄ and concentrated in vacuo. The residue was then dissolved in EtOH (60 mL). After storing for 5 hours at room temperature, the precipitate was collected by filtration and the filter cake was washed with cold EtOH to give the title compound in 8.9 g. MS: (+) m/z 235.46 (M+1).

b) 4-(o-Tolyloxy)phthalic acid

A mixture of 4-(o-tolyloxy)phthalonitrile (8.9 g, 37.8 mmol) and KOH (19 mL, 220.9 mmol, 45% by weight solution) in MeOH (19 mL) was heated to reflux for 3 days. After cooling to room temperature, the reaction mixture was dissolved in H₂O (500 mL). To the solution was added concentrated HCl until pH was less than 1. The resulting mixture was then extracted with EtOAc (100 mL). The organic phase was then dried over MgSO₄ and concentrated in vacuo to give the title compound in 9.8 g. MS: (−) m/z 271.41 (M−1).

c) 2-(1,3-Dioxo-5-(o-tolyloxy)isoindolin-2-yl)acetic acid

A mixture of 4-(o-tolyloxy)phthalic acid (9.5 g, 35.0 mmol) and glycine (2.6 g, 35.0 mmol) was ground thoroughly in a mortar. The powder was then transferred to a flask and heated to 220-240° C. under high vacuum for 30 minutes. The reaction crude was cooled to room temperature to give the title compound in 10.2 g. ¹H NMR (DMSO, 200 MHz): δ=7.89 (d, 1H, J=8.0 Hz), 7.42-7.08 (m, 6H), 4.27 (s, 2H), 2.14 (s, 3H).

d) Methyl 2-(1,3-dioxo-5-(o-tolyloxy)isoindolin-2-yl)acetate

A mixture of 2-(1,3-dioxo-5-(o-tolyloxy)isoindolin-2-yl) acetic acid (10.1 g, 32.5 mmol) and concentrated H₂SO₄ (2.0 mL) in MeOH (41 mL) was heated to reflux with stirring for 18 hours. After cooling to room temperature, the solvent was removed in vacuo. To the residue was added sat'd NaHCO₃ solution (100 mL) and EtOAc (100 mL). The layers were separated and the organic layer was dried over Mg SO₄ and then concentrated in vacuo to give the title compound as white solid in 10.0 g. $^1$H NMR (CDCl₃, 200 MHz): δ=7.78 (d, 1H, J=9.0 Hz), 7.31-7.13 (m, 5H), 6.98 (d, 1H, J=7.4 Hz), 4.40 (s, 2H), 3.75 (s, 3H), 2.18 (s, 3H).

e) Butyl 1,4-dihydroxy-6-(o-tolyloxy)isoquinoline-3-carboxylate

To a stirred solution of methyl 2-(1,3-dioxo-5-(o-tolyloxy) isoindolin-2-yl)acetate (10.0 g, 30.8 mmol) in n-butanol (206 mL) at 95° C. was added 1 N sodium n-butoxide solution (62.0 mL, 62.0 mmol). The resulting mixture was stirred at 95° C. for 2 hours before cooling to room temperature. The solvent was partially removed and the residue was diluted with EtOAc (200 mL) and 2 N HCl (40 mL). The resulting mixture was stirred vigorously for 15 minutes at room temperature and the precipitation was collected by filtration. The filter cake was washed with H₂O and then dried at 70° C. in vacuo to give a yellow solid. The solid obtained was further suspended in EtOAc (300 mL) and the slurry was heated to reflux with stirring for 2 hours. After cooling to room temperature, the precipitate was collected by filtration and then dried in vacuo to give the title compound in 1.6 g. $^1$H NMR (CDCl₃, 200 MHz): δ=10.38 (s, 1H), 8.42-8.32 (m, 2H), 7.43 (s, 1H), 7.34-7.10 (m, 3H), 7.02 (d, 1H, J=7.6 Hz), 4.39 (t, 2H, J=6.6 Hz)), 2.20 (s, 3H), 1.84-1.38 (m, 4H), 0.99 (t, 3H, J=7.2 Hz).

f) Butyl 1-bromo-4-hydroxy-6-(o-tolyloxy)isoquinoline-3-carboxylate

A mixture of butyl 1,4-dihydroxy-6-(o-tolyloxy)isoquinoline-3-carboxylate (1.5 g, 4.2 mmol) and POBr3 (4.9 g, 16.8 mmol) in acetonitrile (32 mL) was heated to reflux for 90 minutes. After cooling to room temperature, the solvent was removed in vacuo. The residue was dissolved in CHCl₃ (200 mL) and to the solution were added NaHCO₃ (10 g) and H₂O (13 mL). The resulting mixture was stirred vigorously at room temperature for 30 minutes before dried over MgSO₄. The mixture was then filtered and the filtrate was concentrated in vacuo and then purified by flash chromatography (0-10% EtOAc/CH₂Cl₂) to give the title compound in 0.9 g. $^1$H NMR (CDCl₃, 200 MHz): δ=11.74 (s, 1H), 8.21 (d, 1H, J=8.4 Hz), 7.52-7.44 (m, 2H), 7.34-7.15 (m, 3H), 7.03 (d, 1H, J=8.8 Hz), 4.46 (t, 2H, J=7.2 Hz)), 2.20 (s, 3H), 1.92-1.77 (m, 2H), 1.56-1.38 (m, 2H), 0.98 (t, 3H, J=7.2 Hz).

g) Butyl 1-cyano-4-hydroxy-6-(o-tolyloxy)isoquinoline-3-carboxylate

Butyl 1-bromo-4-hydroxy-6-(o-tolyloxy)isoquinoline-3-carboxylate (130 mg, 0.30 mmol) and CuCN (54 mg, 0.61 mmol) were suspended in DMF (1.2 mL). The resulting mixture was heated to reflux for 40 minutes and then cooled to room temperature. The reaction crude was poured into CH₂Cl₂ (30 mL) and stirred vigorously for 10 minutes at room temperature. The resulting suspension was filtered through a pad of celite and the filtrate was washed with H₂O and brine sequentially. The organic layer was dried over MgSO₄, concentrated, and purified by flash chromatography (0-30% EtOAc/hexanes) to give the title compound in 65 mg. MS: (−) m/z 375.29 (M−1).

h) 3-(1-Cyano-4-hydroxy-6-(o-tolyloxy)isoquinoline-3-carboxamido)-2,2-dimethylpropanoic acid Butyl 1-cyano-4-hydroxy-6-(o-tolyloxy)isoquinoline-3-carboxylate (11 mg, 0.03 mmol), 3-amino-2,2-dimethyl-propionic acid TFA salt (27.1 mg, 0.12 mmol) and NaOMe (12.3 mg, 0.23 mmol) in EtOH (3 mL) were heated at 150° C. in a microwave for 90 minutes. The solvent was removed in vacuo and the residue was dissolved in H₂O (15 mL) and EtOAc (15 mL). To the stirred mixture was added 1 N hydrochloric acid until pH was 1. The layers were separated and the aqueous layer was extracted twice with EtOAc. The combined organic layers were dried over MgSO₄, concentrated, and purified by flash chromatography (0-25% MeOH/CH₂Cl₂) to give the title compound in 7 mg. MS: (−) m/z 417.94 (M−1).

Example 156

3-[(1-Cyano-7-cyclohexyloxy-4-hydroxy-isoquinoline-3-carbonyl)-amino]-2,2-dimethyl-propionic acid

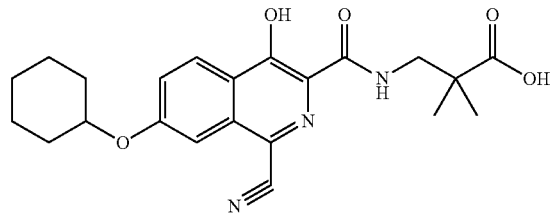 [SMILES: CC(C)(CNC(=O)c1nc(C#N)c2cc(OC3CCCCC3)ccc2c1O)C(=O)O]

a) 3-[(1-Cyano-7-cyclohexyloxy-4-hydroxy-isoquinoline-3-carbonyl)-amino]-2,2-dimethyl-propionic acid tert-butyl ester A mixture of 1-cyano-7-cyclohexyloxy-4-hydroxy-isoquinoline-3-carboxylic acid butyl ester (45 mg, 0.12 mmol) (prepared according to U.S. Pat. No. 7,629,357) and 3-amino-2,2-dimethyl-propionic acid tert-butyl ester (50 mg, 0.29 mmol) in ethanol was microwaved at 140° C. for 1 h. Reaction mixture was quenched with acetic acid (3 equivalents) and concentrated. Residue was purified by silica gel chromatography, eluting with 5-50% EtOAc/hexanes to provide the title compound 55 mg (0.118 mmol) in 98% yield. $^1$H NMR (200 MHz) CDCl₃, δ in ppm: 13.92 (s, 1H), 8.29 (d, J=8.4 Hz, 1H), 7.42 (m, 2H), 4.56 (br s, 1H), 3.55 (d, J=6.2 Hz, 2H), 2.04 (br m, 2H), 1.83 (br m, 2H), 1.56-1.24 (m, 21H).

b) 3-[(1-Cyano-7-cyclohexyloxy-4-hydroxy-isoquinoline-3-carbonyl)-amino]-2,2-dimethyl-propionic acid A mixture of 3-[(1-cyano-7-cyclohexyloxy-4-hydroxy-isoquinoline-3-carbonyl)-amino]-2,2-dimethyl-propionic acid tert-butyl ester (55 mg, 0.118 mmol) in (½) TFA/CH₂Cl₂ (3 mL) was stirred at room temperature for 3 h and concentrated. Residue was taken up with 30 mL of water and the resultant suspension was basified by 1 N NaOH to pH=9-10. The clear solution was then acidified by 1 N HCl to pH=3-4. Precipitate was collected and dried. Crude product was triturated with MeOH (3 mL). Solid was collected and dried in vacuo to provide the title compound 8.6 mg (0.02 mmol) in 18% yield. LC-MS ESI–: 410.00 (M–1)⁻.

Example 157

3-(2-Carboxy-2-methylpropylcarbamoyl)-1-cyano-4-hydroxy-7-phenoxyisoquinoline 2-oxide

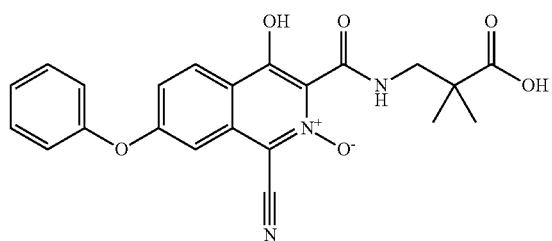

a) 3-[(4-Hydroxy-7-phenoxy-isoquinoline-3-carbonyl)-amino]-2,2-dimethyl-propionic acid ethyl ester To a solution of the 3-amino-2,2-dimethyl-propionic acid ethyl ester (598 mg, 4.12 mmol) in EtOH (9.1 mL) at r.t. were added 4-hydroxy-7-phenoxy-isoquinoline-3-carboxylic acid methyl ester (811 mg, 2.75 mmol) to give suspension solution, the reaction mixture was allowed to reflux for 18 h. After cooled to rt, the solvent was evaporated in vacuo, the crude was purified by silica gel chromatography to give 300 mg of title compound as a yellow oil: MS (m/z) 409.0 (M+1)⁺.

b) 3-[(4-Hydroxy-2-oxy-7-phenoxy-isoquinoline-3-carbonyl)-amino]-2,2-dimethyl-propionic acid ethyl ester To a solution of the 3-[(4-Hydroxy-7-phenoxy-isoquinoline-3-carbonyl)-amino]-2,2-dimethyl-propionic acid ethyl ester (300 mg, 0.73 mmol) in dichloromethane (3.65 mL) at r.t. was added mCPBA (345 mg, 1.54 mmol) to give suspension solution, the reaction mixture was stirred at r.t. After 24 hours, the mixture was filtered and the filtrate was washed by NaHCO₃ solution and water. The dried solution (MgSO₄) was concentrated in vacuo and purified by silica gel chromatography, eluting with 15-50% EtOAc/hexanes, to give product (112.4 mg) as brown oil: MS (m/z) 425.0 (M+1)⁺.

c) 3-[(4-Hydroxy-1-iodo-2-oxy-7-phenoxy-isoquinoline-3-carbonyl)-amino]-2,2-dimethyl-propionic acid ethyl ester To a solution of the 3-[(4-Hydroxy-2-oxy-7-phenoxy-isoquinoline-3-carbonyl)-amino]-2,2-dimethyl-propionic acid ethyl ester (95 mg, 0.22 mmol) in dichloromethane (2.2 mL) was added bis(2,4,6-trimethylpyridine)iodine(I) hexafluorophosphate (230 mg, 0.44 mmol). The reaction mixture was allowed to stir at rt. After 20 h, the mixture was filtered and washed with CH₂Cl₂. The filtrate was concentrated in vacuo and purified by silica gel chromatography over silica gel, eluting with 0-20% EtOAc/CH₂Cl₂, to give product (57.2 mg) as a yellow solid: ¹H NMR (CDCl₃, 200 MHz): δ=11.74 (br, 1H), 8.25 (d, 1H, J=8.2 hz), 7.1-7.45 (m, 7H), 4.20 (q, 2H, J=7.0 Hz), 3.65 (d, 2H, J=5.8 Hz), 1.30-1.35 (m, 9H).

d) 3[(1-Cyano-4-hydroxy-2-oxy-7-phenoxy-isoquinoline-3-carbonyl)-amino]-2,2-dimethyl-propionic acid ethyl ester To a solution of 3-[(4-Hydroxy-1-iodo-2-oxy-7-phenoxy-isoquinoline-3-carbonyl)-amino]-2,2-dimethyl-propionic acid ethyl ester (57.2 mg, 0.1 mmol) in DMF (1 mL) at r.t. was added CuCN (18.6 mg, 0.2 mmol). After the reaction was stirred at 160° C. for 6 min under N₂ atmosphere, the mixture was allowed to cool to r.t. and diluted with dichloromethane. The mixture was stirred for another 15 min, filtered and the filtrate was washed by 0.1 N HCl solution and water. The dried solution (MgSO₄) was concentrated in vacuo to give 35.4 mg of title compound as a yellow solid: MS (m/z) 448.0 (M–1)⁺.

e) 3[(1-Cyano-4-hydroxy-2-oxy-7-phenoxy-isoquinoline-3-carbonyl)-amino]-2,2-dimethyl-propionic acid To a solution of 3-[(1-Cyano-4-hydroxy-2-oxy-7-phenoxy-isoquinoline-3-carbonyl)-amino]-2,2-dimethyl-propionic acid ethyl ester (35.4 mg, 0.078 mmol) in THF (0.44 mL) and EtOH (0.78 mL) was added 2 N NaOH (0.16 mL. 0.31 mmol) and the reaction was allowed to stir at rt. After 18 h, the solvent was concentrated in vacuo to give residue as a solid. The solid was dissolved in water (5 mL), the aqueous solution was acidified by 1N HCl solution, filtered, washed with water, dried to give 26.5 mg of the title compound as white solid: MS (m/z) 420.0 (M–1)⁺.

Example 158

3-(3-Carboxypropylcarbamoyl)-1-cyano-4-hydroxy-7-phenoxyisoquinoline 2-oxide

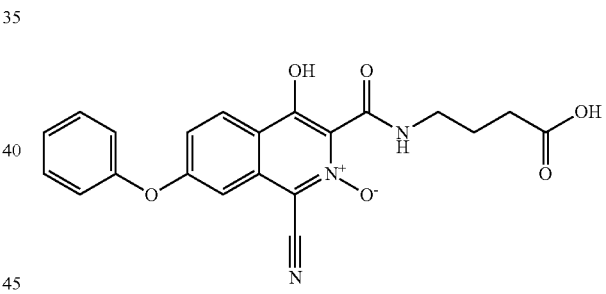

a) 4-[(4-Hydroxy-7-phenoxy-isoquinoline-3-carbonyl)-amino]butyric acid

To a solution of 4-hydroxy-7-phenoxy-isoquinoline-3-carboxylic acid methyl ester (1.08 g, 3.66 mmol) in flask was added 4-Amino-butyric acid (3.77 g, 36.6 mmol) and NaOMe (58 mL, 29.28 mmol, 0.5 M solution in MeOH). The reaction mixture was allowed to reflux. After 24 h, the mixture was cooled to rt, and concentrated in vacuo to give residue as a solid. The solid was dissolved in water (50 mL), extracted with CH₂Cl₂ (2×20 mL). The aqueous solution was acidified by 1N HCl solution, filtered, washed with water, dried to give 1.32 g of title of the compound as a white solid: MS (m/z) 367.0 (M+1)⁺.

b) 4-[(4-Hydroxy-7-phenoxy-isoquinoline-3-carbonyl)-amino]-butyric acid methyl ester To a solution of 4-[(4-hydroxy-7-phenoxy-isoquinoline-3-carbonyl)-amino]-butyric acid (1.32 g, 3.6 mmol) in MeOH (7.2 mL) was added 10% sulfuric acid. The reaction mixture was stirred at reflux for 20 hours. After cooled to rt, the solvent was concentrated in vacuo as a oil and purified by silica gel chromatography over silica gel, eluting with 15-75% EtOAc/hexanes to give product (900 mg) as a colorless oil: MS (m/z) 381.0 (M+1)+.

c) 4-[(4-Hydroxy-2-oxy-7-phenoxy-isoquinoline-3-carbonyl)-amino]-butyric acid methyl ester To a solution of 4-[(4-hydroxy-7-phenoxy-isoquinoline-3-carbonyl)-amino]-butyric acid methyl ester (900 mg, 2.36 mmol) in dichloromethane (11.8 mL) at r.t. were added mCPBA (1.11 g, 4.97 mmol) to give suspension solution, the reaction mixture was stirred at r.t. After 24 hours, the mixture was filtered and the filtrate was washed by NaHCO$_3$ solution and water. The dried solution (MgSO$_4$) was concentrated in vacuo and purified by silica gel chromatography over silica gel, eluting with 15-50% EtOAc/CH$_2$Cl$_2$, to give product (112.4 mg) as brown oil: MS (m/z) 397.0 (M+1)+.

d) 4-[(4-Hydroxy-1-iodo-2-oxy-7-phenoxy-isoquinoline-3-carbonyl)-amino]-butyric acid methyl ester To a solution of the 4-[(4-hydroxy-2-oxy-7-phenoxy-isoquinoline-3-carbonyl)-amino]-butyric acid methyl ester (406 mg, 1.02 mmol) in dichloromethane (10.3 mL) was added bis(2,4,6-trimethylpyridine)iodine(I) hexafluorophosphate (1.05 g, 2.04 mmol). The reaction mixture was allowed to stir at rt. After 20 h, the mixture was filtered and washed with CH$_2$Cl$_2$. The filtrate was concentrated in vacuo and purified by silica gel chromatography over silica gel, eluting with 0-20% EtOAc/CH$_2$Cl$_2$, to give 214 mg of the title compound as a yellow solid: MS (m/z) 523.0 (M+1)+.

e) 4-[(1-Cyano-4-hydroxy-2-oxy-7-phenoxy-isoquinoline-3-carbonyl)-amino]-butyric acid methyl ester To a solution of 4-[(4-hydroxy-1-iodo-2-oxy-7-phenoxy-isoquinoline-3-carbonyl)-amino]-butyric acid methyl ester (46 mg, 0.088 mmol) in DMF (0.44 mL) at r.t. was added CuCN (15.8 mg, 0.176 mmol). After the reaction was stirred at 160° C. for 6 min under N$_2$ atmosphere, the mixture was allowed to cool to r.t. and diluted with dichloromethane. The mixture was stirred for another 15 min, filtered and the filtrate was washed by 0.1 N HCl solution and water. The dried solution (MgSO$_4$) was concentrated in vacuo to give 37 mg of title compound as a yellow solid: MS (m/z) 420.1 (M−1)+.

f) 4-[(1-Cyano-4-hydroxy-2-oxy-7-phenoxy-isoquinoline-3-carbonyl)-amino]-butyric acid To a solution of 4-[(1-cyano-4-hydroxy-2-oxy-7-phenoxy-isoquinoline-3-carbonyl)-amino]-butyric acid methyl ester (37 mg, 0.087 mmol) in THF (0.49 mL) and EtOH (0.87 mL) was added 2 N NaOH (0.17 mL. 0.35 mmol) and the reaction was allowed to stir at rt. After 18 h, the solvent was concentrated in vacuo to give residue as a solid. The solid was dissolved in water (5 mL), the aqueous solution was acidified by 1N HCl solution, filtered, washed with water, dried to give 28.9 mg of the title compound as white solid: MS (m/z) 406.0 (M−1)+.

Example 159

1-{[(1-Cyano-7-cyclohexyloxy-4-hydroxy-isoquinoline-3-carbonyl)-amino]-methyl}-cyclobutanecarboxylic acid

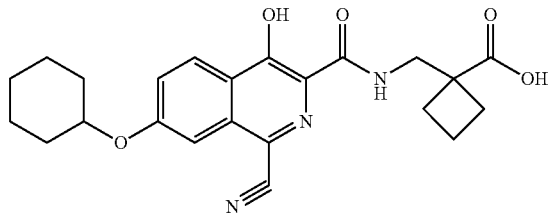 [SMILES: N#Cc1nc(C(=O)NCC2(C(=O)O)CCC2)c(O)c2ccc(OC3CCCCC3)cc12]

A mixture of 1-cyano-7-cyclohexyloxy-4-hydroxy-isoquinoline-3-carboxylic acid butyl ester (20 mg, 0.054 mmol) and 1-aminomethyl-cyclobutanecarboxylic acid (37 mg, 0.22 mmol) in 0.5 M NaOMe/MeOH solution (0.84 mL, 0.42 mmol) was microwaved at 120° C. for 2 h. Reaction mixture was diluted with water (50 mL) and acidified by 1 N HCl to pH=3-4. Precipitate was collected, rinsed with water and dried. Crude product was purified by silica gel chromatography, eluting with 10-100% EtOAc/hexanes, to provide the title compound 8 mg (0.019 mmol) in 35% yield. LC-MS ESI−: 422.03 (M−1)−.

Example 160

3-[(1-Cyano-7-cyclohexanesulfonyl-4-hydroxy-isoquinoline-3-carbonyl)-amino]-2,2-dimethyl-propionic acid

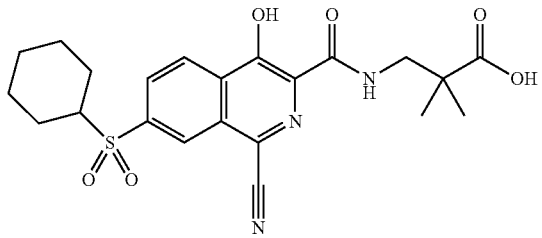 [SMILES: CC(C)(CNC(=O)c1nc(C#N)c2cc(S(=O)(=O)C3CCCCC3)ccc2c1O)C(=O)O]

a) 7-Cyclohexylsulfanyl-1,4-dihydroxy-isoquinoline-3-carboxylic acid butyl ester The regio-mixtures of 6- and 7-cyclohexylsulfanyl-1,4-dihydroxy-isoquinoline-3-carboxylic acid butyl ester (7.0 g) (prepared according to U.S. Pat. No. 7,629,357) was separated by silica gel chromatography, eluting with 0-30% EtOAc/CH$_2$Cl$_2$, to provide the title compound 3.01 g. $^1$H NMR (200 MHz) CDCl$_3$, δ in ppm: 10.45 (br s, 1H), 8.30 (s, 1H), 8.02 (d, J=8.4 Hz, 1H), 7.66 (d, J=8.4 Hz, 1H), 4.4 (t, J=6.6 Hz, 2H), 3.42 (br S, 1H), 2.04 (m, 2H), 1.8-1.3 (m, 12H), 1.00 (t, J=7.2 Hz, 3H).

b) 1-Bromo-7-cyclohexylsulfanyl-4-hydroxy-isoquinoline-3-carboxylic acid butyl ester To a mixture of 7-cyclohexylsulfanyl-1,4-dihydroxy-isoquinoline-3-carboxylic acid butyl ester (2.95 g, 7.87 mmol) in toluene (40 mL) was added POBr3 (3.38 g, 11.8 mmol) was refluxed for 3 h. Reaction mixture was cooled to 0° C. and quenched with saturated NaHCO3 aqueous solution (100 mL). It was stirred for 15 min., and then was extracted with EtOAc. Organic layer was washed with brine, dried over MgSO4, filtered and concentrated to provide the title compound 2.55 g (5.82 mmol), which was used directly to the next reaction without further purification. $^1$H NMR (200 MHz) CDCl3, δ in ppm: 11.85 (s, 1H), 8.23 (d, J=8.8 Hz, 1H), 8.05 (s, 1H), 7.65 (d, J=8.5 Hz, 1H), 4.47 (t, J=7.0 Hz, 2H), 3.46 (br S, 1H), 2.10 (br m, 2H), 1.85-1.42 (m, 12H), 0.99 (t, J=7.1 Hz, 3H).

c) 1-Cyano-7-cyclohexylsulfanyl-4-hydroxy-isoquinoline-3-carboxylic acid butyl ester A mixture of 1-Bromo-7-cyclohexylsulfanyl-4-hydroxy-isoquinoline-3-carboxylic acid butyl ester (686 mg, 1.57 mmol) and CuCN (279 mg, 3.13 mmol) in 3.6 mL of NMP was heated in a 130-135° C. oil bath for 3 h. Reaction mixture was diluted with CH$_2$Cl$_2$ (120 mL) and stirred at room temperature overnight. Then 100 mL of 0.5 N HCl aqueous solution was added and the resultant mixture was stirred vigorously for 30 min Two phases were separated and organic layer was washed with brine, dried over MgSO$_4$, filtered and concentrated. Crude residue was purified by silica gel chromatography, eluting with 5-60% EtOAc/hexanes, to provide the title compound 470 mg (1.22 mmol) in 78% yield. $^1$H NMR (200 MHz) CDCl$_3$, δ in ppm: 12.36 (s, 1H), 8.27 (d, J=8.8 Hz, 1H), 8.01 (s, 1H), 7.68 (d, J=8.8 Hz, 1H), 4.50 (t, J=6.8 Hz, 2H), 3.50 (br m, 1H), 2.10 (m, 2H), 1.87-1.39 (m, 12H), 1.00 (t, J=7.2 Hz, 3H).

d) 1-Cyano-7-cyclohexanesulfonyl-4-hydroxy-isoquinoline-3-carboxylic acid butyl ester A mixture of 1-cyano-7-cyclohexylsulfanyl-4-hydroxy-isoquinoline-3-carboxylic acid butyl ester (325 mg, 0.85 mmol) and mCPBA (526 mg, 3.05 mmol) in CH$_2$Cl$_2$ was stirred at room temperature overnight. The reaction was quenched by adding Na$_2$S$_2$O$_3$ (3.6 equivalents). It was then filtered and rinsed with CH$_2$Cl$_2$. Filtrate was concentrated and purified by silica gel chromatography, eluting with 10-100% EtOAc/hexanes to provide the title compound 297 mg (0.71 mmol) in 84% yield. LC-MS ESI−: 414.99 (M−1)−.

e) 3-[(1-Cyano-7-cyclohexanesulfonyl-4-hydroxy-isoquinoline-3-carbonyl)-amino]-2,2-dimethyl-propionic acid A mixture of 1-cyano-7-cyclohexanesulfonyl-4-hydroxy-isoquinoline-3-carboxylic acid butyl ester (40 mg, 0.096 mmol) and 3-amino-2,2-dimethyl-propionic acid tert-butyl ester (50 mg, 0.29 mmol) in 0.5 M NaOMe/MeOH solution was microwave at 130° C. for 1 h. It was added acetic acid (50 microL) and then concentrated. Residue was purified by silica gel chromatography, eluting with 5-80% EtOAc/hexanes, to give the intermediate 32 mg. This intermediate was then treated with (½) TFA/CH$_2$Cl$_2$ (3 mL). The resultant mixture was stirred at room temperature for 5 h and then concentrated. Residue was treated with water (60 mL) and basified by 1 N NaOH to pH=9-10. It was stirred to homogeneous and then acidified by 1 N HCl to pH=3-4. Precipitate was collected and dried in vacuo to provide the title compound 19.1 mg (0.04 mmol) in 43% yield. LC-MS ESI−: 458.11 (M−1)−.

Example 161

1-{[(1-Cyano-7-cyclohexanesulfonyl-4-hydroxy-isoquinoline-3-carbonyl)-amino]-methyl}-cyclobutanecarboxylic acid

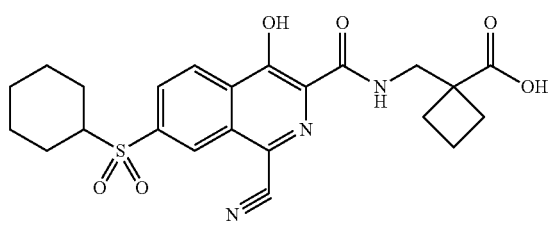 [SMILES: N#Cc1nc(C(=O)NCC2(C(=O)O)CCC2)c(O)c2ccc(S(=O)(=O)C3CCCCC3)cc12]

To a mixture of 1-cyano-7-cyclohexanesulfonyl-4-hydroxy-isoquinoline-3-carboxylic acid butyl ester (30 mg, 0.072 mmol) and 1-aminomethyl-cyclobutanecarboxylic acid (48 mg, 0.29 mmol) (available from Ukrorgsyntez Ltd) in ethanol (0.7 mL) was added NaOMe solid (16 mg, 0.29 mmol). The resultant mixture was microwaved at 140° C. for 1 h. The reaction mixture was then treated with 1 mL of 3 N NaOH aqueous solution and stirred at room temperature for 3 h. Reaction mixture was diluted with water (60 mL) and acidified by 1 N HCl to pH=3-4. Precipitate was collected and purified by silica gel chromatography, eluting with 0-10% MeOH/CH$_2$Cl$_2$ to provide the title compound 6.4 mg (0.014 mmol) in 19% yield. LC-MS ESI−: 470.12 (M−1)−.

Example 162

3-{[7-(3-Benzyl-ureido)-1-cyano-4-hydroxy-isoquinoline-3-carbonyl]-amino}-2,2-dimethyl-propionic acid

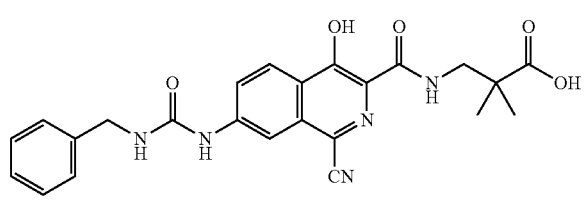 [SMILES: CC(C)(CNC(=O)c1nc(C#N)c2cc(NC(=O)NCc3ccccc3)ccc2c1O)C(=O)O]

a) 7-(3-Benzyl-ureido)-1-cyano-4-hydroxy-isoquinoline-3-carboxylic acid ethyl ester 7-(3-Benzyl-ureido)-1-cyano-4-hydroxy-isoquinoline-3-carboxylic acid ethyl ester was prepared from 7-bromo-1-cyano-4-hydroxy-isoquinoline-3-carboxylic acid ethyl ester under conditions analogous to Example 116(a) using benzylurea. MS ESI(+) m/e: 391.0935 (M+1).

b) 3-{[7-(3-Benzyl-ureido)-1-cyano-4-hydroxy-isoquinoline-3-carbonyl]amino}-2,2-dimethyl-propionic acid ethyl ester 3-{[7-(3-Benzyl-ureido)-1-cyano-4-hydroxy-isoquinoline-3-carbonyl]-amino}-2,2-dimethyl-propionic acid ethyl ester was prepared from 7-(3-Benzyl-ureido)-1-cyano-4-hydroxy-isoquinoline-3-carboxylic acid ethyl ester under conditions analogous to Example 139(d). The isolated product was used immediately in the following reaction.

c) 3-{[7-(3-Benzyl-ureido)-1-cyano-4-hydroxy-isoquinoline-3-carbonyl]amino}-2,2-dimethyl-propionic acid 3-{[7-(3-Benzyl-ureido)-1-cyano-4-hydroxy-isoquinoline-3-carbonyl]-amino}-2,2-dimethyl-propionic acid was prepared from 3-{[7-(3-benzyl-ureido)-1-cyano-4-hydroxy-isoquinoline-3-carbonyl]-amino}-2,2-dimethyl-propionic acid ethyl ester under conditions analogous to Example 139 (e). MS ESI(−) m/e: 460.1889 (M−1), MS ESI(+) m/e: 462.2043 (M+1).

Example 163

(S)-2-[Amino-5-(1-cyano-4-hydroxy-7-phenoxy-isoquinoline-3-carbonyl)-amino]-pentanoic acid 2,2,2-trifluoroacetic acid (1:1)

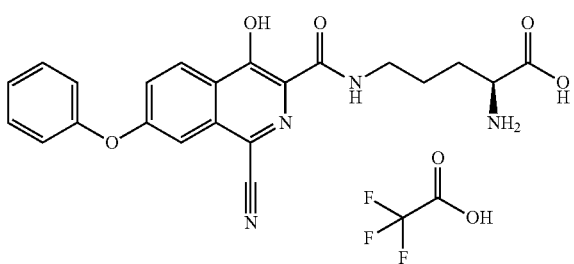 [SMILES: N#Cc1nc(C(=O)NCCC[C@H](N)C(=O)O)c(O)c2ccc(Oc3ccccc3)cc12 ; O=C(O)C(F)(F)F]

The title was prepared according to the procedures disclosed herein using the appropriate starting materials.

Example 164

3-[(7-Benzyl-1-cyano-4-hydroxy-isoquinoline-3-carbonyl)-amino]-2,2-dimethyl-propionic acid

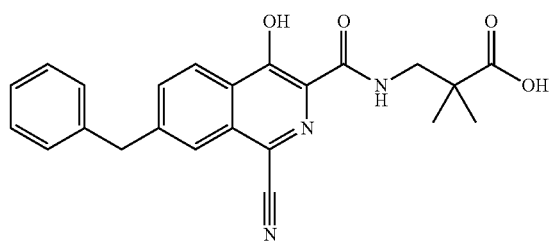 [SMILES: CC(C)(CNC(=O)c1nc(C#N)c2cc(Cc3ccccc3)ccc2c1O)C(=O)O]

a) 7-Benzyl-1-bromo-4-hydroxy-isoquinoline-3-carboxylic acid methyl ester

A mixture of 7-Benzyl-4-hydroxy-isoquinoline-3-carboxylic acid methyl ester (302 mg, 1.03 mmole, prepared according to procedures in U.S. Pat. No. 7,928,120 B2 for example 22c) and N-bromosuccinimide (202 mg, 1.13 mmole) in anhydrous dichloromethane (5 ml) was stirred at room temperature for twenty hours before it was quenched with water, extracted with dichloromethane, washed with brine, dried over anhydrous sodium sulfate, concentrated and purified by flash column chromatography on silica gel with a gradient of ethyl acetate and hexanes to give the title compound as a white solid (259 mg). LC-MS ESI+: 372, 374 ($^{79}$Br/$^{81}$Br) (M+1)$^+$; ESI−: 370, 372 ($^{79}$Br/$^{81}$Br) (M-b) 7-Benzyl-1-cyano-4-hydroxy-isoquinoline-3-carboxylic acid methyl ester A mixture of 7-Benzyl-1-bromo-4-hydroxy-isoquinoline-3-carboxylic acid methyl ester (209 mg, 0.56 mmole) and copper cyanide (101 mg, 1.12 mmole) in anhydrous dimethylformamide (2.2 ml) was stirred at 160° C. for twelve minutes before it was cooled to room temperature, dichloromethane was added and stirred for ten minutes before the suspension was filtered, washed with 0.5 N hydrochloric acid, brine, dried over anhydrous sodium sulfate, concentrated and purified by flash column chromatography on silica gel with a gradient of dichloromethane and hexanes to give the title compound as a white solid (132 mg). LC-MS ESI+: 319 (M+1)$^+$; ESI−: 317 (M−1)$^−$.

c) 3-[(7-Benzyl-1-cyano-4-hydroxy-isoquinoline-3-carbonyl)-amino]-2,2-dimethyl-propionic acid tert-butyl ester A mixture of 7-Benzyl-1-cyano-4-hydroxy-isoquinoline-3-carboxylic acid methyl ester (20 mg, 0.06 mmole) and 3-amino-2,2-dimethyl-propionic acid tert-butyl ester (22 mg, 0.12 mmole) in anhydrous ethanol (0.6 ml) was stirred at 130° C. in a CEM microwave synthesizer for one hour before it was cooled to room temperature, concentrated and purified by flash column chromatography on silica gel with a gradient of dichloromethane and hexanes to give the title compound as a white solid (22 mg). LC-MS ESI+: 460 (M+1)$^+$; ESI−: 458 (M−1)$^−$.

d) 3-[(7-Benzyl-1-cyano-4-hydroxy-isoquinoline-3-carbonyl)-amino]-2,2-dimethyl-propionic acid A mixture of 3-[(7-Benzyl-1-cyano-4-hydroxy-isoquinoline-3-carbonyl)-amino]-2,2-dimethyl-propionic acid tert-butyl ester (22 mg, 0.05 mmole) in a mixture of trifluoroacetic acid (3 ml) and dichloromethane (1 ml) was stirred room temperature for 80 minutes before it was concentrated to give the title compound as a white solid (13 mg). LC-MS ESI−: 402 (M−1)$^−$.

Example 165

3-(3-Chloro-phenyl)-3-[(1-cyano-4-hydroxy-7-phenoxy-isoquinoline-3-carbonyl)-amino]-propionic acid

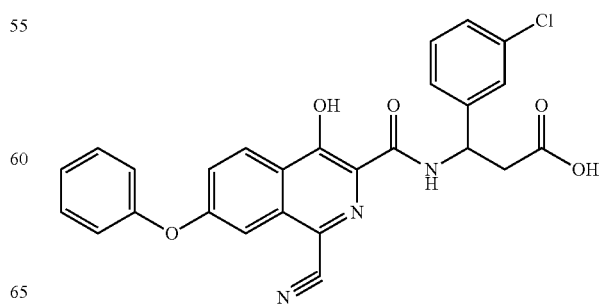

To a mixture of 1-cyano-4-hydroxy-7-phenoxy-isoquinoline-3-carboxylic acid methyl ester (50 mg, 0.16 mmol) and 3-amino-3-(3-chloro-phenyl)-propionic acid (156 mg, 0.78 mmol) (commercially available from Alfa Aesar L19797) in N,N-dimethylacetamide (DMA) (2 mL) was added sodium methoxide (34 mg, 0.62 mmol). The resultant suspension mixture was heated in a 150° C. oil bath for 4 h. After cooled, reaction mixture was diluted with water (50 mL), acidified by 1 N HCl to pH=3-4, and then extracted with EtOAc. Organic layer was washed with brine, dried over MgSO₄, filtered and concentrated. Crude product was purified by silica gel chromatography, eluting with EtOAc/hexanes (10%-100%), to provide the title compound 20 mg (0.04 mmol) in 26% yield. LC-MS ESI–: 486 (M–1)⁻.

Example 166

3-[(1-Cyano-4-hydroxy-7-phenoxy-isoquinoline-3-carbonyl)-amino]-2-cyclopropyl-propionic acid

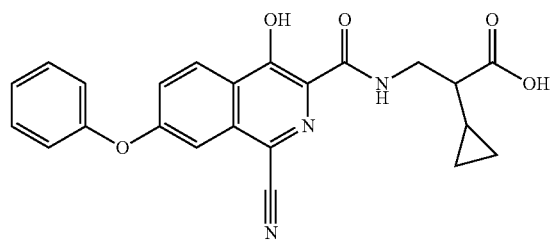 [SMILES: N#Cc1nc(C(=O)NCC(C(=O)O)C2CC2)c(O)c2ccc(Oc3ccccc3)cc12]

a) 3[(1-Cyano-4-hydroxy-7-phenoxy-isoquinoline-3-carbonyl)-amino]-2-cyclopropyl-propionic acid tert-butyl ester To a dry ice/acetone bath cooled solution of cyclopropyl-acetonitrile (1.46 g) and Boc anhydride (4.32 g) in THF (18 mL) was slowly added a solution of LDA (18 mL, 2 M solution) in THF and the reaction was stirred for 2 h in the cold bath. The reaction was then warmed to rt and quenched with diluted citric acid solution, extracted with EtOAc; EtOAc phase was washed with diluted NaCl solution, and dried over anhydrous sodium sulfate, filtered, concentrated and silica gel column purified to give desired product cyano-cyclopropyl-acetic acid tert-butyl ester (1 g), which was mixed with Raney nickel (5 mL, 50% water) in MeOH (50 mL) and stirred under hydrogen balloon at rt overnight. The mixture was then filtered through Celite and concentrated to give crude product amine (1 g). A mixture of this crude amine (84 mg), 4-hydroxy-7-phenoxy-isoquinoline-3-carboxylic acid methyl ester (58 mg) and DBU (0.041 mL) in DMA (1 mL) was heated in an oil bath (140° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product as brown solid (65 mg). LC-MS ESI+: 474 (M+1)⁺.

b) 3[(1-Cyano-4-hydroxy-7-phenoxy-isoquinoline-3-carbonyl)-amino]-2-cyclopropyl-propionic acid A mixture of 3-[(1-cyano-4-hydroxy-7-phenoxy-isoquinoline-3-carbonyl)-amino]-2-cyclopropyl-propionic acid tert-butyl ester (65 mg) and TFA (2 mL) in DCM (2 mL) was stirred at rt for 2 h. The mixture was subsequently concentrated and resulting residue was dissolved in EtOAc, washed with water, diluted NaCl solution and dried over anhydrous sodium sulfate, filtered, concentrated and solids were treated with hot DCM/hexanes (1:1 by volume); solids after cooling were collected via filtration, giving desired product after air-drying as white solids (40 mg). LC-MS ESI+: 418 (M+1)⁺.

Example 167

2-Cyclopropyl-3-[(4-hydroxy-7-phenoxy-isoquinoline-3-carbonyl)-amino]-propionic acid

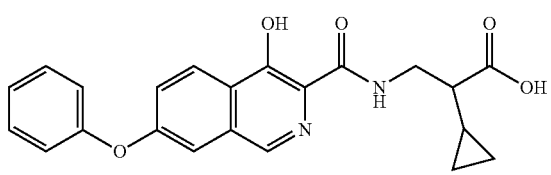 [SMILES: O=C(NCC(C(=O)O)C1CC1)c1ncc2cc(Oc3ccccc3)ccc2c1O]

a) 2-Cyclopropyl-3-[(4-hydroxy-7-phenoxy-isoquinoline-3-carbonyl)-amino]propionic acid tert-butyl ester A mixture of 3-amino-2-cyclopropyl-propionic acid tert-butyl ester (66 mg), 4-hydroxy-7-phenoxy-isoquinoline-3-carboxylic acid methyl ester (35 mg) and DBU (0.027 mL) in DMA (1 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product as brown solid (52 mg). LC-MS ESI+: 449 (M+1)⁺.

b) 2-Cyclopropyl-3-[(4-hydroxy-7-phenoxy-isoquinoline-3-carbonyl)-amino]propionic acid A mixture of 2-cyclopropyl-3-[(4-hydroxy-7-phenoxy-isoquinoline-3-carbonyl)-amino]-propionic acid tert-butyl ester (52 mg) and TFA (2 mL) in DCM (2 mL) was stirred at rt for 3 h; then the mixture was concentrated and resulting residue was treated with water; the solids were collected via filtration and air dried to give desired product as white solids (37 mg). LC-MS ESI+: 393 (M+1)⁺.

Example 168

3-[(1-Cyano-4-hydroxy-7-phenoxy-isoquinoline-3-carbonyl)-amino]-2-phenyl-propionic acid

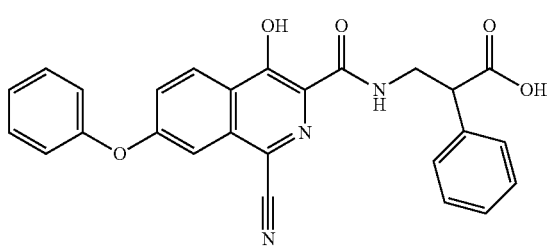 [SMILES: N#Cc1nc(C(=O)NCC(C(=O)O)c2ccccc2)c(O)c2ccc(Oc3ccccc3)cc12]

a) Cyano-phenyl-acetic acid tert-butyl ester

To a dry ice/acetone bath cooled solution of phenyl-acetonitrile (2.64 g) and Boc anhydride (5.5 g) in THF (35 mL) was slowly added a solution of LDA (30 mL, 1.5 M solution) in cyclohexane and the solution was stirred for 2 h in the cold bath; then the reaction was warmed to rt and quenched with diluted citric acid solution, extracted with EtOAc; EtOAc phase was washed with diluted NaCl solution, and dried over anhydrous sodium sulfate, filtered, concentrated and silica gel column purified to give desired product (4.52 g). $^1$H NMR in CDCl$_3$, δ in ppm: 7.42 (m, 5H), 4.61 (s, 1H), 1.45 (s, 9H).

b) 3-Amino-2-phenyl-propionic acid tert-butyl ester

Cyano-phenyl-acetic acid tert-butyl ester (4.52 g) was mixed with Raney nickel (5 mL, 50% water) in MeOH (100 mL) and stirred under hydrogen balloon at rt overnight. The mixture was then filtered through Celite and concentrated to give crude product (4.36 g). $^1$H NMR in CDCl$_3$, δ in ppm: 7.4-7.2 (m, 5H), 3.54 (m, 1H), 3.3-2.9 (br, 2H), 1.41 (s, 9H).

c) 3-[(1-Cyano-4-hydroxy-7-phenoxy-isoquinoline-3-carbonyl)-amino]-2-phenyl-propionic acid tert-butyl ester A mixture of 3-amino-2-phenyl-propionic acid tert-butyl ester (108 mg), 1-cyano-4-hydroxy-7-phenoxy-isoquinoline-3-carboxylic acid methyl ester (52 mg) and DBU (0.036 mL) in DMA (0.5 mL) was heated in an oil bath (150° C.) for 1.5 h. After cooling, the reaction mixture was partitioned between EtOAc and diluted HCl solution; EtOAc phase was separated and washed with water, diluted NaCl solution respectively and dried over anhydrous sodium sulfate solution, filtered, concentrated and silica gel column purified to give desired product as brown solid (60 mg). LC-MS ESI+: 510 (M+1)$^+$.

d) 3-[(1-Cyano-4-hydroxy-7-phenoxy-isoquinoline-3-carbonyl)-amino]-2-phenyl-propionic acid A mixture of 3-[(1-cyano-4-hydroxy-7-phenoxy-isoquinoline-3-carbonyl)-amino]-2-phenyl-propionic acid tert-butyl ester (60 mg) and TFA (2 mL) in DCM (2 mL) was stirred at rt for 3 h. The mixture was concentrated and resulting residue was treated with water; solids were collected via filtration and air dried to give desired product (50 mg). LC-MS ESI+: 454 (M+1)$^+$.

Example 169

3-[(4-Hydroxy-7-phenoxy-isoquinoline-3-carbonyl)-amino]-2-phenyl-propionic acid

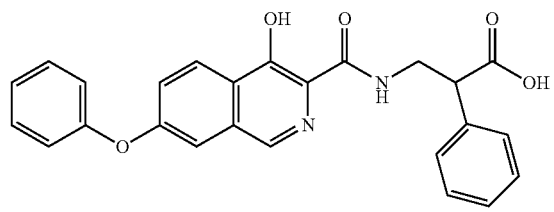 [SMILES: O=C(NCC(C(=O)O)c1ccccc1)c1ncc2cc(Oc3ccccc3)ccc2c1O]

a) 3-[(4-hydroxy-7-phenoxy-isoquinoline-3-carbonyl)-amino]-2-phenyl-propionic acid tert-butyl ester A mixture of 3-amino-2-phenyl-propionic acid tert-butyl ester (90 mg), 4-hydroxy-7-phenoxy-isoquinoline-3-carboxylic acid methyl ester (40 mg) and DBU (0.030 mL) in DMA (1 mL) was heated in an oil bath (150° C.) for 1.5 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product as brown solid (50 mg). LC-MS ESI+: 485 (M+1)$^+$.

b) 3-[(4-hydroxy-7-phenoxy-isoquinoline-3-carbonyl)-amino]-2-phenyl-propionic acid A mixture of 3-[(4-hydroxy-7-phenoxy-isoquinoline-3-carbonyl)-amino]-2-phenyl-propionic acid tert-butyl ester (50 mg) and TFA (2 mL) in DCM (2 mL) was stirred at rt for 3 h; then the mixture was concentrated and resulting residue was treated with water; the solids were collected via filtration and air dried to give desired product as white solids (35 mg). LC-MS ESI+: 429 (M+1)$^+$.

Example 170

3-(S)-[(1-Cyano-4-hydroxy-7-phenoxy-isoquinoline-3-carbonyl)-amino]-3-(2-fluoro-phenyl)-propionic acid

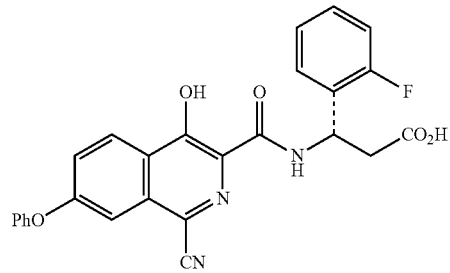 [SMILES: Cc1ccccc1[C@H](CC(=O)O)NC(=O)c1nc(C#N)c2cc(Oc3ccccc3)ccc2c1O]

1-Cyano-4-hydroxy-7-phenoxy-isoquinoline-3-carboxylic acid methyl ester (50 mg, 0.156 mmol) was combined in an oven-dried flask with 3-(S)-amino-3-(2-fluoro-phenyl)-propionic acid (86 mg, 0.468 mmol) (commercially available from Combi-Blocks SS-1800) and N,N-dimethylacetamide (1.5 mL) was added with stirring. Solid sodium methoxide (25 mg, 0.468 mmol) was added and the reaction was heated to 150° C. in an oil bath for approximately five hours. The reaction was cooled and the solution diluted with five volumes of water. The solution was acidified to pH 3 with 1M hydrochloric acid to induce precipitation. Filtration of the

Example 171

3-(S)-[(1-Cyano-4-hydroxy-7-phenoxy-isoquinoline-3-carbonyl)-amino]-3-o-tolyl-propionic acid

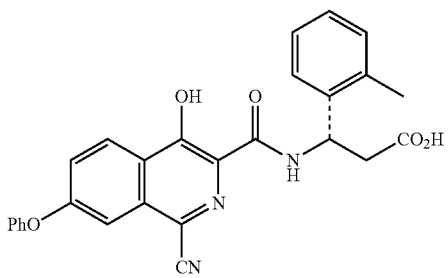

1-Cyano-4-hydroxy-7-phenoxy-isoquinoline-3-carboxylic acid methyl ester (50 mg, 0.156 mmol) was combined in an oven-dried flask with 3-(S)-amino-3-o-tolyl-propionic acid (84 mg, 0.468 mmol) (commercially available from Combi-Blocks SS-1801) and N,N-dimethylacetamide (1.5 mL) was added with stirring. Solid sodium methoxide (25 mg, 0.468 mmol) was added and the reaction was heated to 150° C. in an oil bath for approximately five hours. The reaction was cooled and the solution diluted with five volumes of water. The solution was acidified to pH 3 with 1M hydrochloric acid to induce precipitation. Filtration of the solid followed by vacuum drying provided the desired product in 90% yield. LC-MS ESI−: 466 (M−1)−.

Example 172

3-(S)-[(1-Cyano-4-hydroxy-7-phenoxy-isoquinoline-3-carbonyl)-amino]-3-(4-cyano-phenyl)-propionic acid

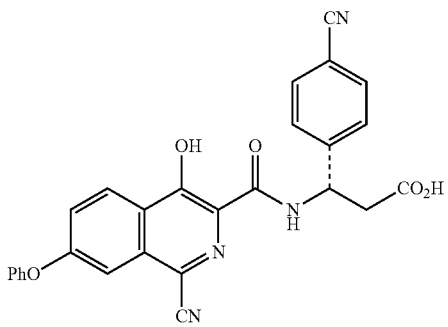 [SMILES: N#Cc1ccc([C@H](CC(=O)O)NC(=O)c2nc(C#N)c3cc(Oc4ccccc4)ccc3c2O)cc1]

1-Cyano-4-hydroxy-7-phenoxy-isoquinoline-3-carboxylic acid methyl ester (50 mg, 0.156 mmol) was combined in an oven-dried flask with 3-(S)-Amino-3-(4-cyano-phenyl)-propionic acid (92 mg, 0.468 mmol) (commercially available from Combi-Blocks SS-1849) and N,N-dimethylacetamide (1.5 mL) was added with stirring. Solid sodium methoxide (25 mg, 0.468 mmol) was added and the reaction was heated to 150° C. in an oil bath for approximately five hours. The reaction was cooled and the solution diluted with five volumes of water. The solution was acidified to pH 3 with 1M hydrochloric acid to induce precipitation. Filtration of the solid followed by vacuum drying provided the desired product in 90% yield. LC-MS ESI−: 477 (M−1)−.

Example 173

3-(4-Chloro-phenyl)-3-[(1-cyano-4-hydroxy-7-phenoxy-isoquinoline-3-carbonyl)-amino]-propionic acid

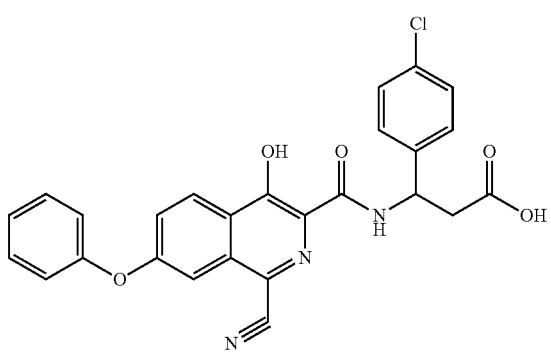 [SMILES: N#Cc1nc(C(=O)NC(CC(=O)O)c2ccc(Cl)cc2)c(O)c2ccc(Oc3ccccc3)cc12]

To a mixture of 1-cyano-4-hydroxy-7-phenoxy-isoquinoline-3-carboxylic acid methyl ester (50 mg, 0.16 mmol) and 3-amino-3-(4-chloro-phenyl)-propionic acid (94 mg, 0.47 mmol) (commercially available from Alfa Aesar L19798) in DMA (2 mL) was added sodium methoxide (25 mg, 0.47 mmol). The resultant suspension mixture was heated in a 150° C. oil bath for 2 h. After cooled, reaction mixture was diluted with water (50 mL) and acidified by 1 N HCl to pH=3-4.

Precipitate was collected, rinsed with water and dried in vacuo. Crude product was purified by silica gel chromatography, eluting with EtOAc/hexanes (5%-100%). Fractions containing the product were collected, concentrated and recrystallized from hot acetonitrile (2 mL) to provide the title compound 14 mg (0.029 mmol) in 18% yield. LC-MS ESI−: 486 (M−1)−.

Example 174

3-[(1-Cyano-4-hydroxy-7-phenoxy-isoquinoline-3-carbonyl)-amino]-3-pyridin-3-yl-propionic acid

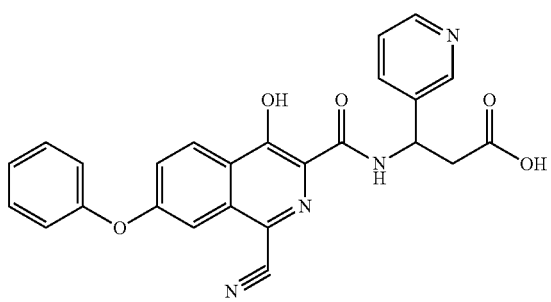 [SMILES: N#Cc1nc(C(=O)NC(CC(=O)O)c2cccnc2)c(O)c2ccc(Oc3ccccc3)cc12]

To a mixture of 1-cyano-4-hydroxy-7-phenoxy-isoquinoline-3-carboxylic acid methyl ester (50 mg, 0.16 mmol) and 3-amino-3-pyridin-3-yl-propionic acid (52 mg, 0.31 mmol)

(commercially available from Combi-Blocks SS-4195) in DMA (2 mL) was added sodium methoxide (17 mg, 0.31 mmol). The resultant suspension mixture was heated in a 150° C. oil bath for 2 h. After cooled, reaction mixture was diluted with water (75 mL) and acidified by 1 N HCl to pH=3-4. Precipitate was collected, rinsed with water and dried in vacuo to provide the title compound 30 mg (0.066 mmol) in 42% yield. LC-MS ESI–: 453 (M–1)⁻.

Example 175

3-(S)-[(1-Cyano-4-hydroxy-7-phenoxy-isoquinoline-3-carbonyl)-amino]-3-pyridin-3-yl-propionic acid

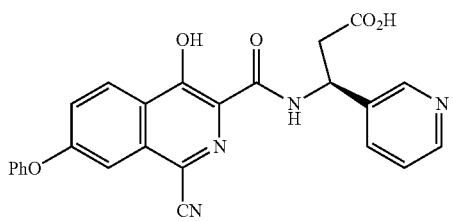 [SMILES: N#Cc1nc(C(=O)N[C@@H](CC(=O)O)c2cccnc2)c(O)c2ccc(Oc3ccccc3)cc12]

a) 3-(S)-[(1-Cyano-4-hydroxy-7-phenoxy-isoquinoline-3-carbonyl)-amino]-3-pyridin-3-yl-propionic acid methyl ester 1-Cyano-4-hydroxy-7-phenoxy-isoquinoline-3-carboxylic acid methyl ester (50 mg, 0.156 mmol) was combined in a CEM microwave tube (10 mL) with (S)-3-amino-3-pyridin-3-yl-propionic acid ethyl ester dihydrochloride (134 mg, 0.5 mmol) (commercially available from AstaTech 46247) and a solution of sodium methoxide in methanol (2 mL, 0.5M, 1 mmol) was added with stirring. The reaction was heated to 140° C. in the CEM microwave apparatus for approximately 90 minutes. The reaction was cooled, concentrated under vacuum and filtered through silica to provide 41 mg of the desired product which was used without additional purification.

b) 3-(S)-[(1-Cyano-4-hydroxy-7-phenoxy-isoquinoline-3-carbonyl)-amino]-3-pyridin-3-yl-propionic acid 3-(S)-[(1-Cyano-4-hydroxy-7-phenoxy-isoquinoline-3-carbonyl)-amino]-3-pyridin-3-yl-propionic acid methyl ester (25 mg, 0.0533 mmol) was dissolved in methanol (2 mL) and tetrahydrofuran (2 mL.) Sodium hydroxide solution (2 mL, 2M) was added and the reaction was permitted to stir overnight at room temperature. After 18 hours, the pH was adjusted to 4 and reaction lyophilized. The crude product was purified by HPLC to provide the title compound in 68% yield. LC-MS ESI+: 455 (M+1)⁺; ESI–: 453 (M–1)⁻.

Example 176

3-(R)-[(1-Cyano-4-hydroxy-7-phenoxy-isoquinoline-3-carbonyl)-amino]-3-pyridin-3-yl-propionic acid

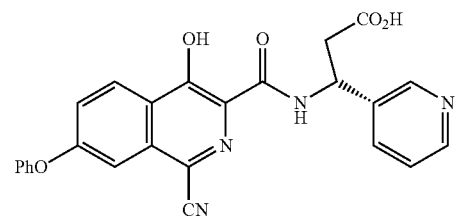

a) 3-(R)-[(1-Cyano-4-hydroxy-7-phenoxy-isoquinoline-3-carbonyl)-amino]-3-pyridin-3-yl-propionic acid methyl ester 1-Cyano-4-hydroxy-7-phenoxy-isoquinoline-3-carboxylic acid methyl ester (50 mg, 0.156 mmol) was combined in a CEM microwave tube (10 mL) with (R)-3-amino-3-pyridin-3-yl-propionic acid ethyl ester dihydrochloride (134 mg, 0.5 mmol) (commercially available from AstaTech 46345) and a solution of sodium methoxide in methanol (2 mL, 0.5M, 1 mmol) was added with stirring. The reaction was heated to 140° C. in the CEM microwave apparatus for approximately 90 minutes. The reaction was cooled, concentrated under vacuum and filtered through silica to provide 49 mg of the desired product which was used without additional purification.

b) 3-(R)-[(1-Cyano-4-hydroxy-7-phenoxy-isoquinoline-3-carbonyl)-amino]-3-pyridin-3-yl-propionic acid 3-(R)-[(1-Cyano-4-hydroxy-7-phenoxy-isoquinoline-3-carbonyl)-amino]-3-pyridin-3-yl-propionic acid methyl ester (25 mg, 0.0533 mmol) was dissolved in methanol (2 mL) and tetrahydrofuran (2 mL.) Sodium hydroxide solution (2 mL, 2M) was added and the reaction was permitted to stir overnight at room temperature. After 18 hours, the pH was adjusted to 4 and reaction lyophilized. The crude product was purified by HPLC to provide the title compound in 80% yield. LC-MS ESI+: 455 (M+1)⁺; ESI−: 453 (M−1)⁻.

Example 177

3{-[1-Cyano-7-(2-fluoro-phenoxy)-4-hydroxy-isoquinoline-3-carbonyl]-amino}-2-cyclopropyl-propionic acid

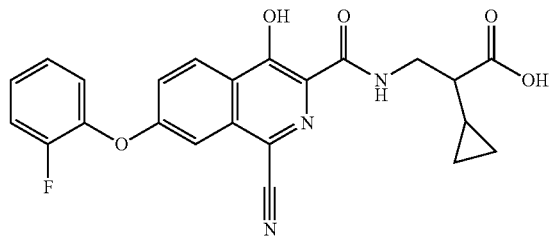 [SMILES: N#Cc1nc(C(=O)NCC(C(=O)O)C2CC2)c(O)c2ccc(Oc3ccccc3F)cc12]

a) 3-{[7-Cyano-7-(2-fluoro-phenoxy)-4-hydroxy-isoquinoline-3-carbonyl]amino}-2-cyclopropyl-propionic acid tert-butyl ester A mixture of 3-amino-2-cyclopropyl-propionic acid tert-butyl ester (15 mg), 1-cyano-7-(2-fluoro-phenoxy)-4-hydroxy-isoquinoline-3-carboxylic acid methyl ester (11 mg) and DBU (0.0074 mL) in DMA (0.5 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product (10 mg). LC-MS ESI+: 492 (M+1)⁺.

b) 3-{[7-Cyano-7-(2-fluoro-phenoxy)-4-hydroxy-isoquinoline-3-carbonyl]amino}-2-cyclopropyl-propionic acid A mixture of 3-{[1-cyano-7-(2-fluoro-phenoxy)-4-hydroxy-isoquinoline-3-carbonyl]-amino}-2-cyclopropyl-propionic acid tert-butyl ester (10 mg) and TFA (2 mL) in DCM (2 mL) was stirred at rt for 3 h; then the mixture was concentrated and resulting residue was treated with water; the solids were collected via filtration and air dried to give desired product (9 mg). LC-MS ESI+: 436 (M+1)⁺.

Example 178

3{-[1-Cyano-4-hydroxy-7-(pyridin-3-yloxy)-isoquinoline-3-carbonyl]-amino}-2-cyclopropyl-propionic acid tert-butyl ester, trifluoro-acetic acid salt

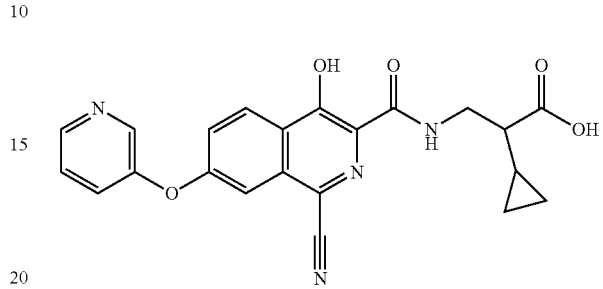

a) 3-{[7-Cyano-4-hydroxy-7-(pyridin-3-yloxy)-isoquinoline-3-carbonyl]amino}-2-cyclopropyl-propionic acid tert-butyl ester A mixture of 3-amino-2-cyclopropyl-propionic acid tert-butyl ester (39 mg), 1-cyano-4-hydroxy-7-(pyridin-3-yloxy)-isoquinoline-3-carboxylic acid ethyl ester (28 mg) and DBU (0.019 mL) in DMA (0.5 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product (21 mg). LC-MS ESI+: 475 (M+1)⁺.

b) 3-{[7-Cyano-4-hydroxy-7-(pyridin-3-yloxy)-isoquinoline-3-carbonyl]amino}-2-cyclopropyl-propionic acid tert-butyl ester, trifluoro-acetic acid salt A mixture of 3-{[1-cyano-4-hydroxy-7-(pyridin-3-yloxy)-isoquinoline-3-carbonyl]-amino}-2-cyclopropyl-propionic acid tert-butyl ester (21 mg) and TFA (2 mL) in DCM (2 mL) was stirred at rt for 3 h; then the mixture was concentrated; resulting residue was treated with water and freeze dried to give desired product (25 mg). LC-MS ESI+: 419 (M+1)⁺.

Example 179

3{-[1-Cyano-7-(4-fluoro-phenoxy)-4-hydroxy-isoquinoline-3-carbonyl]-amino}-2-cyclopropyl-propionic acid

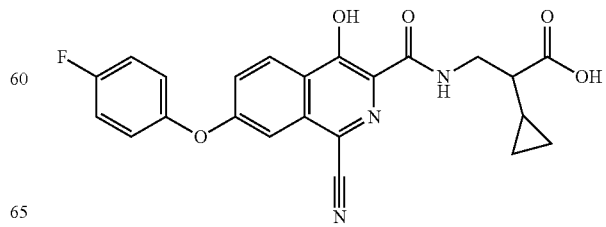

a) 3-{[1-Cyano-7-(4-fluoro-phenoxy)-4-hydroxy-isoquinoline-3-carbonyl]amino}-2-cyclopropyl-propionic acid tert-butyl ester A mixture of 3-amino-2-cyclopropyl-propionic acid tert-butyl ester (20 mg), 1-cyano-7-(4-fluoro-phenoxy)-4-hydroxy-isoquinoline-3-carboxylic acid methyl ester (15 mg) and DBU (10 mg) in DMA (0.3 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product as brown solid (10 mg). LC-MS ESI+: 492 (M+1)+.

b) 3-{[7-Cyano-7-(4-fluoro-phenoxy)-4-hydroxy-isoquinoline-3-carbonyl]amino}-2-cyclopropyl-propionic acid A mixture of 3-{[1-cyano-7-(4-fluoro-phenoxy)-4-hydroxy-isoquinoline-3-carbonyl]-amino}-2-cyclopropyl-propionic acid tert-butyl ester (10 mg) and TFA (1 mL) in DCM (1 mL) was stirred at rt for 3 h; then the mixture was concentrated and resulting residue was treated with water; the solids were collected via filtration and air dried to give desired product (11 mg). LC-MS ESI+: 436 (M+1)+.

Example 180

3{-[1-Cyano-7-(2,6-difluoro-phenoxy)-4-hydroxy-isoquinoline-3-carbonyl]-amino}-2-cyclopropyl-propionic acid

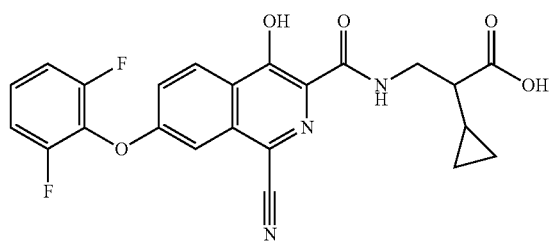 [SMILES: N#Cc1nc(C(=O)NCC(C(=O)O)C2CC2)c(O)c2ccc(Oc3c(F)cccc3F)cc12]

a) 3-{[7-Cyano-7-(2,6-difluoro-phenoxy)-4-hydroxy-isoquinoline-3-carbonyl]amino}-2-cyclopropyl-propionic acid tert-butyl ester A mixture of 3-amino-2-cyclopropyl-propionic acid tert-butyl ester (20 mg), 1-cyano-7-(2,6-difluoro-phenoxy)-4-hydroxy-isoquinoline-3-carboxylic acid ethyl ester (16 mg) and DBU (10 mg) in DMA (0.3 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product as brown solid (10 mg). LC-MS ESI+: 510 (M+1)+.

b) 3-{[7-Cyano-7-(2,6-difluoro-phenoxy)-4-hydroxy-isoquinoline-3-carbonyl]amino}-2-cyclopropyl-propionic acid A mixture of 3-{[1-cyano-7-(4-fluoro-phenoxy)-4-hydroxy-isoquinoline-3-carbonyl]-amino}-2-cyclopropyl-propionic acid tert-butyl ester (10 mg) and TFA (1 mL) in DCM (1 mL) was stirred at rt for 3 h; then the mixture was concentrated and resulting residue was treated with water; the solids were collected via filtration and air dried to give desired product (9 mg). LC-MS ESI+: 454 (M+1)+.

Example 181

3-[(1-Cyano-4-hydroxy-7-phenoxy-isoquinoline-3-carbonyl)-amino]-2-(4-fluoro-phenyl)-propionic acid

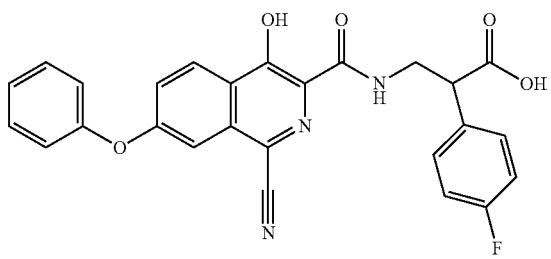 [SMILES: N#Cc1nc(C(=O)NCC(C(=O)O)c2ccc(F)cc2)c(O)c2ccc(Oc3ccccc3)cc12]

To a dry ice/acetone bath cooled solution of (4-fluoro-phenyl)-acetonitrile (3.04 g) and Boc anhydride (5.9 g) in THF (20 mL) was slowly added a solution of LDA (30 mL, 1.5 M solution) in cyclohexane and the solution was stirred for 2 h in the cold bath; then the reaction was warmed to rt and quenched with diluted citric acid solution, extracted with EtOAc; EtOAc phase was washed with diluted NaCl solution, and dried over anhydrous sodium sulfate, filtered, concentrated and silica gel column purified to give cyano-(4-fluoro-phenyl)-acetic acid tert-butyl ester (3.78 g).

Cyano-(4-fluoro-phenyl)-acetic acid tert-butyl ester (3.78 g) was mixed with Raney nickel (5 mL, 50% water) in MeOH (100 mL) and stirred under hydrogen balloon at rt overnight. The mixture was then filtered through Celite, concentrated to give crude, which was silica gel column purified to give 3-amino-2-(4-fluoro-phenyl)-propionic acid tert-butyl ester (1.3 g).

A mixture of 3-amino-2-(4-fluoro-phenyl)-propionic acid tert-butyl ester (1.3 g) and TFA (10 mL) in DCM (10 mL) was stirred at rt for 1.5 h. Then concentrated, HCl aqueous solution (50 mL, 2 M) was added and concentrated; then acetonitrile was added, and concentrated; then ether was added, solids were collected via filtration and air dried to give HCl salt of 3-amino-2-(4-fluoro-phenyl)-propionic acid (1.21 g).

A mixture of HCl salt of 3-amino-2-(4-fluoro-phenyl)-propionic acid (82 mg), 4-hydroxy-7-phenoxy-isoquinoline-3-carboxylic acid methyl ester (40 mg) and NaOMe (41 mg) in DMA (1 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column column-purified to give desired product (19 mg). LC-MS ESI+: 472 (M+1)+.

Example 182

3-[(1-Cyano-4-hydroxy-7-phenoxy-isoquinoline-3-carbonyl)-amino]-2-(2-fluoro-phenyl)-propionic acid

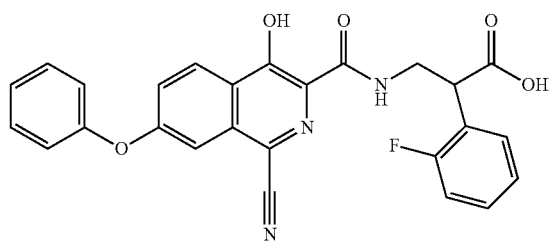 [SMILES: N#Cc1nc(C(=O)NCC(C(=O)O)c2ccccc2F)c(O)c2ccc(Oc3ccccc3)cc12]

To a dry ice/acetone bath cooled solution of (2-fluoro-phenyl)-acetonitrile (2.99 g) and Boc anhydride (5.55 g) in THF (20 mL) was slowly added a solution of LDA (25 mL, 1.5 M solution) in cyclohexane and the solution was stirred for 2 h in the cold bath; then the reaction was warmed to rt and quenched with diluted citric acid solution, extracted with EtOAc; EtOAc phase was washed with diluted NaCl solution, and dried over anhydrous sodium sulfate, filtered, concentrated and silica gel column purified to give cyano-(2-fluoro-phenyl)-acetic acid tert-butyl ester (4.55 g).

Cyano-(2-fluoro-phenyl)-acetic acid tert-butyl ester (4.55 g) was mixed with Raney nickel (3 mL, 50% water) in MeOH (100 mL) and stirred under hydrogen balloon at rt overnight. The mixture was then filtered through celite, concentrated to give crude, which was silica gel column purified to give 3-amino-2-(2-fluoro-phenyl)-propionic acid tert-butyl ester (1.4 g).

A mixture of 3-amino-2-(2-fluoro-phenyl)-propionic acid tert-butyl ester (1.4 g) and TFA (10 mL) in DCM (10 mL) was stirred at rt for 1.5 h, which was then concentrated, co-evaporated with aqueous HCl solution (50 mL, 2 M) and acetonitrile respectively. Ether was added to the resulting mixture; solids were collected via filtration and air dried to give HCl salt of 3-amino-2-(2-fluoro-phenyl)-propionic acid (1.25 g).

A mixture of HCl salt of 3-amino-2-(2-fluoro-phenyl)-propionic acid (82 mg), 4-hydroxy-7-phenoxy-isoquinoline-3-carboxylic acid methyl ester (40 mg) and DBU (0.112 mL) in DMA (1 mL) was heated in an oil bath (150° C.) for 1 h. The reaction mixture was then partitioned between EtOAc and diluted HCl solution, EtOAc phase was separated and washed with water, diluted NaCl solution and dried over anhydrous sodium sulfate solution, filtered, concentrated and silica gel column purified to give desired product (40 mg). LC-MS ESI+: 472 (M+1)+.

Example 183

3-{[(1-Cyano-4-hydroxy-7-phenoxy-isoquinoline-3-carbonyl)-amino]-methyl}-5-methyl-hexanoic acid

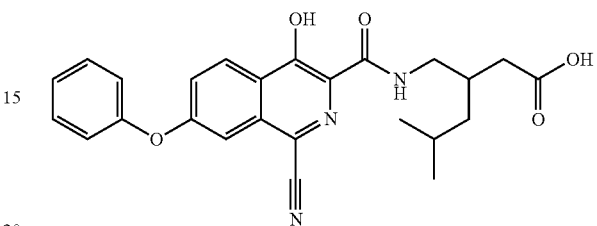

A mixture of 1-cyano-4-hydroxy-7-phenoxy-isoquinoline-3-carboxylic acid methyl ester (50 mg, 0.16 mmole) and 3-(aminomethyl)-5-methylhexanoic acid (249 mg, 1.6 mmole, AK Scientific) in 0.5 M sodium methoxide in methanol (2.5 ml) was refluxed for two days before it was cooled to room temperature, concentrated and dissolved in water, extracted with dichloromethane. The remaining aqueous layer was acidified with 1N hydrochloric chloride, extracted with dichloromethane. The organic layer was dried over anhydrous sodium sulfate, concentrated and purified by flash column chromatography on silica gel with a gradient of dichloromethane and ethyl acetate to give the title compound as a white solid (35 mg). LC-MS ESI+: 448 (M+1)+; ESI−: 446 (M-1)−.

Example 184

4-[(1-Cyano-4-hydroxy-7-phenoxy-isoquinoline-3-carbonyl)-amino]-pentanoic acid

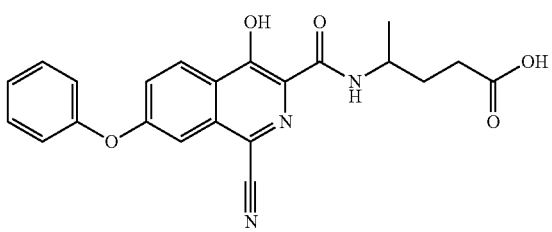 [SMILES: CC(CCC(=O)O)NC(=O)c1nc(C#N)c2cc(Oc3ccccc3)ccc2c1O]

A mixture of 1-cyano-4-hydroxy-7-phenoxy-isoquinoline-3-carboxylic acid methyl ester (50 mg, 0.16 mmole) and 4-amino-pentanoic acid (prepared from hydrolysis of 5-methyl-2-pyrrolidinone in 6 N HCl at reflux for 2 days, followed by lyophilization, 274 mg, 2.4 mmole) in 0.5 M sodium methoxide in methanol (4.6 ml) was refluxed for twenty hours before it was cooled to room temperature, concentrated and dissolved in water, extracted with dichloromethane. The remaining aqueous layer was acidified with 1N hydrochloric chloride, extracted with a mixture of dichloromethane and methanol. The organic layer was dried over anhydrous sodium sulfate, concentrated and purified by flash column chromatography on silica gel with a gradient of dichloromethane and methanol to give the title compound as a white solid (43 mg). LC-MS ESI–: 404 (M–1)⁻.

Example 185

Comparative Data

The compounds shown in below in Table 2 were tested in the HIF-PH assay (above). Compounds of the invention were compared to some previously described HIF prolyl hydroxylase inhibitor compounds. The previously described compounds inhibit PHD1 and PHD2 with similar potency whereas the compounds of the invention selectively inhibit PHD1 over PHD2 with at least a $IC_{50}$ PHD2/$IC_{50}$ PHD1 of at least and up to more than 40.

TABLE 2

| Compound | Name | PHD2/PHD1 |
|---|---|---|
| U.S. Pat. No. 7,928,120; Example 3 | 2-[(1-Cyano-4-hydroxy-7-phenoxy-isoquinoline-3-carbonyl)-amino]-acetic acid | 0.4 |
| 10 | 3-[(1-Cyano-4-hydroxy-7-phenoxy-isoquinoline-3-carbonyl)-amino]-propionic acid | 5 |
| 11 | 3-[(1-Cyano-4-hydroxy-7-phenoxy-isoquinoline-3-carbonyl)-amino]-butyric acid | 41 |
| U.S. Pat. No. 7,323,475; Example D-7 | 2-[(4-Hydroxy-7-phenoxy-isoquinoline-3-carbonyl)-amino]-acetic acid | 1.5 |
| 1 | 3-[(4-Hydroxy-7-phenoxy-isoquinoline-3-carbonyl)-amino]-propionic acid | 11 |
| 6 | 3-[(4-Hydroxy-7-phenoxy-isoquinoline-3-carbonyl)-amino]-3-methyl-butyric acid | 23 |
| 3 | 2-(S)-Hydroxy-3-[(4-hydroxy-7-phenoxy-isoquinoline-3-carbonyl)-amino]-propionic acid | 14 |
| U.S. Pat. No. 7,323,475; Example D-67 | 2-{[4-Hydroxy-7-(pyridin-3-yloxy)-isoquinoline-3-carbonyl]-amino}-acetic acid | 3 |
| 24 | 3-{[4-Hydroxy-7-(pyridin-3-yloxy)-isoquinoline-3-carbonyl]-amino}-propionic acid | 10 |

What is claimed is:

1. A compound of Formula I:

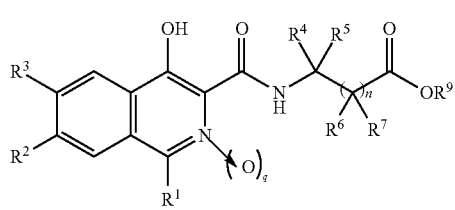

I wherein
n is 1, 2, or 3;
q is 0 or 1;
$R^1$ is hydrogen, cyano, $C_1$-$C_4$ alkyl, aryl, or heteroaryl;
  wherein said $C_1$-$C_4$ alkyl, aryl, or heteroaryl is optionally substituted with 1, 2, or 3 trifluoromethyl, $C_1$-$C_4$ alkyl, or halo;
one of $R^2$ or $R^3$ is -L-$R^8$ and the other is hydrogen;
$R^4$ and $R^5$ are independently hydrogen, halo, $C_1$-$C_4$ alkyl, cycloalkyl, aryl, heterocyclyl, or heteroaryl;
  wherein said $C_1$-$C_4$ alkyl, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;
each $R^6$ and $R^7$ are independently hydrogen, halo, hydroxy, $C_1$-$C_4$ alkyl, $C_1$-$C_4$ alkoxy, amino, substituted amino, acylamino, carboxyl, carboxyl ester, carboxamide, oxycarbonylamino, aminocarbonyloxy, aminocarbonylamino, cycloalkyl, aryl, heterocyclyl, or heteroaryl, or $R^6$ and $R^7$ together with the carbon atom attached thereto, form a carbonyl;
  wherein said $C_1$-$C_4$ alkyl, $C_1$-$C_4$ alkoxy, cycloalkyl, aryl, heterocyclyl, or heteroaryl is optionally substituted with 1, 2, or 3 hydroxy, cyano, halo, nitro, acyl, amino, substituted amino, acylamino, sulfonyl, $C_1$-$C_4$ alkyl, $C_1$-$C_4$ alkoxy, cycloalkyl, cycloalkyloxy, heterocyclyl, heterocyclyloxy, carboxyl, carboxyl ester, carboxamide, oxycarbonylamino, aminocarbonyloxy, aminocarbonylamino, aryl, aryloxy, heteroaryloxy, alkylthio, cycloalkylthio, arylthio, heteroarylthio, heterocyclicthio, or heteroaryl;
or wherein any of $R^4$ and $R^5$, $R^6$ and $R^7$, $R^4$ and $R^6$, or $R^5$ and $R^7$ groups, together with the carbon atom(s) attached thereto, join to form a cycloalkyl, aryl, heterocyclyl, or heteroaryl group, each optionally substituted with 1 to 4 halogen, oxo, $C_1$-$C_4$ alkyl, $C_1$-$C_4$ alkoxy, carboxyl, carboxyl ester, carboxamide, oxycarbonylamino, aminocarbonyloxy, aminocarbonylamino, or aryl;
$R^8$ is cycloalkyl, aryl, or heteroaryl;
  wherein said cycloalkyl, aryl, or heteroaryl is optionally substituted with 1, 2, or 3 $C_1$-$C_4$ alkyl, $C_1$-$C_4$ alkoxy, or halo;
L is a covalent bond, $C_1$-$C_4$ alkylene, —O—, —S—, —SO—, —SO$_2$—, —NH—, —C(O)NH—, —NHC(O)—, —NHC(O)NH—, —O-alkylene-, —NH-alkylene-, or —NHC(O)NH-alkylene; and
$R^9$ is hydrogen or $C_1$-$C_4$ alkyl;
  wherein said $C_1$-$C_4$ alkyl is optionally substituted with 1, 2, or 3 $C_1$-$C_4$ alkoxy, halo, cycloalkyl, heterocyclyl, aryl, or heteroaryl;
or a pharmaceutically acceptable salt, single stereoisomer, mixture of stereoisomers, ester, or tautomer thereof.

2. The compound of claim 1, wherein the compound of Formula I is represented by Formula II:

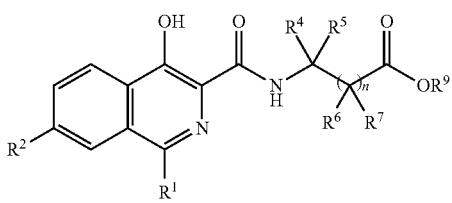

wherein n, $R^1$, $R^2$, $R^4$, $R^5$, $R^7$ and $R^9$ are as defined in claim 1.

3. The compound of claim 1, wherein the compound of Formula I is represented by Formula III:

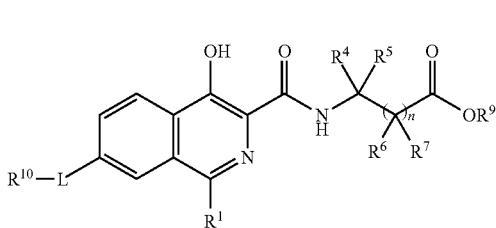

wherein n, L, $R^1$, $R^4$, $R^5$, $R^6$, $R^7$ and $R^9$ are as defined in claim 1, and
$R^{10}$ is aryl optionally substituted with 1, 2, or 3 $C_1$-$C_4$ alkyl, $C_1$-$C_4$ alkoxy, or halo.

4. The compound of claim 1, wherein q is 0.
5. The compound of claim 1, wherein n is 1.
6. The compound of claim 1, wherein n is 2 or 3.
7. The compound of claim 1, wherein $R^9$ is hydrogen.
8. The compound of claim 1, wherein $R^9$ is $C_1$-$C_4$ alkyl.
9. The compound of claim 1, wherein $R^1$ is hydrogen.
10. The compound of claim 1, wherein $R^1$ is cyano.
11. The compound of claim 1, wherein $R^1$ is $C_1$-$C_4$ alkyl, aryl, or heteroaryl;
wherein said $C_1$-$C_4$ alkyl, aryl, or heteroaryl is optionally substituted with 1, 2, or 3 trifluoromethyl, $C_1$-$C_4$ alkyl, or halo.
12. The compound of claim 1, wherein $R^4$ and $R^5$ are independently hydrogen, $C_1$-$C_4$ alkyl, or aryl;
wherein said $C_1$-$C_4$ alkyl is optionally substituted with 1, 2, or 3 hydroxy or aryl;
or wherein $R^4$ and $R^5$ together with the carbon atom attached thereto, join to form a cycloalkyl or heterocyclyl group, optionally substituted with carboxyl ester.
13. The compound of claim 1, wherein $R^4$ and $R^5$ are hydrogen.
14. The compound of claim 1, wherein each $R^6$ and $R^7$ are independently hydrogen, halo, hydroxy, $C_1$-$C_4$ alkyl, $C_1$-$C_4$ alkoxy, aryl, amino, acylamino, or aminocarbonylamino, or wherein $R^6$ and $R^7$ together with the carbon atom attached thereto, form a carbonyl;
wherein said $C_1$-$C_4$ alkyl or aryl, is optionally substituted with 1, 2, or 3 hydroxy, halo, or aryl;
or wherein $R^6$ and $R^7$ together with the carbon atom attached thereto, join to form a cycloalkyl or heterocyclyl group, each optionally substituted with oxo.
15. The compound of claim 1, wherein each $R^6$ and $R^7$ are independently hydrogen, halo, hydroxy, $C_1$-$C_4$ alkyl, $C_1$-$C_4$ alkoxy, aryl, amino, acylamino, or aminocarbonylamino, or $R^6$ and $R^7$ together with the carbon atom attached thereto, form a carbonyl.

16. The compound of claim 1, wherein L is —O—, —S—, —SO$_2$—, —NH—, —C(O)NH—, —NHC(O)—, or —NHC(O)NH—.
17. The compound of claim 1, wherein L is —O— or —S—.
18. The compound of claim 1, wherein L is —O—.
19. The compound of claim 1, wherein L is —O—; $R^9$ is hydrogen; $R^1$ is hydrogen or cyano-; and $R^8$ is aryl.
20. The compound of claim 3, wherein L is —O—; $R^9$ is hydrogen; $R^1$ is hydrogen or cyano-; and $R^{10}$ is aryl.
21. The compound of claim 1, wherein the compound is the trifluoroacetic acid salt thereof.
22. The compound of claim 1, wherein when n is 1 and each $R^6$ and $R^7$ are hydrogen, then $R^1$ is cyano.
23. A compound selected from the group consisting of:
3-[(4-Hydroxy-7-phenoxy-isoquinoline-3-carbonyl)-amino]-propionic acid,
3-[(4-Hydroxy-7-phenoxy-isoquinoline-3-carbonyl)-amino]-2,2-dimethyl-propionic acid,
2-(S)-Hydroxy-3-[(4-hydroxy-7-phenoxy-isoquinoline-3-carbonyl)-amino]-propionic acid,
4-[(4-Hydroxy-7-phenoxy-isoquinoline-3-carbonyl)-amino]-butyric acid,
5-[(4-Hydroxy-7-phenoxy-isoquinoline-3-carbonyl)-amino]-pentanoic acid,
3-[(4-Hydroxy-7-phenoxy-isoquinoline-3-carbonyl)-amino]-3-methyl-butyric acid,
2-(S)-Hydroxy-4-[(4-hydroxy-7-phenoxy-isoquinoline-3-carbonyl)-amino]-butyric acid,
4-[(4-Hydroxy-7-phenoxy-isoquinoline-3-carbonyl)-amino]-2,2-dimethyl-butyric acid,
2-(S)-Amino-3-[(4-hydroxy-7-phenoxy-isoquinoline-3-carbonyl)-amino]-propionic acid,
3-[(1-Cyano-4-hydroxy-7-phenoxy-isoquinoline-3-carbonyl)-amino]-propionic acid,
3-[(1-Cyano-4-hydroxy-7-phenoxy-isoquinoline-3-carbonyl)-amino]-butyric acid,
1-{[(1-Cyano-4-hydroxy-7-phenoxy-isoquinoline-3-carbonyl)-amino]-methyl}-cyclopropanecarboxylic acid,
1{-[(4-Hydroxy-7-phenoxy-isoquinoline-3-carbonyl)-amino]-methyl}-cyclobutanecarboxylic acid,
1-{[(1-Cyano-4-hydroxy-7-phenoxy-isoquinoline-3-carbonyl)-amino]-methyl}-cyclobutanecarboxylic acid,
4-{[(4-Hydroxy-7-phenoxy-isoquinoline-3-carbonyl)-amino]-methyl}-tetrahydro-pyran-4-carboxylic acid,
4-{[(1-Cyano-4-hydroxy-7-phenoxy-isoquinoline-3-carbonyl)-amino]-methyl}-tetrahydro-pyran-4-carboxylic acid,
2-{[(1-Cyano-4-hydroxy-7-phenoxy-isoquinoline-3-carbonyl)-amino]-methyl}-pentanoic acid,
2-{[(1-Cyano-4-hydroxy-7-phenoxy-isoquinoline-3-carbonyl)-amino]-methyl}-2-propyl-pentanoic acid,
1-{[(1-Cyano-4-hydroxy-7-phenoxy-isoquinoline-3-carbonyl)-amino]-methyl}-cyclopentanecarboxylic acid,
3-{[1-Cyano-4-hydroxy-7-(4-methoxy-phenoxy)-isoquinoline-3-carbonyl]-amino}-2,2-dimethyl-propionic acid,
3-{[1-Cyano-4-hydroxy-7-(4-methoxy-phenoxy)-isoquinoline-3-carbonyl]-amino}-3-methyl-butyric acid,
3-{[1-Cyano-7-(2,6-difluoro-phenoxy)-4-hydroxy-isoquinoline-3-carbonyl]-amino}-2,2-dimethyl-propionic acid,
3-{[7-(4-Chloro-3-fluoro-phenoxy)-4-hydroxy-isoquinoline-3-carbonyl]-amino}-2,2-dimethyl-propionic acid,
3-{[4-Hydroxy-7-(pyridin-3-yloxy)-isoquinoline-3-carbonyl]-amino}-propionic acid, 3-{[4-Hydroxy-7-(pyridin-2-yloxy)-isoquinoline-3-carbonyl]-amino}-propionic acid,
1-({[1-Cyano-7-(2,6-difluoro-phenoxy)-4-hydroxy-isoquinoline-3-carbonyl]-amino}-methyl)-cyclobutanecarboxylic acid,
3-{[1-Cyano-4-hydroxy-7-(pyridin-3-yloxy)-isoquinoline-3-carbonyl]-amino}-2,2-dimethyl-propionic acid,
1-({[1-Cyano-4-hydroxy-7-(pyridin-3-yloxy)-isoquinoline-3-carbonyl]-amino}-methyl)-cyclobutanecarboxylic acid,
4-{[(1-Cyano-4-hydroxy-7-phenoxy-isoquinoline-3-carbonyl)-amino]-methyl}-1,1-dioxo-hexahydro-11$^6$-thiopyran-4-carboxylic acid,
4-{[(1-Cyano-4-hydroxy-7-phenoxy-isoquinoline-3-carbonyl)-amino]-methyl}-1-oxo-hexahydro-11$^4$-thiopyran-4-carboxylic acid,
3-{[7-(2-Chloro-5-fluoro-phenoxy)-1-cyano-4-hydroxy-isoquinoline-3-carbonyl]-amino}-2,2-dimethyl-propionic acid,
cis-2-(1-Cyano-4-hydroxy-7-phenoxyisoquinoline-3-carboxamido)cyclohexanecarboxylic acid,
cis-2-[(1-Cyano-4-hydroxy-7-phenoxy-isoquinoline-3-carbonyl)-amino]-cyclopentanecarboxylic acid,
3-(4-Chloro-phenyl)-4-[(1-cyano-4-hydroxy-7-phenoxy-isoquinoline-3-carbonyl)-amino]-butyric acid,
(S)-4-(1-Cyano-4-hydroxy-7-phenoxyisoquinoline-3-carboxamido)-3-hydroxybutanoic acid,
(1-{[(1-Cyano-4-hydroxy-7-phenoxy-isoquinoline-3-carbonyl)-amino]-methyl}-cyclohexyl)-acetic acid,
(R)-3-(1-Cyano-4-hydroxy-7-phenoxyisoquinoline-3-carboxamido)-4-hydroxybutanoic acid,
3-(7-(2-Chlorophenoxy)-1-cyano-4-hydroxyisoquinoline-3-carboxamido)-2,2-dimethylpropanoic acid,
3-{[7-(3-Chloro-phenoxy)-1-cyano-4-hydroxy-isoquinoline-3-carbonyl]-amino}-2,2-dimethyl-propionic acid,
3-{[7-(4-Chloro-phenoxy)-1-cyano-4-hydroxy-isoquinoline-3-carbonyl]-amino}-2,2-dimethyl-propionic acid,
3-{[1-Cyano-7-(2-fluoro-phenoxy)-4-hydroxy-isoquinoline-3-carbonyl]-amino}-2,2-dimethyl-propionic acid,
3-(1-Cyano-7-(3-fluorophenoxy)-4-hydroxyisoquinoline-3-carboxamido)-2,2-dimethylpropanoic acid,
3-(1-Cyano-4-hydroxy-7-(naphthalen-1-yloxy)isoquinoline-3-carboxamido)-2,2-dimethylpropanoic acid,
3-[(1-Cyano-4-hydroxy-7-p-tolyloxy-isoquinoline-3-carbonyl)-amino]-2,2-dimethyl-propionic acid,
(S)-2-Amino-4-(1-cyano-4-hydroxy-7-phenoxyisoquinoline-3-carboxamido)butanoic acid,
4-(1-Cyano-4-hydroxy-7-phenoxyisoquinoline-3-carboxamido)-4-methylpentanoic acid,
(S)-3-[(1-Cyano-4-hydroxy-7-phenoxy-isoquinoline-3-carbonyl)-amino]-3-phenyl-propionic acid,
(R)-3-[(1-Cyano-4-hydroxy-7-phenoxy-isoquinoline-3-carbonyl)-amino]-3-phenyl-propionic acid,
(S)-2-Benzyl-3-[(1-cyano-4-hydroxy-7-phenoxy-isoquinoline-3-carbonyl)-amino]-propionic acid,
(R)-2-Amino-4-(1-cyano-4-hydroxy-7-phenoxyisoquinoline-3-carboxamido)butanoic acid,
(R)-2-Acetylamino-4-[(1-cyano-4-hydroxy-7-phenoxy-isoquinoline-3-carbonyl)-amino]-butyric acid,
(R)-4-(1-Cyano-4-hydroxy-7-phenoxyisoquinoline-3-carboxamido)-2-(3-ethylureido)butanoic acid,
(R)-4-(1-Cyano-4-hydroxy-7-phenoxyisoquinoline-3-carboxamido)-2-(methoxycarbonylamino)butanoic acid,
(R)-4-(1-Cyano-4-hydroxy-7-phenoxyisoquinoline-3-carboxamido)-2-(3,3-dimethylureido)butanoic acid,
(R)-4-(1-Cyano-4-hydroxy-7-phenoxyisoquinoline-3-carboxamido)-2-ureidobutanoic acid,
4-(1-Cyano-4-hydroxy-7-phenoxyisoquinoline-3-carboxamido)-2-oxobutanoic acid,
2-((1-Cyano-4-hydroxy-7-phenoxyisoquinoline-3-carboxamido)methyl)butanoic acid,
2-{[(1-Cyano-4-hydroxy-7-phenoxy-isoquinoline-3-carbonyl)-amino]-methyl}-2-methyl-butyric acid,
3-{[1-Cyano-4-hydroxy-7-(naphthalen-2-yloxy)-isoquinoline-3-carbonyl]-amino}-2,2-dimethyl-propionic acid,
3-{[1-Cyano-4-hydroxy-7-(2-methoxy-phenoxy)-isoquinoline-3-carbonyl]-amino}-2,2-dimethyl-propionic acid,
3-[(1-Cyano-4-hydroxy-7-phenoxy-isoquinoline-3-carbonyl)-amino]-4-methyl-pentanoic acid,
3-{[1-Cyano-7-(2-ethyl-phenoxy)-4-hydroxy-isoquinoline-3-carbonyl]-amino}-2,2-dimethyl-propionic acid,
3-(R)-[(1-Cyano-4-hydroxy-7-phenoxy-isoquinoline-3-carbonyl)-amino]-pentanoic acid,
3-(R)-[(1-Cyano-4-hydroxy-7-phenoxy-isoquinoline-3-carbonyl)-amino]-butyric acid,
3-[(1-Cyano-4-hydroxy-7-phenoxy-isoquinoline-3-carbonyl)-amino]-2,2-difluoro-propionic acid,
3-[(1-Cyano-4-hydroxy-7-phenoxy-isoquinoline-3-carbonyl)-amino]-5-methyl-hexanoic acid,
(S)-3-[(1-Cyano-4-hydroxy-7-phenoxy-isoquinoline-3-carbonyl)-amino]-4-phenyl-butyric acid,
(R)-3-[(1-Cyano-4-hydroxy-7-phenoxy-isoquinoline-3-carbonyl)-amino]-4-phenyl-butyric acid,
(2R,3R)-3-[(1-Cyano-4-hydroxy-7-phenoxy-isoquinoline-3-carbonyl)-amino]-2-methyl-butyric acid,
(2S,3R)-3-[(1-Cyano-4-hydroxy-7-phenoxy-isoquinoline-3-carbonyl)-amino]-2-methyl-butyric acid,
(2S,3S)-3-[(1-Cyano-4-hydroxy-7-phenoxy-isoquinoline-3-carbonyl)-amino]-2-methyl-butyric acid,
(2R,3S)-3-[(1-Cyano-4-hydroxy-7-phenoxy-isoquinoline-3-carbonyl)-amino]-2-methyl-butyric acid,
(S)-3-(1-Cyano-4-hydroxy-7-phenoxyisoquinoline-3-carboxamido)-2-hydroxy-2-methylpropanoic acid,
(2S,3R)-3-(1-Cyano-4-hydroxy-7-phenoxyisoquinoline-3-carboxamido)-2-hydroxy-4-phenylbutanoic acid,
(2R,3R)-3-(1-Cyano-4-hydroxy-7-phenoxyisoquinoline-3-carboxamido)-2-hydroxy-4-phenylbutanoic acid,
3-[(1-Cyano-4-hydroxy-7-phenoxy-isoquinoline-3-carbonyl)-amino]-2-hydroxy-propionic acid,
3-[(1-Cyano-4-hydroxy-7-phenoxy-isoquinoline-3-carbonyl)-amino]-2,2-dimethyl-propionic acid,
3-(S)-[(1-Cyano-4-hydroxy-7-phenoxy-isoquinoline-3-carbonyl)-amino]-butyric acid,
3-[(1-Cyano-4-hydroxy-7-phenoxy-isoquinoline-3-carbonyl)-amino]-2-(S)-hydroxy-propionic acid,
4-[(1-Cyano-4-hydroxy-7-phenoxy-isoquinoline-3-carbonyl)-amino]-butyric acid,
5-[(1-Cyano-4-hydroxy-7-phenoxy-isoquinoline-3-carbonyl)-amino]-pentanoic acid,
3-[(1-Cyano-4-hydroxy-7-phenoxy-isoquinoline-3-carbonyl)-amino]-3-methyl-butyric acid,
4-[(1-Cyano-4-hydroxy-7-phenoxy-isoquinoline-3-carbonyl)-amino]-2-(S)-hydroxy-butyric acid,
4-[(1-Cyano-4-hydroxy-7-phenoxy-isoquinoline-3-carbonyl)-amino]-2,2-dimethyl-butyric acid,
2-(S)-tert-Butoxycarbonylamino-3-[(1-cyano-4-hydroxy-7-phenoxy-isoquinoline-3-carbonyl)-amino]-propionic acid,
2-(S)-Amino-3-[(1-cyano-4-hydroxy-7-phenoxy-isoquinoline-3-carbonyl)-amino]-propionic acid, 2-(S)-Benzyloxycarbonylamino-3-[(1-cyano-4-hydroxy-7-phenoxy-isoquinoline-3-carbonyl)-amino]-propionic acid,
trans-4-[(1-Cyano-4-hydroxy-7-phenoxy-isoquinoline-3-carbonyl)-amino]-cyclohexanecarboxylic acid,
4-[(1-Cyano-4-hydroxy-7-phenoxy-isoquinoline-3-carbonyl)-amino]-3,3-dimethyl-butyric acid,
{1-[(1-Cyano-4-hydroxy-7-phenoxy-isoquinoline-3-carbonyl)-amino]-cyclohexyl}-acetic acid,
3-[(1-Cyano-4-hydroxy-7-phenoxy-isoquinoline-3-carbonyl)-amino]-3-phenyl-propionic acid,
3-[(1-Cyano-4-hydroxy-7-phenoxy-isoquinoline-3-carbonyl)-amino]-2-(R)-methyl-propionic acid,
3-[(1-Cyano-4-hydroxy-7-phenoxy-isoquinoline-3-carbonyl)-amino]-2-(S)-methyl-propionic acid,
4-[(1-Cyano-4-hydroxy-7-phenoxy-isoquinoline-3-carbonyl)-amino]-2-(S)-methoxy-butyric acid,
5-[(1-Cyano-4-hydroxy-7-phenoxy-isoquinoline-3-carbonyl)-amino]-2,2-dimethyl-pentanoic acid,
4-Carboxymethyl-4-[(1-cyano-4-hydroxy-7-phenoxy-isoquinoline-3-carbonyl)-amino]-piperidine-1-carboxylic acid tert-butyl ester,
3-{[7-(2-Chloro-4-fluoro-phenoxy)-1-cyano-4-hydroxy-isoquinoline-3-carbonyl]-amino}-propionic acid,
5-{[7-(2-Chloro-4-fluoro-phenoxy)-1-cyano-4-hydroxy-isoquinoline-3-carbonyl]-amino}-pentanoic acid,
3-{[7-(2-Chloro-4-fluoro-phenoxy)-1-cyano-4-hydroxy-isoquinoline-3-carbonyl]-amino}-2,2-dimethyl-propionic acid,
5-{[7-(2,6-Difluoro-phenoxy)-4-hydroxy-isoquinoline-3-carbonyl]-amino}-pentanoic acid,
3-{[1-Cyano-7-(4-fluoro-phenoxy)-4-hydroxy-isoquinoline-3-carbonyl]-amino}-2,2-dimethyl-propionic acid,
3-{[1-Cyano-7-(4-fluoro-phenoxy)-4-hydroxy-isoquinoline-3-carbonyl]-amino}-3-methyl-butyric acid,
2-(S)-Hydroxy-3-{[4-hydroxy-7-(4-methoxy-phenoxy)-isoquinoline-3-carbonyl]-amino}-propionic acid,
3-{[4-Hydroxy-7-(4-methoxy-phenoxy)-isoquinoline-3-carbonyl]-amino}-2,2-dimethyl-propionic acid,
5-{[4-Hydroxy-7-(4-methoxy-phenoxy)-isoquinoline-3-carbonyl]-amino}-pentanoic acid,
{1-[(1-Cyano-4-hydroxy-7-phenoxy-isoquinoline-3-carbonyl)-amino]-cyclobutyl}-acetic acid,
(R)-3-[(1-Cyano-4-hydroxy-7-phenoxy-isoquinoline-3-carbonyl)-amino]-5-phenylpentanoic acid,
3-[(4-Hydroxy-1-methyl-7-phenoxy-isoquinoline-3-carbonyl)-amino]-propionic acid,
3-{[1-Cyano-6-(2,6-dimethyl-phenoxy)-4-hydroxy-isoquinoline-3-carbonyl]-amino}-propionic acid,
4-{[1-Cyano-6-(2,6-dimethyl-phenoxy)-4-hydroxy-isoquinoline-3-carbonyl]-amino}-butyric acid,
5-{[1-Cyano-6-(2,6-dimethyl-phenoxy)-4-hydroxy-isoquinoline-3-carbonyl]-amino}-pentanoic acid,
3-[(4-Hydroxy-6-phenoxy-isoquinoline-3-carbonyl)-amino]-propionic acid,
4-[(4-Hydroxy-6-phenoxy-isoquinoline-3-carbonyl)-amino]-butyric acid,
5-[(4-Hydroxy-7-phenylsulfanyl-isoquinoline-3-carbonyl)-amino]-pentanoic acid,
4-[(4-Hydroxy-7-phenylsulfanyl-isoquinoline-3-carbonyl)-amino]-butyric acid,
3-{[4-Hydroxy-7-(3-phenyl-ureido)-isoquinoline-3-carbonyl]-amino}-propionic acid,
2(S)-Hydroxy-3-{[4-hydroxy-7-(3-phenyl-ureido)-isoquinoline-3-carbonyl]-amino}-propionic acid,
3-{[7-(4-Fluoro-benzoylamino)-4-hydroxy-isoquinoline-3-carbonyl]-amino}-propionic acid,
4-{[4-Hydroxy-7-(3-phenyl-ureido)-isoquinoline-3-carbonyl]-amino}-butyric acid,
4-{[7-(4-Fluoro-benzoylamino)-4-hydroxy-isoquinoline-3-carbonyl]-amino}-butyric acid,
3-[(1-Cyano-4-hydroxy-7-phenylsulfanyl-isoquinoline-3-carbonyl)-amino]-2,2-dimethyl-propionic acid,
3-[(1-Cyano-4-hydroxy-7-phenethyl-isoquinoline-3-carbonyl)-amino]-2,2-dimethyl-propionic acid,
3-[(1-Cyano-4-hydroxy-6-phenoxy-isoquinoline-3-carbonyl)-amino]-2,2-dimethyl-propionic acid,
5-[(4-Hydroxy-7-phenylamino-isoquinoline-3-carbonyl)-amino]-pentanoic acid,
5-{[4-Hydroxy-7-(4-methoxy-benzylamino)-isoquinoline-3-carbonyl]-amino}-pentanoic acid,
3-{[4-Hydroxy-7-(4-methoxy-benzylamino)-isoquinoline-3-carbonyl]-amino}-2,2-dimethyl-propionic acid,
3-[(4-Hydroxy-7-phenylsulfanyl-isoquinoline-3-carbonyl)-amino]-2,2-dimethyl-propionic acid,
5-[(1-Cyano-4-hydroxy-6-phenoxy-isoquinoline-3-carbonyl)-amino]-pentanoic acid,
3-[(4-Hydroxy-7-phenyl-isoquinoline-3-carbonyl)-amino]-2,2-dimethyl-propionic acid,
3-{[7-(3-Cyclohexyl-ureido)-4-hydroxy-isoquinoline-3-carbonyl]-amino}-propionic acid,
4-{[7-(3-Cyclohexyl-ureido)-4-hydroxy-isoquinoline-3-carbonyl]-amino}-butyric acid,
3-{[7-(4-Fluoro-phenyl)-4-hydroxy-isoquinoline-3-carbonyl]-amino}-propionic acid,
3-{[7-(3-Benzyl-ureido)-4-hydroxy-isoquinoline-3-carbonyl]-amino}-propionic acid,
4-{[7-(3-Benzyl-ureido)-4-hydroxy-isoquinoline-3-carbonyl]-amino}-butyric acid,
3-[(7-Cyclohexanesulfonyl-4-hydroxy-isoquinoline-3-carbonyl)-amino]-propionic acid,
3-{[1-(5-Fluoro-pyridin-3-yl)-4-hydroxy-7-phenoxy-isoquinoline-3-carbonyl]-amino}-2,2-dimethyl-propionic acid,
3-[(1-Cyano-4-hydroxy-7-phenyl-isoquinoline-3-carbonyl)-amino]-propionic acid,
3-[(1-Cyano-4-hydroxy-7-phenyl-isoquinoline-3-carbonyl)-amino]-2,2-dimethyl-propionic acid,
3-{[7-(4-Fluoro-benzoylamino)-4-hydroxy-isoquinoline-3-carbonyl]-amino}-2,2-dimethyl-propionic acid,
3-{[1-Cyano-4-hydroxy-7-(3-phenyl-ureido)-isoquinoline-3-carbonyl]-amino}-2,2-dimethyl-propionic acid,
3-({7-[3-(4-Fluoro-phenyl)-ureido]-4-hydroxy-isoquinoline-3-carbonyl}-amino)-propionic acid,
4-({7-[3-(4-Fluoro-phenyl)-ureido]-4-hydroxy-isoquinoline-3-carbonyl}-amino)-butyric acid,
3-[(4-Hydroxy-7-phenoxy-1-phenyl-isoquinoline-3-carbonyl)-amino]-2,2-dimethyl-propionic acid,
3-[(4-Hydroxy-7-phenoxy-1-phenyl-isoquinoline-3-carbonyl)-amino]-propionic acid,
3-[(4-Hydroxy-7-phenoxy-1-trifluoromethyl-isoquinoline-3-carbonyl)-amino]-propionic acid,
3-[(7-Benzyl-4-hydroxy-isoquinoline-3-carbonyl)-amino]-2,2-dimethyl-propionic acid,
5-{[1-(5-Fluoro-pyridin-3-yl)-4-hydroxy-7-phenoxy-isoquinoline-3-carbonyl]-amino}-pentanoic acid,
4-{[7-(4-Fluoro-phenyl)-4-hydroxy-isoquinoline-3-carbonyl]-amino}-butyric acid,
5-{[7-(4-Fluoro-phenyl)-4-hydroxy-isoquinoline-3-carbonyl]-amino}-pentanoic acid,
3-{[7-(4-Fluoro-phenyl)-4-hydroxy-isoquinoline-3-carbonyl]-amino}-2,2-dimethyl-propionic acid, 3-{[4-Hydroxy-1-(2-methyl-5-trifluoromethyl-2H-pyrazol-3-yl)-7-phenoxy-isoquinoline-3-carbonyl]-amino}-2,2-dimethyl-propionic acid,
3-[(7-Benzyloxy-1-cyano-4-hydroxy-isoquinoline-3-carbonyl)-amino]-3-methyl-butyric acid,
3-[(7-Benzyloxy-1-cyano-4-hydroxy-isoquinoline-3-carbonyl)-amino]-2,2-dimethyl-propionic acid,
1{[(1-Cyano-4-hydroxy-7-phenylsulfanyl-isoquinoline-3-carbonyl)-amino]-methyl}-cyclobutanecarboxylic acid,
3-[(1-Cyano-4-hydroxy-6-o-tolyloxy-isoquinoline-3-carbonyl)-amino]-2,2-dimethyl-propionic acid,
3-[(1-Cyano-7-cyclohexyloxy-4-hydroxy-isoquinoline-3-carbonyl)-amino]-2,2-dimethyl-propionic acid,
3-(2-Carboxy-2-methylpropylcarbamoyl)-1-cyano-4-hydroxy-7-phenoxyisoquinoline 2-oxide,
3-(3-Carboxypropylcarbamoyl)-1-cyano-4-hydroxy-7-phenoxyisoquinoline 2-oxide,
1{[(1-Cyano-7-cyclohexyloxy-4-hydroxy-isoquinoline-3-carbonyl)-amino]-methyl}-cyclobutanecarboxylic acid,
3-[(1-Cyano-7-cyclohexanesulfonyl-4-hydroxy-isoquinoline-3-carbonyl)-amino]-2,2-dimethyl-propionic acid,
1{[(1-Cyano-7-cyclohexanesulfonyl-4-hydroxy-isoquinoline-3-carbonyl)-amino]-methyl}-cyclobutanecarboxylic acid,
3-{[7-(3-Benzyl-ureido)-1-cyano-4-hydroxy-isoquinoline-3-carbonyl]-amino}-2,2-dimethyl-propionic acid,
(S)-2-[Amino-5-(1-cyano-4-hydroxy-7-phenoxy-isoquinoline-3-carbonyl)-amino]-pentanoic acid, 2,2,2-trifluoroacetic acid (1:1),
3-[(7-Benzyl-1-cyano-4-hydroxy-isoquinoline-3-carbonyl)-amino]-2,2-dimethyl-propionic acid,
3-(3-Chloro-phenyl)-3-[(1-cyano-4-hydroxy-7-phenoxy-isoquinoline-3-carbonyl)-amino]-propionic acid,
3-[(1-Cyano-4-hydroxy-7-phenoxy-isoquinoline-3-carbonyl)-amino]-2-cyclopropyl-propionic acid,
2-Cyclopropyl-3-[(4-hydroxy-7-phenoxy-isoquinoline-3-carbonyl)-amino]-propionic acid,
3-[(1-Cyano-4-hydroxy-7-phenoxy-isoquinoline-3-carbonyl)-amino]-2-phenyl-propionic acid,
3-[(4-Hydroxy-7-phenoxy-isoquinoline-3-carbonyl)-amino]-2-phenyl-propionic acid,
3-(S)-[(1-Cyano-4-hydroxy-7-phenoxy-isoquinoline-3-carbonyl)-amino]-3-(2-fluoro-phenyl)-propionic acid,
3-(S)-[(1-Cyano-4-hydroxy-7-phenoxy-isoquinoline-3-carbonyl)-amino]-3-o-tolyl-propionic acid,
3-(S)-[(1-Cyano-4-hydroxy-7-phenoxy-isoquinoline-3-carbonyl)-amino]-3-(4-cyano-phenyl)-propionic acid,
3-(4-Chloro-phenyl)-3-[(1-cyano-4-hydroxy-7-phenoxy-isoquinoline-3-carbonyl)-amino]-propionic acid,
3-[(1-Cyano-4-hydroxy-7-phenoxy-isoquinoline-3-carbonyl)-amino]-3-pyridin-3-yl-propionic acid,
3-(S)-[(1-Cyano-4-hydroxy-7-phenoxy-isoquinoline-3-carbonyl)-amino]-3-pyridin-3-yl-propionic acid,
3-(R)-[(1-Cyano-4-hydroxy-7-phenoxy-isoquinoline-3-carbonyl)-amino]-3-pyridin-3-yl-propionic acid,
3-{[1-Cyano-7-(2-fluoro-phenoxy)-4-hydroxy-isoquinoline-3-carbonyl]-amino}-2-cyclopropyl-propionic acid,
3-{[1-Cyano-4-hydroxy-7-(pyridin-3-yloxy)-isoquinoline-3-carbonyl]-amino}-2-cyclopropyl-propionic acid tert-butyl ester, trifluoro-acetic acid salt,
3-{[1-Cyano-7-(4-fluoro-phenoxy)-4-hydroxy-isoquinoline-3-carbonyl]-amino}-2-cyclopropyl-propionic acid,
3-{[1-Cyano-7-(2,6-difluoro-phenoxy)-4-hydroxy-isoquinoline-3-carbonyl]-amino}-2-cyclopropyl-propionic acid,
3-[(1-Cyano-4-hydroxy-7-phenoxy-isoquinoline-3-carbonyl)-amino]-2-(4-fluoro-phenyl)-propionic acid,
3-[(1-Cyano-4-hydroxy-7-phenoxy-isoquinoline-3-carbonyl)-amino]-2-(2-fluoro-phenyl)-propionic acid,
3-{[(1-Cyano-4-hydroxy-7-phenoxy-isoquinoline-3-carbonyl)-amino]-methyl}-5-methyl-hexanoic acid, and
4-[(1-Cyano-4-hydroxy-7-phenoxy-isoquinoline-3-carbonyl)-amino]-pentanoic acid;

or a pharmaceutically acceptable salt, single stereoisomer, mixture of stereoisomers, ester, or tautomer thereof.

24. A pharmaceutical composition comprising one or more compounds of claim 1, and a pharmaceutically acceptable excipient.

25. A method of inhibiting PHD1 enzyme, the method comprising bringing into contact the PHD1 enzyme and an inhibitory-effective amount of a compound of claim 1.

26. The method of claim 25, wherein the PHD1 enzyme is present with PHD2 and/or PHD3.

27. The method of claim 25, wherein the compound selectively inhibits PHD1 enzyme over PHD2 and/or PHD3.

28. The method of claim 25, wherein the ratio of the $IC_{50}$ for PHD2 over the $IC_{50}$ for PHD1 is greater than or equal to five.

29. The method of claim 25, wherein the ratio of the $IC_{50}$ for PHD2 over the $IC_{50}$ for PHD1 is greater than or equal to eight.

30. The method of claim 25, wherein the ratio of the $IC_{50}$ for PHD2 over the $IC_{50}$ for PHD1 is greater than or equal to ten.

\* \* \* \* \*